(12) United States Patent
Hellmann

(10) Patent No.: US 9,745,591 B2
(45) Date of Patent: Aug. 29, 2017

(54) PLANTS HAVING ALTERED EXPRESSION AND ACTIVITY OF YIELD-RELATED PROTEINS

(71) Applicant: Washington State University, Pullman, WA (US)

(72) Inventor: Hanjo Hellmann, Pullman, WA (US)

(73) Assignee: Washington State University, Pullman, WA (US)

( * ) Notice: Subject to any disclaimer, the term of this patent is extended or adjusted under 35 U.S.C. 154(b) by 110 days.

(21) Appl. No.: 14/519,577

(22) Filed: Oct. 21, 2014

(65) Prior Publication Data

US 2015/0121572 A1    Apr. 30, 2015

Related U.S. Application Data

(60) Provisional application No. 61/895,007, filed on Oct. 24, 2013.

(51) Int. Cl.
    *C12N 15/82* (2006.01)
    *C07K 14/415* (2006.01)

(52) U.S. Cl.
    CPC ........ *C12N 15/8218* (2013.01); *C07K 14/415* (2013.01); *C12N 15/8247* (2013.01); *C12N 15/8261* (2013.01)

(58) Field of Classification Search
    None
    See application file for complete search history.

(56) References Cited

U.S. PATENT DOCUMENTS

2014/0026257 A1    1/2014   Hatzfeld et al.

OTHER PUBLICATIONS

Lechner et al. MATH/BTB CRL3 receptors target the homeodomain-leucine zipper ATHB6 to modulate abscisic acid signaling. Developmental Cell 21, 1116-1128, Dec. 13, 2011.*
Liu et al. Increasing seed mass and oil content in transgenic Arabidopsis by the overexpression of wri1-like gene from *Brassica napus*. Plant Physiol. Biochem. Jan. 2010;48(1):9-15. Epub Oct. 1, 2009.*

* cited by examiner

*Primary Examiner* — Cynthia Collins
(74) *Attorney, Agent, or Firm* — Whitham, Curtis & Cook, P.C.

(57) ABSTRACT

Transgenic plants that have enhanced yield-related traits, such as increased seed oil production, are produced by genetically engineering the plants to down-regulate the expression of at least one BPM protein. Such transgenic plants can, for example, be cultivated and yield higher seed oil production than control plants which have not been genetically engineered for down regulation of a BPM protein.

14 Claims, 38 Drawing Sheets

CUL3a  301 lvtvrdvmtshlremgkqlvtdpekskdpvefvqrllderdkydkiinta 350  SEQ ID NO:65
            |||||||||.|||||||||||||||||||||||||||||||:|||.|
CUL3b  301 lvtvrdvmtlhlremgkqlvtdpekskdpvefvqrllderdkydriinma 350  SEQ ID NO:66
WRI1    30 cssspsssvsssttsspiqseaprpkrakrakkssspsgdkshnpt 55  SEQ ID NO:67
Figure 1A
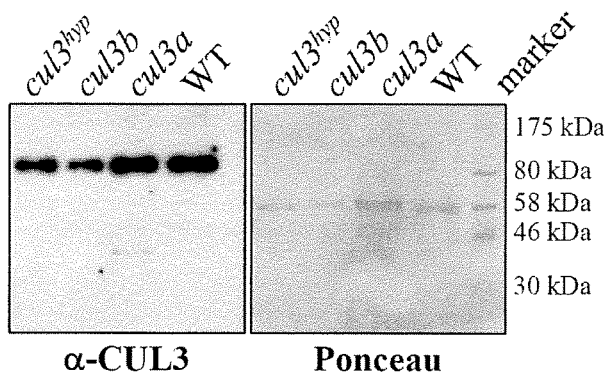
Figure 1B
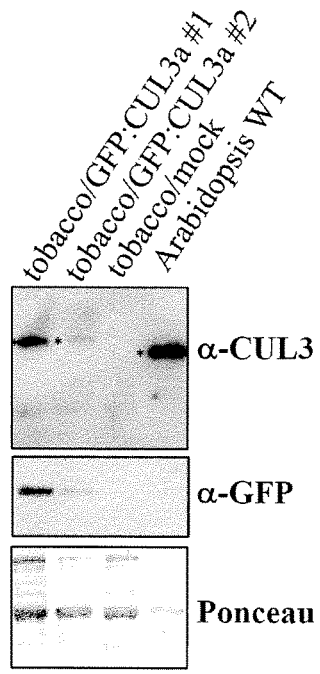
Figure 1C
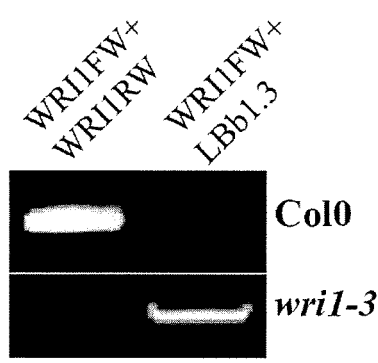
Figure 1D
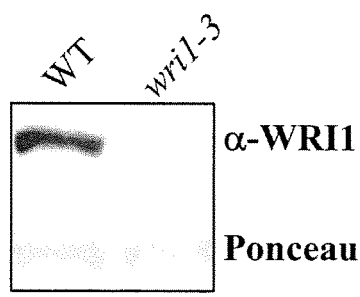
Figure 1E

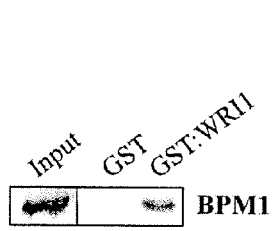
Figure 2A
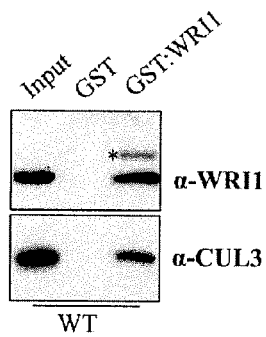
Figure 2B
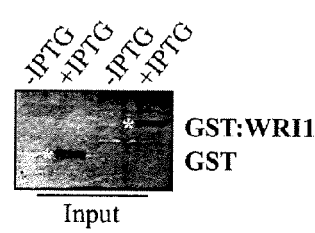
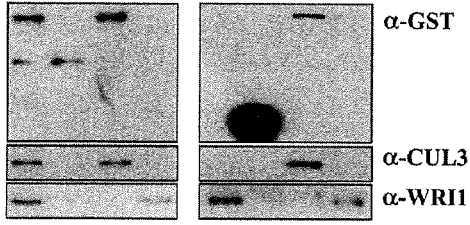
Figure 2F
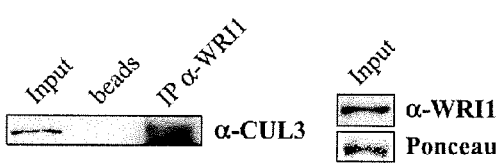
Figure 2G  Figure 2H

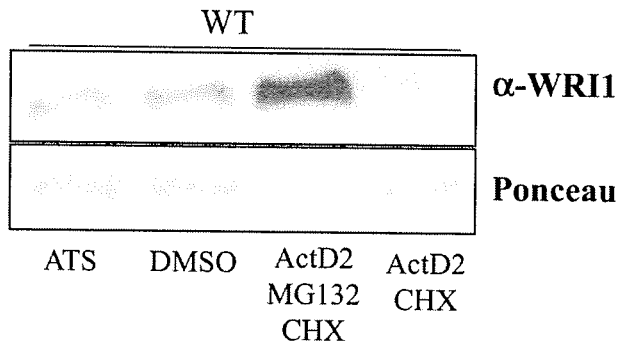
Figure 5A
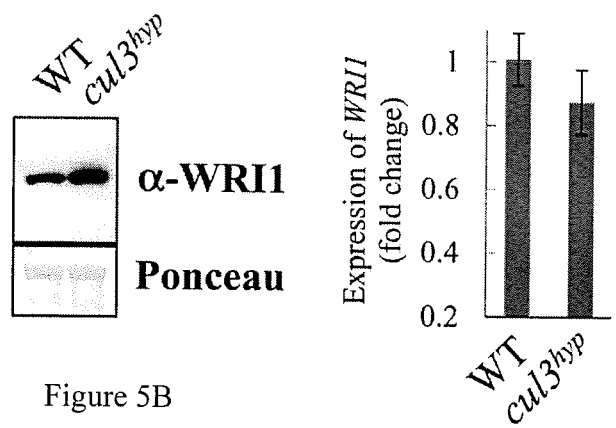
Figure 5B
Figure 5C
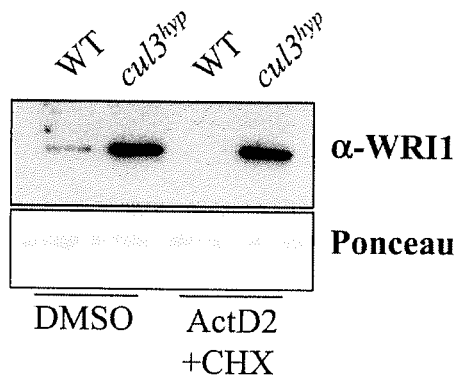
Figure 5D

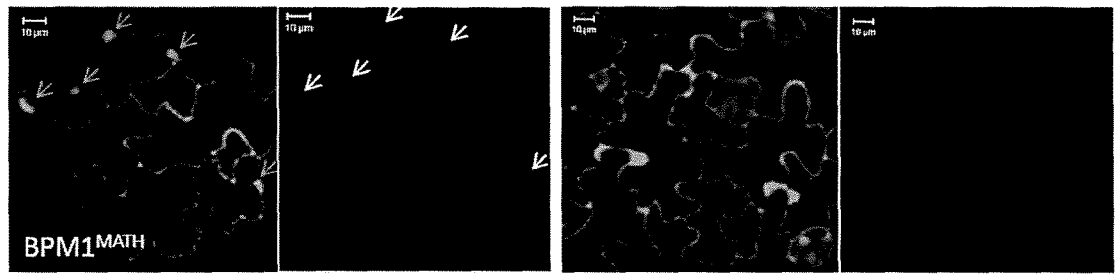
Figure 8A
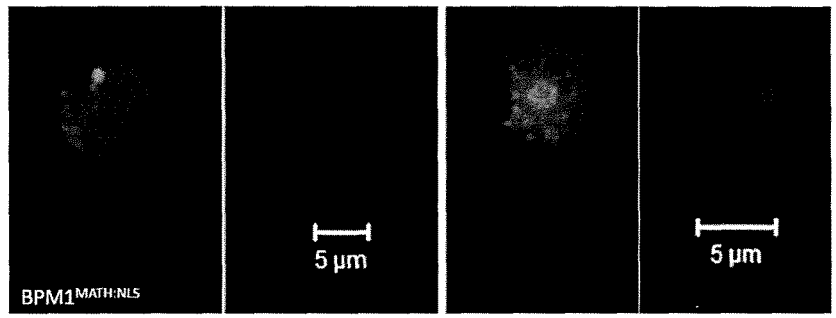
Figure 8B
Figure 8C
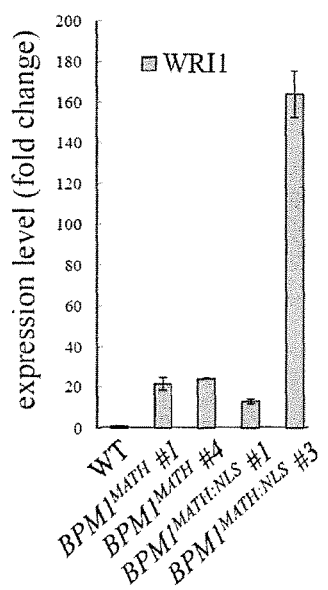

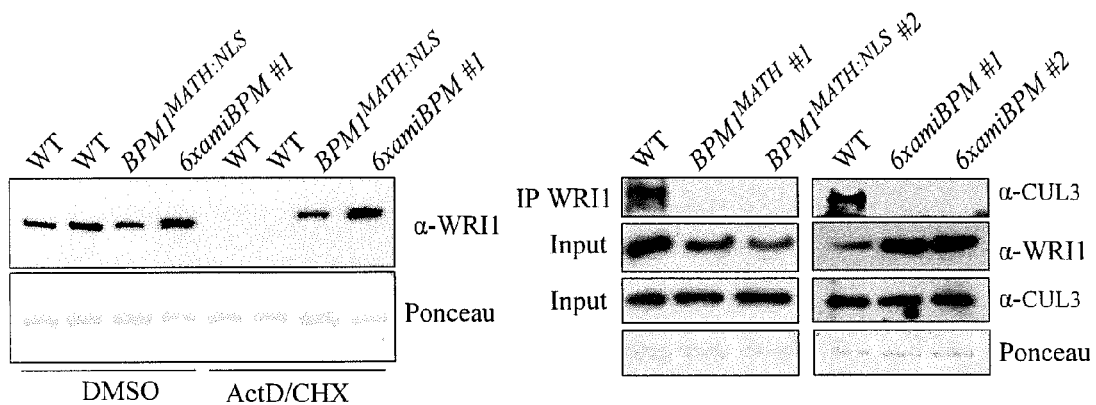
Figure 11A
Figure 11B
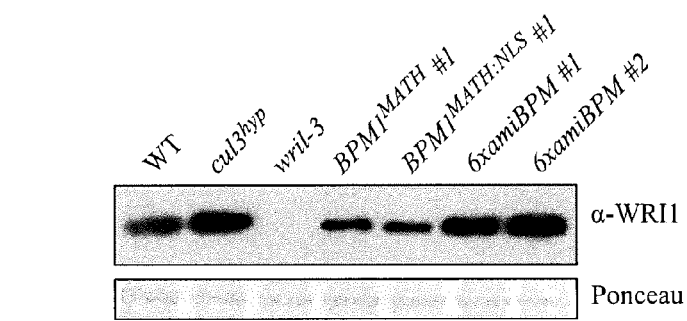
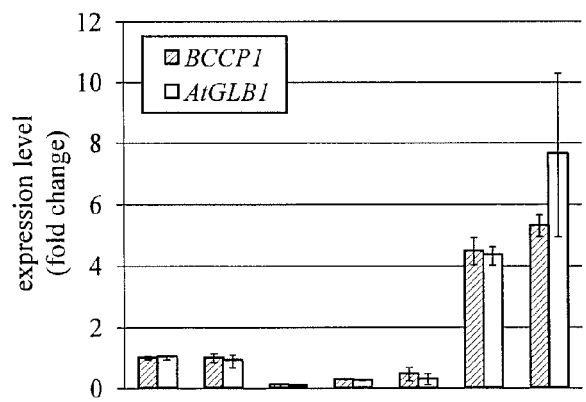
Figure 11C

*Arabidopsis thaliana* (NM_129534; Arabidopsis)
GAAGGCGAAAACAGTTTCCCCCAAATTCTCATAATTTTCACAAACAACCTCTCGTCTTCTAGGTTAATCCAATTTCG
TCGATTCATGAAGTTCACAATTCTCCCATCGGAAAATTCTTCGTAATCGACGACGAAGAGATCATGAGTACCGTCGG
AGGTATAGAGCAGTTGATACCTGATTCCGTTTCAACGTCGTTCATCGAAACGGTGAACGGTTCGCACCAGTTCACGA
TTCAAGGTTACTCTCTAGCCAAAGGCATGAGCCCTGGGAAGTTTATACAGAGCGATATCTTCTCCGTTGGTGGATAC
GATTGGGCGATTTACTTCTATCCTGATGGGAAGAACCCGGAGGACCAGTCCTCGTATATCTCTTTGTTCATCGCTTT
AGCGAGTGATTCTAATGATATTAGGGCTTTGTTGAGCTTACGCTTATGGATCAGAGTGGGAAAGGGAAACATAAGG
TGCATAGTCACTTTGATCGGGCGCTTGAAGGTGGTCCTTATACACTTAAGTATAAAGGAAGCATGTGGGGTTACAAA
CGCTTTTTCAAACGATCAGCTTTAGAAACCTCTGACTACTTAAAGGATGATTGTCTTGTCATCAATTGTACTGTTGG
CGTTGTTAGAGCCCGACTCGAGGGTCCAAAACAGTATGGCATTGTGCTACCCCTGTCGAATATGGGTCAGGGATTGA
AAGACTTGTTAGATTCTGAAGTTGGTTGTGACATAGCTTTCCAAGTCGGAGATGAAACATACAAAGCTCACAAACTG
ATTCTCGCGGCACGCTCCCCAGTTTTTAGAGCTCAGTTTTTTGGACCAATTGGGAATAACAATGTGGATAGAATAGT
GATAGACGACATCGAACCTTCTATCTTCAAGGCTATGCTTAGCTTCATTTACACCGATGTACTTCCTAATGTGCATG
AAATTACCGGGTCAACTTCTGCCAGTTCGTTTACAAACATGATACAACATCTCTTGGCAGCTGCTGACCTCTATGAC
CTTGCAAGGTTAAAGATATTATGTGAAGTTTTGCTATGCGAAAAACTTGATGTTGATAATGTGGCAACAACACTTGC
GTTGGCTGAACAGCACCAATTCTTACAGCTCAAAGCGTTCTGCTTAGAATTTGTTGCATCTCCAGCAAACTTGGGAG
CTGTAATGAAGTCCGAAGGGTTCAAGCACTTGAAACAGAGCTGTCCCACTTTGTTATCTGAGTTGCTGAACACTGTT
GCAGCAGCAGATAAGAGCTCGACGAGTGGACAATCAAACAAGAAAAGAAGTGCGAGCAGTGTATTAGGGTGTGACAC
TACAAATGTGAGGCAATTGAGGAGGAGAACACGAAAAGAAGTGCGAGCAGTGTCTTAGGATCATTACATACCGTATG
CAAAATTCTAGAATTATGCATTGTGTTTCAAGCAGAGTTTATGAATTCCAAGTCATCCCGTGAACTTTTTTACCAGT
GAGAATTATAGAGGCCTGAACTCTGAACCAAACTGTTTGTGTCAATCATTTTACATTTCTGGACAAAAGAAAGTACA
ATCTCCACAAAGAGCTGTGAGAATTGACTCAAAACAAATCCTAAAACTCTGTACCAGATTGTTCAATTTCTCATTAA
ATCCCACAATATGATTTTC (SEQ ID NO:68)

*Brassica rapa* (XM_009143587; Polish Canola)
CTAATCATAACCAAAACCGAAACCTTAGTTAAAATCCGGTAGAATCTCCACAAACCAAAACCATCCGAATACTAAAC
CAAACCAAACCAAATCCAATCGAATTTATTTTGGTTCAGTTCGTCACAATTTTAACCGAATCAAACTAACAAACCAA
ACTTCTACCGAACCCGCAGTCCTAAAGTATCATCTCCAATCAAACGGAGCTTTTATCATTTTCAAAATCAAATCGAC
GGCGACGATGAGCGCATCTCATCCGAATCACGATTCGGTATCAACAACCGTAATGGAGACGGTGAACGGATCGCACC
AATTCACGATCAAAGGCTACTCTCTCGCCAAAGGCATGAGCCCGGGGAGGTACATACAGAGCGACGTCTTCTCCGTG
AACGGATACGACTGGGTGATCTACTTCTACCCCGACGGGAAGAACCCCGAGGAGAACTCCACCTACGTCTCTCTCTT
CATCGCCTTGGCGAGCGATTCGAGCGACATTAGGGCTTTGTTCGAGCTGACGCTGATGGATCAGAGCGGGAGAGGGA
GGCATAAGGTTCATAGTCATTTCGATCGGGCGCTTGAAGGAGGGCCTTATACGCTTAAGTATAAAGGGAGTATGTGG
GGTTACAAACGCTTTTTAAGAAGAACAGCTTTGGAAGCATCTGACTACTTGAAGGATGATTGTCTTATCATCAACTG
TACTGTTGGCGTCGTTAGAGCTCGCCTTGAGGGTCCTAAACAGTTTGGCATTGTGCCACCACCTTCAAACATGGGTC
AGGGATTGAAAGACTTGTTAGACTCTGAACTTGGCTGCGACATTGCTTTCCAAGTCGGAGATGAGACTTACAAAGCT
CACAAACTGATCCTCGCAGCACGCTCGCCGGTCTTTAGAGCTCAGTTCTATGGACCAGTTGGGAATAACAGTGTGGA
TAGAGTAGTCATAGAGGACATGGAGCCTTCAATCTTTAAGGCTATGCTTAGCTTCATCTACACGGATGTACTTCCTG
ATGTGCATGAGATTACAGGGTCTACTTCTACCGCTTCGTTCACGAACATGATACAGCATCTATTGGCAGCTGCTGAC
CTCTATGACCTTGGGAGGTTAAAGATACTGTGTGAAGCTTTTCTATGTGAAGAACTAAACGTTGATAATGTGGCAAC
AACACTTGCACTAGCTGACCAACACCAGTTCTTGCAGCTCAAAGCCTTCTGCTTAAAATTTGTTGCATCTCCAGCAA
ATTTGCGAGCCGTAATGAAGTCAGAAGGTTTCAAGCACTTGAACCAGAGCTGTCCCTCTGTGTTGCCTGAGTTGCTA
AACACAGTTGCAGCAGCGGATAAGAGCTCGACGTCGTCGAGTGGACAGTCAAGCAAGAAAAGAAGTGTGAGCAGTGT
GTTGGGCTGTGATACAAGCACAACAAATGCGAGACAGGTGAGGAGGACGTAGGTAGGATCGACCCAAGTGCAAGTAA
TGCTTTAGTCTGATGCTACTTTGCTAGACTTTTACTTATTGTAATGAAAATAATTGTTTGTAGTATGTCTACAGTT
AGTGTAAAGCTTTAGGCAATGGAACATCTGTTTTGCTTTGCGTGTTTGTAAAAGCTTTGGATAATACTAGGTTAAAA
GCTTTGGAGTTAATAGTCTTTTTTGTTGCA (SEQ ID NO:69)

Figure 22A

*Jatropha curcas* (KK914240.1; Barbados Nut)
ATGGTCGACGTCAAAGCGGATTTCGATAAAGAGTCGTGTTCGAAATCAGTAAACGAGACAGTGAACGGGT
CGCACCAGTTCACCATAAAGGGATATTCTTTGGCGAAAGGGATGGGAGCTGGGAAATGCATATCGAGTGA
TATTTTCACGGTTGGTGGTTACGATTGGGCGATTTACTTTTACCCAGATGGTAAAAACCCTGAAGATAGC
TCCATGTATGTTTCCGTTTTTATTGCCCTGGCGAGCGAAGGAACGGATGTTAGGGCTTTGTTTGAGTTGA
CGTTGGTTGATCAGAGTGGAAACGGGAAGCACAAAGTGCATAGCCACTTTGATCGTGCATTGGAGAGTGG
GCCGTACACTTTGAAGTATAGAGGGAGCATGTGGGGTTACAAGCGTTTCTTTAGAAGGACGACCTTAGAA
AATTCTGATTATATAAAGGATGATTGCCTACTCATGAACTGTACTGTTGGAGTTGTCAGAACTCGTCTTG
TAGGACCAAAACAATGTTTTATTACCATTCCACCCTCAGACATGGGCCAGGGCCTCAAAGAACTCTTGGA
ATCTGAAGTTGGTTGTGACATTGCTTTCCAGGTTGGGGATGAAACATTTAAAGCTCATAAATTGATACTT
GCTGCTCGCTCTCCAGTTTTCAGGGCCCAGTTTTTTGGACTTTTTGGGGATCCTAACCTAGATAAAGTAG
TTGTGAAGGATATTGACCCCTCAATCTTCAAGGCAATGCTACTATTCGTATACACAGACAAACTTCCTGA
TGTACATGAAATTACTGGCACGACGTCTATGTGCACATCCACCAATATGGTGCAGCATCTATTGGCTGCT
GCTGACCTATACAATTTAGATCGATTGAAATTGCTATGTGAATCGAAGTTGTGTGAGGAACTGAGTGCTG
AGACAGTGGCGACGACGCTTGCATTAGCTGAGCAGCATCAGTGTTCGCAGCTTAGGGCCATCTGTTTGAA
ATTTGCTGCAACTCCTGCAAACTTGGGAGCGGTAATGCAATCAGAAGGATTCCGGCACTTAGAAGAAAGC
TGCCCGGCATTGTTGTGTGAGATGCTGAAGACATTTGCATTAGGAGATGAGAATTCAAATCAGTCAGGTC
GGAAGAGGAGTGGGAGCAGCATCTATGGCTAGATCTAGCAACAGATGGGGCTGCAGCAGAATCAGTAAA
TCCCAATGCCAGGCGTTTGAGGAGGCGGTATTAG (SEQ ID NO:70)

*Populus trichocarpa* (XM_002311150.2; California poplar)
ATGGACGATTTCAAGGGAGATGTAGATAAGGAGTCGTGTTCGAAGTCAATAAACGAGACGGTGAATGGGT
CTCACCAGTTTACGATAAAAGGGTATTCATTAGCGAAAGGAATGGGAGCTGGGAGATGCATACCGAGTGA
TGTTTTCAACGTGGGTGGTTATGATTGGGCGATTTATTTTACCCAGATGGGAAAAACCCTGAGGATAGC
TCGATGTATGTGTCGGTTTTTATTGCGTTAGCGAGCGAAGGAACGGATGTTAGGGCTTTGTTCGAGTTGA
CGCTGGTGGATCAGAGTGGGAAAGGGAAGCATAAAGTACATAGTCATTTCGATCGTGCGTTGGAGAGTGG
ACCTTATTCATTGAAGTACAGAGGCAGCATGTGGGGTTACAAACGTTTCTTCCGAAGGACAACCTTGGAA
ACTTCTGATTATCTGAAGGATGACTGCCTTATCATGAACTGCACTGTTGGAGTTGTCAGAACTCGTCTTG
AAGGACCAAAACAGTACTCCATTTCAGTTCCACCTTCAGACATGGGTTGGGGTTTTAAAGAACTACTGGA
GTCTGAATCTGGTTGTGACATAGATTTCCAGGTTGGTGATGAAACATTTAGAGCTCATAAGCTGATCCTT
GCTGCTCGTTCACCTGTTTTCAGAGCTCAATTTTTTGGACTTGTCGGGGATCCTAACATGGATAAAGTAG
TAGTGAAGGATGTTGATCCCTTGATATTCAAGGCAATGCTTCTGTTTATATACACAGACAAACTTCCTGA
TGCACATGAAATAACTGGCTCGACATCAATGTGCACATCCACCAATATGGTGCAGCATCTGTTGGCTGTC
TCTGACCTTTACAATTTAGATCGATTGAAATTGTTATGTGAAGCAAAGTTGTGTGAGGAACTCAGTGCCG
AGAATGTGGCAACAACACTGGCATTGGCTGAGCAGCATCAGTGCATGCAACTGAAGGCCATCTGTTTGAA
ATTTGCAGCAAATCCAGCGAACTTGGGAGCGGTAATGCAGTCAGAAGGGTTCCGACACTTGGAGGAGAGC
TGCCCTTCAATGTTATGTGAGTTGCTGAAGACACTTGCTTCTGGAGATGAGAACTCAAGTCTTCTGTCAG
GTAGGAAGAGGAGTGGCAGCAGTTTACTTGGGGTTGATCTAGCGGATGGGGCTCCAGCAGAATCAGCAAA
TCCCAATGGCAGGCGTTTGAGGAGGCGGTTTTAG (SEQ ID NO:71)

*Theobroma cacao* (XM_007009225.1; cacao tree)
ATGGACGATTTCAAGGACTCGGTATCGAAATCGGTGAGCGAGACTGTGAACGGGTCGCACCAGTTCACGA
TCAAGGGTTACTCGTTGGCGAAAGGGATGGGCCCTGGAAAATGTATAGCCAGCGATGTTTTCACCGTCGG
AGGTTTCGATTGGGTGATTTACTTTTACCCCGACGGTAAAAATCCGGAGGATAGTGCTATGTATGTTTCG
GTTTTCATTGCTCTGGCCAGCGAAGGTACCGATGTCCGTGCACTTTTCGAGCTCACGCTTGTGGACCAGA
GTGGGAAAGGGAAGCATAAGGTTCATAGTCACTTTGATCGGGCGTTGGAGAGTGGACCTTATACGTTGAA
GTATAGAGGGAGCATGTGGGGTTACAAGCGTTTCTTTAGAAGAACAACTTTAGAAACTTCTGACTATATT
AAGGATGATTGCCTAATCATGAACTGCACTGTTGGAGTAGTCAGAACTCGCCTCGAGGGACAAAGCAGT
GTTCTATTTCTGTACCGCCATCAGAAATGGGTCAGAATCTTAAAGCCTTGTTGGAGTCTGAAGTTGGTTG
TGATATCATTTTCCAGGTTGTTGATGAGAAATTTAAAGCACATAAGTTGATCCTTGCTGCCCGCTCACCT
GTTTTTAGAGCGCAGTTTTTTGGGCTTGTTGGGGATCCTAACATGGATAAAGTAGTAGTGGAAGATTTTG
AGCCCTCTATCTTCAAGGCAATGCTTTGTTTATTATACCGACAAGCTTCCTGATGTACAAGAGATTAC
AGGCTCAACGTCCATGTGTATGTCTACCAACATGGTGCAGCATCTTTTGGCTGCTGCTGATCTGTACAAT
TTAGATAGACTCAAAGTGTTGTGCGAGGCAAAATTGTGTGAAGAACTTAATGCTGACACAGTGGCAACAA
CCCTTGCACTAGCTGAGCAGCACCATTGCGCACAGCTTAAGGCCATATGTTTGAAATTTGCTGCAACTCC
AGCAAACTTGGGAGCGGTAATGCAGTCAGAAGGGTTCAGGCACTTGGAGGAATGTTGCCCATCTTTGTTG
TCTGAGCTTTTGAAGACCTTTGCATCAGGTGAGGAGAGCTTGAGTCAGCTGTCCAGTAGGAAGAGGAGTG
GCAGCAGTGTATACGGGATGGATCTAGCAGCAGAAGGTCCTGTGGCAGAATCGGTGAATCCTAATGGCAG
GCGTGTTCGGAGGCGTTGA (SEQ ID NO:72)

Figure 22B

*Citrus clementina* (XM_006435551.1; Clementine)
ATGGGCAATTCGGAGAAAGATTCGACGTCGAAGTCAATTAACGAGACGGTGAACGGGTCCCACCAGTTCA
CGGTAAAAGGTTACTCCCTGGCGAAGGGAATGGGCCCTGGCAAGTGCTTATCGAGCGACGTTTTTACCGT
GGGCGGTTACGATTGGGCGATTTACTTTTACCCCGACGGCAAGAACCCGGAAGATGGGGCTTTGTATGTT
TCGGTGTTTATTGCGTTGGCGAGTGAAGGAACGGACGTGAGGGCGCTGTTTGAGTTAACTTTGGTTGACC
AAAGTGGGAAGGAAAGCATAAAGTTCATAGTCATTTTGATCGAGCGTTAGAGAGTGGCCCGTACACCTT
GAAGTATCGTGGAAGCATGTGGGCTATAAGCGCTTCTTTAAAAGAACATCTCTGGAGACTTCTGATTAT
ATTAAGGATGATTGTCTTCTCATCAACTGCACTGTTGGAGTTGTTAGAAACCGCCTTGAGGGACCAAAAC
AGTATTCCATACCAGTGCCACCGTCAGACATGGGCCAGGGTCTTAAGGATTTGCTAGAGTCTGAAATTGG
ATGTGACATAGTTTTTGAGGTTGGTGATGAAACATTTAAAGCTCATAAACTGATACTTGCTGCTCGCTCT
CCTGTTTTCAGAGCCCAATTCTATGGGCTTGTTGGAGATCGTAACTTGGATAAAGTAGTTGTGAAGGATG
TTGAACCCTCAATCTTCAAGGCAATGCTCCTGTTTATATACACCGATAAATTTCCTGATGTATATGAAAT
TACTGGCACAACATCAATGTGCACAACAACCAACATGGTACAGCATCTACTGGCTGCAGCTGATCTTTAT
AATGTAGATCGATTGAAATTGTTGTGTGAATCAAAATTATGTGAAGAACTAAATGCTGAGACAGTGGCCA
CAACACTCGCACTGGCAGAACAACATCAGTGTCCCCAGCTTAAGGCTATCTGCTTGAAGTTTGCTGCAAC
TCCGGCGAATTTGGGAGTGATAATGCAGTCAGAAGGGTTCAAGCACTTGGAGGAGAGCTGCCCATCACTG
TTGTCCGAGCTCCTGAAGACATTGGCTTCAGGTGATGATACCTCAAGTCTGTCATCAAATAGGAAAAGAA
GTGGCAGCAGTATATATGCACTAGATCTAGCTGGAGATGGGCAGCAGCAGAGTCAGCAAATCCCAATGG
CAGGCGTGTACGAAGGCGGTTTTTAG (SEQ ID NO:73)

*Ricinus communis* (XM_002524172.1; Castor oil plant)
ATGGTTGAATTGAAGTCAGATTCTGATAAAGAGTCATGTTCAATGTCAATAAACGAGACGGTAAATGGGT
CTCACCAATTTTCCATAAAAGGGTATTCTTTAGCGAAAGGAATGGGAGCTGGAAAATGTATAGCAAGTGA
TATTTTCACTGTGGGTGGTTATGATTGGGCGATCTATTTTTACCCAGATGGTAAAAATCCTGAAGATAGT
TCTATGTATGTTTCTGTTTTTGTAGCTTTGGCTAGTGAAGGAACTGATGTTAGGGCTTTGTTTGAGTTGA
CCTTGGTTGATCAAAGCGGAAATGGGAAGCATAAAGTTCACAGTCATTTCGATCGTGCGTTGGAAAGTGG
GCCTTATACTTTGAAGTATAGAGGGAGCATGTGGGGTTACAAGCGTTTCTTTAGAAGAACAACTCTTGAA
AATTCTGATTATATAAAGGATGATTGCCTAATCATGAACTGCACAGTTGGAGTTGTTAGAACCCGTCTTG
AAGGACCAAAGCAGTATTCCATTTCACTTCCGCCGTCAGACATGGGGCAAGGCCTTAAGGAACTGTTAGA
ATCTGAAGTTGGTTGCGACATTGTTTTCCAGGTTGGGGATGAAACATTTAAAGCGCATAAGTTGATACTT
GCTGCTCGTTCCCTGTTTTTAGAGCTCAATTCTTTGGACTTGTTGGGGATCCAAACTTAGATAAAGTAG
TAGTGGAGGATATTGACCCCTCAATTTTCAAGGCAATGCTCCTGTTTATATACACAGACAAGCTTCCTAA
TGTACATGAGATTACTGGCACAACATCAATGTGCACATCCACCAACATGGTGCAGCATTTATTGGCTGCT
GCTGATCTTTACAATTTAGATCAATTGAAATTGTTATGTGAATCAAAATTGTGCGAGGAACTGAGTGCTG
AGACTGTGGCAACAACTCTTGCATTAGCTGAGCAGCATCAATGTTCGCAACTCAAGGTCGTCTGTCTGAA
ATTTGCTGCAAATCCAGCAAACTTGGGAGCGGTAATGCAGTCAGAAGGATTCCGACACTTGGAAGAGAGC
TGCCCTTCATTGTTGTGCGAGATGCTAAAGACATTTGCGTCAGGCGATGAGAACTCAAGTCTTCTATCAA
GTCGGAAGAGGAGCGGAAGCAGTATATATGGGCTAGATATAGCTGCAGATGGGCTGCAGCAGAATCAGC
CAATCCCATGGGCAGGCGAGTAAGGAGGCGTTTTTAG (SEQ ID NO:74)

*Eucalyptus grandis* (KK198759.1; Eucalyptus)
ATGCAGCGCAAAGCGATGTGCGCTCCGATCGGCGGCGGCGGCGGCGACGGCGGGGGGGAGTGCGGCTCGA
CGTCGATCAGCCGGACGGTGAACGGGTCGCACACGTTCACGATCAGCGGCTACTCGCTGGCCAAGGGGAT
GGGGGCCGGGAAGTTCATCGCCAGCGACGTGTTCACCGTCGGGGGCTACGACTGGGCCATCTACTTCTAC
CCCGACGGGAAGAACCCGGAGGACAGCACGACGTACGTGTCCGTGTTCATCGCCCTGGCCAGCGACGGCT
CCGACGTCAGGGCGCTGTTCGAGCTGACCCTGGTCGACCAGAGCGGGAAGGGGAAGCACAAGGTCCACAG
CCACTTCGACCGCGCGCTCCAGAGCGGGCCTTACACGCTCAAGTACCGCGGCAGCATGTGGGGTTACAAG
CGTTTCTTGAAAAGAGTTGCTTTAGAGACTTCTGATTACATCAAGGACGATTGCCTTGTGATGCACTGTA
CTGTCGGGGTTGTGAGAACCCATACCGAGGGCCCCAAACAGTACCGAATTCCTATTCCGCCGTCTGACAT
GGGCCAGTGTCTGAAGGCCCTGTTAGATTCTGAAGTTGGCTGCGACATAGCATTTGTTGTTGGTGACGAA
ACCTTTAGAGCTCATAAACTGATCCTCGCTGCTCGTTCTCCGGTCTTTCGAGCCCAATTTTTTGGTCTTG
TTGGTGATTGCAATATAGAGAAAGTTGTCGTGGAGGATGTTGATCCCTCAATTTTTAAGGCAATGCTCCT
GTTCATTTACATGGACGAAATGCCTGATCTACGTGAAATCACGGGCTCATCCTCTTCTGGTACATTGACT
AACGTAGTGCAGCATCTGTTAGCTGCTGCCGACCGCTACAATCTAGAACGATTGAATTATTATGTGAGT
CGAAATTATGTGAGGAGATTACTGCTGATACAGTGGCTACAACACTTGCCCTAGCAGAGCAGCACCAGTT
TGGACAGCTGAAGGCAATGTGTCTAAAATTTGCTGCGCATCCAACAAACTTGGCGGTGGTAATGCAGTCA
GAAGGCTTCAGGCACTTGGAGGAGAGCTGCCCTTCCTTGTTGTCTGAACTGCTCAAGGCTTTTGTAACGG
TGGATGATTCTTCTGACCGATTTTCAAATAAGAAGAGAGGCACCAGCAGCATTTACGGACTAGATACGGT
GCCAGTTGTGACTGGAGCTGAACATGGGGATATAGATGGAAGGCGTGTGAAGAGGCGGAATTTAGAATGA
(SEQ ID NO:75)

Figure 22C

*Vitis vinifera* (XM_002282500.2; Grape vine)
ATGGTTAATTCCAAGGCCGATATTGAGAGAGACTCGTGTTCGAAGTCGATCAACGAGACGGTGAATGGCT
CGCACCATTTCTTGATAAAGGGTTATTCCCTCGCAAAGGGAATGGGCGCGGGCAAATACATCTCGAGCGA
CACGTTTACCGTTGGAGGATATGATTGGGCAATTTACTTCTATCCTGATGGCAAGAACGCGGAGGATAAT
TCGATGTATGTGTCGGTGTTCATTGCGTTGGCGAGCGAGGGCACTGACGTTAGGGCTTTGTTTGAATTGA
CGTTGTTGGATCAGAGTGGGAAAGGCAAGCACAAAGTACACAGTCATTTTGATCGCGCATTGGAGAGTGG
CCCATATACTTTGAAATATAGAGGAAGCATGTGGGGCTACAAGCGCTTCTTCAGACGGACAACTTTAGAA
ACATCTGATTTTATCAAGGATGATTGCCTTGCTATGCATTGCACTGTTGGGGTTGTCAGAACTCGTGTTG
AGGGGCCTAAACAGTATACCATTCCTATACCACCTTCAGACATTGGTCAGAGTCTTAAGGACTTGCTAGA
ATCTGAAGTTGGTTGTGACATAACTTTTCAGGTTGCAGATGAGACATTCAAAGCTCATAAGTTGATACTT
GCTGCTCGTTCTCCTGTATTTAGAGCTCAGTTTTTGGACTTGTTGGAAATCCTAATATGGATAAAGTTG
TAGTGGAGGATGTTGAACCCTCTATCTTTAAGGCGATGCTCCTGTTTATTTACTCAGACAAGCTTCCTGA
TGTAGACGAAATTACAGGCTCAGCGTCTGTGTGCACATCCACAATAATGGTTCAGCACTTACTAGCTGCT
GCTGACCGCTTTGGTTTAGATCGTCTGAAACTATTATGTGAATCAAAATTGTGTAAAGAAGTCAGTGCTG
AAACGGTGGCCACAACACTTGCCCTAGCTGAGCAGCATCGTTGTCCACAACTTAAAGCCATCTGTTTGAA
ATTTGCAGCCACTCCGTCAATCTTGGGAGCGGTAATGCAATCAGAAGGGTTTGGGTACTTGGAAGAGTGC
TGCCCCTCATTGTTATCTGAGCTGCTTGGAGTGATTGCATCAGTAGATGAAACTTGACGATGCTCTCGA
GTAAGAAGAGAAGTGGCAGCAGCATATTAGGGTTAGATCTACCAGCAGATGGAGCTCCAGCAGAATCAGC
CAGTGGCAGGCGCATAAGGAGGCGGTTTTAG (SEQ ID NO:76)

*Prunus persica* (XM_007217988.1; Peach)
ATGCCGAATCACAAATCGTCCAGAGGGGCTCAATTGGGTGAAGCCATGTCGAATTCGAAGCCTGGAGTCG
ACCAGGAGTCGTGTTCGAGATCGATCAGCGAGACTGTCAATGGGTCTCACCGGTTCACGATAAAGGGGTA
TTCTTTGGCCAAAGGGATGGGTGCCGGAAAGTACATAATGAGCGATACGTTTACGGTGGGTGGCTACGAT
TGGGCAATTTACTTCTACCCGACGGCAAAAATCCTGAGGATAGTTCCACGTACGTCTCCGTTTTCATTG
CTCTGGTCAGTGAGGGTACGGATGTGAGGGCTTTGTTCGAGCTGACTTTGGTGGACCAGACCAAGAGTGG
GAAGGACAAGGTGCATAGCCACTTTGATCGCGCGCTCGAGAGCGGGCCGTACACGTTGAAGTACAGAGGC
AGCATGTGGGGTTACAAGAGATTTTTCAAAAGATCAGCCCTCGAAACTTCTGAGTTTCTAAGGGATGATT
GCCTTGTATTGAACTGCACTGTTGGAGTTGTCAGAACTCGCCTTGAGCGACCAAAACAATTTTCAATTAC
TGTACCATCATCAGACATGGGTCAAGATCTTAAGGACTTTCTAGACTCTGAAGCTGGTTGTGACATAGTT
TTTCAGGTTGGCGATGAATTGTTTAAAGCTCACAAGTTGATACTTGCTGCCCGTTCTCCTGTATTTAGAG
CACAGTTTTTTGGACTTGTCGGGGATTGTAGCATAGATAAAGTAGTTGTGAAGGATGTTGAGCCCTTTAT
CTTCAAGGCAATGCTTCTGTTTATTTACACGGACAAACTTCCTGATGTACACGAAGTTATGGGCTCATCA
CCATTGTGCACATTCACTGTCATGGTGCAGCATCTTTTGGCTGCCGCGGACCTGTATAATCTAGAACGAC
TGAAAGTATTGTGTGAATCAAAGTTGTGTGAAGAAATCACTACTGAAACAGTTGCGACCACACTTGCTCT
AGCTGAACAACATCACTGTCCGCAGCTCAAGGCTGTGTGCTTAAAATTTGCAGCAAATCCTGCAAACTTA
GGAGCTGTGATGCAATCAGATGGGTACAAGCATCTAGAAGAGAGCTGCCCCTCAATGTTGCTGGAGTTGC
TAGAGACATTTGCAGCAGTGGATGAGAGCTCAAGTCTTCTGTCAAGTAGGAAGAGGAGTGGCAGCAGCAT
ATATGGGCTAGACTTGCCAGCAGATGGTGGCGGGCTGTAGCAGAATCAGCAAATCCCAATGGAAGGCGT
GTGAGGCGGCGGTATTAG (SEQ ID NO:77)

*Phaseolus vulgaris* (XM_007163402.1; String bean)
ATGGCGGAATTGGAGGAGGACCGGATGGGGGATTTCAAGCCCTTCTCGGAGGGCTCTTCGTGCTCACGTT
CGATCAGCGAAACGGTGAATGGCTCTCACCAATTCACGATAAAGGGGTACTCTCTCGCAAAGGGGATGGG
TGCTGGGAAGTACATCATGAGCGACAGTTTTAGCGTTGGTGGTTACGATTGGGCAATTTACTTCTACCCT
GATGGGAAGAACCCCGAGGACAATTCCATGTACGTTTCGGTCTTCATAGCTCTCGCTAGCGACGGAACCG
ATGTTAGGGCTCTGTTCAAGTTGACGCTGGTGGATCAGAGTGAGAAGGGAAACGATAAGGTCCATAGCCA
TTTCGATAGGCCTCTTGACGGTGGACCGTACACCTTGAAGTATAGAGGCAGCATGTGGGGTTACAAGCGT
TTCTTCAGAAGAAATTTACTTGAATCTTCAGAGTATCTAAAAGACGATTGCCTTGTCATGCATTGCACTG
TTGGTGTTGTCAAAACTCGTTTTGAGGGATCTAAACAAGGTGTTACTGTGCCACAGTCAGACATGGGCCG
AAATTTTAAGGACTTGCTGGACTCAGAGGTTGGTTGCGACATAGTTTTCAAGGTTAAAAGCGAAAGCTTC
AAAGCTCATAAGTTAATACTTGCGGCCCGATCTCCTGTGTTTAGAGCACAGTTTTTTGGACTTGTTGGGG
ATCCTAGCTTAGAGGAAGTAGTGGTAGAGGATATTGAGCCTTTTATCTTCAAGGCAATGCTTCTCTTCAT
TTATTCTGACAAACTTCCAGACATCTATGAAGTTATGGACTCAATGAATGTCTGCTCATATGCCGTCATG
GTGCAGCATCTCTTGGCTGCTGCTGATCTCTATAATCTTGACCGGCTCAAACTGCTTTGTGAATCAAAAT
TGTGTGAAGAAATCAATACTGACAATGTAGCCACGACACTTGCCCTGGCAGAGCAACACAACTGTCCACA
GCTTAAGGCAATCTGTTTAAAATTTATTGCCAATCCAGCAAATTTGGGAGCTGTAATGCAGTCGGAAGCT
TTTGTGCATTTGAAAGAGAGCTGCCCCGCAATGTTGTTGGAGCTGCTGGAGACATTTGCCTCAGTGGACG
ATAACTCAAGCCTGACATTGAGCAGAAAGAGAAGTGGCAGTAGCATATATGCTCAAGATTTGGCAGACGG
GGCAGCTACTGAATCAGTTAATCCAAATGGCAGGCGAGTAAGGAGGCGAACATAA (SEQ ID NO:78)

Figure 22D

*Glycine max* (XM_003552724.2; Soybean)
ATGGCGGAATTGGAGGAGGAGCGGATGGGGGATTTCAAGCCCTTCTCGGAAGGTTCTTCGTGCTCGCGTT
CGATCAGCGAAACCGTGAACGGCTCGCACCAATTCACGATAAAGGGTTACTCTTTGGCCAAAGGGATGGG
TGCTGGAAAGTACATCATGAGCGACACTTTCACCGTTGGTGGTTACGATTGGGCTATTTACTTCTACCCC
GATGGGAAGAACCCTGAGGACAATTCCATGTACGTTTCGGTCTTTATTGCGCTCGCTAGCGACGGAACCG
ATGTTAGGGCTTTGTTCAAGTTGACGCTGGTGGATCAGAGTGAGAAGGGGAATGATAAAGTTCATAGCCA
TTTCGATCGCCCTCTCGAGAGTGGACCTTATACCTTGAAGTATAAAGGCAGCATGTGGGGTTACAAACGC
TTCTTCAGAAGAACACAACTGGAAACCTCAGAGTATCTAAAAAATGATTGCCTTGTCATGCATTGCACTG
TTGGTGTTGTTAAAACTCGTTTTGAGGGATCTAAACAGGGTGTTATTGTGCCACAGTCAGACATGGGCCG
GGATTTTAAGGACTTGTTGGAATCTGAGGTCGGTTGTGACATACTTTTCAAGGTCAAAAGTGAAAGCTTC
AAAGCTCATAAGTTGATACTTGCAGCCCGATCTCCTGTGTTTAGAGCCCAGTTTTTTGGGCTTGTTGGGG
ATCCTACCTTAGAGGAAGTAGTGGTAGAGGATATTGAGCCCTTTATCTTCAAGGCAATGCTTCTCTTTGT
TTACTCTGACAAACTTCCTGGCATATATGAGGTTATGGACTCAATGCCCTTGTGCTCATACACCGTCATG
GTGCAGCATCTCTTGGCTGCTGCTGATCTCTATAATCTTGATCGGCTCAAACTGCTTTGCGAATCAAAAT
TGTGTGAAGAAATCAATACTGACAATGTGGCCACAACACTTGCGCTGGCAGAGCAACATCACTGTCCACA
GCTTAAGGCAATCTGTTTAAAATATATTGCAAATCCTGCAAACTTGGGAGCTGTAATGCAGTCAGAAGCT
TTTGTGCATTTGAAAGAGAGCTGCCCCTCAATGCTGTTGGAATTGCTGGAGACATTTGCATCAGTGGATG
ATAACTCAGGCCAGACATTGAGCAGAAAGAGAAGTGGCAGTAGCATATATGGGCAAGATTTAGCAGACGG
GGCAGCTGCTGAATCAGTTAATCCAAATGGCAGGCGAGTAAGGAGGCGGACATAA (SEQ ID NO:79)

*Phoenix dactylifera* (XM_008787313.1;date palm)
ATGGCGAAGCTCGAGGAGGAGCAGGGAGGATTGAACAACCGTCAGCTCAATCCGCTGAACGTGTCGCGGT
CTCGGTCGGTGTGCGAGACGGTAAACGGGTCGCACCGGTACACGGTGAAGGGGTTCTCGCTGGCGAAGGG
GATGGGTCCTGGAAGGTACCTGTCCAGCGACACCTTCACCGTGGGGGGATTCCAGTGGGCCGTCTACTTC
TATCCGACGGCAAGAACCCGGAGGACAACTCCCTTTATGTCTCGGTGTTCATTGCCCTGGCGAGCGAGG
GGACCGACGTGAGGGCGCTCTTCGAACTCACTCTGCTCGACCAGAACGGCAAGGGGAGGCACAAGGTGCA
CAGCCACTTCGATCGGGCGCTGGAGGCCGGGCCCTACACGCTCAAGTACCGGGGGAGCATGTGGGGTTAC
AAGCGGTTTTACAGGAGGACATCCTTAGAAACATCGGATTATCTCAAGGATGATTGTCTAATTATGAACT
GCACAGTGGGTGTTGTTAGAAACCATATTGAAACACCAACACAGCTTTCAATTTCTGTACCACCACCTGA
CTTGGGTCAGTGTCTCAAGGAGTTGTTCATATCTGGCATTGGTTCTGACATAGATTTTGAGGTTGGTGAT
GAGACATTTAAAGCTCACAAGCAGATTCTTGCTGCTCGCTCGCCAGTTTTTAGTGCACAATTTTTTGGTC
TTATCGGGAATCCAAATGTGGACAAAATTGTTGTGGAGGATGTTGAACCTCCTATTTTCAAGGCCATGCT
TCTGTTTATATATTCAGATGAACTCCCTGATGTGCATGATCTAACTGGATCTGTTTCTATGTGCACATCC
ACGATTATGGTACAACATTTATTGGCTGCAGCAGATAGATATGGACTGGAACGTCTGAAGCTGTTATGCG
AAGCAAAACTGTGCGAAGAAGTCACTGCTGATACTGTAGCAACAACCTTGGCCCTGGCAGAGCAACACCA
ATGTGCTCAATTGAAGGCTGTCTGCTTAAAATTTACAGCAGCTCGAGAAAACTTGGGAGCTGTTATGCAG
ACTGAAGGGTTCAATTACTTGGAGGCGACGTGCCCATCTTTGCTGTCAGACTTGTTGGCAACTGTTGCTG
TGGCCGGATGATGACTCTAGTCCTATCAGCAGGAAGAGGAGCGGTAGCAGTAACATAGGGCTCAATTTAAT
GGACAGTGTTGATTTGAATGGGAGGCGTATGAAAAGGCGGATGTAG (SEQ ID NO:80)

*Fragaria vesca* subsp. *vesca* (XM_004307418.1; Strawberry)
ATGCCACCGATTCAGAAACACTCCCTCCGCGGCGCGCAATTGGGCGGTAGAATCTCATCCATGAAGTCGA
AGCTCGAAAACGACGAGTCGTGTTCGCGGTCGATCAGCGAGACCGTGAACGGCTCCCACCGGTTCACCAT
AAAGGGGTATTCCTTGGCCAAAGGAATGGGCGCCGGGAAATACATACTCAGCGACACTTTCACCGTCGGC
GGTTACGATTGGGCGATTTACTTTTACCCCGACGGTAAAAACCCCGAGGATAGCTCCGTCTACGTCTCCG
TCTTCATTGCGCTGGTGAGCGAAGGCACCGACGTGAGGGCCTTGTTTGAGCTCACCTTGGTGGACCAGAG
CAACAGCGGCAAGGACAAGGTCCATAGTCACTTTGATCGTGCCCTTGAGAGCGGGCCTTACACGTTGAAG
TACCGTGGAAGCATGTGGGGTTACAAGCGATTCTTCAGAAGATCAGCCCTTGAAACGTCCGAGTTTCTAA
AGGATGATTCCCTTGTGTTGAACTGCACTGTTGGAGTCGTCAGAACTCGCCTAGAGTGTCCGAAACATTT
TGCAATTACTGTACCACCATCAGACATGGGTGAAGGTCTTAAGGCCTTTCTAGACTCTGGAGCTGGTTGC
GACCTGGTTTTTCAGGTTGGCGATGAGGAATTCAAAGCTCACAAGTTGATACTTGCTGCTCGTTCTCCTG
TATTCAAAGCACAGTTTTTTGGACATCTTGGAGATTCGAGTGTAGATAAAGTAGTCGTGAAGGATGTTGA
GCCCTTCATCTTCAAGGCAATGCTTCTTTTTATACGGGACAAACTTCCTGATATCCGTGAAGTTACA
GGTTCATCATCTTTGTGCACATTCACTGTCATGGTGCAGCATCTGTTGGCTGCTGCAGACCTGTATGACC
TAGAGCGACTGAAGTTGTTGTGTGAATCAATGTTGTGTGAAGAAATCACGACTGAAACAGTGGCAACCAC
ATTGGCCCTTGCTGAGCAGCATCACTGTCCACAGCTGAAGGCTGTGTGTCTAAAGTTTGCGGCAAAGTCA
ACAAACTTGGGAGCTGTAATGCAGTCAGATGGATACAAGCATCTAGAAGAGAGCTGCCCCTCAGTGTTAC
AGGAGCTGCTGAAGACATTTGCATCTGTCGATGCCAATGAGAATTCAAATTCAAGTAAGAAGAGGAGTGG
CAGCAGCATATATGGGCTAGACTTGCCAGCAGATGGCAGTGGGGCAGTAGCAGAATCAGCAAATCCCAAT
GGTAGGCGGTTGAGGCCGCGGCGATATTAA (SEQ ID NO:81)

Figure 22E

*Malus domestica* (XM_008373804.1; Apple)
ATGCCGCCGATTCGGAAACATTCCAGAGGGGCGAAATCGGGTGAATCCATGGGGAATTCGAAGCCTGGGT
TCGACCAGGAATCGTGCTCGAGATCGATCAGCGAGACTGTGAACGGCTCCCACCGGTTCACGATAAAGGG
GTATTCGCTGGCCAAAGGGATGGGAGCCGGGAAGTACCTGATGAGCGATACGTTCACGGTGGGCGGATAC
GATTGGGCAATTTACTTTTACCCCGACGGTAAAAACCCCGAGGATAGCAACGCGTACGTCTCGGTTTTCA
TTGCTTTGGTTAGTGAGGGTACGGATGTGAGGGCTCTGTTCGAGCTGACGTTGGTGGATCAGACGGACAG
TGGGAAGGACAAGGTGCACAGTCACTTTGATCGCGCTCTCGAGGGCGGGCCGTACACGCTGAAGTACAGA
GGCAGCATGTGGGGTTACAAGAAATTCTTCAGAAGATCAATCCTAGAAACTTCTGAGTTCCTTAAGGATG
ATTGCCTTGTATTGAACTGCACTGTTGGAGTTGTCAGAACTCGCCTTGAGCAACCAAAACAATTTACAAT
CACTGTTCCATCATCAGACATGGGACGAGACCTAAAGGACTTTCTAGATTCTGAAGCTGGTTGTGACATA
GTTTTTCAGGTTGGTGATGAACAGTTTAAAGCTCACAAGTTGATACTTGCTGCTCGGTCTCGTGTATTTA
GAGCGCAGTTTTATGGACTTGTCGGGGATTGTAACGTAGATAAAGTAGTTGTGAAGGATGTTGAGCCCTT
CATCTTCAAGGCAATGCTTCTCTTTATTTACACGGACAAACTTCCTGATACACACGAAGTTATGGGCTCA
TCACCTTTGTGCACATTCACTGTCATGGTGCAGCATCTGTTGGCAGCTGCAGACCTGTATAATCTAGATC
GACTGAAATTGTTGTGTGAATCAAAGTTATGTGAAGAAATCACTACTGAGACAGTGGCGACTACACTTGC
GCTTGCTGAACAGCATCAATGCCGACAGCTTAAGGATGTCTGTCTTAAATTTACAGCAAATCCGTCGAAC
TTGGGAGCTGTAATGCAATCAGAAGGGTACAAGCATCTAGAAGAGAGCTGCCCATCAATGTTGGTAGAGC
TGCTGGAGACATTTGCAGCGGTGGATGACAATTCTAGTCTTCTGTCAAGTCGGAAGAGGAGTGGCAGCAG
CATATATGGACTAGATTTGCCAGCAGATGGGGTGGGACTGCAGCAGAATCAGCAAATCCCAATGGTAGG
CGCGTGAGGCGGCGGTTTTAG (SEQ ID NO:82)

*Solanum lycopersicum* (XM_004239865.1; tomato)
ATGAACCAAATTTCCGTCGACCGTGCCGGGAAGGATTCATCATCCAAGTCTGTAAACGAAACGGTGAATG
GGTCTCACCATTTTACCATCAGGGGTTACTCTTTGGCCAAAGGAATGGGACCGGGAAAGTACATATCTAG
CGACATTTTCACCGTTGGTGGGTATGATTGGGCAATTTATTTCTACCCAGATGGTAAAAACATAGAGGAT
TCTTCAATGTATGTGTCTGTTTTTATAGCATTGGCTAGCGAAGGAACGGATGTTAGGGCGTTGTTTGAGT
TGACGATGTTGGATCAGAGTGGAAAAGTGAAACATAAAGTTCATAGCCATTTTGATCGGGCATTGGAAAG
TGGACCTTATACTTTGAAATATAGAGGAAGCATGTGGGGTTACAAACGATTTTTTAGAAGAGCAAGTTTA
GAAACTTCTGACTACCTGAAGGATGATTGCCTTTCCATGCACTGTACTGTTGGAGTTGTCAGAACTCGTG
TTGAAGGCCCCAAAAATTATAGTGTTACAATTCCACCTTCAGACATGGGTCAAAGTCTCAAATACTTGCT
GGATGCTGAACTTGGTTGTGATATAGTTTTCCGGGTTGGAGAAGAGGCATTTAAGGGTCATAAGTTGATA
CTTGCTGCTCGGTCTCCTGTATTTAGAGCACAATTCTTTGGCCTTATTGGGAATCCTAAAACGGACGAAG
TGGAAATTGAGGATATTGAACCCTCAGTCTTCAAGGCTATGCTTCAGTACATTTATTCTGATGAACTTCC
AGATTTGATTGAAATTACTGGCTCTACTTCAACTTGCACTTCTACGATAGTGACACAGCATCTATTGGCA
GCAGCCGATCGATTTGGTGTAGATAGGTTGAAAGAGTTATGTGAGGCGAAATTGTGTGAAGAAGTTAATG
TGGATACTGTGGCAACAACTCTTTCTCTTGCTGAGCAGCATCGGTGCCCACAACTCAAGGCCATCTGTTT
GAAATTTGCAGCTACAAACTTGGGAGTGGTCATGCAGAAAGATGGATTCAAGCACTTGGAAGAGAGTTGC
CCCTTATTGTTGTCAGAGCTGCTGGAAACAGTAGCATCCGTCGATGAGAAGCCAAGTCTGACGTCTAGCA
AGAAAAGGAATAGCAGCAGCAGCATCTTTGGACTGGATCTGGCTGCAGATGGCGCGGCAGCAGATTCTGT
TAACCTTACCGCTAGGCGGGTGAGGAGGAGGATGTAA (SEQ ID NO:83)

*Solanum tuberosum* (XM_006355629.1, potato)
ATGAACCAAATTTCCATCGACCGTGCCGGAAACGATTCGTCATCCAAGTCTGTAAACGAAACGGTGAATG
GGTCTCACCATTTTACCATCAGGGGTTACTCTTTGGCCAAAGGAATGGGACCTGGAAAGTACATATCTAG
CGACATTTTCACCGTTGGTGGGTATGATTGGGCAATTTATTTCTACCCAGATGGTAAAAACATAGAGGAT
TCTTCCATGTATGTGTCTGTTTTTATAGCATTGGCTAGCGAAGGAACAGATGTTAGGGCGTTGTTTGAGT
TGACGATGTTGGATCAGAGTGGAAAAGTGAAACATAAAGTTCATAGCCATTTTGATCGGGCATTGGAAAG
TGGACCTTATACTTTGAAATATAGAGGAAGCATGTGGGGTTACAAACGATTTTTTAGAAGAGCAAGTTTA
GAAATGTCTGACTACCTGAAGGATGATTGCCTTTCCATGCACTGTACTGTTGGAGTTGTCAGAACTCGTG
TTGAAGGCCCAAAAGATTATAGTGTTACAATTCCACCATCAGACATGGGCCAAAGTCTCAAATACTTGCT
GGATGCTGAACTTGGTTGTGATATAGTTTTCCGGGTTGGAGAAGAGGCATTTAAGGGTCATAAGTTGATA
CTTGCTGCTCGGTCTCCTGTGTTTAGAGCCCAATTCTTTGGCCTTATTGGGAATCCTAAAACGGACGAAG
TGGAAATTGAGGATATTGAACCCTCAGTCTTCAAGGCTATGCTCCAGTACATTTATTCTGATGAGCTTCC
AGATTTAATTGAAATTACTGGCTCTACTTCAACTTGCACTTCTACGATAGTGATGCAGCATTTATTGGCA
GCAGCTGATCGATTTGGTTTGGATAGGTTGAAAGAGTTATGTGAGGCGAAATTGTGTGAAGAAGTCAATG
TGGATACTGTGGCAACAACTCTTTCTCTTGCTGAGCAGCATCGATGCCCACAACTCAAGGCCATCTGTTT
GAAATTTGCAGCTACAAACTTGGGAGTGGTCATGCAGAAAGATGGATTCAAGCACTTAGAAGAGCTGC
CCCTTACTGTTGTCAGAGCTGCTGGAAACAGTGGCATCCGTCGATGAGAAGCCAAGTCTGACGTCTAGCA
AGAAAAGGAGTAGCAGCAGCAGCATCTTTGGACTAGATCTGGCTGCAGATGGCGCAGCAGCAGATTCTGT
TAACCTTACCGTTAGGCGGGTGAGGAGGAGGATGTAA (SEQ ID NO:84)

Figure 22F

*Oryza brachyantha* (XM_006657321.1; Oryza)
ATGACGGTGCCGCCGCCGACGCCGCCCCCTCGTGGTCTCGCTCCGTCACGGAGACCGTGCGGGGATCTC
ACCAGTACACCGTCAAGGGCTTCTCCATGGCCAAGGGCATGGGCCCCGGCCGCTACGTCACCAGCGACAC
CTTCGCCGTCGGCGGCTACCACTGGGCCGTCTACCTCTACCCCGACGGTAAGAACCCCGAGGACAACGCC
AACTACGTCTCCGTCTTCGTCGCCCTCGCCTCCGACGGGGCCGACGTCCGCGCCCTCTTCGAGCTCACCC
TCCTCGACCAGTCCGGCCGCGGACGCCACAAGGTCCATTCCCATTTCGACCGATCCCTGCAGGCCGGACC
CTACACCCTCAAGTACCGAGGCTCCATGTGGGGTTACAAGCGCTTCTACAGAAGATCACTCCTAGAATCT
TCCGACTTTCTCAAGGACGATTGCCTTGTAATGAACTGCACAGTAGGCGTCGTCAAGAACCGTCTCGAAA
CCCCAAAGAACATTCAGATCCACATTCCGCCTTCTGACATGGGCCGTTGCTTCAAGAACCTTCTCAACCT
CGGCATTGGATGTGACATAACTTTCGAGGTTGGTGATGACACAGTCCAGGCACACAAGTGGATTCTTGCT
GCTCGCTCCCGGTATTCAAAGCCCAATTCTTTGGTCCTATTGGGAATCCTGACCTACACTCGGTCACTG
TGGAGGATGTTGAACCTGTTGTTTCAAGGCGATGGTGAATTTCATATACTCCGATGAACTTCCTAGTAT
TCATGAACTAGCTGGATCTGTCTCAACATGGACATCGACAGTAGTAGTACAGCATTTGTTGGCAGCAGCT
GATAGATATGGATTAGATCGGCTACGTCTCCTATGCGAGGAAAAGTTATGTGATGAACTCACAGCTGAAA
CAGTTGCAACAACCTTAGCCCTAGCTGAACAACATCATTGTACTCAGCTGAAATCTGCTTGCCTAAAGTT
CACTGCCGTTCGGGAAAATCTGGGAGCTGTGATGGAGACAGAAGGATTTAACTACTTGGAGGAGACATGC
CCGTCCCTACTGTCCGACTTGTTGGCTACTGTCGCAGTGGTGGATGATGATTCTGCAACATTAAACCGGA
AGAGGGGAGTCAGTGGTAACGAAGGAGCGAATCCCGTGGAGAGCGTGGAGGCTAGTGAAAGGCGCATCCG
CAGGAGGGTTTAG (SEQ ID NO:85)

*Brachypodium distachyon* (XM_003557665.1; Brachypodium)
ATGGCGGCGGTGCCGCGGCCGTCGTGGTCGCGCTCGGTCAGCGAGACGGTGCGGGGTCGCACCAGTACA
CCGTCAAGGGCTTCTCCCTCGCCAAGGGCATCGGTCCCGGCCGCCACCTCGCCAGCGACACCTTCGCCGT
CGGCGGCTACGACTGGGCCGTCTACCTCTACCCCGACGGCAAGAACCCCGAGGACAACGCCAGCTACGTC
TCCGTCTTCGTCGCCCTCGCCTCCGAGGGCACCGACGTCCGCGCCCTCTTCGAGCTCACCCTCCTCGACC
AGTCCGGCCGCGCACGCCACAAGGTCCACTCCCACTTCGACCGCTCCATGCAGGCCGGACCGTACACCCT
CAAGTACAGGGGATCCATGTGGGGTTACAAGAGGTTCTACAGAAGGTCACAGTTAGAAACATCAGATTTT
CTAAAGAACGATTGCCTAGTAATGAACTGCACAGTAGGTGTTGTCAAGACTCGGCTCGAAACACCAAAGA
ACATCCAGATTAACGTTCCTCCATCTGACATCGGCCGTTGCTTCAAGGAGCTCCTCAGACTCCGCATTGG
CTGTGACATAACATTTGAAGTAGGTGACGAGAAGGTCCAGGCACATAAATGGATTCTTGCTGCTCGTTCC
CCAGTATTCAAAGCCCAATTCTTTGGACCAATTGGTAAAGCTGACTTGGACAGAGTTGTTGTGGAGGATG
TTGAACCTATCGTCTTCAAGGCAATGGTGAATTTCATATACTCTGATGAGCTTCCTAGTATTCATGAACT
AGCTGGATCTTTCTCAATGTGGACATCAACTGCAGTTATACAGCATTTGTTGGCAGCAGCTGATAGATAT
GGATTGGACCGGCTACGAATACTATGTGAGGCACAGTTATGTGATGGGCTTACTGCTGAAACAGTTGCGA
CAACCTTAGCCCTGGCTGAACAGCATCATTGTGCTCAGCTCAAGTCAGCCTGCTTAAAGTTTACTGCTGT
CCGAGAAAATCTTGGAGTTGTGATGGAGACTGATGGGTTAACTACTTGGAGGAGACATGCCCATCCCTG
CTGTCTGATTTGTTAGCAACCGTCGCGGTAGTGGACGATGATCCTACATCTGTTAACCGGAAAAGGGGAG
TTTGTATCAACGAAGATGTGAATCCAGTTGAAAGTGTTGAGGCTAGTGACAGGCGCATCCGCAGGAGGGT
TTAG (SEQ ID NO:86)

*Oryza sativa* Japonica Group (NM_001065212.1, rice)
ATGACGGCGGCGGCGTCGTGGTCCCGGTCGGTGACGGAGACGGTGCGGGGGTCTCACCAGTACACGGTGA
AGGGGTTCTCGATGGCGAAGGGCGTAGGGGCCGGGCGGTACGTGAGCAGCGACACCTTCGCGGTGGGCGG
CTACCACTGGGCCGTCTACCTCTACCCCGACGGCAAGAACCCCGAGGACAACGCCAACTACGTCTCCGTC
TTCGTCGCCCTCGCCTCCGACGGCGCCGACGTCCGCGCCCTCTTCGAGCTCACCCTCCTCGACCAGTCCG
GCCGCGGCCGCCACAAGGTCCACTCCCACTTCGACCGATCCCTCCAGGCCGGACCCTACACCCTCAAGTA
CCGAGGCTCCATGTGGGGCTACAAGCGCTTCTACCGAAGATCACTCTTAGAATCATCCGACTTTCTCAAG
GACGACTGCCTCGTTATGAACTGCACTGTAGGCGTCGTCAAGAACCGTCTCGAAACACCAAAGAACATCC
ACATCAATATTCCTCCATCCGACATGGGCCGTTGCTTCAACAACCTCCTCAATCTCCGCATCGGCTGTGA
CGTATCTTTTGAGGTGGGTGATGAAAGAGTCCAGGCGCACAAGTGGATTCTTGCTGCCCGCTCCCCTGTA
TTCAAAGCCCAATTCTTTGGTCCTATTGGGAATCCTGACCTACACACAGTCATTGTCGAGGATGTAGAAC
CTCTTGTCTTCAAGGCAATGGTGAATTTCATATACTCTGATGAACTTCCTAGTATTCATGAACTAGCTGG
ATCTGTCTCAACTTGGACATCGACAGTAGTAGTACAGCATTTGTTGGCGCTGCTGACAGATATGGACTA
GATCGGCTACGTCTGCTATGCGAGGAAAAGTTATGTGATGAACTCACTGCTGAAACAGTTGCAACAACTT
TAGCCCTAGCTGAACAACATCATTGTACTCAGCTGAAATCTGCTTGTCTGAAGTTCACTGCTGTTCGGGA
AAATCTGGGAGCTGTGATGGAGACAGAAGGATTTAATTACTTGGAGGAGACATGCCCGTCCCTGCTATCT
GACTTGTTAGCTACTGTCGCAGTAGTGGATGATGATGCTGCGTCATTCAACCGGAAGAGGGGAGTCGGTG
GTAACGAAGGAGCGAATCCTGTGGAGAGCGTGGAGGCTAGTGATAGGCGCATCCGCAGGAGGGTTTAG
(SEQ ID NO:87)

Figure 22G

*Hordeum vulgare* subsp. vulgare (AK363044.1, barley)
ATGGCGGTGCCGCGGCCGTCATGGTCGCGGTCGGTCACAGAGACCGTGCGGGGTTCGCACCAGTACACCG
TCAAGGGATTCTCCCTCGCCAAGGGCATCGGCCCCGGCCGGCACCTCTCCAGTGACACCTTCGCCGTCGG
CGGCTATGACTGGGCCGTCTACCTCTACCCGGACGGGAAGAACCAAGAGGACAACGCCAACTACGTCTCC
GTGTTCGTCGCCCTCGCCTCCGAGGGTACCGACGTCCGCGCCCTCTTCGAGCTCACCCTCCTCGACCAGT
CCGGCCGCGCCCGCCACAAGGTCCACTCCCATTTCGATCGATCCATGCAGGCCGGACCATACACCCTCAA
GTACAGAGGATCCATGTGGGGTTACAAGAGATTCTACAGAAGGACACAGTTAGAAGCATCAGATTTTTTA
AAGGATGATTGCCTAGTAATGAACTGCACAGTAGGTGTCGTCAAGAACCGTCTCGAAACACCGAAGAATA
TCCAGATTAATGTCCCCCCATCTGATATTGGTCGTTACTTCAAGGAACTCCTCAAACTCCACATTGGCTG
CGACATAACTTTTGAAGTAGGTGATGAGAAAGTCCAGGCACATAAATGGATTCTTGCTGCTCGCTCCCCT
GTGTTCAAAGCCCAATTCTTTGGACCTATTGGTAAACCTGACTTGGACAGAGTTGTTGTGGAGGATGTTG
AACCTATCGTCTTCAAGGCAATGGTGAATTTCATATATTCTGATGAGCTTCCTAGTATTCATGAAGTAGC
TGGATCTTTCTCAATGTGGACATCTACTGCGGTAACACAACATCTGTTGGCAGCAGCTGATAGATATGGA
TTGGACCGGCTACGAATCCTATGTGAGGCAAAGTTATGTGATGAACTCACTTCTGAAACAGTAGCGACAA
CCTTAGCCCTAGCTGAACAGCACCACTGTGCTCAGCTCAAGTCTGCCTGTCTAAAGTTCACTGCTGTTCG
ACAAAATCTGGGAGCTGTGATGGAGACAGAAGGGTTTAATTACTTGGAGGAGACTTGCCCATCCTTGCTG
TCTGATTTGTTAGCAACAGTCGCAGTAGTGGATGATGATCCTGCATCTGTTAACCGGAAAAGGGGAGTTT
GTATCAATGAAGATGCGAATCCCGTCGAAAGCGTTGAGGCTAGTGACAGGCGCACCCGCAGGAGGGTTTA
G (SEQ ID NO:88)

*Selaginella moellendorffii* (XM_002961536.1; spikemoss)
ATGGCACGGACGTCGGTAGTCTTGCAGGACGATTCAGGGCAAGTGGTCGGGAGTCCCACATCCACGGCAA
CGCCTTCCCGATCTCGATGCATCACAGAGACTGTGAATGGATCTCACCATTTCACGATCCATGGCTATTC
CCTGGCCAAAGGGATGGGCGTAGGGAAGTACATTGCGAGCGACACATTCACGGTTGGGGGCTACCAGTGG
GCGATCTACTTCTATCCGGATGGGAAGAACACCGAGGACAACTCGCTCTACGTGTCGGTGTTCATAGCTC
TGGCAAGTGAAGGGACGGATGTGAGGGCGCTGTTCGAGCTGACGCTTCTGGATCAAAGCGGCAAGAACAA
GCATAAGATCCACAGCCACTTTGATCGTTCGCTGGAGAGTGGTCCTTACACACTGAAGTATCGAGGCAGT
ATGTGGGGTTACAAGCGCTTCTTCAGACGGGCCGTGCTCGAGACGTCCGATTTTCTGAAAGACGACAGTC
TTTCAATCACCTGCACGGTCGGCGTCGTAGTTTCCTCCATGCAAGCCTTGAAGCAACACTCTTTGTTAGT
TCCGGAATCCGATATTGGCCAACATTTCCTGTCTTTGTTGGAAAGTGGTGAAGGAACGGACGTTAACTTT
AACGTAAAAGGGGAGGCATTCAGTGCTCACAAGTTGTTACTGGCTGCGAGATCCCCAGTGTTCAAAGCGC
AGCTGTTTGGACCCATGAAGGACGAGAATGGTGACGTGATCGAAATCGACGACATGGAACCACCTGTCTT
CAAGGCCATGCTACACTTTATATATAAAGACAGTCTGCCCGATACCAACGAGATGACAGGGTCTTCGTCA
CAGTCGACGGCGACGATGATGGCTCAGCATTTACTCGCAGCCGCAGATAGGTTTTGCCTGGATCGTTTAA
GACTTTTGTGCGAGTCCAGGCTCTGTGAACAGATCACTGTTGACACAGTGGCGACTACGCTTGCGTTGGC
AGACCAACACCATGCATCTCAGCTCAAAAATGTCTGCCTCAAGTTCGCTGCTTCCAACCTTGCAGTGGTG
ATGCAGTCTGATGGTTTTGAGTACCTGCGTGAGAGCTGCCCGTCATTACAATCCGAGCTCCTCAAGACGG
TCGCGGGAGTAGAAGAAGAAGCCAAGGCTGGAACAAAGAACAGGACCGTCTGGACGCACGTCGCAGATGG
TGGCGACGGATTGGGAAGGCGCGTGCGGCAAAAGATCTGA (SEQ ID NO:89)

*Medicago truncatula* (CM001223.2; Barrel Clover)
ATGGGTAAGATTCTCCGAGAAACCGCGAAACCATCTTCCAATCCATCATCACCATCTTCCTCATCGGAAC
CGGCGACAACTTCTTCGACATCGATAACCGAAACAGTGAAAGGCTCGCACCAGTTCAAGATCACTGGGTA
CTCGCTTTCGAAAGGGATCGGGATTGGGAAATACATAGCGTCGGATATCTTTTCGGTTGGTGGGTACGAT
TGGGCCATTTATTTCTACCCTGATGGAAAGAGTGTTGAGGATAATGCTACCTATGTGTCGCTTTTCATTG
CGCTTGCGAGTGATGGGACTGATGTTAGGGCTCTTTTTGAGTTGACCCTTTTGGATCAGAGTGGGAAAGA
GAGGCATAAGGTTCATAGCCATTTTGAGAGGACTCTTGAAAGTGGACCTTATACCTTGAAATACCGCGGT
AGTATGTGGGGTTACAAGCGGTTTTTTAAGAGGACAGCTTTAGAGACATCTGATTACCTTAAAGATGATT
GCCTTTCTGTTAATTGTAGTGTTGGTGTTGTGAGGTCACGCACGGAAGGCCCAAAGATATATTCCATTGC
AATACCACCTTCTAACATTGGTCACCAATTTGGTCAACTGCTGGAAAATGGTAAAGGAAGTGATGTGAGC
TTTGAAGTGGATGGGAAGTTTTCACTGCTCATAAATTGGTGCTAGCAGCTCGTTCACCTGTTTTCAGAG
CCCAGCTTTTTGGTCCTATGAGAGATCAAAGTACCCAGTCTATTAAAGTTGAAGACATGGAAGCTCCAGT
TTTTAAGGCATTGCTTCATTTTATGTACTGGGACTCGCTGCCTGACATGCAAGAGCTTACTGGGATGAAC
ACAAAATGGGCAACAACCTTGATGGCCCAACATCTTCTAGCGGCTGCTGATCGTTATGCCTTAGAGAGGC
TCAGGCTTATATGTGAAGCGAGTCTATGTGAAGATGTTGCCATTAATACCGTGGCTACAACTTTAGCCTT
GGCAGAGCAACACCACTGTTTCCAGCTGAAAGCAGTCTGTCTCAAGTTTATTGCCACCTCTGAAAATCTC
AGAGCTGTGATGCAAACTGATGGATTTGAGTACTTGAAGGAAAGTTGCCCATCTGTTCTGACTGAGCTAC
TGGAGTACGTGGCTAGATTTACTGAGCATTCGGACTTTTTGTGCAAGCACAGGAATGAAGCAATACTTGA
TGGTAGCGACATAAATGGAAGGCGGGTGAAGCAAAGGCTTTAG (SEQ ID NO:90)

Figure 22H

*Coffea canephora* (HG739095.1; Robusta coffee)
ATGGGAAGGGTTTACAATGGAGAAACCTCCAACCCGTCGTCTTCCACAACGGCGTCAACATCGCCGCCGC
CGGTGACGACGTCGACGTCGATCACGGAGACTGTGAATGGAACGCACGATTTTAAGATCACGGGGTATTC
CTTGTCCAAGGGAATTGGGATTGGCAAGTACGTAGCGTCTGATATTTTCATGGTGGGAGGCTATGCGTGG
GCGATCTATTTCTATCCTGATGGGAAAGCGTGGAGGACAATGCGACGTATGTTTCCTTGTTTATTGCGC
TAGCCAGCGAGGGAACGGACGTTAGAGCGCTGTTTGAACTGACGCTTATGGATCAGAGCGGGAGAGCGAG
GCATAAGATTCATAGCCATTTCGGAAGGGCTTTAGAGAGTGGGCCTTACACGTTAAATACCGCGGAAGC
ATGTGGGGCTATAAGCGGTTTTTTAAGAGAACTGCACTAGAAACATCAGACTATCTGAAGAATGATTGTC
TTCAGGTTCATTGTTGTGTTGGTGTAGTTAGATCCCAAACTGAGGGACCCAAAATCTACTCTATACCGCT
TCCACCTTCGGACATTGGTCAACATTTTGGGCAGCTACTGGAATGTGGAAAGGGAACTGATGTAAATTTT
GAAGTCAATGGAGAAAAATTTTCTGCTCACAAGTTGGTTCTTGCTGCGCGCTCACCTGTATTTAGAGCTC
AACTATTTGGCCCAATGAAAGATCATGACACACAATGTATTCGAGTTAAGACATGGAAGCTCCTGTTTT
TAAGGCTCTACTTCATTTCATATACTGGGATTGCTTACCCGATATGGAAGAACTTACTGGTTTGAACTCA
AAAGGGGCTACAAGCTTGATGGCTCAACATCTGCTTGCTGCTGCAGATAGATATGGTTTGGATAGGCTCA
GGTTGATATGTGAAGCTAATCTCTGCGAGGATGTTGCCATAAATACTGTTGCTACTACGCTGGCCCTTGC
AGAGCAGCATCACTGTTTCCAGCTGAAGTCTGTATGCCTAAAATTTGTTGCCATGCCAGAAAATCTTAGG
GCTGTTATGCAGACAGACGGGTTTGAATACCTAAAAGAAAGTTGTCCAAGCGTGCTCACAGAATTGTTGG
AGTATGTAGCTAGGATCAATGAGCATTCTGTCAGTGTGAACAAGCAATTGACTGATGGTATATTGGACGG
GAGTGATGTCAATGGTCGGCGGGTGAAGCAGAGATTGTAG (SEQ ID NO:91)

*Zea mays* (NM_001148597.1; corn)
ATGGCGATTCCGCCGCGGACTCCTTCCCCGCCGCCATCGTGGTCGCGCTCTGTAACCGAGACCGTTCGGG
GGTCCCACCAGTTCACCGTACGGGGCTACTCCCTCGCCAAGGGCATGGGCCCCGGCCGCTACCTCGCCAG
CGACGTCTTCGCCGTCGGAGGATACCACTGGGCCGTCTACCTCTACCCCGACGGCAAGAACGCCGAGGAC
AACTCCAACTACGTCTCCGTTTTCGTCGCCCTCGCTTCCGACGGCATCGACGTCCGAGCCCTCTTCGAGC
TCACCCTCCTCGACCAGTCCGGCCGCGGCTGCCACAAGGTTCACTCGCACTTTGACCGCTCGCTCAAGTT
CGGCCCATACACCCTCAAGTACAGGGGATCCATGTGGGGTTACAAGCGCTTCTACAAAAGAACACTCTTG
GAAGAATCTGATTTCTTAAAGAATGATTGCCTAGTGATGAACTGCACAGTAGGTGTTGTCAAGAACCGTA
TAGAAACACCAAAGGACATCCAGATTCATGTTCCACGATCAGACATGGGCCGCTGCTTCAAGGAGCTCCT
CAGCCGCTGCATTGGATGTGACATAACATTCGAAGTGCGAGATGAGAAAGTCAGGGCACACAAGTGGATT
CTTGCTGCTCGCTCCCCAGTATTTAAAGCCCAGTTCTTTGGTCCTATTGGAAAGCCTGACCTGCACACGG
TTGTTGTGGAGGATGTGGAACCTGTTGTCTTCAAGGCAATGGTGAACTTCATTTACGCTGATGAACTCCC
CAGCATTCCTGAGCTAGCTGGGTCTGCCTCAACGTGGACATCAACAGTAGTAGTACAGCATTTGTTGGCA
GCAGCTGATAGATATGGACTGGTCCGTCTGCGTATCCTGTGTGAATCAAAGCTCTGTGATGAACTGACTC
CTGAAACTGTCGCAACAACTTTAGCCCTTGCTGAACAGCACCATTGTGCTGAGCTGAAGTCTGCATGTCT
AAAGTTCATTGCTTTGCGAGGAAATTTGGGAGCTGTTATGGAGACGGAAGGCTTTGATTACCTGGAGGAT
ACATGCCCGTCCCTACTATCTGACTTGTTAGCTACTGTGGCAGTCGTGGACGACGATCTTGCATCCCTTA
ACCGAAAAGGGGAGTCAGCGGGAACCAAGTCATGGCTCTAGTGGGAAGCGTTGAAAGGCGCACCCGGAG
GAAGCTTTAG (SEQ ID NO:92)

*Sorghum bicolor* (XM_002461247.1; Sorghum)
ATGGCGATTCCGCCGCGGACTCCTCCCCCGCCGCCATCGTGGTCGCGCTACGTCACCGAGACCGTGAAGG
GGTCCCACCAGTTCACCGTCCGGGGCTTCTCCCTCGCCAAGGGCATGGGCCCCGGCCGCCACCTCGCCAG
CGACATCTTCGCTGTCGGAGGATACCACTGGGCCGTCTACTTCTACCCCGACGGCAAGAACGCCGAGGAC
AACTCCAACTACGTCTCCGTCTTCGTCGCCCTCGCCTCCGACGGCATCGACGTCCGAGCCCTCTTCGACC
TCACCCTCCTCGACCAGTCCGGCCGCGGCCGCCACAAGATTCACTCGCACTTTGGCCGCAAGCTAGATTC
CGGCCCATACACCCTCAAGTACAGGGGCTCCATGTGGGGTTACAAACGCTTCTACAAAAGATCACTCTTG
GAAGCATCTGATTTCTTAAAGAATGATTGCCTAGTGATGAACTGCACAGTAGGTGTTGTCAAGAACCGTA
TGGAAACACCAAAGGACATCCAGATTCATGTTCCACGATCAGACATGGGCCACTGCTTCAAGGAGCTCCT
CAGCCGCGGCATTGGATGTGACATAACCTTCGAAGTGCGCGACGAGAAAGTCAGGGCACACAAGTGGATT
CTTGCTGCTCGCTCCCCAGTATTTAAAGCCCAGTTCTTTGGTCCTATTGGAAAGCCTGACCTGCACACGG
TTGTCGTGGAGGATGTGGAACCTGTCGTCTTCAAGGCAATGGTGAACTTCATGTACACTGATGAACTCCC
CAGCATTCTGAGCTAGCTGGATCTGCCTCAACATGGACATCAACAGTAGTAGTACAGCATTTGTTGGCA
GCAGCTGATAGATATGGACTGGACCGTCTTCGTATCCTGTGTGAATCAAAGCTATGTGATGAACTGACTC
CTGAAACTGTCGCAACAACCTTAGCCCTTGCTGAACAACACCATTGCGCTGAGCTGAAGTCTGCCTGTCT
AAGGTTTGCTGCTGTGCGAGAAAATTTGGGAGCTGTTATGGGGACGGAAGGCTTTGATTACTTGGAAGAG
ACATGCCCGTCCCTACTATCCGACTTGTTAGCTACTGTGGCAGAAGTGGACGATGATCCTGCATCCCTTG
ACCGAAAAGGGGAGTTTGCGGTAACCAAGTCTTGGCTCCAGTGGAAAGTGTCGAGGCTACTGAAAGGCG
CACCCGGAGGAGGCTTTAG (SEQ ID NO:93)

Figure 22I

Cucumis melo (XM_008460321.1, muskmelon)
ATGGGCACGATTAAATCTTGCAGGGATACCTCTAAATCCTACTCAAATCTTCGGTCGCCGACGCCTCCAC
CAGTGACTTTTTCAACTTCTCGTTTCGAGACCGTCAATGGATCGCATGAGTTCAAGATCAATGGGTATTC
CCTTAATAAAGGGATGGGGATTGGGAAATACATCGCGTCTGATACCTTTATGGTTGGGGGATATGCGTTT
GCTATATATTTTTACCCAGACGGGAAGAGCGTCGAGGATAACGCATCGTATGTCTCGGTTTTTATAGCGT
TGGCTAGTGAAGGGACTGACGTTAGAGCCCTTTTTGAATTGACGTTGTTGGATCAAAGTGGGAAGGAGAA
CCACAAGGTGCACAGCCATTTCGAGAGAAGACTCGAGAGTGGTCCTTATACGCTTAAATATCGAGGAAGC
ATGTGGGGGTATAAACGTTATTTTAAAAGAACAGTTTTAGAAACATCCGACTTCCTAAAGGACGACTGCC
TTGAAATCCACTGTGTAGTTGGTGTTGTTAAGTCCCATACAGAGGGACCAAAGATTTACTCCATAACACC
ACCACCTTCTGATATAGGCCAGCATTTTGGGAAGCTTTTGGAGAGTGGGAAACTAACTGATGTGAACTTT
GAAGTAGATGGGGAAACATTTTCTGCCCACAAGTTAGTTCTTGCTGCGCGGTCACCTGTCTTTAGGGCAC
AACTCTTTGGCCCTCTGAAGGACCAGAATACTGAGTGTATAAAAGTCGAAGATATGGAAGCCCCAGTATT
TAAGGCATTGCTTCATTTCATATACTGGGATGCTCTACCAGATATGCAAGAAATTGTAGGTTTAAACTCA
AAATGGGCTTCCACTCTGATGTCCCAGCATCTACTTGCGGCAGCAGACAGATATGCACTTGACAGACTCA
AATTGCTATGCGAGGCTAAACTTTGTGAGGACGTTGCTATAAATACAGTGGCAACGACATTGGCATTGGC
TGAGCAGCATCACTGTTTCCAACTAAAAGCTGTATGTTTGAAAGTCATTGCATTGCCGGAGAATTTGAGA
GCTGTAATGCAAACGGAGGGGTTTGAATATTTGAAAGAGAGCTGCCCATCGGTTCTCACTGAACTACTAG
AATATGTAGCAAGGGTGACGGAGCATGCAGTGATTACTTGCAGCGGGTATGGAAATGGAACAGTGTTAGA
TGGTAGTTACGTGAATGGAAGACGGGTAAGGCAGAGGTTGTATTGA (SEQ ID NO:94)

Figure 22J

SEQUENCE LISTING

<160> NUMBER OF SEQ ID NOS: 94

<210> SEQ ID NO 1
<211> LENGTH: 408
<212> TYPE: PRT
<213> ORGANISM: Arabidopsis thaliana

<400> SEQUENCE: 1

Met Ser Thr Val Gly Gly Ile Glu Gln Leu Ile Pro Asp Ser Val Ser
1               5                   10                  15

Thr Ser Phe Ile Glu Thr Val Asn Gly Ser His Gln Phe Thr Ile Gln
            20                  25                  30

Gly Tyr Ser Leu Ala Lys Gly Met Ser Pro Gly Lys Phe Ile Gln Ser
            35                  40                  45

Asp Ile Phe Ser Val Gly Gly Tyr Asp Trp Ala Ile Tyr Phe Tyr Pro
 50                  55                  60

Asp Gly Lys Asn Pro Glu Asp Gln Ser Ser Tyr Ile Ser Leu Phe Ile
 65                  70                  75                  80

Ala Leu Ala Ser Asp Ser Asn Asp Ile Arg Ala Leu Phe Glu Leu Thr
                85                  90                  95

Leu Met Asp Gln Ser Gly Lys Gly Lys His Lys Val His Ser His Phe
               100                 105                 110

Asp Arg Ala Leu Glu Gly Gly Pro Tyr Thr Leu Lys Tyr Lys Gly Ser
               115                 120                 125

Met Trp Gly Tyr Lys Arg Phe Phe Lys Arg Ser Ala Leu Glu Thr Ser
               130                 135                 140

Asp Tyr Leu Lys Asp Asp Cys Leu Val Ile Asn Cys Thr Val Gly Val
145                 150                 155                 160

Val Arg Ala Arg Leu Glu Gly Pro Lys Gln Tyr Gly Ile Val Leu Pro
               165                 170                 175

Leu Ser Asn Met Gly Gln Gly Leu Lys Asp Leu Leu Asp Ser Glu Val
               180                 185                 190

Gly Cys Asp Ile Ala Phe Gln Val Gly Asp Glu Thr Tyr Lys Ala His
               195                 200                 205

Lys Leu Ile Leu Ala Ala Arg Ser Pro Val Phe Arg Ala Gln Phe Phe
               210                 215                 220

Gly Pro Ile Gly Asn Asn Val Asp Arg Ile Val Ile Asp Asp Ile
225                 230                 235                 240

Glu Pro Ser Ile Phe Lys Ala Met Leu Ser Phe Ile Tyr Thr Asp Val
               245                 250                 255

Leu Pro Asn Val His Glu Ile Thr Gly Ser Thr Ser Ala Ser Ser Phe
               260                 265                 270

Thr Asn Met Ile Gln His Leu Leu Ala Ala Asp Leu Tyr Asp Leu
               275                 280                 285

Ala Arg Leu Lys Ile Leu Cys Glu Val Leu Leu Cys Glu Lys Leu Asp
               290                 295                 300

Val Asp Asn Val Ala Thr Thr Leu Ala Leu Ala Glu Gln His Gln Phe
305                 310                 315                 320

Leu Gln Leu Lys Ala Phe Cys Leu Glu Phe Val Ala Ser Pro Ala Asn
               325                 330                 335

Leu Gly Ala Val Met Lys Ser Glu Gly Phe Lys His Leu Lys Gln Ser
               340                 345                 350

Cys Pro Thr Leu Leu Ser Glu Leu Leu Asn Thr Val Ala Ala Ala Asp
               355                 360                 365

Lys Ser Ser Thr Ser Gly Gln Ser Asn Lys Lys Arg Ser Ala Ser Ser
               370                 375                 380

Val Leu Gly Cys Asp Thr Asn Val Arg Gln Leu Arg Arg Arg Thr
385                 390                 395                 400

Arg Lys Glu Val Arg Ala Val Ser
               405

<210> SEQ ID NO 2
<211> LENGTH: 399
<212> TYPE: PRT
<213> ORGANISM: Brassica rapa -continued

<400> SEQUENCE: 2

Met Ser Ala Ser His Pro Asn His Asp Ser Val Ser Thr Thr Val Met
1               5                   10                  15

Glu Thr Val Asn Gly Ser His Gln Phe Thr Ile Lys Gly Tyr Ser Leu
            20                  25                  30

Ala Lys Gly Met Ser Pro Gly Arg Tyr Ile Gln Ser Asp Val Phe Ser
        35                  40                  45

Val Asn Gly Tyr Asp Trp Val Ile Tyr Phe Tyr Pro Asp Gly Lys Asn
    50                  55                  60

Pro Glu Glu Asn Ser Thr Tyr Val Ser Leu Phe Ile Ala Leu Ala Ser
65                  70                  75                  80

Asp Ser Ser Asp Ile Arg Ala Leu Phe Glu Leu Thr Leu Met Asp Gln
                85                  90                  95

Ser Gly Arg Gly Arg His Lys Val His Ser His Phe Asp Arg Ala Leu
            100                 105                 110

Glu Gly Gly Pro Tyr Thr Leu Lys Tyr Lys Gly Ser Met Trp Gly Tyr
        115                 120                 125

Lys Arg Phe Leu Arg Arg Thr Ala Leu Glu Ala Ser Asp Tyr Leu Lys
    130                 135                 140

Asp Asp Cys Leu Ile Ile Asn Cys Thr Val Gly Val Val Arg Ala Arg
145                 150                 155                 160

Leu Glu Gly Pro Lys Gln Phe Gly Ile Val Pro Pro Ser Asn Met
                165                 170                 175

Gly Gln Gly Leu Lys Asp Leu Leu Asp Ser Glu Leu Gly Cys Asp Ile
            180                 185                 190

Ala Phe Gln Val Gly Asp Glu Thr Tyr Lys Ala His Lys Leu Ile Leu
        195                 200                 205

Ala Ala Arg Ser Pro Val Phe Arg Ala Gln Phe Tyr Gly Pro Val Gly
    210                 215                 220

Asn Asn Ser Val Asp Arg Val Val Ile Glu Asp Met Glu Pro Ser Ile
225                 230                 235                 240

Phe Lys Ala Met Leu Ser Phe Ile Tyr Thr Asp Val Leu Pro Asp Val
                245                 250                 255

His Glu Ile Thr Gly Ser Thr Ser Thr Ala Ser Phe Thr Asn Met Ile
            260                 265                 270

Gln His Leu Leu Ala Ala Ala Asp Leu Tyr Asp Leu Gly Arg Leu Lys
        275                 280                 285

Ile Leu Cys Glu Ala Phe Leu Cys Glu Glu Leu Asn Val Asp Asn Val
    290                 295                 300

Ala Thr Thr Leu Ala Leu Ala Asp Gln His Gln Phe Leu Gln Leu Lys
305                 310                 315                 320

Ala Phe Cys Leu Lys Phe Val Ala Ser Pro Ala Asn Leu Arg Ala Val
                325                 330                 335

Met Lys Ser Glu Gly Phe Lys His Leu Asn Gln Ser Cys Pro Ser Val
            340                 345                 350

Leu Pro Glu Leu Leu Asn Thr Val Ala Ala Ala Asp Lys Ser Ser Thr
        355                 360                 365

Ser Ser Ser Gly Gln Ser Ser Lys Lys Arg Ser Val Ser Ser Val Leu
    370                 375                 380

Gly Cys Asp Thr Ser Thr Thr Asn Ala Arg Gln Val Arg Arg Thr
385                 390                 395

<210> SEQ ID NO 3

```
<211> LENGTH: 407
<212> TYPE: PRT
<213> ORGANISM: Jatropha curcas

<400> SEQUENCE: 3

Met Val Asp Val Lys Ala Asp Phe Asp Lys Glu Ser Cys Ser Lys Ser
1               5                   10                  15

Val Asn Glu Thr Val Asn Gly Ser His Gln Phe Thr Ile Lys Gly Tyr
            20                  25                  30

Ser Leu Ala Lys Gly Met Gly Ala Gly Lys Cys Ile Ser Ser Asp Ile
        35                  40                  45

Phe Thr Val Gly Gly Tyr Asp Trp Ala Ile Tyr Phe Tyr Pro Asp Gly
    50                  55                  60

Lys Asn Pro Glu Asp Ser Ser Met Tyr Val Ser Val Phe Ile Ala Leu
65              70                  75                  80

Ala Ser Glu Gly Thr Asp Val Arg Ala Leu Phe Glu Leu Thr Leu Val
                85                  90                  95

Asp Gln Ser Gly Asn Gly Lys His Lys Val His Ser His Phe Asp Arg
            100                 105                 110

Ala Leu Glu Ser Gly Pro Tyr Thr Leu Lys Tyr Arg Gly Ser Met Trp
        115                 120                 125

Gly Tyr Lys Arg Phe Phe Arg Arg Thr Thr Leu Glu Asn Ser Asp Tyr
    130                 135                 140

Ile Lys Asp Asp Cys Leu Leu Met Asn Cys Thr Val Gly Val Val Arg
145                 150                 155                 160

Thr Arg Leu Val Gly Pro Lys Gln Cys Phe Ile Thr Ile Pro Pro Ser
                165                 170                 175

Asp Met Gly Gln Gly Leu Lys Glu Leu Leu Glu Ser Glu Val Gly Cys
            180                 185                 190

Asp Ile Ala Phe Gln Val Gly Asp Glu Thr Phe Lys Ala His Lys Leu
        195                 200                 205

Ile Leu Ala Ala Arg Ser Pro Val Phe Arg Ala Gln Phe Phe Gly Leu
    210                 215                 220

Phe Gly Asp Pro Asn Leu Asp Lys Val Val Lys Asp Ile Asp Pro
225                 230                 235                 240

Ser Ile Phe Lys Ala Met Leu Leu Phe Val Tyr Thr Asp Lys Leu Pro
                245                 250                 255

Asp Val His Glu Ile Thr Gly Thr Thr Ser Met Cys Thr Ser Thr Asn
            260                 265                 270

Met Val Gln His Leu Leu Ala Ala Asp Leu Tyr Asn Leu Asp Arg
        275                 280                 285

Leu Lys Leu Leu Cys Glu Ser Lys Leu Cys Glu Glu Leu Ser Ala Glu
    290                 295                 300

Thr Val Ala Thr Thr Leu Ala Leu Ala Glu Gln His Gln Cys Ser Gln
305                 310                 315                 320

Leu Arg Ala Ile Cys Leu Lys Phe Ala Ala Thr Pro Ala Asn Leu Gly
                325                 330                 335

Ala Val Met Gln Ser Glu Gly Phe Arg His Leu Glu Glu Ser Cys Pro
            340                 345                 350

Ala Leu Leu Cys Glu Met Leu Lys Thr Phe Ala Leu Gly Asp Glu Asn
        355                 360                 365

Ser Asn Gln Ser Gly Arg Lys Arg Ser Gly Ser Ile Tyr Gly Leu
    370                 375                 380

Asp Leu Ala Thr Asp Gly Ala Ala Ala Glu Ser Val Asn Pro Asn Ala
```

```
                385                 390                 395                 400
Arg Arg Leu Arg Arg Tyr
                405

<210> SEQ ID NO 4
<211> LENGTH: 407
<212> TYPE: PRT
<213> ORGANISM: Populus trichocarpa

<400> SEQUENCE: 4

Met Asp Asp Phe Lys Gly Asp Val Asp Lys Glu Ser Cys Ser Lys Ser
1               5                   10                  15

Ile Asn Glu Thr Val Asn Gly Ser His Gln Phe Thr Ile Lys Gly Tyr
            20                  25                  30

Ser Leu Ala Lys Gly Met Gly Ala Gly Arg Cys Ile Pro Ser Asp Val
        35                  40                  45

Phe Asn Val Gly Gly Tyr Asp Trp Ala Ile Tyr Phe Tyr Pro Asp Gly
    50                  55                  60

Lys Asn Pro Glu Asp Ser Ser Met Tyr Val Ser Val Phe Ile Ala Leu
65                  70                  75                  80

Ala Ser Glu Gly Thr Asp Val Arg Ala Leu Phe Glu Leu Thr Leu Val
                85                  90                  95

Asp Gln Ser Gly Lys Gly Lys His Lys Val His Ser His Phe Asp Arg
            100                 105                 110

Ala Leu Glu Ser Gly Pro Tyr Ser Leu Lys Tyr Arg Gly Ser Met Trp
        115                 120                 125

Gly Tyr Lys Arg Phe Phe Arg Arg Thr Thr Leu Glu Thr Ser Asp Tyr
    130                 135                 140

Leu Lys Asp Asp Cys Leu Ile Met Asn Cys Thr Val Gly Val Val Arg
145                 150                 155                 160

Thr Arg Leu Glu Gly Pro Lys Gln Tyr Ser Ile Ser Val Pro Pro Ser
                165                 170                 175

Asp Met Gly Trp Gly Phe Lys Glu Leu Leu Ser Glu Ser Gly Cys
            180                 185                 190

Asp Ile Asp Phe Gln Val Gly Asp Glu Thr Phe Arg Ala His Lys Leu
        195                 200                 205

Ile Leu Ala Ala Arg Ser Pro Val Phe Arg Ala Gln Phe Phe Gly Leu
    210                 215                 220

Val Gly Asp Pro Asn Met Asp Lys Val Val Lys Asp Val Asp Pro
225                 230                 235                 240

Leu Ile Phe Lys Ala Met Leu Leu Phe Ile Tyr Thr Asp Lys Leu Pro
                245                 250                 255

Asp Ala His Glu Ile Thr Gly Ser Thr Ser Met Cys Thr Ser Thr Asn
            260                 265                 270

Met Val Gln His Leu Leu Ala Val Ser Asp Leu Tyr Asn Leu Asp Arg
        275                 280                 285

Leu Lys Leu Leu Cys Glu Ala Lys Leu Cys Glu Glu Leu Ser Ala Glu
    290                 295                 300

Asn Val Ala Thr Thr Leu Ala Leu Ala Glu Gln His Gln Cys Met Gln
305                 310                 315                 320

Leu Lys Ala Ile Cys Leu Lys Phe Ala Ala Asn Pro Ala Asn Leu Gly
                325                 330                 335

Ala Val Met Gln Ser Glu Gly Phe Arg His Leu Glu Glu Ser Cys Pro
            340                 345                 350
```

```
Ser Met Leu Cys Glu Leu Leu Lys Thr Leu Ala Ser Gly Asp Glu Asn
            355                 360                 365

Ser Ser Leu Leu Ser Gly Arg Lys Arg Ser Gly Ser Ser Leu Leu Gly
    370                 375                 380

Val Asp Leu Ala Asp Gly Ala Pro Ala Glu Ser Ala Asn Pro Asn Gly
385                 390                 395                 400

Arg Arg Leu Arg Arg Phe
                405

<210> SEQ ID NO 5
<211> LENGTH: 402
<212> TYPE: PRT
<213> ORGANISM: Theobroma cacao

<400> SEQUENCE: 5

Met Asp Asp Phe Lys Asp Ser Val Ser Lys Ser Val Ser Glu Thr Val
1               5                   10                  15

Asn Gly Ser His Gln Phe Thr Ile Lys Gly Tyr Ser Leu Ala Lys Gly
            20                  25                  30

Met Gly Pro Gly Lys Cys Ile Ala Ser Asp Val Phe Thr Val Gly Gly
        35                  40                  45

Phe Asp Trp Val Ile Tyr Phe Tyr Pro Asp Gly Lys Asn Pro Glu Asp
    50                  55                  60

Ser Ala Met Tyr Val Ser Val Phe Ile Ala Leu Ala Ser Glu Gly Thr
65                  70                  75                  80

Asp Val Arg Ala Leu Phe Glu Leu Thr Leu Val Asp Gln Ser Gly Lys
                85                  90                  95

Gly Lys His Lys Val His Ser His Phe Asp Arg Ala Leu Glu Ser Gly
            100                 105                 110

Pro Tyr Thr Leu Lys Tyr Arg Gly Ser Met Trp Gly Tyr Lys Arg Phe
        115                 120                 125

Phe Arg Arg Thr Thr Leu Glu Thr Ser Asp Tyr Ile Lys Asp Asp Cys
    130                 135                 140

Leu Ile Met Asn Cys Thr Val Gly Val Val Arg Thr Arg Leu Glu Gly
145                 150                 155                 160

Pro Lys Gln Cys Ser Ile Ser Val Pro Pro Ser Glu Met Gly Gln Asn
                165                 170                 175

Leu Lys Ala Leu Leu Glu Ser Glu Val Gly Cys Asp Ile Ile Phe Gln
            180                 185                 190

Val Val Asp Glu Lys Phe Lys Ala His Lys Leu Ile Leu Ala Ala Arg
        195                 200                 205

Ser Pro Val Phe Arg Ala Gln Phe Gly Leu Val Gly Asp Pro Asn
    210                 215                 220

Met Asp Lys Val Val Glu Asp Phe Glu Pro Ser Ile Phe Lys Ala
225                 230                 235                 240

Met Leu Leu Phe Ile Tyr Thr Asp Lys Leu Pro Asp Val Gln Glu Ile
                245                 250                 255

Thr Gly Ser Thr Ser Met Cys Met Ser Thr Asn Met Val Gln His Leu
            260                 265                 270

Leu Ala Ala Ala Asp Leu Tyr Asn Leu Asp Arg Leu Lys Val Leu Cys
        275                 280                 285

Glu Ala Lys Leu Cys Glu Glu Leu Asn Ala Asp Thr Val Ala Thr Thr
    290                 295                 300

Leu Ala Leu Ala Glu Gln His His Cys Ala Gln Leu Lys Ala Ile Cys
305                 310                 315                 320
```

Leu Lys Phe Ala Ala Thr Pro Ala Asn Leu Gly Ala Val Met Gln Ser
                325                 330                 335

Glu Gly Phe Arg His Leu Glu Glu Cys Cys Pro Ser Leu Leu Ser Glu
            340                 345                 350

Leu Leu Lys Thr Phe Ala Ser Gly Glu Glu Ser Leu Ser Gln Leu Ser
        355                 360                 365

Ser Arg Lys Arg Ser Gly Ser Ser Val Tyr Gly Met Asp Leu Ala Ala
370                 375                 380

Glu Gly Pro Val Ala Glu Ser Val Asn Pro Asn Gly Arg Arg Val Arg
385                 390                 395                 400

Arg Arg

<210> SEQ ID NO 6
<211> LENGTH: 404
<212> TYPE: PRT
<213> ORGANISM: Citrus clementina

<400> SEQUENCE: 6

Met Gly Asn Ser Glu Lys Asp Ser Thr Ser Lys Ser Ile Asn Glu Thr
1               5                   10                  15

Val Asn Gly Ser His Gln Phe Thr Val Lys Gly Tyr Ser Leu Ala Lys
            20                  25                  30

Gly Met Gly Pro Gly Lys Cys Leu Ser Ser Asp Val Phe Thr Val Gly
        35                  40                  45

Gly Tyr Asp Trp Ala Ile Tyr Phe Tyr Pro Gly Lys Asn Pro Glu
    50                  55                  60

Asp Gly Ala Leu Tyr Val Ser Val Phe Ile Ala Leu Ala Ser Glu Gly
65                  70                  75                  80

Thr Asp Val Arg Ala Leu Phe Glu Leu Thr Leu Val Asp Gln Ser Gly
                85                  90                  95

Lys Gly Lys His Lys Val His Ser His Phe Asp Arg Ala Leu Glu Ser
            100                 105                 110

Gly Pro Tyr Thr Leu Lys Tyr Arg Gly Ser Met Trp Gly Tyr Lys Arg
        115                 120                 125

Phe Phe Lys Arg Thr Ser Leu Glu Thr Ser Asp Tyr Ile Lys Asp Asp
130                 135                 140

Cys Leu Leu Ile Asn Cys Thr Val Gly Val Val Arg Asn Arg Leu Glu
145                 150                 155                 160

Gly Pro Lys Gln Tyr Ser Ile Pro Val Pro Pro Ser Asp Met Gly Gln
                165                 170                 175

Gly Leu Lys Asp Leu Leu Glu Ser Glu Ile Gly Cys Asp Ile Val Phe
            180                 185                 190

Glu Val Gly Asp Glu Thr Phe Lys Ala His Lys Leu Ile Leu Ala Ala
        195                 200                 205

Arg Ser Pro Val Phe Arg Ala Gln Phe Tyr Gly Leu Val Gly Asp Arg
210                 215                 220

Asn Leu Asp Lys Val Val Val Lys Asp Val Glu Pro Ser Ile Phe Lys
225                 230                 235                 240

Ala Met Leu Leu Phe Ile Tyr Thr Asp Lys Phe Pro Asp Val Tyr Glu
                245                 250                 255

Ile Thr Gly Thr Thr Ser Met Cys Thr Thr Thr Asn Met Val Gln His
            260                 265                 270

Leu Leu Ala Ala Ala Asp Leu Tyr Asn Val Asp Arg Leu Lys Leu Leu
        275                 280                 285

```
Cys Glu Ser Lys Leu Cys Glu Leu Asn Ala Glu Thr Val Ala Thr
        290                 295                 300

Thr Leu Ala Leu Ala Glu Gln His Gln Cys Pro Gln Leu Lys Ala Ile
305                 310                 315                 320

Cys Leu Lys Phe Ala Ala Thr Pro Ala Asn Leu Gly Val Ile Met Gln
            325                 330                 335

Ser Glu Gly Phe Lys His Leu Glu Glu Ser Cys Pro Ser Leu Leu Ser
            340                 345                 350

Glu Leu Leu Lys Thr Leu Ala Ser Gly Asp Asp Thr Ser Ser Leu Ser
        355                 360                 365

Ser Asn Arg Lys Arg Ser Gly Ser Ile Tyr Ala Leu Asp Leu Ala
        370                 375                 380

Gly Asp Gly Ala Ala Glu Ser Ala Asn Pro Asn Gly Arg Arg Val
385                 390                 395                 400

Arg Arg Arg Phe

<210> SEQ ID NO 7
<211> LENGTH: 408
<212> TYPE: PRT
<213> ORGANISM: Ricinus communis

<400> SEQUENCE: 7

Met Val Glu Leu Lys Ser Asp Ser Asp Lys Glu Ser Cys Ser Met Ser
1               5                   10                  15

Ile Asn Glu Thr Val Asn Gly Ser His Gln Phe Ser Ile Lys Gly Tyr
            20                  25                  30

Ser Leu Ala Lys Gly Met Gly Ala Gly Lys Cys Ile Ala Ser Asp Ile
        35                  40                  45

Phe Thr Val Gly Gly Tyr Asp Trp Ala Ile Tyr Phe Tyr Pro Asp Gly
    50                  55                  60

Lys Asn Pro Glu Asp Ser Ser Met Tyr Val Ser Val Phe Val Ala Leu
65                  70                  75                  80

Ala Ser Glu Gly Thr Asp Val Arg Ala Leu Phe Glu Leu Thr Leu Val
                85                  90                  95

Asp Gln Ser Gly Asn Gly Lys His Lys Val His Ser His Phe Asp Arg
            100                 105                 110

Ala Leu Glu Ser Gly Pro Tyr Thr Leu Lys Tyr Arg Gly Ser Met Trp
        115                 120                 125

Gly Tyr Lys Arg Phe Phe Arg Arg Thr Thr Leu Glu Asn Ser Asp Tyr
    130                 135                 140

Ile Lys Asp Asp Cys Leu Ile Met Asn Cys Thr Val Gly Val Val Arg
145                 150                 155                 160

Thr Arg Leu Glu Gly Pro Lys Gln Tyr Ser Ile Ser Leu Pro Pro Ser
                165                 170                 175

Asp Met Gly Gln Gly Leu Lys Glu Leu Leu Glu Ser Glu Val Gly Cys
            180                 185                 190

Asp Ile Val Phe Gln Val Gly Asp Glu Thr Phe Lys Ala His Lys Leu
        195                 200                 205

Ile Leu Ala Ala Arg Ser Pro Val Phe Arg Ala Gln Phe Phe Gly Leu
    210                 215                 220

Val Gly Asp Pro Asn Leu Asp Lys Val Val Val Glu Asp Ile Asp Pro
225                 230                 235                 240

Ser Ile Phe Lys Ala Met Leu Leu Phe Ile Tyr Thr Asp Lys Leu Pro
                245                 250                 255
```

```
Asn Val His Glu Ile Thr Gly Thr Thr Ser Met Cys Thr Ser Thr Asn
            260                 265                 270

Met Val Gln His Leu Leu Ala Ala Ala Asp Leu Tyr Asn Leu Asp Gln
            275                 280                 285

Leu Lys Leu Leu Cys Glu Ser Lys Leu Cys Glu Glu Leu Ser Ala Glu
290             295                 300

Thr Val Ala Thr Leu Ala Leu Ala Glu Gln His Gln Cys Ser Gln
305             310                 315                 320

Leu Lys Val Val Cys Leu Lys Phe Ala Ala Asn Pro Ala Asn Leu Gly
                325                 330                 335

Ala Val Met Gln Ser Glu Gly Phe Arg His Leu Glu Glu Ser Cys Pro
            340                 345                 350

Ser Leu Leu Cys Glu Met Leu Lys Thr Phe Ala Ser Gly Asp Glu Asn
            355                 360                 365

Ser Ser Leu Leu Ser Ser Arg Lys Arg Ser Gly Ser Ser Ile Tyr Gly
            370                 375                 380

Leu Asp Ile Ala Ala Asp Gly Ala Ala Ala Glu Ser Ala Asn Pro Met
385                 390                 395                 400

Gly Arg Arg Val Arg Arg Phe
                405

<210> SEQ ID NO 8
<211> LENGTH: 419
<212> TYPE: PRT
<213> ORGANISM: Eucalyptus grandis

<400> SEQUENCE: 8

Met Gln Arg Lys Ala Met Cys Ala Pro Ile Gly Gly Gly Gly Gly Asp
1               5                   10                  15

Gly Gly Gly Glu Cys Gly Ser Thr Ser Ile Ser Arg Thr Val Asn Gly
            20                  25                  30

Ser His Thr Phe Thr Ile Ser Gly Tyr Ser Leu Ala Lys Gly Met Gly
            35                  40                  45

Ala Gly Lys Phe Ile Ala Ser Asp Val Phe Thr Val Gly Gly Tyr Asp
50                  55                  60

Trp Ala Ile Tyr Phe Tyr Pro Asp Gly Lys Asn Pro Glu Asp Ser Thr
65                  70                  75                  80

Thr Tyr Val Ser Val Phe Ile Ala Leu Ala Ser Asp Gly Ser Asp Val
                85                  90                  95

Arg Ala Leu Phe Glu Leu Thr Leu Val Asp Gln Ser Gly Lys Gly Lys
            100                 105                 110

His Lys Val His Ser His Phe Asp Arg Ala Leu Gln Ser Gly Pro Tyr
            115                 120                 125

Thr Leu Lys Tyr Arg Gly Ser Met Trp Gly Tyr Lys Arg Phe Leu Lys
            130                 135                 140

Arg Val Ala Leu Glu Thr Ser Asp Tyr Ile Lys Asp Cys Leu Val
145                 150                 155                 160

Met His Cys Thr Val Gly Val Val Arg Thr His Thr Glu Gly Pro Lys
                165                 170                 175

Gln Tyr Arg Ile Pro Ile Pro Pro Ser Asp Met Gly Gln Cys Leu Lys
            180                 185                 190

Ala Leu Leu Asp Ser Glu Val Gly Cys Asp Ile Ala Phe Val Val Gly
            195                 200                 205

Asp Glu Thr Phe Arg Ala His Lys Leu Ile Leu Ala Ala Arg Ser Pro
```

-continued

```
                210                 215                 220
Val Phe Arg Ala Gln Phe Phe Gly Leu Val Gly Asp Cys Asn Ile Glu
225                 230                 235                 240

Lys Val Val Glu Asp Val Asp Pro Ser Ile Phe Lys Ala Met Leu
            245                 250                 255

Leu Phe Ile Tyr Met Asp Glu Met Pro Asp Leu Arg Glu Ile Thr Gly
                260                 265                 270

Ser Ser Ser Gly Thr Leu Thr Asn Val Val Gln His Leu Leu Ala
            275                 280                 285

Ala Ala Asp Arg Tyr Asn Leu Glu Arg Leu Lys Leu Leu Cys Glu Ser
            290                 295                 300

Lys Leu Cys Glu Glu Ile Thr Ala Asp Thr Val Ala Thr Thr Leu Ala
305                 310                 315                 320

Leu Ala Glu Gln His Gln Phe Gly Gln Leu Lys Ala Met Cys Leu Lys
                325                 330                 335

Phe Ala Ala His Pro Thr Asn Leu Ala Val Val Met Gln Ser Glu Gly
                340                 345                 350

Phe Arg His Leu Glu Glu Ser Cys Pro Ser Leu Leu Ser Glu Leu Leu
            355                 360                 365

Lys Ala Phe Val Thr Val Asp Ser Ser Asp Arg Phe Ser Asn Lys
370                 375                 380

Lys Arg Gly Thr Ser Ser Ile Tyr Gly Leu Asp Thr Val Pro Val Val
385                 390                 395                 400

Thr Gly Ala Glu His Gly Asp Ile Asp Gly Arg Arg Val Lys Arg Arg
                405                 410                 415

Asn Leu Glu

<210> SEQ ID NO 9
<211> LENGTH: 406
<212> TYPE: PRT
<213> ORGANISM: Vitis vinifera

<400> SEQUENCE: 9

Met Val Asn Ser Lys Ala Asp Ile Glu Arg Asp Ser Cys Ser Lys Ser
1               5                   10                  15

Ile Asn Glu Thr Val Asn Gly Ser His His Phe Leu Ile Lys Gly Tyr
            20                  25                  30

Ser Leu Ala Lys Gly Met Gly Ala Gly Lys Tyr Ile Ser Ser Asp Thr
        35                  40                  45

Phe Thr Val Gly Gly Tyr Asp Trp Ala Ile Tyr Phe Tyr Pro Asp Gly
    50                  55                  60

Lys Asn Ala Glu Asp Asn Ser Met Tyr Val Ser Val Phe Ile Ala Leu
65              70                  75                  80

Ala Ser Glu Gly Thr Asp Val Arg Ala Leu Phe Glu Leu Thr Leu Leu
                85                  90                  95

Asp Gln Ser Gly Lys Gly Lys His Lys Val His Ser His Phe Asp Arg
            100                 105                 110

Ala Leu Glu Ser Gly Pro Tyr Thr Leu Lys Tyr Arg Gly Ser Met Trp
        115                 120                 125

Gly Tyr Lys Arg Phe Phe Arg Arg Thr Thr Leu Glu Thr Ser Asp Phe
    130                 135                 140

Ile Lys Asp Asp Cys Leu Ala Met His Cys Thr Val Gly Val Val Arg
145                 150                 155                 160

Thr Arg Val Glu Gly Pro Lys Gln Tyr Thr Ile Pro Ile Pro Pro Ser
```

```
                        165                 170                 175
Asp Ile Gly Gln Ser Leu Lys Asp Leu Leu Glu Ser Glu Val Gly Cys
                180                 185                 190

Asp Ile Thr Phe Gln Val Ala Asp Glu Thr Phe Lys Ala His Lys Leu
                195                 200                 205

Ile Leu Ala Ala Arg Ser Pro Val Phe Arg Ala Gln Phe Phe Gly Leu
            210                 215                 220

Val Gly Asn Pro Asn Met Asp Lys Val Val Glu Asp Val Glu Pro
225                 230                 235                 240

Ser Ile Phe Lys Ala Met Leu Leu Phe Ile Tyr Ser Asp Lys Leu Pro
                245                 250                 255

Asp Val Asp Glu Ile Thr Gly Ser Ala Ser Val Cys Thr Ser Thr Ile
                260                 265                 270

Met Val Gln His Leu Leu Ala Ala Ala Asp Arg Phe Gly Leu Asp Arg
                275                 280                 285

Leu Lys Leu Leu Cys Glu Ser Lys Leu Cys Lys Glu Val Ser Ala Glu
            290                 295                 300

Thr Val Ala Thr Thr Leu Ala Leu Ala Glu Gln His Arg Cys Pro Gln
305                 310                 315                 320

Leu Lys Ala Ile Cys Leu Lys Phe Ala Thr Pro Ser Ile Leu Gly
                325                 330                 335

Ala Val Met Gln Ser Glu Gly Phe Gly Tyr Leu Glu Gly Cys Cys Pro
                340                 345                 350

Ser Leu Leu Ser Glu Leu Leu Gly Val Ile Ala Ser Val Asp Glu Asn
            355                 360                 365

Leu Thr Met Leu Ser Ser Lys Lys Arg Ser Gly Ser Ser Ile Leu Gly
            370                 375                 380

Leu Asp Leu Pro Ala Asp Gly Ala Pro Ala Glu Ser Ala Ser Gly Arg
385                 390                 395                 400

Arg Ile Arg Arg Arg Phe
                405

<210> SEQ ID NO 10
<211> LENGTH: 425
<212> TYPE: PRT
<213> ORGANISM: Prunus persica

<400> SEQUENCE: 10

Met Pro Asn His Lys Ser Ser Arg Gly Ala Gln Leu Gly Glu Ala Met
1               5                   10                  15

Ser Asn Ser Lys Pro Gly Val Asp Gln Glu Ser Cys Ser Arg Ser Ile
                20                  25                  30

Ser Glu Thr Val Asn Gly Ser His Arg Phe Thr Ile Lys Gly Tyr Ser
            35                  40                  45

Leu Ala Lys Gly Met Gly Ala Gly Lys Tyr Ile Met Ser Asp Thr Phe
        50                  55                  60

Thr Val Gly Gly Tyr Asp Trp Ala Ile Tyr Phe Tyr Pro Asp Gly Lys
65                  70                  75                  80

Asn Pro Glu Asp Ser Ser Thr Tyr Val Ser Val Phe Ile Ala Leu Val
                85                  90                  95

Ser Glu Gly Thr Asp Val Arg Ala Leu Phe Glu Leu Thr Leu Val Asp
            100                 105                 110

Gln Thr Lys Ser Gly Lys Asp Lys Val His Ser His Phe Asp Arg Ala
        115                 120                 125
```

```
Leu Glu Ser Gly Pro Tyr Thr Leu Lys Tyr Arg Gly Ser Met Trp Gly
    130                 135                 140

Tyr Lys Arg Phe Phe Lys Arg Ser Ala Leu Glu Thr Ser Glu Phe Leu
145                 150                 155                 160

Arg Asp Asp Cys Leu Val Leu Asn Cys Thr Val Gly Val Val Arg Thr
                165                 170                 175

Arg Leu Glu Arg Pro Lys Gln Phe Ser Ile Thr Val Pro Ser Ser Asp
            180                 185                 190

Met Gly Gln Asp Leu Lys Asp Phe Leu Asp Ser Glu Ala Gly Cys Asp
        195                 200                 205

Ile Val Phe Gln Val Gly Asp Glu Leu Phe Lys Ala His Lys Leu Ile
    210                 215                 220

Leu Ala Ala Arg Ser Pro Val Phe Arg Ala Gln Phe Phe Gly Leu Val
225                 230                 235                 240

Gly Asp Cys Ser Ile Asp Lys Val Val Val Lys Asp Val Glu Pro Phe
                245                 250                 255

Ile Phe Lys Ala Met Leu Leu Phe Ile Tyr Thr Asp Lys Leu Pro Asp
            260                 265                 270

Val His Glu Val Met Gly Ser Ser Pro Leu Cys Thr Phe Thr Val Met
        275                 280                 285

Val Gln His Leu Leu Ala Ala Ala Asp Leu Tyr Asn Leu Glu Arg Leu
    290                 295                 300

Lys Val Leu Cys Glu Ser Lys Leu Cys Glu Glu Ile Thr Thr Glu Thr
305                 310                 315                 320

Val Ala Thr Thr Leu Ala Leu Ala Glu Gln His His Cys Pro Gln Leu
                325                 330                 335

Lys Ala Val Cys Leu Lys Phe Ala Ala Asn Pro Ala Asn Leu Gly Ala
            340                 345                 350

Val Met Gln Ser Asp Gly Tyr Lys His Leu Glu Glu Ser Cys Pro Ser
        355                 360                 365

Met Leu Leu Glu Leu Leu Glu Thr Phe Ala Ala Val Asp Glu Ser Ser
    370                 375                 380

Ser Leu Leu Ser Ser Arg Lys Arg Ser Gly Ser Ser Ile Tyr Gly Leu
385                 390                 395                 400

Asp Leu Pro Ala Asp Gly Gly Ala Val Ala Glu Ser Ala Asn Pro
                405                 410                 415

Asn Gly Arg Arg Val Arg Arg Tyr
            420                 425

<210> SEQ ID NO 11
<211> LENGTH: 414
<212> TYPE: PRT
<213> ORGANISM: Phaseolus vulgaris

<400> SEQUENCE: 11

Met Ala Glu Leu Glu Glu Asp Arg Met Gly Asp Phe Lys Pro Phe Ser
1               5                   10                  15

Glu Gly Ser Ser Cys Ser Arg Ser Ile Ser Glu Thr Val Asn Gly Ser
                20                  25                  30

His Gln Phe Thr Ile Lys Gly Tyr Ser Leu Ala Lys Gly Met Gly Ala
            35                  40                  45

Gly Lys Tyr Ile Met Ser Asp Ser Phe Ser Val Gly Gly Tyr Asp Trp
        50                  55                  60

Ala Ile Tyr Phe Tyr Pro Asp Gly Lys Asn Pro Glu Asp Asn Ser Met
65                  70                  75                  80
```

```
Tyr Val Ser Val Phe Ile Ala Leu Ala Ser Asp Gly Thr Asp Val Arg
                85                  90                  95

Ala Leu Phe Lys Leu Thr Leu Val Asp Gln Ser Glu Lys Gly Asn Asp
                100                 105                 110

Lys Val His Ser His Phe Asp Arg Pro Leu Asp Gly Pro Tyr Thr
                115                 120                 125

Leu Lys Tyr Arg Gly Ser Met Trp Gly Tyr Lys Arg Phe Phe Arg Arg
130                 135                 140

Asn Leu Leu Glu Ser Ser Glu Tyr Leu Lys Asp Asp Cys Leu Val Met
145                 150                 155                 160

His Cys Thr Val Gly Val Val Lys Thr Arg Phe Glu Gly Ser Lys Gln
                165                 170                 175

Gly Val Thr Val Pro Gln Ser Asp Met Gly Arg Asn Phe Lys Asp Leu
                180                 185                 190

Leu Asp Ser Glu Val Gly Cys Asp Ile Val Phe Lys Val Lys Ser Glu
                195                 200                 205

Ser Phe Lys Ala His Lys Leu Ile Leu Ala Ala Arg Ser Pro Val Phe
                210                 215                 220

Arg Ala Gln Phe Phe Gly Leu Val Gly Asp Pro Ser Leu Glu Glu Val
225                 230                 235                 240

Val Val Glu Asp Ile Glu Pro Phe Ile Phe Lys Ala Met Leu Leu Phe
                245                 250                 255

Ile Tyr Ser Asp Lys Leu Pro Asp Ile Tyr Glu Val Met Asp Ser Met
                260                 265                 270

Asn Val Cys Ser Tyr Ala Val Met Val Gln His Leu Leu Ala Ala Ala
                275                 280                 285

Asp Leu Tyr Asn Leu Asp Arg Leu Lys Leu Leu Cys Glu Ser Lys Leu
290                 295                 300

Cys Glu Glu Ile Asn Thr Asp Asn Val Ala Thr Thr Leu Ala Leu Ala
305                 310                 315                 320

Glu Gln His Asn Cys Pro Gln Leu Lys Ala Ile Cys Leu Lys Phe Ile
                325                 330                 335

Ala Asn Pro Ala Asn Leu Gly Ala Val Met Gln Ser Glu Ala Phe Val
                340                 345                 350

His Leu Lys Glu Ser Cys Pro Ala Met Leu Leu Glu Leu Leu Glu Thr
                355                 360                 365

Phe Ala Ser Val Asp Asp Asn Ser Ser Leu Thr Leu Ser Arg Lys Arg
370                 375                 380

Ser Gly Ser Ser Ile Tyr Ala Gln Asp Leu Ala Asp Gly Ala Ala Thr
385                 390                 395                 400

Glu Ser Val Asn Pro Asn Gly Arg Arg Val Arg Arg Thr
                405                 410

<210> SEQ ID NO 12
<211> LENGTH: 414
<212> TYPE: PRT
<213> ORGANISM: Glycine max

<400> SEQUENCE: 12

Met Ala Glu Leu Glu Glu Arg Met Gly Asp Phe Lys Pro Phe Ser
1               5                   10                  15

Glu Gly Ser Ser Cys Ser Arg Ser Ile Ser Glu Thr Val Asn Gly Ser
                20                  25                  30

His Gln Phe Thr Ile Lys Gly Tyr Ser Leu Ala Lys Gly Met Gly Ala
```

```
                35                  40                  45
Gly Lys Tyr Ile Met Ser Asp Thr Phe Thr Val Gly Gly Tyr Asp Trp
 50                  55                  60

Ala Ile Tyr Phe Tyr Pro Asp Gly Lys Asn Pro Glu Asp Asn Ser Met
 65                  70                  75                  80

Tyr Val Ser Val Phe Ile Ala Leu Ala Ser Asp Gly Thr Asp Val Arg
                 85                  90                  95

Ala Leu Phe Lys Leu Thr Leu Val Asp Gln Ser Glu Lys Gly Asn Asp
                100                 105                 110

Lys Val His Ser His Phe Asp Arg Pro Leu Glu Ser Gly Pro Tyr Thr
            115                 120                 125

Leu Lys Tyr Lys Gly Ser Met Trp Gly Tyr Lys Arg Phe Phe Arg Arg
130                 135                 140

Thr Gln Leu Glu Thr Ser Glu Tyr Leu Lys Asn Asp Cys Leu Val Met
145                 150                 155                 160

His Cys Thr Val Gly Val Val Lys Thr Arg Phe Glu Gly Ser Lys Gln
                165                 170                 175

Gly Val Ile Val Pro Gln Ser Asp Met Gly Arg Asp Phe Lys Asp Leu
                180                 185                 190

Leu Glu Ser Glu Val Gly Cys Asp Ile Leu Phe Lys Val Lys Ser Glu
            195                 200                 205

Ser Phe Lys Ala His Lys Leu Ile Leu Ala Ala Arg Ser Pro Val Phe
210                 215                 220

Arg Ala Gln Phe Phe Gly Leu Val Gly Asp Pro Thr Leu Glu Glu Val
225                 230                 235                 240

Val Val Glu Asp Ile Glu Pro Phe Ile Phe Lys Ala Met Leu Leu Phe
                245                 250                 255

Val Tyr Ser Asp Lys Leu Pro Gly Ile Tyr Glu Val Met Asp Ser Met
                260                 265                 270

Pro Leu Cys Ser Tyr Thr Val Met Val Gln His Leu Leu Ala Ala Ala
            275                 280                 285

Asp Leu Tyr Asn Leu Asp Arg Leu Lys Leu Leu Cys Glu Ser Lys Leu
290                 295                 300

Cys Glu Glu Ile Asn Thr Asp Asn Val Ala Thr Thr Leu Ala Leu Ala
305                 310                 315                 320

Glu Gln His His Cys Pro Gln Leu Lys Ala Ile Cys Leu Lys Tyr Ile
                325                 330                 335

Ala Asn Pro Ala Asn Leu Gly Ala Val Met Gln Ser Glu Ala Phe Val
                340                 345                 350

His Leu Lys Glu Ser Cys Pro Ser Met Leu Leu Glu Leu Leu Glu Thr
            355                 360                 365

Phe Ala Ser Val Asp Asp Asn Ser Gly Gln Thr Leu Ser Arg Lys Arg
370                 375                 380

Ser Gly Ser Ser Ile Tyr Gly Gln Asp Leu Ala Asp Gly Ala Ala Ala
385                 390                 395                 400

Glu Ser Val Asn Pro Asn Gly Arg Arg Val Arg Arg Thr
                405                 410

<210> SEQ ID NO 13
<211> LENGTH: 411
<212> TYPE: PRT
<213> ORGANISM: Phoenix dactylifera

<400> SEQUENCE: 13
```

```
Met Ala Lys Leu Glu Glu Gln Gly Gly Leu Asn Asn Arg Gln Leu
1               5                   10                  15

Asn Pro Leu Asn Val Ser Arg Ser Arg Ser Val Cys Glu Thr Val Asn
            20                  25                  30

Gly Ser His Arg Tyr Thr Val Lys Gly Phe Ser Leu Ala Lys Gly Met
        35                  40                  45

Gly Pro Gly Arg Tyr Leu Ser Ser Asp Thr Phe Thr Val Gly Gly Phe
    50                  55                  60

Gln Trp Ala Val Tyr Phe Tyr Pro Asp Gly Lys Asn Pro Glu Asp Asn
65                  70                  75                  80

Ser Leu Tyr Val Ser Val Phe Ile Ala Leu Ala Ser Glu Gly Thr Asp
                85                  90                  95

Val Arg Ala Leu Phe Glu Leu Thr Leu Leu Asp Gln Asn Gly Lys Gly
            100                 105                 110

Arg His Lys Val His Ser His Phe Asp Arg Ala Leu Glu Ala Gly Pro
            115                 120                 125

Tyr Thr Leu Lys Tyr Arg Gly Ser Met Trp Gly Tyr Lys Arg Phe Tyr
        130                 135                 140

Arg Arg Thr Ser Leu Glu Thr Ser Asp Tyr Leu Lys Asp Asp Cys Leu
145                 150                 155                 160

Ile Met Asn Cys Thr Val Gly Val Val Arg Asn His Ile Glu Thr Pro
                165                 170                 175

Thr Gln Leu Ser Ile Ser Val Pro Pro Asp Leu Gly Gln Cys Leu
            180                 185                 190

Lys Glu Leu Phe Ile Ser Gly Ile Gly Ser Asp Ile Asp Phe Glu Val
            195                 200                 205

Gly Asp Glu Thr Phe Lys Ala His Lys Gln Ile Leu Ala Ala Arg Ser
    210                 215                 220

Pro Val Phe Ser Ala Gln Phe Phe Gly Leu Ile Gly Asn Pro Asn Val
225                 230                 235                 240

Asp Lys Ile Val Val Glu Asp Val Glu Pro Pro Ile Phe Lys Ala Met
                245                 250                 255

Leu Leu Phe Ile Tyr Ser Asp Glu Leu Pro Asp Val His Asp Leu Thr
            260                 265                 270

Gly Ser Val Ser Met Cys Thr Ser Thr Ile Met Val Gln His Leu Leu
    275                 280                 285

Ala Ala Ala Asp Arg Tyr Gly Leu Glu Arg Leu Lys Leu Leu Cys Glu
    290                 295                 300

Ala Lys Leu Cys Glu Glu Val Thr Ala Asp Thr Val Ala Thr Thr Leu
305                 310                 315                 320

Ala Leu Ala Glu Gln His Gln Cys Ala Gln Leu Lys Ala Val Cys Leu
            325                 330                 335

Lys Phe Thr Ala Ala Arg Glu Asn Leu Gly Ala Val Met Gln Thr Glu
            340                 345                 350

Gly Phe Asn Tyr Leu Glu Ala Thr Cys Pro Ser Leu Leu Ser Asp Leu
        355                 360                 365

Leu Ala Thr Val Ala Val Ala Asp Asp Ser Ser Pro Ile Ser Arg
    370                 375                 380

Lys Arg Ser Gly Ser Ser Asn Ile Gly Leu Asn Leu Met Asp Ser Val
385                 390                 395                 400

Asp Leu Asn Gly Arg Arg Met Lys Arg Met
            405                 410
```

```
<210> SEQ ID NO 14
<211> LENGTH: 429
<212> TYPE: PRT
<213> ORGANISM: Fragaria vesca

<400> SEQUENCE: 14

Met Pro Pro Ile Gln Lys His Ser Leu Arg Gly Ala Gln Leu Gly Gly
1               5                   10                  15

Arg Ile Ser Ser Met Lys Ser Lys Leu Glu Asn Asp Glu Ser Cys Ser
            20                  25                  30

Arg Ser Ile Ser Glu Thr Val Asn Gly Ser His Arg Phe Thr Ile Lys
        35                  40                  45

Gly Tyr Ser Leu Ala Lys Gly Met Gly Ala Gly Lys Tyr Ile Leu Ser
    50                  55                  60

Asp Thr Phe Thr Val Gly Gly Tyr Asp Trp Ala Ile Tyr Phe Tyr Pro
65                  70                  75                  80

Asp Gly Lys Asn Pro Glu Asp Ser Ser Val Tyr Val Ser Val Phe Ile
                85                  90                  95

Ala Leu Val Ser Glu Gly Thr Asp Val Arg Ala Leu Phe Glu Leu Thr
            100                 105                 110

Leu Val Asp Gln Ser Asn Ser Gly Lys Asp Lys Val His Ser His Phe
        115                 120                 125

Asp Arg Ala Leu Glu Ser Gly Pro Tyr Thr Leu Lys Tyr Arg Gly Ser
130                 135                 140

Met Trp Gly Tyr Lys Arg Phe Phe Arg Arg Ser Ala Leu Glu Thr Ser
145                 150                 155                 160

Glu Phe Leu Lys Asp Asp Ser Leu Val Leu Asn Cys Thr Val Gly Val
                165                 170                 175

Val Arg Thr Arg Leu Glu Cys Pro Lys His Phe Ala Ile Thr Val Pro
            180                 185                 190

Pro Ser Asp Met Gly Glu Gly Leu Lys Ala Phe Leu Asp Ser Gly Ala
        195                 200                 205

Gly Cys Asp Leu Val Phe Gln Val Gly Asp Glu Glu Phe Lys Ala His
210                 215                 220

Lys Leu Ile Leu Ala Ala Arg Ser Pro Val Phe Lys Ala Gln Phe Phe
225                 230                 235                 240

Gly His Leu Gly Asp Ser Ser Val Asp Lys Val Val Lys Asp Val
                245                 250                 255

Glu Pro Phe Ile Phe Lys Ala Met Leu Leu Phe Ile Tyr Gly Asp Lys
            260                 265                 270

Leu Pro Asp Ile Arg Glu Val Thr Gly Ser Ser Ser Leu Cys Thr Phe
        275                 280                 285

Thr Val Met Val Gln His Leu Leu Ala Ala Ala Asp Leu Tyr Asp Leu
290                 295                 300

Glu Arg Leu Lys Leu Leu Cys Glu Ser Met Leu Cys Glu Glu Ile Thr
305                 310                 315                 320

Thr Glu Thr Val Ala Thr Thr Leu Ala Leu Ala Glu Gln His His Cys
                325                 330                 335

Pro Gln Leu Lys Ala Val Cys Leu Lys Phe Ala Ala Lys Ser Thr Asn
            340                 345                 350

Leu Gly Ala Val Met Gln Ser Asp Gly Tyr Lys His Leu Glu Glu Ser
        355                 360                 365

Cys Pro Ser Val Leu Gln Glu Leu Leu Lys Thr Phe Ala Ser Val Asp
370                 375                 380
```

```
Ala Asn Glu Asn Ser Asn Ser Ser Lys Lys Arg Ser Gly Ser Ser Ile
385                 390                 395                 400

Tyr Gly Leu Asp Leu Pro Ala Asp Gly Ser Gly Ala Val Ala Glu Ser
            405                 410                 415

Ala Asn Pro Asn Gly Arg Arg Leu Arg Pro Arg Arg Tyr
            420                 425

<210> SEQ ID NO 15
<211> LENGTH: 426
<212> TYPE: PRT
<213> ORGANISM: Malus domestica

<400> SEQUENCE: 15

Met Pro Pro Ile Arg Lys His Ser Arg Gly Ala Lys Ser Gly Glu Ser
1               5                   10                  15

Met Gly Asn Ser Lys Pro Gly Phe Asp Gln Glu Ser Cys Ser Arg Ser
            20                  25                  30

Ile Ser Glu Thr Val Asn Gly Ser His Arg Phe Thr Ile Lys Gly Tyr
        35                  40                  45

Ser Leu Ala Lys Gly Met Gly Ala Gly Lys Tyr Leu Met Ser Asp Thr
    50                  55                  60

Phe Thr Val Gly Gly Tyr Asp Trp Ala Ile Tyr Phe Tyr Pro Asp Gly
65                  70                  75                  80

Lys Asn Pro Glu Asp Ser Asn Ala Tyr Val Ser Val Phe Ile Ala Leu
                85                  90                  95

Val Ser Glu Gly Thr Asp Val Arg Ala Leu Phe Glu Leu Thr Leu Val
            100                 105                 110

Asp Gln Thr Asp Ser Gly Lys Asp Lys Val His Ser His Phe Asp Arg
        115                 120                 125

Ala Leu Glu Gly Gly Pro Tyr Thr Leu Lys Tyr Arg Gly Ser Met Trp
    130                 135                 140

Gly Tyr Lys Lys Phe Phe Arg Arg Ser Ile Leu Glu Thr Ser Glu Phe
145                 150                 155                 160

Leu Lys Asp Asp Cys Leu Val Leu Asn Cys Thr Val Gly Val Val Arg
                165                 170                 175

Thr Arg Leu Glu Gln Pro Lys Gln Phe Thr Ile Thr Val Pro Ser Ser
            180                 185                 190

Asp Met Gly Arg Asp Leu Lys Asp Phe Leu Asp Ser Glu Ala Gly Cys
        195                 200                 205

Asp Ile Val Phe Gln Val Gly Asp Glu Gln Phe Lys Ala His Lys Leu
    210                 215                 220

Ile Leu Ala Ala Arg Ser Arg Val Phe Arg Ala Gln Phe Tyr Gly Leu
225                 230                 235                 240

Val Gly Asp Cys Asn Val Asp Lys Val Val Lys Asp Val Glu Pro
                245                 250                 255

Phe Ile Phe Lys Ala Met Leu Leu Phe Ile Tyr Thr Asp Lys Leu Pro
            260                 265                 270

Asp Thr His Glu Val Met Gly Ser Ser Pro Leu Cys Thr Phe Thr Val
        275                 280                 285

Met Val Gln His Leu Leu Ala Ala Ala Asp Leu Tyr Asn Leu Asp Arg
    290                 295                 300

Leu Lys Leu Leu Cys Glu Ser Lys Leu Cys Glu Glu Ile Thr Thr Glu
305                 310                 315                 320

Thr Val Ala Thr Thr Leu Ala Leu Ala Glu Gln His Gln Cys Arg Gln
                325                 330                 335
```

Leu Lys Asp Val Cys Leu Lys Phe Thr Ala Asn Pro Ser Asn Leu Gly
            340                 345                 350

Ala Val Met Gln Ser Glu Gly Tyr Lys His Leu Glu Glu Ser Cys Pro
            355                 360                 365

Ser Met Leu Val Glu Leu Leu Glu Thr Phe Ala Ala Val Asp Asp Asn
370                 375                 380

Ser Ser Leu Leu Ser Ser Arg Lys Arg Ser Gly Ser Ser Ile Tyr Gly
385                 390                 395                 400

Leu Asp Leu Pro Ala Asp Gly Gly Thr Ala Ala Glu Ser Ala Asn
            405                 410                 415

Pro Asn Gly Arg Arg Val Arg Arg Phe
            420                 425

<210> SEQ ID NO 16
<211> LENGTH: 408
<212> TYPE: PRT
<213> ORGANISM: Solanum lycopersicum

<400> SEQUENCE: 16

Met Asn Gln Ile Ser Val Asp Arg Ala Gly Lys Asp Ser Ser Ser Lys
1               5                   10                  15

Ser Val Asn Glu Thr Val Asn Gly Ser His His Phe Thr Ile Arg Gly
            20                  25                  30

Tyr Ser Leu Ala Lys Gly Met Gly Pro Gly Lys Tyr Ile Ser Ser Asp
            35                  40                  45

Ile Phe Thr Val Gly Gly Tyr Asp Trp Ala Ile Tyr Phe Tyr Pro Asp
50                  55                  60

Gly Lys Asn Ile Glu Asp Ser Ser Met Tyr Val Ser Val Phe Ile Ala
65                  70                  75                  80

Leu Ala Ser Glu Gly Thr Asp Val Arg Ala Leu Phe Glu Leu Thr Met
            85                  90                  95

Leu Asp Gln Ser Gly Lys Val Lys His Lys Val His Ser His Phe Asp
            100                 105                 110

Arg Ala Leu Glu Ser Gly Pro Tyr Thr Leu Lys Tyr Arg Gly Ser Met
            115                 120                 125

Trp Gly Tyr Lys Arg Phe Phe Arg Arg Ala Ser Leu Glu Thr Ser Asp
            130                 135                 140

Tyr Leu Lys Asp Asp Cys Leu Ser Met His Cys Thr Val Gly Val Val
145                 150                 155                 160

Arg Thr Arg Val Glu Gly Pro Lys Asn Tyr Ser Val Thr Ile Pro Pro
            165                 170                 175

Ser Asp Met Gly Gln Ser Leu Lys Tyr Leu Leu Asp Ala Glu Leu Gly
            180                 185                 190

Cys Asp Ile Val Phe Arg Val Gly Glu Glu Ala Phe Lys Gly His Lys
            195                 200                 205

Leu Ile Leu Ala Ala Arg Ser Pro Val Phe Arg Ala Gln Phe Phe Gly
            210                 215                 220

Leu Ile Gly Asn Pro Lys Thr Asp Glu Val Glu Ile Glu Asp Ile Glu
225                 230                 235                 240

Pro Ser Val Phe Lys Ala Met Leu Gln Tyr Ile Tyr Ser Asp Glu Leu
            245                 250                 255

Pro Asp Leu Ile Glu Ile Thr Gly Ser Thr Ser Thr Cys Thr Ser Thr
            260                 265                 270

Ile Val Thr Gln His Leu Leu Ala Ala Ala Asp Arg Phe Gly Val Asp

```
              275                 280                 285
Arg Leu Lys Glu Leu Cys Glu Ala Lys Leu Cys Glu Val Asn Val
    290                 295                 300

Asp Thr Val Ala Thr Thr Leu Ser Leu Ala Glu Gln His Arg Cys Pro
305                 310                 315                 320

Gln Leu Lys Ala Ile Cys Leu Lys Phe Ala Ala Thr Asn Leu Gly Val
                    325                 330                 335

Val Met Gln Lys Asp Gly Phe Lys His Leu Glu Glu Ser Cys Pro Leu
                340                 345                 350

Leu Leu Ser Glu Leu Leu Glu Thr Val Ala Ser Val Asp Glu Lys Pro
            355                 360                 365

Ser Leu Thr Ser Ser Lys Lys Arg Asn Ser Ser Ser Ile Phe Gly
    370                 375                 380

Leu Asp Leu Ala Ala Asp Gly Ala Ala Asp Ser Val Asn Leu Thr
385                 390                 395                 400

Ala Arg Arg Val Arg Arg Met
                405

<210> SEQ ID NO 17
<211> LENGTH: 408
<212> TYPE: PRT
<213> ORGANISM: Solanum tuberosum

<400> SEQUENCE: 17

Met Asn Gln Ile Ser Ile Asp Arg Ala Gly Asn Asp Ser Ser Ser Lys
1               5                   10                  15

Ser Val Asn Glu Thr Val Asn Gly Ser His His Phe Thr Ile Arg Gly
            20                  25                  30

Tyr Ser Leu Ala Lys Gly Met Gly Pro Gly Lys Tyr Ile Ser Ser Asp
        35                  40                  45

Ile Phe Thr Val Gly Gly Tyr Asp Trp Ala Ile Tyr Phe Tyr Pro Asp
    50                  55                  60

Gly Lys Asn Ile Glu Asp Ser Ser Met Tyr Val Ser Val Phe Ile Ala
65                  70                  75                  80

Leu Ala Ser Glu Gly Thr Asp Val Arg Ala Leu Phe Glu Leu Thr Met
                85                  90                  95

Leu Asp Gln Ser Gly Lys Val Lys His Lys Val His Ser His Phe Asp
            100                 105                 110

Arg Ala Leu Glu Ser Gly Pro Tyr Thr Leu Lys Tyr Arg Gly Ser Met
        115                 120                 125

Trp Gly Tyr Lys Arg Phe Phe Arg Arg Ala Ser Leu Glu Met Ser Asp
    130                 135                 140

Tyr Leu Lys Asp Asp Cys Leu Ser Met His Cys Thr Val Gly Val Val
145                 150                 155                 160

Arg Thr Arg Val Glu Gly Pro Lys Asp Tyr Ser Val Thr Ile Pro Pro
                165                 170                 175

Ser Asp Met Gly Gln Ser Leu Lys Tyr Leu Leu Asp Ala Glu Leu Gly
            180                 185                 190

Cys Asp Ile Val Phe Arg Val Gly Glu Glu Ala Phe Lys Gly His Lys
        195                 200                 205

Leu Ile Leu Ala Ala Arg Ser Pro Val Phe Arg Ala Gln Phe Phe Gly
    210                 215                 220

Leu Ile Gly Asn Pro Lys Thr Asp Glu Val Glu Ile Glu Asp Ile Glu
225                 230                 235                 240
```

```
Pro Ser Val Phe Lys Ala Met Leu Gln Tyr Ile Tyr Ser Asp Glu Leu
                245                 250                 255

Pro Asp Leu Ile Glu Ile Thr Gly Ser Thr Ser Thr Cys Thr Ser Thr
            260                 265                 270

Ile Val Met Gln His Leu Leu Ala Ala Ala Asp Arg Phe Gly Leu Asp
        275                 280                 285

Arg Leu Lys Glu Leu Cys Glu Ala Lys Leu Cys Glu Glu Val Asn Val
    290                 295                 300

Asp Thr Val Ala Thr Thr Leu Ser Leu Ala Glu Gln His Arg Cys Pro
305                 310                 315                 320

Gln Leu Lys Ala Ile Cys Leu Lys Phe Ala Ala Thr Asn Leu Gly Val
                325                 330                 335

Val Met Gln Lys Asp Gly Phe Lys His Leu Glu Glu Ser Cys Pro Leu
            340                 345                 350

Leu Leu Ser Glu Leu Leu Glu Thr Val Ala Ser Val Asp Glu Lys Pro
        355                 360                 365

Ser Leu Thr Ser Ser Lys Lys Arg Ser Ser Ser Ser Ile Phe Gly
    370                 375                 380

Leu Asp Leu Ala Ala Asp Gly Ala Ala Ala Asp Ser Val Asn Leu Thr
385                 390                 395                 400

Val Arg Arg Val Arg Arg Met
                405

<210> SEQ ID NO 18
<211> LENGTH: 400
<212> TYPE: PRT
<213> ORGANISM: Oryza brachyantha

<400> SEQUENCE: 18

Met Thr Val Pro Pro Thr Pro Pro Ser Trp Ser Arg Ser Val
1               5                   10                  15

Thr Glu Thr Val Arg Gly Ser His Gln Tyr Thr Val Lys Gly Phe Ser
            20                  25                  30

Met Ala Lys Gly Met Gly Pro Gly Arg Tyr Val Thr Ser Asp Thr Phe
        35                  40                  45

Ala Val Gly Gly Tyr His Trp Ala Val Tyr Leu Tyr Pro Asp Gly Lys
    50                  55                  60

Asn Pro Glu Asp Asn Ala Asn Tyr Val Ser Val Phe Val Ala Leu Ala
65                  70                  75                  80

Ser Asp Gly Ala Asp Val Arg Ala Leu Phe Glu Leu Thr Leu Leu Asp
                85                  90                  95

Gln Ser Gly Arg Gly Arg His Lys Val His Ser His Phe Asp Arg Ser
            100                 105                 110

Leu Gln Ala Gly Pro Tyr Thr Leu Lys Tyr Arg Gly Ser Met Trp Gly
        115                 120                 125

Tyr Lys Arg Phe Tyr Arg Arg Ser Leu Leu Glu Ser Ser Asp Phe Leu
    130                 135                 140

Lys Asp Asp Cys Leu Val Met Asn Cys Thr Val Gly Val Val Lys Asn
145                 150                 155                 160

Arg Leu Glu Thr Pro Lys Asn Ile Gln Ile His Ile Pro Pro Ser Asp
                165                 170                 175

Met Gly Arg Cys Phe Lys Asn Leu Leu Asn Leu Gly Ile Gly Cys Asp
            180                 185                 190

Ile Thr Phe Glu Val Gly Asp Asp Thr Val Gln Ala His Lys Trp Ile
        195                 200                 205
```

```
Leu Ala Ala Arg Ser Pro Val Phe Lys Ala Gln Phe Phe Gly Pro Ile
    210                 215                 220

Gly Asn Pro Asp Leu His Ser Val Thr Val Glu Asp Val Glu Pro Val
225                 230                 235                 240

Val Phe Lys Ala Met Val Asn Phe Ile Tyr Ser Asp Glu Leu Pro Ser
                245                 250                 255

Ile His Glu Leu Ala Gly Ser Val Ser Thr Trp Thr Ser Thr Val Val
            260                 265                 270

Val Gln His Leu Leu Ala Ala Asp Arg Tyr Gly Leu Asp Arg Leu
        275                 280                 285

Arg Leu Leu Cys Glu Glu Lys Leu Cys Asp Glu Leu Thr Ala Glu Thr
    290                 295                 300

Val Ala Thr Thr Leu Ala Leu Ala Glu Gln His His Cys Thr Gln Leu
305                 310                 315                 320

Lys Ser Ala Cys Leu Lys Phe Thr Ala Val Arg Glu Asn Leu Gly Ala
                325                 330                 335

Val Met Glu Thr Glu Gly Phe Asn Tyr Leu Glu Glu Thr Cys Pro Ser
            340                 345                 350

Leu Leu Ser Asp Leu Leu Ala Thr Val Ala Val Asp Asp Ser
        355                 360                 365

Ala Thr Leu Asn Arg Lys Arg Gly Val Ser Gly Asn Glu Gly Ala Asn
370                 375                 380

Pro Val Glu Ser Val Glu Ala Ser Glu Arg Arg Ile Arg Arg Val
385                 390                 395                 400

<210> SEQ ID NO 19
<211> LENGTH: 397
<212> TYPE: PRT
<213> ORGANISM: Brachypodium distachyon

<400> SEQUENCE: 19

Met Ala Ala Val Pro Arg Pro Ser Trp Ser Arg Ser Val Ser Glu Thr
1               5                   10                  15

Val Arg Gly Ser His Gln Tyr Thr Val Lys Gly Phe Ser Leu Ala Lys
            20                  25                  30

Gly Ile Gly Pro Gly Arg His Leu Ala Ser Asp Thr Phe Ala Val Gly
        35                  40                  45

Gly Tyr Asp Trp Ala Val Tyr Leu Tyr Pro Asp Gly Lys Asn Pro Glu
    50                  55                  60

Asp Asn Ala Ser Tyr Val Ser Val Phe Val Ala Leu Ala Ser Glu Gly
65                  70                  75                  80

Thr Asp Val Arg Ala Leu Phe Glu Leu Thr Leu Leu Asp Gln Ser Gly
                85                  90                  95

Arg Ala Arg His Lys Val His Ser His Phe Asp Arg Ser Met Gln Ala
            100                 105                 110

Gly Pro Tyr Thr Leu Lys Tyr Arg Gly Ser Met Trp Gly Tyr Lys Arg
        115                 120                 125

Phe Tyr Arg Arg Ser Gln Leu Glu Thr Ser Asp Phe Leu Lys Asn Asp
    130                 135                 140

Cys Leu Val Met Asn Cys Thr Val Gly Val Lys Thr Arg Leu Glu
145                 150                 155                 160

Thr Pro Lys Asn Ile Gln Ile Asn Val Pro Ser Asp Ile Gly Arg
                165                 170                 175

Cys Phe Lys Glu Leu Leu Arg Leu Arg Ile Gly Cys Asp Ile Thr Phe
```

```
            180                 185                 190
Glu Val Gly Asp Glu Lys Val Gln Ala His Lys Trp Ile Leu Ala Ala
            195                 200                 205

Arg Ser Pro Val Phe Lys Ala Gln Phe Phe Gly Pro Ile Gly Lys Ala
            210                 215                 220

Asp Leu Asp Arg Val Val Glu Asp Val Glu Pro Ile Val Phe Lys
225                 230                 235                 240

Ala Met Val Asn Phe Ile Tyr Ser Asp Glu Leu Pro Ser Ile His Glu
                245                 250                 255

Leu Ala Gly Ser Phe Ser Met Trp Thr Ser Thr Ala Val Ile Gln His
            260                 265                 270

Leu Leu Ala Ala Ala Asp Arg Tyr Gly Leu Asp Arg Leu Arg Ile Leu
        275                 280                 285

Cys Glu Ala Gln Leu Cys Asp Gly Leu Thr Ala Glu Thr Val Ala Thr
    290                 295                 300

Thr Leu Ala Leu Ala Glu Gln His His Cys Ala Gln Leu Lys Ser Ala
305                 310                 315                 320

Cys Leu Lys Phe Thr Ala Val Arg Glu Asn Leu Gly Val Val Met Glu
                325                 330                 335

Thr Asp Gly Phe Asn Tyr Leu Glu Glu Thr Cys Pro Ser Leu Leu Ser
            340                 345                 350

Asp Leu Leu Ala Thr Val Ala Val Val Asp Asp Pro Thr Ser Val
        355                 360                 365

Asn Arg Lys Arg Gly Val Cys Ile Asn Glu Asp Val Asn Pro Val Glu
    370                 375                 380

Ser Val Glu Ala Ser Asp Arg Arg Ile Arg Arg Val
385                 390                 395

<210> SEQ ID NO 20
<211> LENGTH: 395
<212> TYPE: PRT
<213> ORGANISM: Oryza sativa

<400> SEQUENCE: 20

Met Thr Ala Ala Ala Ser Trp Ser Arg Ser Val Thr Glu Thr Val Arg
1               5                   10                  15

Gly Ser His Gln Tyr Thr Val Lys Gly Phe Ser Met Ala Lys Gly Val
            20                  25                  30

Gly Ala Gly Arg Tyr Val Ser Ser Asp Thr Phe Ala Val Gly Gly Tyr
        35                  40                  45

His Trp Ala Val Tyr Leu Tyr Pro Asp Gly Lys Asn Pro Glu Asp Asn
    50                  55                  60

Ala Asn Tyr Val Ser Val Phe Val Ala Leu Ala Ser Asp Gly Ala Asp
65                  70                  75                  80

Val Arg Ala Leu Phe Glu Leu Thr Leu Leu Asp Gln Ser Gly Arg Gly
                85                  90                  95

Arg His Lys Val His Ser His Phe Asp Arg Ser Leu Gln Ala Gly Pro
            100                 105                 110

Tyr Thr Leu Lys Tyr Arg Gly Ser Met Trp Gly Tyr Lys Arg Phe Tyr
        115                 120                 125

Arg Arg Ser Leu Leu Glu Ser Ser Asp Phe Leu Lys Asp Asp Cys Leu
    130                 135                 140

Val Met Asn Cys Thr Val Gly Val Val Lys Asn Arg Leu Glu Thr Pro
145                 150                 155                 160
```

```
Lys Asn Ile His Ile Asn Ile Pro Pro Ser Asp Met Gly Arg Cys Phe
                165                 170                 175

Asn Asn Leu Leu Asn Leu Arg Ile Gly Cys Asp Val Ser Phe Glu Val
            180                 185                 190

Gly Asp Glu Arg Val Gln Ala His Lys Trp Ile Leu Ala Ala Arg Ser
        195                 200                 205

Pro Val Phe Lys Ala Gln Phe Phe Gly Pro Ile Gly Asn Pro Asp Leu
    210                 215                 220

His Thr Val Ile Val Glu Asp Val Glu Pro Leu Val Phe Lys Ala Met
225                 230                 235                 240

Val Asn Phe Ile Tyr Ser Asp Glu Leu Pro Ser Ile His Glu Leu Ala
                245                 250                 255

Gly Ser Val Ser Thr Trp Thr Ser Thr Val Val Gln His Leu Leu
            260                 265                 270

Ala Ala Ala Asp Arg Tyr Gly Leu Asp Arg Leu Arg Leu Leu Cys Glu
        275                 280                 285

Glu Lys Leu Cys Asp Glu Leu Thr Ala Glu Thr Val Ala Thr Thr Leu
    290                 295                 300

Ala Leu Ala Glu Gln His His Cys Thr Gln Leu Lys Ser Ala Cys Leu
305                 310                 315                 320

Lys Phe Thr Ala Val Arg Glu Asn Leu Gly Ala Val Met Glu Thr Glu
                325                 330                 335

Gly Phe Asn Tyr Leu Glu Glu Thr Cys Pro Ser Leu Leu Ser Asp Leu
            340                 345                 350

Leu Ala Thr Val Ala Val Val Asp Asp Ala Ala Ser Phe Asn Arg
        355                 360                 365

Lys Arg Gly Val Gly Gly Asn Glu Gly Ala Asn Pro Val Glu Ser Val
    370                 375                 380

Glu Ala Ser Asp Arg Arg Ile Arg Arg Val
385                 390                 395

<210> SEQ ID NO 21
<211> LENGTH: 396
<212> TYPE: PRT
<213> ORGANISM: Hordeum vulgare

<400> SEQUENCE: 21

Met Ala Val Pro Arg Pro Ser Trp Ser Arg Ser Val Thr Glu Thr Val
1               5                   10                  15

Arg Gly Ser His Gln Tyr Thr Val Lys Gly Phe Ser Leu Ala Lys Gly
            20                  25                  30

Ile Gly Pro Gly Arg His Leu Ser Ser Asp Thr Phe Ala Val Gly Gly
        35                  40                  45

Tyr Asp Trp Ala Val Tyr Tyr Pro Asp Gly Lys Asn Gln Glu Asp
    50                  55                  60

Asn Ala Asn Tyr Val Ser Val Phe Val Ala Leu Ala Ser Glu Gly Thr
65                  70                  75                  80

Asp Val Arg Ala Leu Phe Glu Leu Thr Leu Leu Asp Gln Ser Gly Arg
                85                  90                  95

Ala Arg His Lys Val His Ser Phe Asp Arg Ser Met Gln Ala Gly
            100                 105                 110

Pro Tyr Thr Leu Lys Tyr Arg Gly Ser Met Trp Gly Tyr Lys Arg Phe
        115                 120                 125

Tyr Arg Arg Thr Gln Leu Glu Ala Ser Asp Phe Leu Lys Asp Asp Cys
    130                 135                 140
```

Leu Val Met Asn Cys Thr Val Gly Val Val Lys Asn Arg Leu Glu Thr
145                 150                 155                 160

Pro Lys Asn Ile Gln Ile Asn Val Pro Pro Ser Asp Ile Gly Arg Tyr
                165                 170                 175

Phe Lys Glu Leu Leu Lys Leu His Ile Gly Cys Asp Ile Thr Phe Glu
            180                 185                 190

Val Gly Asp Glu Lys Val Gln Ala His Lys Trp Ile Leu Ala Ala Arg
        195                 200                 205

Ser Pro Val Phe Lys Ala Gln Phe Phe Gly Pro Ile Gly Lys Pro Asp
    210                 215                 220

Leu Asp Arg Val Val Glu Asp Val Glu Pro Ile Val Phe Lys Ala
225                 230                 235                 240

Met Val Asn Phe Ile Tyr Ser Asp Glu Leu Pro Ser Ile His Glu Val
                245                 250                 255

Ala Gly Ser Phe Ser Met Trp Thr Ser Thr Ala Val Thr Gln His Leu
            260                 265                 270

Leu Ala Ala Ala Asp Arg Tyr Gly Leu Asp Arg Leu Arg Ile Leu Cys
        275                 280                 285

Glu Ala Lys Leu Cys Asp Glu Leu Thr Ser Glu Thr Val Ala Thr Thr
290                 295                 300

Leu Ala Leu Ala Glu Gln His His Cys Ala Gln Leu Lys Ser Ala Cys
305                 310                 315                 320

Leu Lys Phe Thr Ala Val Arg Gln Asn Leu Gly Ala Val Met Glu Thr
                325                 330                 335

Glu Gly Phe Asn Tyr Leu Glu Glu Thr Cys Pro Ser Leu Leu Ser Asp
            340                 345                 350

Leu Leu Ala Thr Val Ala Val Val Asp Asp Pro Ala Ser Val Asn
        355                 360                 365

Arg Lys Arg Gly Val Cys Ile Asn Glu Asp Ala Asn Pro Val Glu Ser
    370                 375                 380

Val Glu Ala Ser Asp Arg Arg Thr Arg Arg Val
385                 390                 395

<210> SEQ ID NO 22
<211> LENGTH: 409
<212> TYPE: PRT
<213> ORGANISM: Selaginella moellendorffii

<400> SEQUENCE: 22

Met Ala Arg Thr Ser Val Val Leu Gln Asp Asp Ser Gly Gln Val Val
1               5                   10                  15

Gly Ser Pro Thr Ser Thr Ala Thr Pro Ser Arg Ser Arg Cys Ile Thr
                20                  25                  30

Glu Thr Val Asn Gly Ser His His Phe Thr Ile His Gly Tyr Ser Leu
            35                  40                  45

Ala Lys Gly Met Gly Val Gly Lys Tyr Ile Ala Ser Asp Thr Phe Thr
        50                  55                  60

Val Gly Gly Tyr Gln Trp Ala Ile Tyr Phe Tyr Pro Asp Gly Lys Asn
65                  70                  75                  80

Thr Glu Asp Asn Ser Leu Tyr Val Ser Val Phe Ile Ala Leu Ala Ser
                85                  90                  95

Glu Gly Thr Asp Val Arg Ala Leu Phe Glu Leu Thr Leu Leu Asp Gln
            100                 105                 110

Ser Gly Lys Asn Lys His Lys Ile His Ser His Phe Asp Arg Ser Leu

```
            115                 120                 125
Glu Ser Gly Pro Tyr Thr Leu Lys Tyr Arg Gly Ser Met Trp Gly Tyr
    130                 135                 140

Lys Arg Phe Phe Arg Arg Ala Val Leu Glu Thr Ser Asp Phe Leu Lys
145                 150                 155                 160

Asp Asp Ser Leu Ser Ile Thr Cys Thr Val Gly Val Val Ser Ser
                165                 170                 175

Met Gln Ala Leu Lys Gln His Ser Leu Leu Val Pro Glu Ser Asp Ile
                180                 185                 190

Gly Gln His Phe Leu Ser Leu Leu Glu Ser Gly Glu Gly Thr Asp Val
                195                 200                 205

Asn Phe Asn Val Lys Gly Glu Ala Phe Ser Ala His Lys Leu Leu Leu
    210                 215                 220

Ala Ala Arg Ser Pro Val Phe Lys Ala Gln Leu Phe Gly Pro Met Lys
225                 230                 235                 240

Asp Glu Asn Gly Asp Val Ile Glu Ile Asp Asp Met Glu Pro Val
                245                 250                 255

Phe Lys Ala Met Leu His Phe Ile Tyr Lys Asp Ser Leu Pro Asp Thr
                260                 265                 270

Asn Glu Met Thr Gly Ser Ser Gln Ser Thr Ala Thr Met Met Ala
                275                 280                 285

Gln His Leu Leu Ala Ala Ala Asp Arg Phe Cys Leu Asp Arg Leu Arg
    290                 295                 300

Leu Leu Cys Glu Ser Arg Leu Cys Glu Gln Ile Thr Val Asp Thr Val
305                 310                 315                 320

Ala Thr Thr Leu Ala Leu Ala Asp Gln His His Ala Ser Gln Leu Lys
                325                 330                 335

Asn Val Cys Leu Lys Phe Ala Ala Ser Asn Leu Ala Val Val Met Gln
                340                 345                 350

Ser Asp Gly Phe Glu Tyr Leu Arg Glu Ser Cys Pro Ser Leu Gln Ser
                355                 360                 365

Glu Leu Leu Lys Thr Val Ala Gly Val Glu Glu Ala Lys Ala Gly
    370                 375                 380

Thr Lys Asn Arg Thr Val Trp Thr His Val Ala Asp Gly Gly Asp Gly
385                 390                 395                 400

Leu Gly Arg Arg Val Arg Gln Lys Ile
                405

<210> SEQ ID NO 23
<211> LENGTH: 410
<212> TYPE: PRT
<213> ORGANISM: Medicago truncatula

<400> SEQUENCE: 23

Met Gly Lys Ile Leu Arg Glu Thr Ala Lys Pro Ser Ser Asn Pro Ser
1               5                   10                  15

Ser Pro Ser Ser Ser Glu Pro Ala Thr Thr Ser Ser Thr Ser Ile
                20                  25                  30

Thr Glu Thr Val Lys Gly Ser His Gln Phe Lys Ile Thr Gly Tyr Ser
                35                  40                  45

Leu Ser Lys Gly Ile Gly Ile Gly Lys Tyr Ile Ala Ser Asp Ile Phe
    50                  55                  60

Ser Val Gly Gly Tyr Asp Trp Ala Ile Tyr Phe Tyr Pro Asp Gly Lys
65                  70                  75                  80
```

```
Ser Val Glu Asp Asn Ala Thr Tyr Val Ser Leu Phe Ile Ala Leu Ala
                85                  90                  95

Ser Asp Gly Thr Asp Val Arg Ala Leu Phe Glu Leu Thr Leu Leu Asp
            100                 105                 110

Gln Ser Gly Lys Glu Arg His Lys Val His Ser His Phe Glu Arg Thr
        115                 120                 125

Leu Glu Ser Gly Pro Tyr Thr Leu Lys Tyr Arg Gly Ser Met Trp Gly
    130                 135                 140

Tyr Lys Arg Phe Phe Lys Arg Thr Ala Leu Glu Thr Ser Asp Tyr Leu
145                 150                 155                 160

Lys Asp Asp Cys Leu Ser Val Asn Cys Ser Val Gly Val Val Arg Ser
                165                 170                 175

Arg Thr Glu Gly Pro Lys Ile Tyr Ser Ile Ala Ile Pro Pro Ser Asn
            180                 185                 190

Ile Gly His Gln Phe Gly Gln Leu Leu Glu Asn Gly Lys Gly Ser Asp
        195                 200                 205

Val Ser Phe Glu Val Asp Gly Glu Val Phe Thr Ala His Lys Leu Val
    210                 215                 220

Leu Ala Ala Arg Ser Pro Val Phe Arg Ala Gln Leu Phe Gly Pro Met
225                 230                 235                 240

Arg Asp Gln Ser Thr Gln Ser Ile Lys Val Glu Asp Met Glu Ala Pro
                245                 250                 255

Val Phe Lys Ala Leu Leu His Phe Met Tyr Trp Asp Ser Leu Pro Asp
            260                 265                 270

Met Gln Glu Leu Thr Gly Met Asn Thr Lys Trp Ala Thr Thr Leu Met
        275                 280                 285

Ala Gln His Leu Leu Ala Ala Asp Arg Tyr Ala Leu Glu Arg Leu
    290                 295                 300

Arg Leu Ile Cys Glu Ala Ser Leu Cys Glu Asp Val Ala Ile Asn Thr
305                 310                 315                 320

Val Ala Thr Thr Leu Ala Leu Ala Glu Gln His His Cys Phe Gln Leu
                325                 330                 335

Lys Ala Val Cys Leu Lys Phe Ile Ala Thr Ser Glu Asn Leu Arg Ala
            340                 345                 350

Val Met Gln Thr Asp Gly Phe Glu Tyr Leu Lys Glu Ser Cys Pro Ser
        355                 360                 365

Val Leu Thr Glu Leu Leu Glu Tyr Val Ala Arg Phe Thr Glu His Ser
    370                 375                 380

Asp Phe Leu Cys Lys His Arg Asn Glu Ala Ile Leu Asp Gly Ser Asp
385                 390                 395                 400

Ile Asn Gly Arg Arg Val Lys Gln Arg Leu
                405                 410

<210> SEQ ID NO 24
<211> LENGTH: 409
<212> TYPE: PRT
<213> ORGANISM: Coffea canephora

<400> SEQUENCE: 24

Met Gly Arg Val Tyr Asn Gly Glu Thr Ser Asn Pro Ser Ser Ser Thr
1               5                   10                  15

Thr Ala Ser Thr Ser Pro Pro Val Thr Ser Thr Ser Ile Thr
            20                  25                  30

Glu Thr Val Asn Gly Thr His Asp Phe Lys Ile Thr Gly Tyr Ser Leu
        35                  40                  45
```

```
Ser Lys Gly Ile Gly Ile Gly Lys Tyr Val Ala Ser Asp Ile Phe Met
     50                  55                  60
Val Gly Gly Tyr Ala Trp Ala Ile Tyr Phe Tyr Pro Asp Gly Lys Ser
 65                  70                  75                  80
Val Glu Asp Asn Ala Thr Tyr Val Ser Leu Phe Ile Ala Leu Ala Ser
                 85                  90                  95
Glu Gly Thr Asp Val Arg Ala Leu Phe Glu Leu Thr Leu Met Asp Gln
                100                 105                 110
Ser Gly Arg Ala Arg His Lys Ile His Ser His Phe Gly Arg Ala Leu
            115                 120                 125
Glu Ser Gly Pro Tyr Thr Leu Lys Tyr Arg Gly Ser Met Trp Gly Tyr
130                 135                 140
Lys Arg Phe Phe Lys Arg Thr Ala Leu Glu Thr Ser Asp Tyr Leu Lys
145                 150                 155                 160
Asn Asp Cys Leu Gln Val His Cys Cys Val Gly Val Val Arg Ser Gln
                165                 170                 175
Thr Glu Gly Pro Lys Ile Tyr Ser Ile Pro Leu Pro Pro Ser Asp Ile
                180                 185                 190
Gly Gln His Phe Gly Gln Leu Leu Glu Cys Gly Lys Gly Thr Asp Val
            195                 200                 205
Asn Phe Glu Val Asn Gly Glu Lys Phe Ser Ala His Lys Leu Val Leu
210                 215                 220
Ala Ala Arg Ser Pro Val Phe Arg Ala Gln Leu Phe Gly Pro Met Lys
225                 230                 235                 240
Asp His Asp Thr Gln Cys Ile Arg Val Glu Asp Met Glu Ala Pro Val
                245                 250                 255
Phe Lys Ala Leu Leu His Phe Ile Tyr Trp Asp Cys Leu Pro Asp Met
                260                 265                 270
Glu Glu Leu Thr Gly Leu Asn Ser Lys Gly Ala Thr Ser Leu Met Ala
            275                 280                 285
Gln His Leu Leu Ala Ala Ala Asp Arg Tyr Gly Leu Asp Arg Leu Arg
290                 295                 300
Leu Ile Cys Glu Ala Asn Leu Cys Glu Asp Val Ala Ile Asn Thr Val
305                 310                 315                 320
Ala Thr Thr Leu Ala Leu Ala Glu Gln His His Cys Phe Gln Leu Lys
                325                 330                 335
Ser Val Cys Leu Lys Phe Val Ala Met Pro Glu Asn Leu Arg Ala Val
                340                 345                 350
Met Gln Thr Asp Gly Phe Glu Tyr Leu Lys Glu Ser Cys Pro Ser Val
            355                 360                 365
Leu Thr Glu Leu Leu Glu Tyr Val Ala Arg Ile Asn Glu His Ser Val
370                 375                 380
Ser Val Asn Lys Gln Leu Thr Asp Gly Ile Leu Asp Gly Ser Asp Val
385                 390                 395                 400
Asn Gly Arg Arg Val Lys Gln Arg Leu
                405

<210> SEQ ID NO 25
<211> LENGTH: 399
<212> TYPE: PRT
<213> ORGANISM: Zea mays

<400> SEQUENCE: 25

Met Ala Ile Pro Pro Arg Thr Pro Ser Pro Pro Pro Ser Trp Ser Arg
```

-continued

```
1               5                   10                  15
Ser Val Thr Glu Thr Val Arg Gly Ser His Gln Phe Thr Val Arg Gly
            20                  25                  30

Tyr Ser Leu Ala Lys Gly Met Gly Pro Gly Arg Tyr Leu Ala Ser Asp
            35                  40                  45

Val Phe Ala Val Gly Gly Tyr His Trp Ala Val Tyr Leu Tyr Pro Asp
 50                     55                  60

Gly Lys Asn Ala Glu Asp Asn Ser Asn Tyr Val Ser Val Phe Val Ala
 65                 70                  75                  80

Leu Ala Ser Asp Gly Ile Asp Val Arg Ala Leu Phe Glu Leu Thr Leu
                85                  90                  95

Leu Asp Gln Ser Gly Arg Gly Cys His Lys Val His Ser His Phe Asp
                100                 105                 110

Arg Ser Leu Lys Phe Gly Pro Tyr Thr Leu Lys Tyr Arg Gly Ser Met
                115                 120                 125

Trp Gly Tyr Lys Arg Phe Tyr Lys Arg Thr Leu Leu Glu Glu Ser Asp
            130                 135                 140

Phe Leu Lys Asn Asp Cys Leu Val Met Asn Cys Thr Val Gly Val Val
145                 150                 155                 160

Lys Asn Arg Ile Glu Thr Pro Lys Asp Ile Gln Ile His Val Pro Arg
                165                 170                 175

Ser Asp Met Gly Arg Cys Phe Lys Glu Leu Leu Ser Arg Cys Ile Gly
                180                 185                 190

Cys Asp Ile Thr Phe Glu Val Arg Asp Glu Lys Val Arg Ala His Lys
                195                 200                 205

Trp Ile Leu Ala Ala Arg Ser Pro Val Phe Lys Ala Gln Phe Phe Gly
        210                 215                 220

Pro Ile Gly Lys Pro Asp Leu His Thr Val Val Glu Asp Val Glu
225                 230                 235                 240

Pro Val Val Phe Lys Ala Met Val Asn Phe Ile Tyr Ala Asp Glu Leu
                245                 250                 255

Pro Ser Ile Pro Glu Leu Ala Gly Ser Ala Ser Thr Trp Thr Ser Thr
                260                 265                 270

Val Val Val Gln His Leu Leu Ala Ala Asp Arg Tyr Gly Leu Val
        275                 280                 285

Arg Leu Arg Ile Leu Cys Glu Ser Lys Leu Cys Asp Glu Leu Thr Pro
        290                 295                 300

Glu Thr Val Ala Thr Thr Leu Ala Leu Ala Glu Gln His His Cys Ala
305                 310                 315                 320

Glu Leu Lys Ser Ala Cys Leu Lys Phe Ile Ala Leu Arg Gly Asn Leu
                325                 330                 335

Gly Ala Val Met Glu Thr Glu Gly Phe Asp Tyr Leu Glu Asp Thr Cys
                340                 345                 350

Pro Ser Leu Leu Ser Asp Leu Leu Ala Thr Val Ala Val Val Asp Asp
                355                 360                 365

Asp Leu Ala Ser Leu Asn Arg Lys Arg Gly Val Ser Gly Asn Gln Val
        370                 375                 380

Met Ala Leu Val Gly Ser Val Glu Arg Arg Thr Arg Arg Lys Leu
385                 390                 395
```

<210> SEQ ID NO 26
<211> LENGTH: 402
<212> TYPE: PRT
<213> ORGANISM: Sorghum bicolor

<400> SEQUENCE: 26

```
Met Ala Ile Pro Pro Arg Thr Pro Pro Pro Ser Trp Ser Arg
1               5                   10                  15

Tyr Val Thr Glu Thr Val Lys Gly Ser His Gln Phe Thr Val Arg Gly
                20                  25                  30

Phe Ser Leu Ala Lys Gly Met Gly Pro Gly Arg His Leu Ala Ser Asp
            35                  40                  45

Ile Phe Ala Val Gly Gly Tyr His Trp Ala Val Tyr Phe Tyr Pro Asp
    50                  55                  60

Gly Lys Asn Ala Glu Asp Asn Ser Asn Tyr Val Ser Val Phe Val Ala
65                  70                  75                  80

Leu Ala Ser Asp Gly Ile Asp Val Arg Ala Leu Phe Asp Leu Thr Leu
                85                  90                  95

Leu Asp Gln Ser Gly Arg Gly Arg His Lys Ile His Ser His Phe Gly
                100                 105                 110

Arg Lys Leu Asp Ser Gly Pro Tyr Thr Leu Lys Tyr Arg Gly Ser Met
            115                 120                 125

Trp Gly Tyr Lys Arg Phe Tyr Lys Arg Ser Leu Leu Glu Ala Ser Asp
    130                 135                 140

Phe Leu Lys Asn Asp Cys Leu Val Met Asn Cys Thr Val Gly Val Val
145                 150                 155                 160

Lys Asn Arg Met Glu Thr Pro Lys Asp Ile Gln Ile His Val Pro Arg
                165                 170                 175

Ser Asp Met Gly His Cys Phe Lys Glu Leu Leu Ser Arg Gly Ile Gly
            180                 185                 190

Cys Asp Ile Thr Phe Glu Val Arg Asp Glu Lys Val Arg Ala His Lys
    195                 200                 205

Trp Ile Leu Ala Ala Arg Ser Pro Val Phe Lys Ala Gln Phe Phe Gly
    210                 215                 220

Pro Ile Gly Lys Pro Asp Leu His Thr Val Val Glu Asp Val Glu
225                 230                 235                 240

Pro Val Val Phe Lys Ala Met Val Asn Phe Met Tyr Thr Asp Glu Leu
                245                 250                 255

Pro Ser Ile Ser Glu Leu Ala Gly Ser Ala Ser Thr Trp Thr Ser Thr
            260                 265                 270

Val Val Val Gln His Leu Leu Ala Ala Asp Arg Tyr Gly Leu Asp
            275                 280                 285

Arg Leu Arg Ile Leu Cys Glu Ser Lys Leu Cys Asp Glu Leu Thr Pro
290                 295                 300

Glu Thr Val Ala Thr Thr Leu Ala Leu Ala Glu Gln His His Cys Ala
305                 310                 315                 320

Glu Leu Lys Ser Ala Cys Leu Arg Phe Ala Ala Val Arg Glu Asn Leu
                325                 330                 335

Gly Ala Val Met Gly Thr Glu Gly Phe Asp Tyr Leu Glu Glu Thr Cys
            340                 345                 350

Pro Ser Leu Leu Ser Asp Leu Leu Ala Thr Val Ala Glu Val Asp Asp
            355                 360                 365

Asp Pro Ala Ser Leu Asp Arg Lys Arg Gly Val Cys Gly Asn Gln Val
    370                 375                 380

Leu Ala Pro Val Glu Ser Val Glu Ala Thr Glu Arg Arg Thr Arg Arg
385                 390                 395                 400

Arg Leu
```

<210> SEQ ID NO 27
<211> LENGTH: 411
<212> TYPE: PRT
<213> ORGANISM: Cucumis melo

<400> SEQUENCE: 27

```
Met Gly Thr Ile Lys Ser Cys Arg Asp Thr Ser Lys Ser Tyr Ser Asn
1               5                   10                  15

Leu Arg Ser Pro Thr Pro Pro Val Thr Phe Ser Thr Ser Arg Phe
            20                  25                  30

Glu Thr Val Asn Gly Ser His Glu Phe Lys Ile Asn Gly Tyr Ser Leu
                35                  40                  45

Asn Lys Gly Met Gly Ile Gly Lys Tyr Ile Ala Ser Asp Thr Phe Met
50                  55                  60

Val Gly Gly Tyr Ala Phe Ala Ile Tyr Phe Tyr Pro Asp Gly Lys Ser
65                  70                  75                  80

Val Glu Asp Asn Ala Ser Tyr Val Ser Val Phe Ile Ala Leu Ala Ser
                85                  90                  95

Glu Gly Thr Asp Val Arg Ala Leu Phe Glu Leu Thr Leu Leu Asp Gln
            100                 105                 110

Ser Gly Lys Glu Asn His Lys Val His Ser His Phe Glu Arg Arg Leu
        115                 120                 125

Glu Ser Gly Pro Tyr Thr Leu Lys Tyr Arg Gly Ser Met Trp Gly Tyr
130                 135                 140

Lys Arg Tyr Phe Lys Arg Thr Val Leu Glu Thr Ser Asp Phe Leu Lys
145                 150                 155                 160

Asp Asp Cys Leu Glu Ile His Cys Val Val Gly Val Val Lys Ser His
                165                 170                 175

Thr Glu Gly Pro Lys Ile Tyr Ser Ile Thr Pro Pro Ser Asp Ile
            180                 185                 190

Gly Gln His Phe Gly Lys Leu Leu Glu Ser Gly Lys Leu Thr Asp Val
        195                 200                 205

Asn Phe Glu Val Asp Gly Glu Thr Phe Ser Ala His Lys Leu Val Leu
210                 215                 220

Ala Ala Arg Ser Pro Val Phe Arg Ala Gln Leu Phe Gly Pro Leu Lys
225                 230                 235                 240

Asp Gln Asn Thr Glu Cys Ile Lys Val Glu Asp Met Glu Ala Pro Val
                245                 250                 255

Phe Lys Ala Leu Leu His Phe Ile Tyr Trp Asp Ala Leu Pro Asp Met
            260                 265                 270

Gln Glu Ile Val Gly Leu Asn Ser Lys Trp Ala Ser Thr Leu Met Ser
        275                 280                 285

Gln His Leu Leu Ala Ala Ala Asp Arg Tyr Ala Leu Asp Arg Leu Lys
290                 295                 300

Leu Leu Cys Glu Ala Lys Leu Cys Glu Asp Val Ala Ile Asn Thr Val
305                 310                 315                 320

Ala Thr Thr Leu Ala Leu Ala Glu Gln His His Cys Phe Gln Leu Lys
                325                 330                 335

Ala Val Cys Leu Lys Val Ile Ala Leu Pro Glu Asn Leu Arg Ala Val
            340                 345                 350

Met Gln Thr Glu Gly Phe Glu Tyr Leu Lys Glu Ser Cys Pro Ser Val
        355                 360                 365

Leu Thr Glu Leu Leu Glu Tyr Val Ala Arg Val Thr Glu His Ala Val
```

```
               370                 375                 380
Ile Thr Cys Ser Gly Tyr Gly Asn Gly Thr Val Leu Asp Gly Ser Tyr
385                 390                 395                 400

Val Asn Gly Arg Arg Val Arg Gln Arg Leu Tyr
                405                 410

<210> SEQ ID NO 28
<211> LENGTH: 285
<212> TYPE: PRT
<213> ORGANISM: Artificial Sequence
<220> FEATURE:
<223> OTHER INFORMATION: Artificial consensus sequence

<400> SEQUENCE: 28

Met Glu Ser Ser Lys Ser Ile Ser Glu Thr Val Asn Gly Ser His Gln
1               5                  10                  15

Phe Thr Ile Lys Gly Tyr Ser Leu Ala Lys Gly Met Gly Gly Lys Tyr
                20                  25                  30

Ile Ser Asp Ile Phe Thr Val Gly Gly Tyr Asp Trp Ala Ile Tyr Phe
            35                  40                  45

Tyr Pro Asp Gly Lys Asn Pro Glu Asp Tyr Val Ser Val Phe Ile Ala
        50                  55                  60

Leu Ala Ser Glu Gly Thr Asp Val Arg Ala Leu Phe Glu Leu Thr Leu
65                  70                  75                  80

Val Asp Gln Ser Gly Lys Gly Lys His Lys Val His Ser His Phe Asp
                85                  90                  95

Arg Ala Leu Glu Ser Gly Pro Tyr Thr Leu Lys Tyr Arg Gly Ser Met
            100                 105                 110

Trp Gly Tyr Lys Arg Phe Phe Arg Arg Thr Leu Glu Thr Ser Asp Tyr
        115                 120                 125

Leu Lys Asp Asp Cys Leu Ile Met Asn Cys Thr Val Gly Val Val Arg
130                 135                 140

Leu Glu Gly Pro Lys Gln Tyr Ser Ile Val Pro Pro Ser Asp Met Gly
                145                 150                 155                 160

Gln Leu Lys Glu Leu Leu Glu Ser Glu Val Gly Cys Asp Ile Phe Val
            165                 170                 175

Gly Asp Glu Phe Lys Ala His Lys Leu Ile Leu Ala Ala Arg Ser Pro
        180                 185                 190

Val Phe Arg Ala Gln Phe Phe Gly Leu Val Gly Asp Pro Leu Asp Lys
    195                 200                 205

Val Val Val Glu Asp Val Glu Pro Ile Phe Lys Ala Met Leu Phe Thr
210                 215                 220

Asp Leu Pro Asp Val Glu Ile Thr Gly Ser Thr Ser Met Cys Thr Ser
225                 230                 235                 240

Thr Val Met Val Gln His Leu Leu Ala Ala Asp Arg Tyr Leu Asp
                245                 250                 255

Arg Leu Lys Leu Leu Cys Glu Leu Cys Glu Glu Leu Ser Glu Thr
            260                 265                 270

Val Ala Thr Thr Leu Ala Leu Ala Glu Gln His His Cys
        275                 280                 285

<210> SEQ ID NO 29
<211> LENGTH: 44
<212> TYPE: DNA
<213> ORGANISM: Artificial Sequence
<220> FEATURE:
<223> OTHER INFORMATION: Synthetic primer
```

-continued

<400> SEQUENCE: 29
taatacgact cactataggg agaatgttca agatctgtgg gtac     44

<210> SEQ ID NO 30
<211> LENGTH: 25
<212> TYPE: DNA
<213> ORGANISM: Artificial Sequence
<220> FEATURE:
<223> OTHER INFORMATION: Synthetic primer

<400> SEQUENCE: 30
ctacatttct agactggacc tcctg     25

<210> SEQ ID NO 31
<211> LENGTH: 47
<212> TYPE: DNA
<213> ORGANISM: Artificial Sequence
<220> FEATURE:
<223> OTHER INFORMATION: Synthetic primer

<400> SEQUENCE: 31
tcgtcctcag tggacgctta gagagcactt ctagactgga cctcctg     47

<210> SEQ ID NO 32
<211> LENGTH: 50
<212> TYPE: DNA
<213> ORGANISM: Artificial Sequence
<220> FEATURE:
<223> OTHER INFORMATION: Synthetic primer

<400> SEQUENCE: 32
acgcttacgc tcagatggct caccgtcgtc gtcctcacgt ggacgcttag     50

<210> SEQ ID NO 33
<211> LENGTH: 50
<212> TYPE: DNA
<213> ORGANISM: Artificial Sequence
<220> FEATURE:
<223> OTHER INFORMATION: Synthetic primer

<400> SEQUENCE: 33
cacgaccgtc cttagaacgc tcgtcacgct cacgcttacg ctcagatggc     50

<210> SEQ ID NO 34
<211> LENGTH: 38
<212> TYPE: DNA
<213> ORGANISM: Artificial Sequence
<220> FEATURE:
<223> OTHER INFORMATION: Synthetic primer

<400> SEQUENCE: 34
agaaagctgg gtcacgacgg ttaccaccac gaccgtcc     38

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
atgaagaagc gcttaaccac     20

<210> SEQ ID NO 36

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
tcagaccaaa tagttacaag                                               20

<210> SEQ ID NO 37
<211> LENGTH: 21
<212> TYPE: DNA
<213> ORGANISM: Artificial Sequence
<220> FEATURE:
<223> OTHER INFORMATION: Synthetic primer

<400> SEQUENCE: 37
cctgccatgt atgttgccat t                                             21

<210> SEQ ID NO 38
<211> LENGTH: 22
<212> TYPE: DNA
<213> ORGANISM: Artificial Sequence
<220> FEATURE:
<223> OTHER INFORMATION: Synthetic primer

<400> SEQUENCE: 38
aatcgagcac aataccggtt gt                                            22

<210> SEQ ID NO 39
<211> LENGTH: 18
<212> TYPE: DNA
<213> ORGANISM: Artificial Sequence
<220> FEATURE:
<223> OTHER INFORMATION: Synthetic primer

<400> SEQUENCE: 39
attggcgtct actcttgt                                                 18

<210> SEQ ID NO 40
<211> LENGTH: 18
<212> TYPE: DNA
<213> ORGANISM: Artificial Sequence
<220> FEATURE:
<223> OTHER INFORMATION: Synthetic primer

<400> SEQUENCE: 40
aatgatgctg ctctgcta                                                 18

<210> SEQ ID NO 41
<211> LENGTH: 18
<212> TYPE: DNA
<213> ORGANISM: Artificial Sequence
<220> FEATURE:
<223> OTHER INFORMATION: Synthetic primer

<400> SEQUENCE: 41
taatcggcac agacttga                                                 18

<210> SEQ ID NO 42
<211> LENGTH: 20
<212> TYPE: DNA
<213> ORGANISM: Artificial Sequence
<220> FEATURE:
<223> OTHER INFORMATION: Synthetic primer

<400> SEQUENCE: 42
```

-continued actcgcatat tgttctaagc                                        20

<210> SEQ ID NO 43
<211> LENGTH: 19
<212> TYPE: DNA
<213> ORGANISM: Artificial Sequence
<220> FEATURE:
<223> OTHER INFORMATION: Synthetic primer

<400> SEQUENCE: 43
caccagttca cgattcaag                                         19

<210> SEQ ID NO 44
<211> LENGTH: 19
<212> TYPE: DNA
<213> ORGANISM: Artificial Sequence
<220> FEATURE:
<223> OTHER INFORMATION: Synthetic primer

<400> SEQUENCE: 44
ccaccaacgg agaagatat                                         19

<210> SEQ ID NO 45
<211> LENGTH: 18
<212> TYPE: DNA
<213> ORGANISM: Artificial Sequence
<220> FEATURE:
<223> OTHER INFORMATION: Synthetic primer

<400> SEQUENCE: 45
tcctgatggc aagaatcc                                          18

<210> SEQ ID NO 46
<211> LENGTH: 18
<212> TYPE: DNA
<213> ORGANISM: Artificial Sequence
<220> FEATURE:
<223> OTHER INFORMATION: Synthetic primer

<400> SEQUENCE: 46
cgaagtggct atgaacct                                          18

<210> SEQ ID NO 47
<211> LENGTH: 18
<212> TYPE: DNA
<213> ORGANISM: Artificial Sequence
<220> FEATURE:
<223> OTHER INFORMATION: Synthetic primer

<400> SEQUENCE: 47
ttaggctcag gttgttgt                                          18

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
tcatccttca tctgttggta                                        20

<210> SEQ ID NO 49
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 49
gcataaggtt catagccatt                                              20

<210> SEQ ID NO 50
<211> LENGTH: 18
<212> TYPE: DNA
<213> ORGANISM: Artificial Sequence
<220> FEATURE:
<223> OTHER INFORMATION: Synthetic primer

<400> SEQUENCE: 50
agatgtctca agcaagga                                                18

<210> SEQ ID NO 51
<211> LENGTH: 18
<212> TYPE: DNA
<213> ORGANISM: Artificial Sequence
<220> FEATURE:
<223> OTHER INFORMATION: Synthetic primer

<400> SEQUENCE: 51
gagcaacaag aagcagag                                                18

<210> SEQ ID NO 52
<211> LENGTH: 18
<212> TYPE: DNA
<213> ORGANISM: Artificial Sequence
<220> FEATURE:
<223> OTHER INFORMATION: Synthetic primer

<400> SEQUENCE: 52
ccacaacgat ccatttcc                                                18

<210> SEQ ID NO 53
<211> LENGTH: 16
<212> TYPE: DNA
<213> ORGANISM: Artificial Sequence
<220> FEATURE:
<223> OTHER INFORMATION: Synthetic primer

<400> SEQUENCE: 53
cagccaaatc gtcact                                                  16

<210> SEQ ID NO 54
<211> LENGTH: 16
<212> TYPE: DNA
<213> ORGANISM: Artificial Sequence
<220> FEATURE:
<223> OTHER INFORMATION: Synthetic primer

<400> SEQUENCE: 54
gttccggtat ggtcag                                                  16

<210> SEQ ID NO 55
<211> LENGTH: 25
<212> TYPE: DNA
<213> ORGANISM: Artificial Sequence
<220> FEATURE:
<223> OTHER INFORMATION: Synthetic primer

<400> SEQUENCE: 55
ctttcaccgt cttaggaaca aacag                                        25
```

```
<210> SEQ ID NO 56
<211> LENGTH: 28
<212> TYPE: DNA
<213> ORGANISM: Artificial Sequence
<220> FEATURE:
<223> OTHER INFORMATION: Synthetic primer

<400> SEQUENCE: 56
taggaacaga gtttcgatgt ctgagaac                                    28

<210> SEQ ID NO 57
<211> LENGTH: 18
<212> TYPE: DNA
<213> ORGANISM: Artificial Sequence
<220> FEATURE:
<223> OTHER INFORMATION: Synthetic primer

<400> SEQUENCE: 57
cggaggataa ctcgtctt                                               18

<210> SEQ ID NO 58
<211> LENGTH: 20
<212> TYPE: DNA
<213> ORGANISM: Artificial Sequence
<220> FEATURE:
<223> OTHER INFORMATION: Synthetic primer

<400> SEQUENCE: 58
aatggctatg aaccttatgc                                             20

<210> SEQ ID NO 59
<211> LENGTH: 22
<212> TYPE: DNA
<213> ORGANISM: Artificial Sequence
<220> FEATURE:
<223> OTHER INFORMATION: Synthetic primer

<400> SEQUENCE: 59
ctggaggttt tgaggctggt ta                                          22

<210> SEQ ID NO 60
<211> LENGTH: 21
<212> TYPE: DNA
<213> ORGANISM: Artificial Sequence
<220> FEATURE:
<223> OTHER INFORMATION: Synthetic primer

<400> SEQUENCE: 60
ccaagggtga aagcaagaag a                                           21

<210> SEQ ID NO 61
<211> LENGTH: 18
<212> TYPE: DNA
<213> ORGANISM: Artificial Sequence
<220> FEATURE:
<223> OTHER INFORMATION: Synthetic primer

<400> SEQUENCE: 61
aagtgaactg ttgttgtt                                               18

<210> SEQ ID NO 62
<211> LENGTH: 20
<212> TYPE: DNA
<213> ORGANISM: Artificial Sequence
<220> FEATURE:
```

<223> OTHER INFORMATION: Synthetic primer

<400> SEQUENCE: 62
cgtcttctta ttgttattgg                                               20

<210> SEQ ID NO 63
<211> LENGTH: 19
<212> TYPE: DNA
<213> ORGANISM: Artificial Sequence
<220> FEATURE:
<223> OTHER INFORMATION: Synthetic primer

<400> SEQUENCE: 63
ttccaataat tacctcctt                                                19

<210> SEQ ID NO 64
<211> LENGTH: 19
<212> TYPE: DNA
<213> ORGANISM: Artificial Sequence
<220> FEATURE:
<223> OTHER INFORMATION: Synthetic primer

<400> SEQUENCE: 64
tttaacacaa ctttcaaag                                                19

<210> SEQ ID NO 65
<211> LENGTH: 50
<212> TYPE: PRT
<213> ORGANISM: Arabidopsis thaliana

<400> SEQUENCE: 65

Leu Val Thr Val Arg Asp Val Met Thr Ser His Leu Arg Glu Met Gly
1               5                   10                  15

Lys Gln Leu Val Thr Asp Pro Glu Lys Ser Lys Asp Pro Val Glu Phe
            20                  25                  30

Val Gln Arg Leu Leu Asp Glu Arg Asp Lys Tyr Asp Lys Ile Ile Asn
        35                  40                  45

Thr Ala
    50

<210> SEQ ID NO 66
<211> LENGTH: 50
<212> TYPE: PRT
<213> ORGANISM: Arabidopsis thaliana

<400> SEQUENCE: 66

Leu Val Thr Val Arg Asp Val Met Thr Leu His Leu Arg Glu Met Gly
1               5                   10                  15

Lys Gln Leu Val Thr Asp Pro Glu Lys Ser Lys Asp Pro Val Glu Phe
            20                  25                  30

Val Gln Arg Leu Leu Asp Glu Arg Asp Lys Tyr Asp Arg Ile Ile Asn
        35                  40                  45

Met Ala
    50

<210> SEQ ID NO 67
<211> LENGTH: 46
<212> TYPE: PRT
<213> ORGANISM: Arabidopsis thaliana

<400> SEQUENCE: 67

Cys Ser Ser Ser Pro Ser Ser Ser Val Ser Ser Ser Thr Thr Thr Ser

```
 1               5                   10                  15
Ser Pro Ile Gln Ser Glu Ala Pro Arg Pro Lys Arg Ala Lys Arg Ala
                20                  25                  30
Lys Lys Ser Ser Pro Ser Gly Asp Lys Ser His Asn Pro Thr
                35                  40                  45
```

<210> SEQ ID NO 68
<211> LENGTH: 1636
<212> TYPE: DNA
<213> ORGANISM: Arabidopsis thaliana

<400> SEQUENCE: 68

```
gaaggcgaaa acagtttccc ccaaattctc ataattttca caaacaacct ctcgtcttct      60
aggttaatcc aatttcgtcg attcatgaag ttcacaattc tcccatcgga aaattcttcg    120
taatcgacga cgaagagatc atgagtaccg tcggaggtat agagcagttg atacctgatt    180
ccgtttcaac gtcgttcatc gaaacggtga acggttcgca ccagttcacg attcaaggtt    240
actctctagc caaaggcatg agccctggga agtttataca gagcgatatc ttctccgttg    300
gtggatacga ttgggcgatt tacttctatc ctgatgggaa gaacccggag gaccagtcct    360
cgtatatctc tttgttcatc gctttagcga gtgattctaa tgatattagg gctttgtttg    420
agcttacgct tatggatcag agtgggaaag gaaacataa ggtgcatagt cactttgatc    480
gggcgcttga aggtggtcct tatacactta agtataaagg aagcatgtgg ggttacaaac    540
gcttttttcaa acgatcagct ttagaaacct ctgactactt aaaggatgat tgtcttgtca    600
tcaattgtac tgttggcgtt gttagagccc gactcgaggg tccaaaacag tatggcattg    660
tgctaccoct gtcgaatatg ggtcagggat tgaaagactt gttagattct gaagttggtt    720
gtgacatagc tttccaagtc ggagatgaaa catacaaagc tcacaaactg attctcgcgg    780
cacgctcccc agttttttaga gctcagtttt ttggaccaat tgggaataac aatgtggata    840
gaatagtgat agacgacatc gaaccttcta tcttcaaggc tatgcttagc ttcatttaca    900
ccgatgtact tcctaatgtg catgaaatta ccgggtcaac ttctgccagt tcgtttacaa    960
acatgataca catctcttg gcagctgctg acctctatga ccttgcaagg ttaaagatat   1020
tatgtgaagt tttgctatgc gaaaaacttg atgttgataa tgtggcaaca acacttgcgt   1080
tggctgaaca gcaccaattc ttacagctca aagcgttctg cttagaattt gttgcatctc   1140
cagcaaactt gggagctgta atgaagtccg aagggttcaa gcacttgaaa cagagctgtc   1200
ccactttgtt atctgagttg ctgaacactg ttgcagcagc agataagagc tcgacgagtg   1260
gacaatcaaa caagaaaaga agtgcgagca gtgtattagg gtgtgacact acaaatgtga   1320
ggcaattgag gaggagaaca cgaaaagaag tgcgagcagt gtcttaggat cattacatac   1380
cgtatgcaaa attctagaat tatgcattgt gtttcaagca gagtttatga attccaagtc   1440
atcccgtgaa cttttttacc agtgagaatt atagaggcct gaactctgaa ccaaactgtt   1500
tgtgtcaatc atttacatt tctggacaaa agaaagtaca atctccacaa agagctgtga   1560
gaattgactc aaaacaaatc ctaaaactct gtaccagatt gttcaatttc tcattaaatc   1620
ccacaatatg attttc                                                    1636
```

<210> SEQ ID NO 69
<211> LENGTH: 1647
<212> TYPE: DNA
<213> ORGANISM: Brassica rapa

<400> SEQUENCE: 69

-continued

```
ctaatcataa ccaaaaccga aaccttagtt aaaatccggt agaatctcca caaaccaaaa      60
ccatccgaat actaaaccaa accaaaccaa atccaatcga attttattttg gttcagttcg    120 tcacaatttt aaccgaatca aactaacaaa ccaaacttct accgaacccg cagtcctaaa    180
gtatcatctc caatcaaacg gagcttttat cattttcaaa atcaaatcga cggcgacgat    240
gagcgcatct catccgaatc acgattcggt atcaacaacc gtaatggaga cggtgaacgg    300
atcgcaccaa ttcacgatca aaggctactc tctcgccaaa ggcatgagcc cggggaggta    360
catacagagc gacgtcttct ccgtgaacgg atacgactgg gtgatctact tctaccccga    420
cgggaagaac cccgaggaga actccaccta cgtctctctc ttcatcgcct ggcgagcga    480 ttcgagcgac attagggctt tgttcgagct gacgctgatg gatcagagcg ggagagggag    540
gcataaggtt catagtcatt tcgatcgggc gcttgaagga gggccttata cgcttaagta    600
taaagggagt atgtgggggtt acaaacgctt tttaagaaga acagctttgg aagcatctga    660
ctacttgaag gatgattgtc ttatcatcaa ctgtactgtt ggcgtcgtta gagctcgcct    720
tgagggtcct aaacagtttg gcattgtgcc accaccttca aacatgggtc agggattgaa    780
agacttgtta gactctgaac ttggctgcga cattgctttc caagtcggag atgagactta    840
caaagctcac aaactgatcc tcgcagcacg ctcgccggtc tttagagctc agttctatgg    900
accagttggg aataacagtg tggatagagt agtcatagag gacatggagc cttcaatctt    960
taaggctatg cttagcttca tctacacgga tgtacttcct gatgtgcatg agattacagg   1020
gtctacttct accgcttcgt tcacgaacat gatacagcat ctattggcag ctgctgacct   1080
ctatgacctt gggaggttaa agatactgtg tgaagctttt ctatgtgaag aactaaacgt   1140
tgataatgtg gcaacaacac ttgcactagc tgaccaacac cagttcttgc agctcaaagc   1200
cttctgctta aaatttgttg catctccagc aaatttgcga gccgtaatga agtcagaagg   1260
tttcaagcac ttgaaccaga gctgtccctc tgtgttgcct gagttgctaa acacagttgc   1320
agcagcggat aagagctcga cgtcgtcgag tggacagtca agcaagaaaa gaagtgtgag   1380
cagtgtgttg ggctgtgata caagcacaac aaatgcgaga caggtgagga ggacgtaggt   1440
aggatcgacc caagtgcaag taatgcttta gtctgatgct actttgctag acttttact   1500 tattgtaatg aaaataattg tttgtagtat gtctacagtt agtgtaaagc tttaggcaat   1560
ggaacatctg ttttgctttg cgtgtttgta aaagctttgg ataatactag gttaaaagct   1620
ttggagttaa tagtctttttt tgttgca                                      1647
```

<210> SEQ ID NO 70
<211> LENGTH: 1224
<212> TYPE: DNA
<213> ORGANISM: Jatropha curcas

<400> SEQUENCE: 70

```
atggtcgacg tcaaagcgga tttcgataaa gagtcgtgtt cgaaatcagt aaacgagaca     60
gtgaacgggt cgcaccagtt caccataaag ggatattctt tggcgaaagg gatgggagct    120
gggaaatgca tatcgagtga tattttcacg gttggtggtt acgattgggc gatttacttt    180
tacccagatg gtaaaaaccc tgaagatagc tccatgtatg tttccgtttt tattgccctg    240
gcgagcgaag gaacggatgt tagggctttg tttgagttga cgttggttga tcagagtgga    300
aacgggaagc acaaagtgca tagccacttt tgatcgtgcat tggagagtgg gccgtacact    360
ttgaagtata gagggagcat gtgggggttac aagcgttttct ttagaaggac gaccttagaa    420
```

```
aattctgatt atataaagga tgattgccta ctcatgaact gtactgttgg agttgtcaga      480
actcgtcttg taggaccaaa acaatgtttt attaccattc caccctcaga catgggccag      540
ggcctcaaag aactcttgga atctgaagtt ggttgtgaca ttgctttcca ggttggggat      600
gaaacattta aagctcataa attgatactt gctgctcgct ctccagtttt cagggcccag      660
ttttttggac ttttttgggga tcctaaccta gataaagtag ttgtgaagga tattgaccccc    720
tcaatcttca aggcaatgct actattcgta tacacagaca aacttcctga tgtacatgaa      780
attactggca cgacgtctat gtgcacatcc accaatatgg tgcagcatct attggctgct      840
gctgacctat acaatttaga tcgattgaaa ttgctatgtg aatcgaagtt gtgtgaggaa      900
ctgagtgctg agacagtggc gacgacgctt gcattagctg agcagcatca gtgttcgcag      960
cttagggcca tctgtttgaa atttgctgca actcctgcaa acttgggagc ggtaatgcaa     1020
tcagaaggat tccggcactt agaagaaagc tgcccggcat tgttgtgtga gatgctgaag     1080
acatttgcat taggagatga gaattcaaat cagtcaggtc ggaagaggag tgggagcagc     1140
atctatgggc tagatctagc aacagatggg gctgcagcag aatcagtaaa tcccaatgcc     1200
aggcgtttga ggaggcggta ttag                                            1224

<210> SEQ ID NO 71
<211> LENGTH: 1224
<212> TYPE: DNA
<213> ORGANISM: Populus trichocarpa

<400> SEQUENCE: 71
atggacgatt tcaagggaga gtagataag gagtcgtgtt cgaagtcaat aaacgagacg       60
gtgaatgggt ctcaccagtt tacgataaaa gggtattcat tagcgaaagg aatgggagct      120
gggagatgca taccgagtga tgttttcaac gtgggtggt atgattgggc gatttatttt       180
tacccagatg ggaaaaaccc tgaggatagc tcgatgtatg tgtcggtttt tattgcgtta      240
gcgagcgaag gaacggatgt tagggctttg ttcgagttga cgctggtgga tcagagtggg      300
aaagggaagc ataaagtaca tagtcatttc gatcgtgcgt tggagagtgg accttattca      360
ttgaagtaca gaggcagcat gtggggttac aaacgtttct tccgaaggac aaccttggaa      420
acttctgatt atctgaagga tgactgcctt atcatgaact gcactgttgg agttgtcaga      480
actcgtcttg aaggaccaaa acagtactcc atttcagttc caccttcaga catgggttgg      540
ggttttaaag aactactgga gtctgaatct ggttgtgaca tagatttcca ggttggtgat      600
gaaacattta gagctcataa gctgatcctt gctgctcgtt caccgtgttt cagagctcaa      660
ttttttggac ttgtcgggga tcctaacatg gataaagtag tagtgaagga tgttgatccc     720
ttgatattca aggcaatgct tctgttttata tacacagaca aacttcctga tgcacatgaa     780
ataactggct cgacatcaat gtgcacatcc accaatatgg tgcagcatct gttggctgtc     840
tctgaccttt acaatttaga tcgattgaaa ttgttatgtg aagcaaagtt gtgtgaggaa     900
ctcagtgccg agaatgtggc aacaacactg gcattggctg agcagcatca gtgcatgcaa     960
ctgaaggcca tctgtttgaa atttgcagca aatccagcga acttgggagc ggtaatgcag    1020
tcagaagggt tccgacactt ggaggagagc tgcccttcaa tgttatgtga gttgctgaag    1080
acacttgctt ctggagatga gaactcaagt cttctgtcag gtaggaagag gagtggcagc    1140
agtttacttg ggttttgatct agcggatggg gctccagcag aatcagcaaa tcccaatggc    1200
aggcgtttga ggaggcggtt ttag                                            1224
```

<210> SEQ ID NO 72
<211> LENGTH: 1209
<212> TYPE: DNA
<213> ORGANISM: Theobroma cacao

<400> SEQUENCE: 72

| | | | | | |
|---|---|---|---|---|---|
| atggacgatt | tcaaggactc | ggtatcgaaa | tcggtgagcg | agactgtgaa | cgggtcgcac | 60 |
| cagttcacga | tcaagggtta | ctcgttggcg | aaagggatgg | gccctggaaa | atgtatagcc | 120 |
| agcgatgttt | tcaccgtcgg | aggtttcgat | tgggtgattt | acttttaccc | cgacggtaaa | 180 |
| aatccggagg | atagtgctat | gtatgtttcg | gttttcattg | ctctggccag | cgaaggtacc | 240 |
| gatgtccgtg | cacttttcga | gctcacgctt | gtggaccaga | gtgggaaagg | gaagcataag | 300 |
| gttcatagtc | actttgatcg | ggcgttggag | agtggacctt | atacgttgaa | gtatagaggg | 360 |
| agcatgtggg | gttacaagcg | tttctttaga | gaacaactt | tagaaacttc | tgactatatt | 420 |
| aaggatgatt | gcctaatcat | gaactgcact | gttggagtag | tcagaactcg | cctcgaggga | 480 |
| ccaaagcagt | gttctatttc | tgtaccgcca | tcagaaatgg | gtcagaatct | aaagccttg | 540 |
| ttggagtctg | aagttggttg | tgatatcatt | ttccaggttg | ttgatgagaa | atttaaagca | 600 |
| cataagttga | tccttgctgc | ccgctcacct | gtttttagag | cgcagttttt | tgggcttgtt | 660 |
| ggggatccta | acatggataa | agtagtagtg | gaagattttg | agccctctat | cttcaaggca | 720 |
| atgcttttgt | ttatttatac | cgacaagctt | cctgatgtac | aagagattac | aggctcaacg | 780 |
| tccatgtgta | tgtctaccaa | catggtgcag | catcttttgg | ctgctgctga | tctgtacaat | 840 |
| ttagatagac | tcaaagtgtt | gtgcgaggca | aaattgtgtg | aagaacttaa | tgctgacaca | 900 |
| gtggcaacaa | cccttgcact | agctgagcag | caccattgcg | cacagcttaa | ggccatatgt | 960 |
| ttgaaatttg | ctgcaactcc | agcaaacttg | ggagcggtaa | tgcagtcaga | agggttcagg | 1020 |
| cacttggagg | aatgttgccc | atctttgttg | tctgagcttt | tgaagacctt | tgcatcaggt | 1080 |
| gaggagagct | tgagtcagct | gtccagtagg | aagaggagtg | gcagcagtgt | atacgggatg | 1140 |
| gatctagcag | cagaaggtcc | tgtggcagaa | tcggtgaatc | ctaatggcag | gcgtgttcgg | 1200 |
| aggcgttga | | | | | | 1209 |

<210> SEQ ID NO 73
<211> LENGTH: 1215
<212> TYPE: DNA
<213> ORGANISM: Citrus clementina

<400> SEQUENCE: 73

| | | | | | |
|---|---|---|---|---|---|
| atgggcaatt | cggagaaaga | ttcgacgtcg | aagtcaatta | cgagacggt | gaacgggtcc | 60 |
| caccagttca | cggtaaaagg | ttactccctg | gcgaagggaa | tgggccctgg | caagtgctta | 120 |
| tcgagcgacg | ttttttaccgt | gggcggttac | gattgggcga | tttactttta | ccccgacggc | 180 |
| aagaacccgg | aagatggggc | tttgtatgtt | tcggtgttta | ttgcgttggc | gagtgaagga | 240 |
| acggacgtga | gggcgctgtt | tgagttaact | ttggttgacc | aaagtgggaa | aggaaagcat | 300 |
| aaagttcata | gtcatttga | tcgagcgtta | gagagtggcc | cgtacacctt | gaagtatcgt | 360 |
| ggaagcatgt | ggggctataa | gcgcttcttt | aaaagaacat | ctctggagac | ttctgattat | 420 |
| attaaggatg | attgtcttct | catcaactgc | actgttggag | ttgttagaaa | ccgccttgag | 480 |
| ggaccaaaac | agtattccat | accagtgcca | ccgtcagaca | tgggccaggg | tcttaaggat | 540 |
| ttgctagagt | ctgaaattgg | atgtgacata | gttttgaggg | ttggtgatga | aacatttaaa | 600 |
| gctcataaac | tgatacttgc | tgctcgctct | cctgttttca | gagcccaatt | ctatgggctt | 660 |

```
gttggagatc gtaacttgga taaagtagtt gtgaaggatg ttgaaccctc aatcttcaag      720
gcaatgctcc tgtttatata caccgataaa tttcctgatg tatatgaaat tactggcaca      780
acatcaatgt gcacaacaac caacatggta cagcatctac tggctgcagc tgatctttat      840
aatgtagatc gattgaaatt gttgtgtgaa tcaaaattat gtgaagaact aaatgctgag      900
acagtggcca caacactcgc actggcagaa caacatcagt gtccccagct taaggctatc      960
tgcttgaagt ttgctgcaac tccggcgaat ttgggagtga taatgcagtc agaagggttc     1020
aagcacttgg aggagagctg cccatcactg ttgtccgagc tcctgaagac attggcttca     1080
ggtgatgata cctcaagtct gtcatcaaat aggaaaagaa gtggcagcag tatatatgca     1140
ctagatctag ctggagatgg ggcagcagca gagtcagcaa atcccaatgg caggcgtgta     1200
cgaaggcggt tttag                                                      1215

<210> SEQ ID NO 74
<211> LENGTH: 1227
<212> TYPE: DNA
<213> ORGANISM: Ricinus communis

<400> SEQUENCE: 74
atggttgaat tgaagtcaga ttctgataaa gagtcatgtt caatgtcaat aaacgagacg       60
gtaaatgggt ctcaccaatt ttccataaaa gggtattctt tagcgaaagg aatgggagct      120
ggaaaatgta tagcaagtga tattttcact gtgggtggtg atgattgggc gatctatttt      180
tacccagatg gtaaaaatcc tgaagatagt tctatgtatg tttctgtttt tgtagctttg      240
gctagtgaag gaactgatgt tagggctttg tttgagttga ccttggttga tcaaagcgga      300
aatgggaagc ataaagttca cagtcatttc gatcgtgcgt tggaaagtgg gccttatact      360
ttgaagtata gagggagcat gtggggttac aagcgtttct ttagaagaac aactcttgaa      420
aattctgatt atataaagga tgattgccta atcatgaact gcacagttgg agttgttaga      480
acccgtcttg aaggaccaaa gcagtattcc atttcacttc cgccgtcaga catggggcaa      540
ggccttaagg aactgttaga atctgaagtt ggttgcgaca ttgttttcca ggttggggat      600
gaaacattta aagcgcataa gttgatactt gctgctcgtt cccctgtttt tagagctcaa      660
ttctttggac ttgttgggga tccaaactta gataaagtag tagtggagga tattgacccc      720
tcaattttca aggcaatgct cctgtttata tacacagaca agcttcctaa tgtacatgag      780
attactggca caacatcaat gtgcacatcc accaacatgg tgcagcattt attggctgct      840
gctgatcttt acaatttaga tcaattgaaa ttgttatgtg aatcaaaatt gtgcgaggaa      900
ctgagtgctg agactgtggc aacaactctt gcattagctg agcagcatca atgttcgcaa      960
ctcaaggtcg tctgtctgaa atttgctgca aatccagcaa acttgggagc ggtaatgcag     1020
tcagaaggat tccgacactt ggaagagagc tgcccttcat tgttgtgcga gatgctaaag     1080
acatttgcgt caggcgatga gaactcaagt cttctatcaa gtcggaagag gagcggaagc     1140
agtatatatg ggctagatat agctgcagat ggggctgcag cagaatcagc caatcccatg     1200
ggcaggcgag taaggaggcg ttttttag                                        1227

<210> SEQ ID NO 75
<211> LENGTH: 1260
<212> TYPE: DNA
<213> ORGANISM: Eucalyptus grandis

<400> SEQUENCE: 75
atgcagcgca aagcgatgtg cgctccgatc ggcggcggcg gcggcgacgg cggggggggag       60
```

```
tgcggctcga cgtcgatcag ccggacggtg aacgggtcgc acacgttcac gatcagcggc    120
tactcgctgg ccaaggggat gggggccggg aagttcatcg ccagcgacgt gttcaccgtc    180
gggggctacg actgggccat ctacttctac cccgacggga agaacccgga ggacagcacg    240
acgtacgtgt ccgtgttcat cgccctggcc agcgacggct ccgacgtcag ggcgctgttc    300
gagctgaccc tggtcgacca gagcgggaag gggaagcaca aggtccacag ccacttcgac    360
cgcgcgctcc agagcgggcc ttacacgctc aagtaccgcg gcagcatgtg gggttacaag    420
cgtttcttga aaagagttgc tttagagact tctgattaca tcaaggacga ttgccttgtg    480
atgcactgta ctgtcggggt tgtgagaacc cataccgagg gccccaaaca gtaccgaatt    540
cctattccgc cgtctgacat gggccagtgt ctgaaggccc tgttagattc tgaagttggc    600
tgcgacatag catttgttgt tggtgacgaa acctttagag ctcataaact gatcctcgct    660
gctcgttctc cggtctttcg agcccaattt ttttggtcttg ttggtgattg caatatagag    720
aaagttgtcg tggaggatgt tgatccctca atttttaagg caatgctcct gttcatttac    780
atggacgaaa tgcctgatct acgtgaaatc acgggctcat cctcttctgg tacattgact    840
aacgtagtgc agcatctgtt agctgctgcc gaccgctaca atctagaacg attgaaatta    900
ttatgtgagt cgaaattatg tgaggagatt actgctgata cagtggctac aacacttgcc    960
ctagcagagc agcaccagtt tggacagctg aaggcaatgt gtctaaaatt tgctgcgcat   1020
ccaacaaact tggcggtggt aatgcagtca gaaggcttca ggcacttgga ggagagctgc   1080
ccttccttgt tgtctgaact gctcaaggct tttgtaacgg tggatgattc ttctgaccga   1140 tttttcaaata agaagagagg caccagcagc atttacggac tagatacggt gccagttgtg   1200
actggagctg aacatgggga tatagatgga aggcgtgtga agaggcggaa tttagaatga   1260
```

<210> SEQ ID NO 76
<211> LENGTH: 1221
<212> TYPE: DNA
<213> ORGANISM: Vitis vinifera

<400> SEQUENCE: 76

```
atggttaatt ccaaggccga tattgagaga gactcgtgtt cgaagtcgat caacgagacg     60
gtgaatggct cgcaccattt cttgataaag ggttattccc tcgcaaaggg aatgggcgcg    120
ggcaaataca tctcgagcga cacgtttacc gttggaggat atgattgggc aatttacttc    180
tatcctgatg gcaagaacgc ggaggataat tcgatgtatg tgtcggtgtt cattgcgttg    240
gcgagcgagg gcactgacgt tagggctttg tttgaattga cgttgttgga tcagagtggg    300
aaaggcaagc acaaagtaca cagtcatttt gatcgcgcat tggagagtgg cccatatact    360
ttgaaatata gaggaagcat gtggggctac aagcgcttct tcagacggac aactttagaa    420
acatctgatt ttatcaagga tgattgcctt gctatgcatt gcactgttgg ggttgtcaga    480
actcgtgttg aggggcctaa acagtatacc attcctatac caccttcaga cattggtcag    540
agtcttaagg acttgctaga atctgaagtt ggttgtgaca taacttttca ggttgcagat    600
gagacattca aagctcataa gttgatactt gctgctcgtt ctcctgtatt tagagctcag    660
ttttttggac ttgttggaaa tcctaatatg gataaagttg tagtggagga tgttgaaccc    720
tctatcttta aggcgatgct cctgtttatt tactcagaca gcttcctga tgtagacgaa    780 attacaggct cagcgtctgt gtgcacatcc acaataatgg ttcagcactt actagctgct    840
gctgaccgct ttggtttaga tcgtctgaaa ctattatgtg aatcaaaatt gtgtaaagaa    900
```

```
gtcagtgctg aaacggtggc cacaacactt gccctagctg agcagcatcg ttgtccacaa    960
cttaaagcca tctgtttgaa atttgcagcc actccgtcaa tcttgggagc ggtaatgcaa   1020
tcagaagggt ttgggtactt ggaagagtgc tgcccctcat tgttatctga gctgcttgga   1080
gtgattgcat cagtagatga aaacttgacg atgctctcga gtaagaagag aagtggcagc   1140
agcatattag ggttagatct accagcagat ggagctccag cagaatcagc cagtggcagg   1200
cgcataagga ggcggtttta g                                             1221
```

<210> SEQ ID NO 77
<211> LENGTH: 1278
<212> TYPE: DNA
<213> ORGANISM: Prunus persica

<400> SEQUENCE: 77

```
atgccgaatc acaaatcgtc cagaggggct caattgggtg aagccatgtc gaattcgaag     60
cctggagtcg accaggagtc gtgttcgaga tcgatcagcg agactgtcaa tgggtctcac    120
cggttcacga taaaggggta ttcttttggcc aaagggatgg gtgccggaaa gtacataatg    180
agcgatacgt ttacggtggg tggctacgat tgggcaattt acttctaccc cgacggcaaa    240
aatcctgagg atagttccac gtacgtctcc gttttcattg ctctggtcag tgagggtacg    300
gatgtgaggg ctttgttcga gctgactttg gtggaccaga ccaagagtgg aaggacaaag    360
gtgcatagcc actttgatcg cgcgctcgag agcgggccgt acacgttgaa gtacagaggc    420
agcatgtggg gttacaagag attttttcaaa agatcagccc tcgaaacttc tgagtttcta    480
agggatgatt gccttgtatt gaactgcact gttggagttg tcagaactcg ccttgagcga    540
ccaaaacaat tttcaattac tgtaccatca tcagacatgg gtcaagatct taaggacttt    600
ctagactctg aagctggttg tgacatagtt tttcaggttg gcgatgaatt gtttaaagct    660
cacaagttga tacttgctgc ccgttctcct gtatttagag cacagttttt tggacttgtc    720
ggggattgta gcatagataa agtagttgtg aaggatgttg agcccttttat cttcaaggca    780
atgcttctgt ttatttacac ggacaaactt cctgatgtac acgaagttat gggctcatca    840
ccattgtgca cattcactgt catggtgcag catcttttgg ctgccgcgga cctgtataat    900
ctagaacgac tgaaagtatt gtgtgaatca agttgtgtg aagaaatcac tactgaaaca    960
gttgcgacca cacttgctct agctgaacaa catcactgtc cgcagctcaa ggctgtgtgc   1020
ttaaaattg cagcaaatcc tgcaaactta ggagctgtga tgcaatcaga tgggtacaag   1080
catctagaag agagctgccc ctcaatgttg ctggagttgc tagagacatt tgcagcagtg   1140
gatgagagct caagtcttct gtcaagtagg aagaggagtg gcagcagcat atatgggcta   1200
gacttgccag cagatggtgg cggggctgta gcagaatcag caaatcccaa tggaaggcgt   1260
gtgaggcggc ggtattag                                                1278
```

<210> SEQ ID NO 78
<211> LENGTH: 1245
<212> TYPE: DNA
<213> ORGANISM: Phaseolus vulgaris

<400> SEQUENCE: 78

```
atggcggaat tggaggagga ccggatgggg gatttcaagc ccttctcgga gggctcttcg     60
tgctcacgtt cgatcagcga aacggtgaat ggctctcacc aattcacgat aaagggtac    120
tctctcgcaa aggggatggg tgctgggaag tacatcatga gcgacagttt tagcgttggt    180
ggttacgatt gggcaattta cttctaccct gatgggaaga accccgagga caattccatg    240
```

```
tacgtttcgg tcttcatagc tctcgctagc gacggaaccg atgttagggc tctgttcaag      300
ttgacgctgg tggatcagag tgagaaggga acgataagg tccatagcca tttcgatagg      360
cctcttgacg gtggaccgta caccttgaag tatagaggca gcatgtgggg ttacaagcgt      420
ttcttcagaa gaaatttact tgaatcttca gagtatctaa aagacgattg ccttgtcatg      480
cattgcactg ttggtgttgt caaaactcgt tttgagggat ctaaacaagg tgttactgtg      540
ccacagtcag acatgggccg aaattttaag gacttgctgg actcagaggt tggttgcgac      600
atagttttca aggttaaaag cgaaagcttc aaagctcata agttaatact tgcggcccga      660
tctcctgtgt ttagagcaca gttttttgga cttgttgggg atcctagctt agaggaagta      720
gtggtagagg atattgagcc ttttatcttc aaggcaatgc ttctcttcat ttattctgac      780
aaacttccag acatctatga agttatggac tcaatgaatg tctgctcata tgccgtcatg      840
gtgcagcatc tcttggctgc tgctgatctc tataatcttg accggctcaa actgctttgt      900
gaatcaaaat tgtgtgaaga aatcaatact gacaatgtag ccacgacact tgccctggca      960
gagcaacaca actgtccaca gcttaaggca atctgtttaa aatttattgc caatccagca     1020
aatttgggag ctgtaatgca gtcggaagct tttgtgcatt tgaaagagag ctgccccgca     1080
atgttgttgg agctgctgga gacatttgcc tcagtggacg ataactcaag cctgacattg     1140
agcagaaaga gaagtggcag tagcatatat gctcaagatt tggcagacgg ggcagctact     1200
gaatcagtta atccaaatgg caggcgagta aggaggcgaa cataa                    1245

<210> SEQ ID NO 79
<211> LENGTH: 1245
<212> TYPE: DNA
<213> ORGANISM: Glycine max

<400> SEQUENCE: 79
atggcggaat tggaggagga gcggatgggg gatttcaagc ccttctcgga aggttcttcg       60
tgctcgcgtt cgatcagcga aaccgtgaac ggctcgcacc aattcacgat aaagggttac      120
tctttggcca aagggatggg tgctggaaag tacatcatga gcgacacttt caccgttggt      180
ggttacgatt gggctattta cttctacccc gatgggaaga accctgagga caattccatg      240
tacgtttcgg tctttattgc gctcgctagc gacggaaccg atgttagggc tttgttcaag      300
ttgacgctgg tggatcagag tgagaagggg aatgataaag ttcatagcca tttcgatcgc      360
cctctcgaga gtggacctta taccttgaag tataaaggca gcatgtgggg ttacaaacgc      420
ttcttcagaa gaacacaact ggaaacctca gagtatctaa aaaatgattg ccttgtcatg      480
cattgcactg ttggtgttgt taaaactcgt tttgagggat ctaaacaggg tgttattgtg      540
ccacagtcag acatgggccg ggattttaag gacttgttgg aatctgaggt cggttgtgac      600 atactttttca aggtcaaaag tgaaagcttc aaagctcata agttgatact tgcagcccga      660
tctcctgtgt ttagagccca gttttttggg cttgttgggg atcctacctt agaggaagta      720
gtggtagagg atattgagcc ctttatcttc aaggcaatgc ttctctttgt ttactctgac      780
aaacttcctg gcatatatga ggttatggac tcaatgccct tgtgctcata caccgtcatg      840
gtgcagcatc tcttggctgc tgctgatctc tataatcttg atcggctcaa actgctttgc      900
gaatcaaaat tgtgtgaaga aatcaatact gacaatgtgg ccacaacact tgcgctggca      960
gagcaacatc actgtccaca gcttaaggca atctgtttaa aatatattgc aaatcctgca     1020
aacttgggag ctgtaatgca gtcagaagct tttgtgcatt tgaaagagag ctgccccctca    1080
```

| | |
|---|---|
| atgctgttgg aattgctgga gacatttgca tcagtggatg ataactcagg ccagacattg | 1140 |
| agcagaaaga gaagtggcag tagcatatat gggcaagatt tagcagacgg ggcagctgct | 1200 |
| gaatcagtta atccaaatgg caggcgagta aggaggcgga cataa | 1245 |

<210> SEQ ID NO 80
<211> LENGTH: 1236
<212> TYPE: DNA
<213> ORGANISM: Phoenix dactylifera

<400> SEQUENCE: 80

| | |
|---|---|
| atggcgaagc tcgaggagga gcagggagga ttgaacaacc gtcagctcaa tccgctgaac | 60 |
| gtgtcgcggt ctcggtcggt gtgcgagacg gtaaacgggt cgcaccggta cacggtgaag | 120 |
| gggttctcgc tggcgaaggg gatgggtcct ggaaggtacc tgtccagcga cacctt cacc | 180 |
| gtgggggat tccagtgggc cgtctacttc tatcccgacg gcaagaaccc ggaggacaac | 240 |
| tcccttatg tctcggtgtt cattgccctg gcgagcgagg ggaccgacgt gagggcgctc | 300 |
| ttcgaactca ctctgctcga ccagaacggc aaggggagga caaggtgca cagccacttc | 360 |
| gatcgggcgc tggaggccgg gccctacacg ctcaagtacc gggggagcat gtggggttac | 420 |
| aagcggtttt acaggaggac atccttagaa acatcggatt atctcaagga tgattgtcta | 480 |
| attatgaact gcacagtggg tgttgttaga aaccatattg aaacaccaac acagctttca | 540 |
| atttctgtac caccacctga cttgggtcag tgtctcaagg agttgttcat atctggcatt | 600 |
| ggttctgaca tagattttga ggttggtgat gagacattta aagctcacaa gcagattctt | 660 |
| gctgctcgct cgccagtttt tagtgcacaa tttttggtc ttatcgggaa tccaaatgtg | 720 |
| gacaaaattg ttgtggagga tgttgaacct cctattttca aggccatgct tctgtttata | 780 |
| tattcagatg aactccctga tgtgcatgat ctaactggat ctgtttctat gtgcacatcc | 840 |
| acgattatgg tacaacattt attggctgca gcagatagat atggactgga acgtctgaag | 900 |
| ctgttatgcg aagcaaaact gtgcgaagaa gtcactgctg atactgtagc aacaaccttg | 960 |
| gccctggcag agcaacacca atgtgctcaa ttgaaggctg tctgcttaaa atttacagca | 1020 |
| gctcgagaaa acttgggagc tgttatgcag actgaagggt tcaattactt ggaggcgacg | 1080 |
| tgcccatctt tgctgtcaga cttgttggca actgttgctg tggcggatga tgactctagt | 1140 |
| cctatcagca ggaagaggag cggtagcagt aacatagggc tcaatttaat ggacagtgtt | 1200 |
| gatttgaatg ggaggcgtat gaaaaggcgg atgtag | 1236 |

<210> SEQ ID NO 81
<211> LENGTH: 1290
<212> TYPE: DNA
<213> ORGANISM: Fragaria vesca

<400> SEQUENCE: 81

| | |
|---|---|
| atgccaccga ttcagaaaca ctccctccgc ggcgcgcaat tgggcggtag aatctcatcc | 60 |
| atgaagtcga agctcgaaaa cgacgagtcg tgttcgcggt cgatcagcga gaccgtgaac | 120 |
| ggctcccacc ggttcaccat aaagggtat tccttggcca aggaatggg cgccgggaaa | 180 |
| tacatactca gcgacacttt caccgtcggc ggttacgatt gggcgattta ctttacccc | 240 |
| gacggtaaaa accccgagga tagctccgtc tacgtctccg tcttcattgc gctggtgagc | 300 |
| gaaggcaccg acgtgagggc cttgtttgag ctcaccttgg tggaccagag caacagcggc | 360 |
| aaggacaagg tccatagtca ctttgatcgt gcccttgaga gcgggcctta cacgttgaag | 420 |
| taccgtggaa gcatgtgggg ttacaagcga ttcttcagaa gatcagccct tgaaacgtcc | 480 |

| | |
|---|---|
| gagtttctaa aggatgattc ccttgtgttg aactgcactg ttggagtcgt cagaactcgc | 540 |
| ctagagtgtc cgaaacattt tgcaattact gtaccaccat cagacatggg tgaaggtctt | 600 |
| aaggcctttc tagactctgg agctggttgc gacctggttt ttcaggttgg cgatgaggaa | 660 |
| ttcaaagctc acaagttgat acttgctgct cgttctcctg tattcaaagc acagtttttt | 720 |
| ggacatcttg gagattcgag tgtagataaa gtagtcgtga aggatgttga gcccttcatc | 780 |
| ttcaaggcaa tgcttctttt tatatacggg gacaaacttc ctgatatccg tgaagttaca | 840 |
| ggttcatcat ctttgtgcac attcactgtc atggtgcagc atctgttggc tgctgcagac | 900 |
| ctgtatgacc tagagcgact gaagttgttg tgtgaatcaa tgttgtgtga agaaatcacg | 960 |
| actgaaacag tggcaaccac attggccctt gctgagcagc atcactgtcc acagctgaag | 1020 |
| gctgtgtgtc taaagtttgc ggcaaagtca acaaacttgg gagctgtaat gcagtcagat | 1080 |
| ggatacaagc atctagaaga gagctgcccc tcagtgttac aggagctgct gaagacattt | 1140 |
| gcatctgtcg atgccaatga gaattcaaat tcaagtaaga gaggagtgg cagcagcata | 1200 |
| tatgggctag acttgccagc agatggcagt ggggcagtag cagaatcagc aaatcccaat | 1260 |
| ggtaggcggt tgaggccgcg gcgatattaa | 1290 |

<210> SEQ ID NO 82
<211> LENGTH: 1281
<212> TYPE: DNA
<213> ORGANISM: Malus domestica

<400> SEQUENCE: 82

| | |
|---|---|
| atgccgccga ttcggaaaca ttccagaggg gcgaaatcgg gtgaatccat ggggaattcg | 60 |
| aagcctgggt tcgaccagga atcgtgctcg agatcgatca gcgagactgt gaacggctcc | 120 |
| caccggttca cgataaaggg gtattcgctg gccaaaggga tgggagccgg gaagtacctg | 180 |
| atgagcgata cgttcacggt gggcggatac gattgggcaa tttacttta ccccgacggt | 240 |
| aaaaaccccg aggatagcaa cgcgtacgtc tcggttttca ttgctttggt tagtgagggt | 300 |
| acggatgtga gggctctgtt cgagctgacg ttggtggatc agacggacag tgggaaggac | 360 |
| aaggtgcaca gtcactttga tcgcgctctc gagggcgggc cgtacacgct gaagtacaga | 420 |
| ggcagcatgt ggggttacaa gaaattcttc agaagatcaa tcctagaaac ttctgagttc | 480 |
| cttaaggatg attgccttgt attgaactgc actgttggag ttgtcagaac tcgccttgag | 540 |
| caaccaaaac aatttacaat cactgttcca tcatcagaca tgggacgaga cctaaaggac | 600 |
| tttctagatt ctgaagctgg ttgtgacata gttttcagg ttggtgatga acagtttaaa | 660 |
| gctcacaagt tgatacttgc tgctcggtct cgtgtattta gagcgcagtt ttatggactt | 720 |
| gtcggggatt gtaacgtaga taagtagtt gtgaaggatg ttgagccctt catcttcaag | 780 |
| gcaatgcttc tctttattta cacggacaaa cttcctgata cacacgaagt tatgggctca | 840 |
| tcacctttgt gcacattcac tgtcatggtg cagcatctgt tggcagctgc agacctgtat | 900 |
| aatctagatc gactgaaatt gttgtgtgaa tcaaagttat gtgaagaaat cactactgag | 960 |
| acagtggcga ctacacttgc gcttgctgaa cagcatcaat gccgacagct taaggatgtc | 1020 |
| tgtcttaaat ttacagcaaa tccgtcgaac ttggagctg taatgcaatc agaagggtac | 1080 |
| aagcatctag aagagagctg cccatcaatg ttggtagagc tgctggagac atttgcagcg | 1140 |
| gtggatgaca attctagtct tctgtcaagt cggaagagga gtggcagcag catatatgga | 1200 |
| ctagatttgc cagcagatgg gggtgggact gcagcagaat cagcaaatcc caatggtagg | 1260 |

-continued

```
cgcgtgaggc ggcggtttta g                                        1281
```

<210> SEQ ID NO 83
<211> LENGTH: 1227
<212> TYPE: DNA
<213> ORGANISM: Solanum lycopersicum

<400> SEQUENCE: 83

```
atgaaccaaa tttccgtcga ccgtgccggg aaggattcat catccaagtc tgtaaacgaa    60
acggtgaatg ggtctcacca ttttaccatc aggggttact ctttggccaa aggaatggga   120
ccgggaaagt acatatctag cgacattttc accgttggtg ggtatgattg gcaatttat    180
ttctacccag atggtaaaaa catagaggat tcttcaatgt atgtgtctgt ttttatagca   240
ttggctagcg aaggaacgga tgttagggcg ttgtttgagt tgacgatgtt ggatcagagt   300
ggaaaagtga acataaagt tcatagccat tttgatcggg cattggaaag tggaccttat   360
actttgaaat atagaggaag catgtggggt tacaaacgat tttttagaag agcaagttta   420
gaaacttctg actacctgaa ggatgattgc ctttccatgc actgtactgt ggagttgtc    480
agaactcgtg ttgaaggccc caaaaattat agtgttacaa ttccaccttc agacatgggt   540
caaagtctca atacttgct ggatgctgaa cttggttgtg atatagtttt ccgggttgga    600
gaagaggcat ttaagggtca taagttgata cttgctgctc ggtctcctgt atttagagca   660
caattctttg gccttattgg gaatcctaaa acggacgaag tggaaattga ggatattgaa   720
ccctcagtct tcaaggctat gcttcagtac atttattctg atgaacttcc agatttgatt   780
gaaattactg gctctacttc aacttgcact tctacgatag tgacacagca tctattggca   840
gcagccgatc gatttggtgt agataggttg aaagagttat gtgaggcgaa attgtgtgaa   900
gaagttaatg tggatactgt ggcaacaact ctttctcttg ctgagcagca tcggtgccca   960
caactcaagg ccatctgttt gaaatttgca gctacaaact tgggagtggt catgcagaaa  1020
gatggattca agcacttgga agagagttgc cccttattgt tgtcagagct gctgaaaaca  1080
gtagcatccg tcgatgagaa gccaagtctg acgtctagca agaaaaggaa tagcagcagc  1140
agcatctttg gactggatct ggctgcagat ggcgcggcag cagattctgt taaccttacc  1200
gctaggcggg tgaggaggag gatgtaa                                     1227
```

<210> SEQ ID NO 84
<211> LENGTH: 1227
<212> TYPE: DNA
<213> ORGANISM: Solanum tuberosum

<400> SEQUENCE: 84

```
atgaaccaaa tttccatcga ccgtgccgga aacgattcgt catccaagtc tgtaaacgaa    60
acggtgaatg ggtctcacca ttttaccatc aggggttact ctttggccaa aggaatggga   120
cctggaaagt acatatctag cgacattttc accgttggtg ggtatgattg gcaatttat    180
ttctacccag atggtaaaaa catagaggat tcttccatgt atgtgtctgt ttttatagca   240
ttggctagcg aaggaacaga tgttagggcg ttgtttgagt tgacgatgtt ggatcagagt   300
ggaaaagtga acataaagt tcatagccat tttgatcggg cattggaaag tggaccttat   360
actttgaaat atagaggaag catgtggggt tacaaacgat tttttagaag agcaagttta   420
gaaatgtctg actacctgaa ggatgattgc ctttccatgc actgtactgt ggagttgtc    480
agaactcgtg ttgaaggccc aaaagattat agtgttacaa ttccaccatc agacatgggc   540
caaagtctca atacttgct ggatgctgaa cttggttgtg atatagtttt ccgggttgga    600
```

-continued

```
gaagaggcat ttaagggtca taagttgata cttgctgctc ggtctcctgt gtttagagcc    660
caattctttg gccttattgg gaatcctaaa acggacgaag tggaaattga ggatattgaa    720
ccctcagtct tcaaggctat gctccagtac atttattctg atgagcttcc agatttaatt    780
gaaattactg gctctacttc aacttgcact tctacgatag tgatgcagca tttattggca    840
gcagctgatc gatttggttt ggataggttg aaagagttat gtgaggcgaa attgtgtgaa    900
gaagtcaatg tggatactgt ggcaacaact ctttctcttg ctgagcagca tcgatgccca    960
caactcaagg ccatctgttt gaaatttgca gctacaaact gggagtggt catgcagaaa   1020 gatggattca agcacttaga agagagctgc cccttactgt tgtcagagct gctggaaaca   1080
gtggcatccg tcgatgagaa gccaagtctg acgtctagca agaaaaggag tagcagcagc   1140
agcatctttg gactagatct ggctgcagat ggcgcagcag cagattctgt taaccttacc   1200
gttaggcggg tgaggaggag gatgtaa                                       1227
```

<210> SEQ ID NO 85
<211> LENGTH: 1203
<212> TYPE: DNA
<213> ORGANISM: Oryza brachyantha

<400> SEQUENCE: 85

```
atgacggtgc cgccgccgac gccgccccc tcgtggtctc gctccgtcac ggagaccgtg     60
cggggatctc accagtacac cgtcaagggc ttctccatgg ccaagggcat gggccccggc   120
cgctacgtca ccagcgacac cttcgccgtc ggcggctacc actgggccgt ctacctctac   180
cccgacggta agaaccccga ggacaacgcc aactacgtct ccgtcttcgt cgccctcgcc   240
tccgacgggg ccgacgtccg cgccctcttc gagctcaccc tcctcgacca gtccggccgc   300
ggacgccaca aggtccattc ccatttcgac cgatccctgc aggccggacc ctacaccctc   360
aagtaccgag gctccatgtg gggttacaag cgcttctaca agatcactcc ctagaatct    420 tccgactttc tcaaggacga ttgccttgta atgaactgca cagtaggcgt cgtcaagaac   480
cgtctcgaaa ccccaaagaa cattcagatc cacattccgc cttctgacat gggccgttgc   540
ttcaagaacc ttctcaacct cggcattgga tgtgacataa ctttcgaggt tggtgatgac   600
acagtccagg cacacaagtg gattcttgct gctcgctccc cggtattcaa agcccaattc   660
tttggtccta ttgggaatcc tgacctacac tcggtcactg tggaggatgt tgaacctgtt   720
gttttcaagg cgatggtgaa tttcatatac tccgatgaac ttcctagtat tcatgaacta   780
gctggatctg tctcaacatg gacatcgaca gtagtagtac agcatttgtt ggcagcagct   840
gatagatatg gattagatcg gctacgtctc ctatgcgagg aaaagttatg tgatgaactc   900
acagctgaaa cagttgcaac aaccttagcc ctagctgaac aacatcattg tactcagctg   960
aaatctgctt gcctaaagtt cactgccgtt cgggaaaatc tgggagctgt gatggagaca  1020
gaaggattta actacttgga ggagacatgc ccgtccctac tgtccgactt gttggctact  1080
gtcgcagtgg tggatgatga ttctgcaaca ttaaaccgga agaggggagt cagtggtaac  1140
gaaggagcga atcccgtgga gagcgtggag gctagtgaaa ggcgcatccg caggagggtt  1200
tag                                                                1203
```

<210> SEQ ID NO 86
<211> LENGTH: 1194
<212> TYPE: DNA
<213> ORGANISM: Brachypodium distachyon

```
<400> SEQUENCE: 86
atggcggcgg tgccgcggcc gtcgtggtcg cgctcggtca gcgagacggt gcggggtcg      60 caccagtaca ccgtcaaggg cttctccctc gccaagggca tcggtcccgg ccgccacctc    120
gccagcgaca ccttcgccgt cggcggctac gactgggccg tctacctcta ccccgacggc    180
aagaaccccg aggacaacgc cagctacgtc tccgtcttcg tcgccctcgc ctccgagggc    240
accgacgtcc gcgccctctt cgagctcacc ctcctcgacc agtccggccg cgcacgccac    300
aaggtccact cccacttcga ccgctccatg caggccggac cgtacaccct caagtacagg    360
ggatccatgt ggggttacaa gaggttctac agaaggtcac agttagaaac atcagatttt    420
ctaaagaacg attgcctagt aatgaactgc acagtaggtg ttgtcaagac tcggctcgaa    480
acaccaaaga acatccagat taacgttcct ccatctgaca tcggccgttg cttcaaggag    540
ctcctcagac tccgcattgg ctgtgacata acatttgaag taggtgacga aaggtccag    600 gcacataaat ggattcttgc tgctcgttcc ccagtattca agcccaatt ctttggacca    660 attggtaaag ctgacttgga cagagttgtt gtggaggatg ttgaacctat cgtcttcaag    720
gcaatggtga atttcatata ctctgatgag cttcctagta ttcatgaact agctggatct    780
ttctcaatgt ggacatcaac tgcagttata cagcatttgt tggcagcagc tgatagatat    840
ggattggacc ggctacgaat actatgtgag gcacagttat gtgatgggct tactgctgaa    900
acagttgcga caaccttagc cctggctgaa cagcatcatt gtgctcagct caagtcagcc    960
tgcttaaagt ttactgctgt ccgagaaaat cttggagttg tgatggagac tgatgggttt   1020
aactacttgg aggagacatg cccatccctg ctgtctgatt tgttagcaac cgtcgcggta   1080
gtggacgatg atcctacatc tgttaaccgg aaaaggggag tttgtatcaa cgaagatgtg   1140
aatccagttg aaagtgttga ggctagtgac aggcgcatcc gcaggagggt ttag         1194

<210> SEQ ID NO 87
<211> LENGTH: 1188
<212> TYPE: DNA
<213> ORGANISM: Oryza sativa

<400> SEQUENCE: 87
atgacggcgg cggcgtcgtg gtcccggtcg gtgacggaga cggtgcgggg gtctcaccag      60
tacacggtga aggggttctc gatggcgaag ggcgtagggg ccgggcggta cgtgagcagc     120
gacaccttcg cggtgggcgg ctaccactgg gccgtctacc tctaccccga cggcaagaac     180
cccgaggaca cgccaactac gtctccgtc ttcgtcgccc tcgcctccga cggcgccgac     240
gtccgcgccc tcttcgagct caccctcctc gaccagtccg gcgcggccg ccacaaggtc     300 cactcccact cgaccgatc cctccaggcc ggaccctaca ccctcaagta ccgaggctcc     360
atgtggggct acaagcgctt ctaccgaaga tcactcttag aatcatccga ctttctcaag     420
gacgactgcc tcgttatgaa ctgcactgta ggcgtcgtca agaaccgtct cgaaacacca     480
aagaacatcc acatcaatat tcctccatcc gacatgggcc gttgcttcaa caacctcctc     540
aatctccgca tcggctgtga cgtatctttt gaggtgggtg atgaaagagt ccaggcgcac     600
aagtggattc ttgctgcccg ctcccctgta ttcaaagccc aattctttgg tcctattggg     660
aatcctgacc tacacacagt cattgtcgag gatgtagaac ctcttgtctt caaggcaatg     720
gtgaatttca tatactctga tgaacttcct agtattcatg aactagctgg atctgtctca     780
acttggacat cgacagtagt agtacagcat ttgttggcgg ctgctgacag atatggacta     840
gatcggctac gtctgctatg cgaggaaaag ttatgtgatg aactcactgc tgaaacagtt     900
```

```
gcaacaactt tagccctagc tgaacaacat cattgtactc agctgaaatc tgcttgtctg      960
aagttcactg ctgttcggga aaatctggga gctgtgatgg agacagaagg atttaattac     1020
ttggaggaga catgcccgtc cctgctatct gacttgttag ctactgtcgc agtagtggat     1080
gatgatgctg cgtcattcaa ccggaagagg ggagtcggtg gtaacgaagg agcgaatcct     1140
gtggagagcg tggaggctag tgataggcgc atccgcagga gggtttag                  1188
```

<210> SEQ ID NO 88
<211> LENGTH: 1191
<212> TYPE: DNA
<213> ORGANISM: Hordeum vulgare

<400> SEQUENCE: 88

```
atggcggtgc cgcggccgtc atggtcgcgg tcggtcacag agaccgtgcg gggttcgcac       60
cagtacaccg tcaagggatt ctccctcgcc aagggcatcg gccccggccg gcacctctcc      120
agtgacacct tcgccgtcgg cggctatgac tgggccgtct acctctaccc ggacgggaag      180
aaccaagagg acaacgccaa ctacgtctcc gtgttcgtcg ccctcgcctc cgagggtacc      240
gacgtccgcg ccctcttcga gctcaccctc ctcgaccagt ccggccgcgc cgccacaaag      300
gtccactccc atttcgatcg atccatgcag gccggaccat acaccctcaa gtacagagga      360
tccatgtggg gttacaagag attctacaga aggacacagt tagaagcatc agattttta      420 aaggatgatt gcctagtaat gaactgcaca gtaggtgtcg tcaagaaccg tctcgaaaca      480
ccgaagaata tccagattaa tgtccccca tctgatattg gtcgttactt caaggaactc      540
ctcaaactcc acattggctg cgacataact tttgaagtag gtgatgagaa agtccaggca      600
cataaatgga ttcttgctgc tcgctcccct gtgttcaaag cccaattctt tggacctatt      660
ggtaaacctg acttggacag agttgttgtg gaggatgttg aacctatcgt cttcaaggca      720
atggtgaatt tcatatattc tgatgagctt cctagtattc atgaagtagc tggatctttc      780
tcaatgtgga catctactgc ggtaacacaa catctgttgg cagcagctga tagatatgga      840
ttggaccggc tacgaatcct atgtgaggca aagttatgtg atgaactcac ttctgaaaca      900
gtagcgacaa ccttagccct agctgaacag caccactgtg ctcagctcaa gtctgcctgt      960
ctaaagttca ctgctgttcg acaaaatctg ggagctgtga tggagacaga agggtttaat     1020
tacttggagg agacttgccc atccttgctg tctgatttgt tagcaacagt cgcagtagtg     1080
gatgatgatc ctgcatctgt taaccggaaa aggggagttt gtatcaatga agatgcgaat     1140
cccgtcgaaa gcgttgaggc tagtgacagg cgcacccgca ggagggttta g              1191
```

<210> SEQ ID NO 89
<211> LENGTH: 1230
<212> TYPE: DNA
<213> ORGANISM: Selaginella moellendorffii

<400> SEQUENCE: 89

```
atggcacgga cgtcggtagt cttgcaggac gattcagggc aagtggtcgg gagtcccaca       60
tccacggcaa cgccttcccg atctcgatgc atcacagaga ctgtgaatgg atctcaccat      120
ttcacgatcc atggctattc cctggccaaa gggatgggcg tagggaagta cattgcgagc      180
gacacattca cggttggggg ctaccagtgg gcgatctact tctatccgga tgggaagaac      240
accgaggaca actcgctcta cgtgtcggtg ttcatagctc tggcaagtga agggacggat      300
gtgagggcgc tgttcgagct gacgcttctg gatcaaagcg gcaagaacaa gcataagatc      360
```

```
cacagccact tgatcgttc gctggagagt ggtccttaca cactgaagta tcgaggcagt    420
atgtggggtt acaagcgctt cttcagacgg gccgtgctcg agacgtccga ttttctgaaa    480
gacgacagtc tttcaatcac ctgcacggtc ggcgtcgtag tttcctccat gcaagccttg    540
aagcaacact ctttgttagt tccggaatcc gatattggcc acatttcct gtctttgttg     600 gaaagtggtg aaggaacgga cgttaacttt aacgtaaaag gggaggcatt cagtgctcac    660
aagttgttac tggctgcgag atccccagtg ttcaaagcgc agctgtttgg acccatgaag    720
gacgagaatg gtgacgtgat cgaaatcgac gacatggaac cacctgtctt caaggccatg    780 ctacactta tatataaaga cagtctgccc gataccaacg agatgacagg gtcttcgtca     840
cagtcgacgg cgacgatgat ggctcagcat ttactcgcag ccgcagatag gttttgcctg    900
gatcgtttaa gacttttgtg cgagtccagg ctctgtgaac agatcactgt tgacacagtg    960
gcgactacgc ttgcgttggc agaccaacac catgcatctc agctcaaaaa tgtctgcctc    1020
aagttcgctg cttccaacct tgcagtggtg atgcagtctg atggttttga gtacctgcgt    1080
gagagctgcc cgtcattaca atccgagctc ctcaagacgg tcgcgggagt agaagaagaa    1140
gccaaggctg aacaaagaa caggaccgtc tggacgcacg tcgcagatgg tggcgacgga    1200
ttgggaaggc gcgtgcggca aagatctga                                    1230

<210> SEQ ID NO 90
<211> LENGTH: 1233
<212> TYPE: DNA
<213> ORGANISM: Medicago truncatula

<400> SEQUENCE: 90
atgggtaaga ttctccgaga aaccgcgaaa ccatcttcca atccatcatc accatcttcc    60
tcatcggaac cggcgacaac ttcttcgaca tcgataaccg aaacagtgaa aggctcgcac    120
cagttcaaga tcactgggta ctcgctttcg aaagggatcg ggattgggaa atacatagcg    180
tcggatatct tttcgttgg tgggtacgat tgggccattt attctaccc tgatggaaag     240 agtgttgagg ataatgctac ctatgtgtcg cttttcattg cgcttgcgag tgatgggact    300
gatgttaggc ctcttttga gttgaccctt ttggatcaga gtgggaaaga gaggcataag    360
gttcatagcc attttgagag gactcttgaa agtggacctt ataccttgaa ataccgcggt    420
agtatgtggg gttacaagcg gttttttaag aggacagctt tagagacatc tgattacctt    480
aaagatgatt gcctttctgt taattgtagt gttggtgttg tgaggtcacg cacggaaggc    540
ccaaagatat attccattgc aataccacct tctaacattg gtcaccaatt tggtcaactg    600
ctggaaaatg gtaaaggaag tgatgtgagc tttgaagtgg atgggaagt tttcactgct    660 cataaattgg tgctagcagc tcgttcacct gtttttcagag cccagctttt tggtcctatg    720
agagatcaaa gtacccagtc tattaaagtt gaagacatgg aagctccagt tttaaggca    780 ttgcttcatt ttatgtactg ggactcgctg cctgacatgc aagagcttac tgggatgaac    840
acaaaatggg caacaacctt gatggcccaa catcttctag cggctgctga tcgttatgcc    900
ttagagaggc tcaggcttat atgtgaagcg agtctatgtg aagatgttgc cattaatacc    960
gtggctacaa ctttagcctt ggcagagcaa caccactgtt tccagctgaa agcagtctgt    1020
ctcaagttta ttgccacctc tgaaaatctc agagctgtga tgcaaactga tggatttgag    1080
tacttgaagg aaagttgccc atctgttctg actgagctac tggagtacgt ggctagattt    1140
actgagcatt cggactttt gtgcaagcac aggaatgaag caatacttga tggtagcgac    1200
ataaatggaa ggcgggtgaa gcaaaggctt tag                                1233
```

<210> SEQ ID NO 91
<211> LENGTH: 1230
<212> TYPE: DNA
<213> ORGANISM: Coffea canephora

<400> SEQUENCE: 91

| | | | | | |
|---|---|---|---|---|---|
| atgggaaggg | tttacaatgg | agaaacctcc | aacccgtcgt | cttccacaac | ggcgtcaaca | 60 |
| tcgccgccgc | cggtgacgac | gtcgacgtcg | atcacggaga | ctgtgaatgg | aacgcacgat | 120 |
| tttaagatca | cggggtattc | cttgtccaag | ggaattggga | ttggcaagta | cgtagcgtct | 180 |
| gatattttca | tggtgggagg | ctatgcgtgg | gcgatctatt | tctatcctga | tgggaaaagc | 240 |
| gtggaggaca | atgcgacgta | tgtttccttg | tttattgcgc | tagccagcga | gggaacggac | 300 |
| gttagagcgc | tgtttgaact | gacgcttatg | gatcagagcg | ggagagcgag | gcataagatt | 360 |
| catagccatt | tcggaagggc | tttagagagt | gggccttaca | cgttaaaata | ccgcggaagc | 420 |
| atgtggggct | ataagcggtt | ttttaagaga | actgcactag | aaacatcaga | ctatctgaag | 480 |
| aatgattgtc | ttcaggttca | ttgttgtgtt | ggtgtagtta | gatcccaaac | tgagggaccc | 540 |
| aaaatctact | ctataccgct | tccaccttcg | gacattggtc | aacattttgg | gcagctactg | 600 |
| gaatgtggaa | agggaactga | tgtaaatttt | gaagtcaatg | gagaaaaatt | ttctgctcac | 660 |
| aagttggttc | ttgctgcgcg | ctcacctgta | tttagagctc | aactatttgg | cccaatgaaa | 720 |
| gatcatgaca | cacaatgtat | tcgagttgaa | gacatggaag | ctcctgttt | taaggctcta | 780 |
| cttcatttca | tatactggga | ttgcttaccc | gatatggaag | aacttactgg | tttgaactca | 840 |
| aaagggcta | caagcttgat | ggctcaacat | ctgcttgctg | ctgcagatag | atatggtttg | 900 |
| gataggctca | ggttgatatg | tgaagctaat | ctctgcgagg | atgttgccat | aaatactgtt | 960 |
| gctactacgc | tggcccttgc | agagcagcat | cactgtttcc | agctgaagtc | tgtatgccta | 1020 |
| aaatttgttg | ccatgccaga | aaatcttagg | gctgttatgc | agacagacgg | gtttgaatac | 1080 |
| ctaaaagaaa | gttgtccaag | cgtgctcaca | gaattgttgg | agtatgtagc | taggatcaat | 1140 |
| gagcattctg | tcagtgtgaa | caagcaattg | actgatggta | tattggacgg | gagtgatgtc | 1200 |
| aatggtcggc | gggtgaagca | gagattgtag | | | | 1230 |

<210> SEQ ID NO 92
<211> LENGTH: 1200
<212> TYPE: DNA
<213> ORGANISM: Zea mays

<400> SEQUENCE: 92

| | | | | | |
|---|---|---|---|---|---|
| atggcgattc | cgccgcggac | tccttccccg | ccgccatcgt | ggtcgcgctc | tgtaaccgag | 60 |
| accgttcggg | ggtcccacca | gttcaccgta | cggggctact | ccctcgccaa | gggcatgggc | 120 |
| cccggccgct | acctcgccag | cgacgtcttc | gccgtcggag | gataccactg | gccgtctac | 180 |
| ctctaccccg | acggcaagaa | cgccgaggac | aactccaact | acgtctccgt | tttcgtcgcc | 240 |
| ctcgcttccg | acggcatcga | cgtccgagcc | ctcttcgagc | tcaccctcct | cgaccagtcc | 300 |
| ggccgcggct | gccacaaggt | tcactcgcac | tttgaccgct | cgctcaagtt | cggcccatac | 360 |
| accctcaagt | acaggggatc | catgtggggt | tacaagcgct | tctacaaaag | aacactcttg | 420 |
| gaagaatctg | atttcttaaa | gaatgattgc | ctagtgatga | actgcacagt | aggtgttgtc | 480 |
| aagaaccgta | tagaaacacc | aaaggacatc | cagattcatg | ttccacgatc | agacatgggc | 540 |
| cgctgcttca | aggagctcct | cagccgctgc | attggatgtg | acataacatt | cgaagtgcga | 600 |

```
gatgagaaag tcagggcaca caagtggatt cttgctgctc gctccccagt atttaaagcc    660
cagttctttg gtcctattgg aaagcctgac ctgcacacgg ttgttgtgga ggatgtggaa    720
cctgttgtct tcaaggcaat ggtgaacttc atttacgctg atgaactccc cagcattcct    780
gagctagctg gtctgcctc aacgtggaca tcaacagtag tagtacagca tttgttggca    840
gcagctgata gatatggact ggtccgtctg cgtatcctgt gtgaatcaaa gctctgtgat    900
gaactgactc ctgaaactgt cgcaacaact ttagcccttg ctgaacagca ccattgtgct    960
gagctgaagt ctgcatgtct aaagttcatt gctttgcgag gaaatttggg agctgttatg   1020
gagacgaaag ctttgatta cctggaggat acatgcccgt ccctactatc tgacttgtta   1080
gctactgtgg cagtcgtgga cgacgatctt gcatccctta accgaaaaag gggagtcagc   1140
gggaaccaag tcatggctct agtgggaagc gttgaaaggc gcacccggag gaagctttag   1200
```

```
<210> SEQ ID NO 93
<211> LENGTH: 1209
<212> TYPE: DNA
<213> ORGANISM: Sorghum bicolor

<400> SEQUENCE: 93
```

```
atggcgattc cgccgcggac tcctcccccg ccgccatcgt ggtcgcgcta cgtcaccgag     60
accgtgaagg ggtcccacca gttcaccgtc cggggcttct ccctcgccaa gggcatgggc    120
cccggccgcc acctcgccag cgacatcttc gctgtcggag gataccactg gccgtctac    180 ttctaccccg acggcaagaa cgccgaggac aactccaact acgtctccgt cttcgtcgcc    240
ctcgcctccg acggcatcga cgtccagcc ctcttcgacc tcacctcct cgaccagtcc    300 ggccgcggcc gccacaagat tcactcgcac tttggccgca agctagattc cggcccatac    360 acctcaagt acaggggctc catgtggggt tacaaacgct tctacaaaag atcactcttg    420
gaagcatctg atttcttaaa gaatgattgc ctagtgatga actgcacagt aggtgttgtc    480
aagaaccgta tggaaacacc aaaggacatc cagattcatg ttccacgatc agacatgggc    540
cactgcttca aggagctcct cagccgcggc attggatgtg acataacctt cgaagtgcgc    600
gacgagaaag tcagggcaca caagtggatt cttgctgctc gctccccagt atttaaagcc    660
cagttctttg gtcctattgg aaagcctgac ctgcacacgg ttgtcgtgga ggatgtggaa    720
cctgtcgtct tcaaggcaat ggtgaacttc atgtacactg atgaactccc cagcatttct    780
gagctagctg gatctgcctc aacatggaca tcaacagtag tagtacagca tttgttggca    840
gcagctgata gatatggact ggaccgtctt cgtatcctgt gtgaatcaaa gctatgtgat    900
gaactgactc ctgaaactgt cgcaacaacc ttagcccttg ctgaacaaca ccattgcgct    960
gagctgaagt ctgcctgtct aaggtttgct gctgtgcgag aaaatttggg agctgttatg   1020
gggacggaag ctttgatta cttggaagag acatgcccgt ccctactatc cgacttgtta   1080
gctactgtgg cagaagtgga cgatgatcct gcatccctg accgaaaaag gggagtttgc   1140
ggtaaccaag tcttggctcc agtggaaagt gtcgaggcta ctgaaaggcg cacccggagg   1200
aggcttag                                                           1209
```

```
<210> SEQ ID NO 94
<211> LENGTH: 1236
<212> TYPE: DNA
<213> ORGANISM: Cucumis melo

<400> SEQUENCE: 94
```

```
atgggcacga ttaaatcttg cagggatacc tctaaatcct actcaaatct tcggtcgccg     60
```

```
acgcctccac cagtgacttt ttcaacttct cgtttcgaga ccgtcaatgg atcgcatgag    120
ttcaagatca atgggtattc ccttaataaa gggatgggga ttgggaaata catcgcgtct    180
gataccttta tggttggggg atatgcgttt gctatatatt tttacccaga cgggaagagc    240
gtcgaggata acgcatcgta tgtctcggtt tttatagcgt tggctagtga agggactgac    300
gttagagccc tttttgaatt gacgttgttg gatcaaagtg ggaaggagaa ccacaaggtg    360
cacagccatt tcgagagaag actcgagagt ggtccttata cgcttaaata tcgaggaagc    420
atgtgggggt ataaacgtta ttttaaaaga acagttttag aaacatccga cttcctaaag    480
gacgactgcc ttgaaatcca ctgtgtagtt ggtgttgtta agtcccatac agagggacca    540
aagatttact ccataacacc accaccttct gatataggcc agcattttgg gaagcttttg    600
gagagtggga aactaactga tgtgaacttt gaagtagatg gggaaacatt ttctgcccac    660
aagttagttc ttgctgcgcg gtcacctgtc tttagggcac aactctttgg ccctctgaag    720
gaccagaata ctgagtgtat aaaagtcgaa gatatgaag ccccagtatt taaggcattg    780
cttcatttca tatactggga tgctctacca gatatgcaag aaattgtagg tttaaactca    840
aaatgggctt ccactctgat gtcccagcat ctacttgcgg cagcagacag atatgcactt    900
gacagactca aattgctatg cgaggctaaa ctttgtgagg acgttgctat aaatacagtg    960
gcaacgacat tggcattggc tgagcagcat cactgtttcc aactaaaagc tgtatgtttg   1020
aaagtcattg cattgccgga gaatttgaga gctgtaatgc aaacggaggg gtttgaatat   1080
ttgaaagaga gctgcccatc ggttctcact gaactactag aatatgtagc aagggtgacg   1140
gagcatgcag tgattacttg cagcgggtat ggaaatggaa cagtgttaga tggtagttac   1200
gtgaatggaa gacgggtaag gcagaggttg tattga                             1236
```

PLANTS HAVING ALTERED EXPRESSION AND ACTIVITY OF YIELD-RELATED PROTEINS

This invention was made with government support under MCB1020673 awarded by the National Science Foundation. The government has certain rights in the invention.

BACKGROUND OF THE INVENTION

Field of the Invention

Embodiments of the invention generally relate to enhanced yield-related traits in plants. In particular, the invention provides plants that have been genetically engineered to down-regulate expression or reduce the activity of BPM proteins, resulting in enhanced yield-related traits including without limitation enhanced seed oil production, as well as products made by or from the plants.

Background of the Invention

Under field conditions, plant performance, for example in terms of growth, development, biomass accumulation and seed generation, depends on a plant's tolerance and acclimation ability to numerous environmental conditions, changes and stresses. There has always been a need for improving plant traits in crop cultivation. Breeding strategies foster crop properties to withstand biotic and abiotic stresses, to improve nutrient use efficiency and to alter other intrinsic crop specific yield parameters.

Plants are sessile organisms and consequently need to cope with various environmental stresses. Biotic stresses such as plant pests and pathogens on the one hand, and abiotic environmental stresses on the other hand are major limiting factors for plant growth and productivity (Boyer, 1982; Bohnert et al., 1995), thereby limiting plant cultivation and geographical distribution. Plants exposed to different stresses typically have low yields of plant material, like seeds, fruit or other produces. Crop losses and crop yield losses caused by abiotic and biotic stresses represent a significant economic and political factor and contribute to food shortages, particularly in many underdeveloped countries.

Conventional means for crop and horticultural improvements today utilize selective breeding techniques to identify plants with desirable characteristics. Advances in molecular biology have allowed for the production of transgenic plants with enhanced yield-related traits. Various yield-related traits in plants are important to many industries worldwide. In particular, plant seed oils are an important source of calories for human nutrition, as feedstocks for non-food uses such as soaps and polymers, and can serve as a high-energy biofuel. World production from oilseed crops in 2011 reached a value near US$120 billion with plant oil consumption expected to double by 2040 (Bates et al., 2013). As a result, methods for increasing seed oil biosynthesis have been an important research topic. However, previous attempts to modulate the transcription levels of factors critical for seed oil biosynthesis, such as WRINKLED1 (WRI1), resulted in relatively low increases in seed oil content (Liu et al., 2010; Shen et al., 2010; Pouvreau et al., 2011).

Effective regulatory mechanisms to time and control developmental and physiological processes in response to environmental cues are of utmost importance to plants due to their sessile life style. A mechanism that allows plants to quickly and flexibly respond is the ubiquitin (UBQ) proteasome pathway (Hua and Vierstra, 2011). It is highly conserved among eukaryotes and requires the concerted activities of an E1 UBQ activating enzyme, a UBQ conjugating enzyme E2, and an E3 UBQ ligase. While E1 and E2 activate the UBQ to modify target substrates, the E3 ligase binds the E2 and a substrate protein to facilitate transfer of the UBQ moiety. Upon building up a UBQ chain on the substrate, the ubiquitylated protein is marked for degradation via the 26S proteasome (Hua and Vierstra, 2011).

CUL3-based RING E3 ligases (CRL3) have been described only recently and mainly with respect to their basic architecture (Figueroa et al., 2005; Gingerich et al., 2005; Weber et al., 2005; Gingerich et al., 2007). They are composed of a cullin 3 protein, as the scaffolding subunit, that binds in its C-terminal region the RING-finger protein RBX1, while its N-terminal part is recognized by proteins containing a BTB/POZ (Broad complex, Tramtrack, Bric-a-brac/Pox virus and Zinc finger) fold (Figueroa et al., 2005; Weber et al., 2005). BTB/POZ proteins comprise a diverse group of proteins within *Arabidopsis* and rice, containing 80 and 149 members, respectively (Gingerich et al., 2007). They have been divided into 12 subgroups based on their secondary domains (Gingerich et al., 2007). While the BTB/POZ fold is required for assembly with the cullin and to interact with other BTB/POZ proteins, the secondary domain may function as an adaptor to allow binding of a substrate and delivery to the CRL3 core for ubiquitylation.

Based on its role as the central scaffolding subunit that assembles with potentially many BTB/POZ proteins, it is not surprising that the loss of CUL3 causes an embryo lethal phenotype. Reduced amounts of functional cullin 3 protein affects red light and ethylene signaling and impacts plant development (Dieterle et al., 2005; Thomann et al., 2009).

One BTB/POZ subfamily is the BPM (BTB/POZ-MATH) family that contains a BTB/POZ fold in their C-terminal region, and a MATH (Meprin and TRAF [tumor necrosis factor receptor associated factor] homolog) domain located within the first 200 amino acids of their N-terminal region. BPM proteins are known in the art and may also be referred to as MATH-BTB/POZ proteins. The family comprises six members in *Arabidopsis*, all of which have molecular weights between 40-50 kDa (Weber et al., 2005). A recent study of *Brassica rapa* provided a phylogenetic analysis of select BPM proteins, but there has yet to be any functional characterization of these genes in the *Brassica* species (Zhao et al., 2013). In *Zea mays*, it was found that the loss of a BPM protein resulted in defects in female gametophyte development (Juranić et al., 2012). However, there has been no study linking the downregulation of BPM proteins to enhanced yield-related traits.

SUMMARY OF THE INVENTION

Based on the surprising finding that BPM proteins assemble widely with ERF/AP2 transcription factors, and as demonstrated with a selected member of this family, WRI1, that the interaction is a requirement to destabilize WRI1 in plants, embodiments of the invention provide genetically engineered plants having increased yield-related traits, in particular and without limitation, seed oil production as compared to non-transgenic plants or other control plants which have not been genetically engineered as described herein, wherein at least one BPM protein is down-regulated or its activity reduced, and methods of making the same. Aspects of the invention also relate to methods of producing and recovering seed oil in plants. Although increased expression of polypeptides containing BTB/POZ domains has been implicated in modifying plant yield-related traits (U.S. patent application Ser. No. 13/818,858), no study has suggested or shown that down-regulating the expression of such polypeptides comprising a MATH domain can enhance yield-related traits.

An embodiment the invention provides transgenic plants, wherein the plants are genetically engineered so as to down-regulate expression or reduce the activity of at least one BPM (BTB/POZ-MATH) protein as compared to a control plant such as a non-transgenic plant or a plant in which the expression or activity of a BPM protein has not been reduced through the genetic engineering described herein. In preferred embodiments, the transgenic plant is of the Brassicaceae family, in particular, *Arabidopsis thaliana*. In some embodiments, the transgenic plant exhibits enhanced yield-related traits as compared to a control plant. In exemplary embodiments, the transgenic plant of the claimed invention exhibits increased seed oil production as compared to a control plant.

Another aspect of the invention provides a method for recovering seed oil from a transgenic plant comprising cultivating said transgenic plant under conditions promoting plant growth and development, wherein said transgenic plant is genetically engineered to down-regulate expression or reduce the activity of at least one BPM protein as compared to a control plant; and recovering seed oil from the transgenic plant. In preferred embodiments, the transgenic plant is of the Brassicaceae family, in particular, *Arabidopsis thaliana*. In some embodiments, said step of genetically engineering comprises introducing artificial microRNA (amiRNA) to down-regulate said BPM protein. In still other embodiments, said step of genetically engineering comprises the expression of an exogenous MATH domain to compete with BPM protein.

Additional aspects of the invention provide a method for enhancing yield-related traits in a plant comprising genetically engineering the plant so as to down-regulate expression or reduce the activity of at least one BPM protein as compared to a control plant. In some embodiments, the method of the invention results in increased seed oil production in the transgenic plant as compared to a control plant. In preferred embodiments, the transgenic plant is of the Brassicaceae family, in particular, *Arabidopsis thaliana*. In some embodiments, the step of genetically engineering comprises introducing artificial microRNA (amiRNA) to down-regulate the BPM protein. In still other embodiments, the step of genetically engineering comprises the expression of an exogenous MATH domain to compete with BPM protein.

Further embodiments of the invention relate to a product produced by or from a transgenic plant which is genetically engineered to down-regulate expression or reduce the activity of at least one BPM protein as compared to a control plant.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

FIG. 1A-E: Verification of α-CUL3 and α-WRI1 antibodies. (A) Upper sequence: partial alignment of *Arabidopsis* CUL3a and CUL3b sequences (SEQ ID NO:65 and SEQ ID NO:66, respectively). Lower sequence: *Arabidopsis* WRI1 (SEQ ID NO:67). The peptide sequences used for antibody generation are highlighted with arrows. (B) Western blot analysis in WT, cul3a, cul3b and cul3$^{hyp}$ backgrounds with α-CUL3. (C) The specificity of α-CUL3 was confirmed by Western blot analysis in transient expression assays with a GFP:CUL3a construct in tobacco. (D) PCR identification of homozygous T-DNA mutant wri1-3. A WRI1 gene-specific product was amplified in WT but not in wri1-3, while one T-DNA specific product was amplified in wri1-3 but not in WT. (E) WRI1 is detectable in WT but not in wri1-3.

FIG. 2A-H: Interaction studies of WRI1 with BPM and CUL3 proteins. (A) BPM1 interacts with ERF4, RAV1 and DREB1a, but only poorly with ERF1 in Y2H assays. SDII, medium for transformation selection; SDIV, medium for test of interaction. Pictures of single spots were taken seven days after transformation. (B) WRI1 can assemble with itself in Y2H assay, as well as with representative members of the BPM family, BPM1, BPM3, BPM4, and BPM5. (C) In vitro translated and [$^{35}$S]-methionine labeled BPM1 protein was used in pull-down assay with *E. coli* expressed and GST and GST:WRI1. (D) Pulldown experiments with in *E. coli* expressed GST: WRI1 results in the precipitation of WRI1 and CUL3, while GST alone was ineffective. Asterisks indicate GST:WRI1 band, while the band below is plant WRI1. Pulldowns were first tested with α-WRI1, and then with α-CUL3 after the membrane had been stripped. (E) Silver-stained SDS-PAGE gel to illustrate the IPTG-induced expression of purified GST and GST: WRI1 proteins from *E. coli*. (F) Pulldown experiments with purified proteins show that His:WRI1 can precipitate GST:CUL3a if GST:BPM1 is present in the assay (left blot), while this is not the case when GST alone is used (right blot). Blots were probed first with a α-GST antibody, before stripped and subsequently probed with α-CUL3 and α-WRI1. PD, pulldown. (G) IP experiments with α-WRI1 antibody shows co-precipitation of CUL3 with WRI1 from *Arabidopsis* wild type (WT) protein extract. If not otherwise stated in this and subsequent figures 30 μg of total protein extract were loaded as input, and experiments were done with 14-days old seedlings. (H) WRI1 is present in the plant extract used for the IP shown in (G).

FIG. 5A-D: Stability and expression level of WRI1 in WT and cul3$^{hyp}$. (A) Treatment of WT plants with ActD2 (6 h) and CHX (3 h) inhibitors shows instability of WRI1. This is blocked by co-treatment with MG132 (6 h). (B) WRI1 protein accumulates in cul3$^{hyp}$ double mutants in comparison to WT. (C) Expression of WRI1 is comparable to WT in cul3$^{hyp}$ plants. (D) WRI1 protein is more stable in cul3$^{hyp}$ than in WT. Error bars in this and all subsequent figures represent standard deviation.

Figure 6:
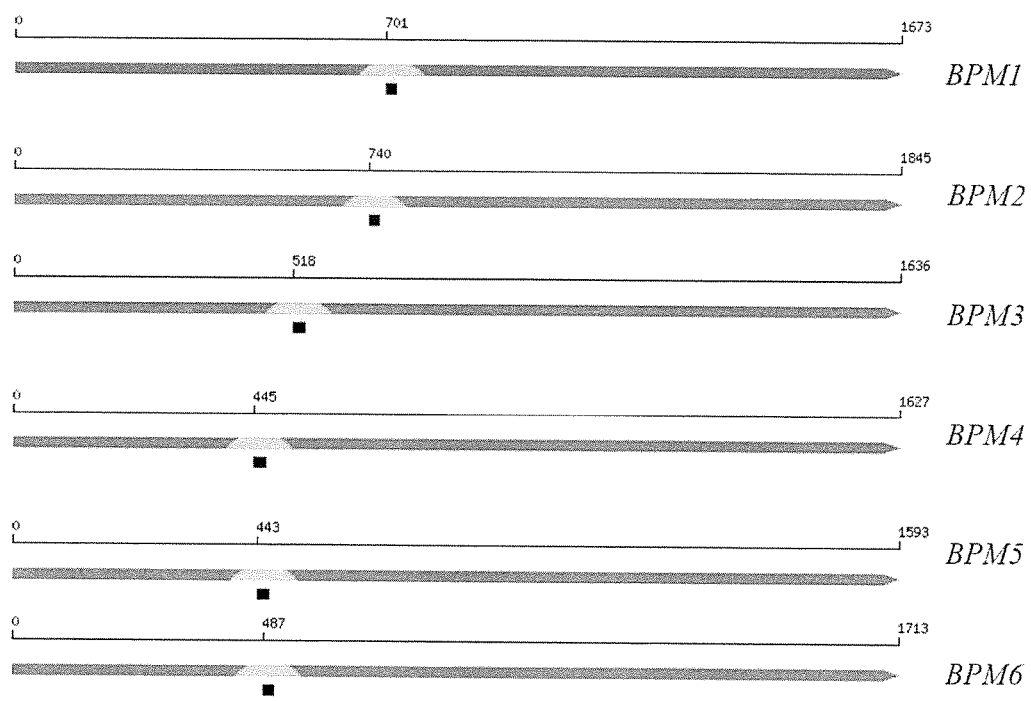

FIG. 6: Predicted target sites for artificial microRNA (squares) on the different BPM genes. Numbers indicate base pairs.

FIG. 7A-D: Generation of 6×amiBPM and MATH-overexpressing lines and their impact on WRI1 protein levels. (A, B) qRT-PCR analysis show significantly reduced expression levels for six BPMs is in two representative 6×amiBPM lines compared to WT. (C) Expression levels of BPM1$^{MATH}$ show significant increases in two BPM1$^{MATH}$ lines, and two BPM1$^{MATH:NLS}$ lines compared to WT. (D) WRI1 protein content is strongly reduced in MATH-overexpressing lines when compared to WT, while both 6×amiBPM lines display increased WRI1 levels. All asterisks in this and subsequent figures indicate the statistical significant difference of at least p<0.05 (One-way ANOVA) to WT.

FIG. 8A-C: Sub-cellular localization of GFP:BPM1$^{MATH}$ and GFP:BPM1$^{MATH:NLS}$. (A) Transient expression analysis of GFP:BPM1$^{MATH}$ in tobacco demonstrates that the fusion protein is present in the cytosol and nucleus (bar=5 μm). (B) GFP:BPM1$^{MATH:NLS}$ fusion protein is strictly localized to the nucleus (bar=10 μm). Arrows indicate nuclei. (C) The expression level of WRI1 in WT and two individual lines of GFP:BPM1$^{MATH}$, GFP:BPM1$^{MATH:NLS}$.

FIG. 9A-G: Phenotype analysis of WT, two 6×amiBPM lines, and MATH-overexpressing lines. (A) Primary root lengths of 2-weeks old *Arabidopsis* seedlings is strongly reduced in all transgenic lines when compared to WT (n=45). (B) Specifically 6×amiBPM plants have reduced numbers of lateral roots development (2-weeks old seedlings; n=45). (C) Root phenotype of WT and two 6×amiBPM lines. Picture was taken 14-days post-germination. (D) Overview of rosette phenotypes from WT and transgenic lines. Picture was taken 33 days after germination. (E) All transgenic lines are late flowering. Data were taken for 33-day-old plants (n=30). (F) Rosette leaf number at time of flowering (n=10). (G) Rosette area of 25-day-old *Arabidopsis* plants for each genetic background (n=30).

Figure 10:
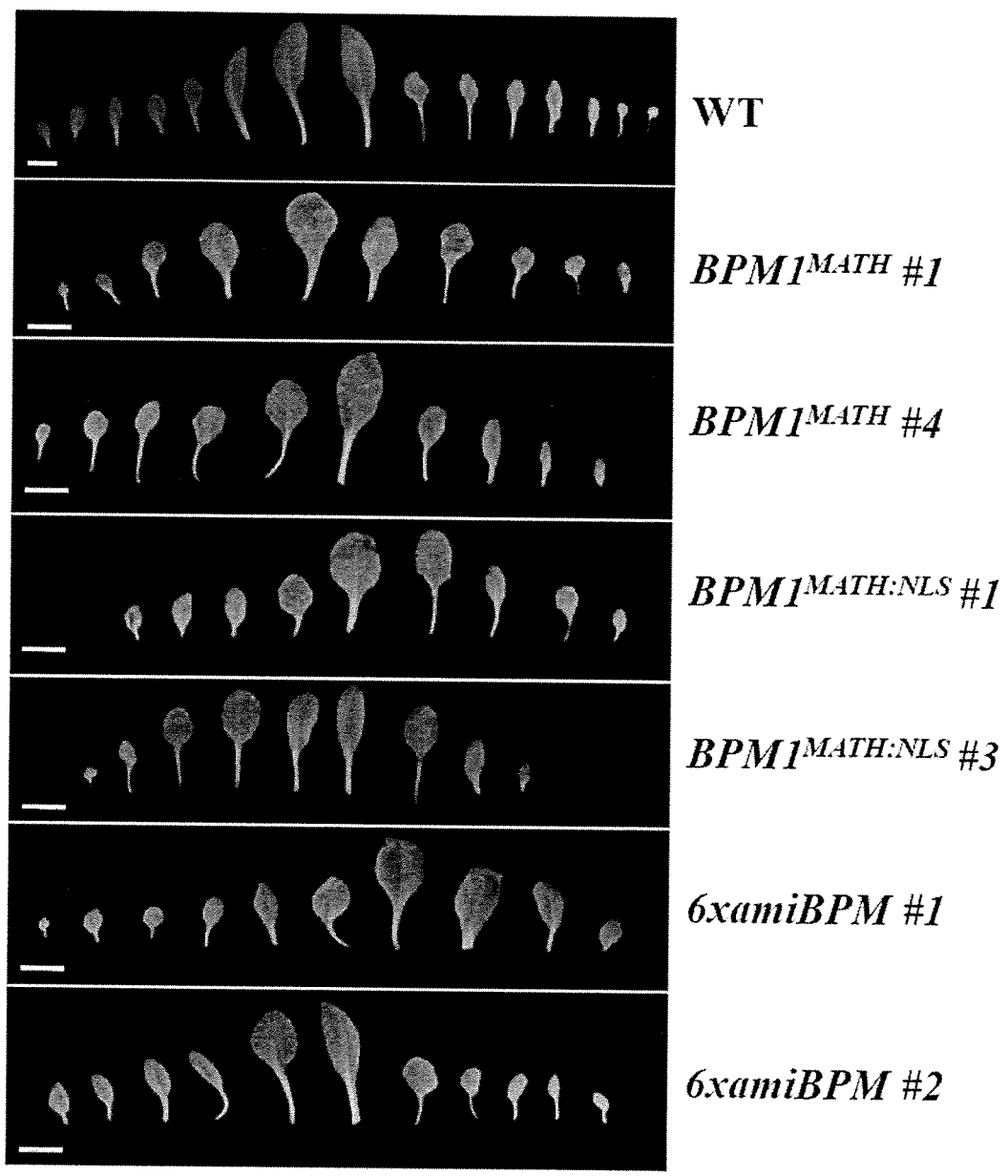

FIG. 10: Rosette leaf phenotype on the time of primary inflorescence. 6×amiBPM and MATH-overexpressing plants develop less and shorter leaves then WT. Leaves of transgenic plants frequently developed wider blades (scale=1 cm).

FIG. 11A-G: Studies of WRI1's protein level, WRI1's transcriptional activity, and complex assembly at the DNA level. (A) WRI1 protein is stabilized in MATH overexpressing and 6×amiBPM lines. (B) CUL3 could be precipitated with α-WRI1 from WT plant extracts but not from BPM1$^{MATH}$ (left half) or 6×amiBPM (right half) extracts. Input was tested for presence of WRI1 and CUL3 proteins using the respective antibodies. (C) Protein levels of WRI1, and expression of two WRI1 target genes, AtGLB1 and BCCP1, in WT and the different transgenic backgrounds. (D-G) ChIP-qPCR analysis on WT, two 6×amiBPM lines, and wri1-3 shows enrichment of the two WRI1 target promoters proBCCP1 and proAtGLB1 in WT (D) but not in a wri1-3 mutant (G) after IP with either α-WRI1 or α-CUL3 antibodies. While no enrichment was detectable in samples derived from α-CUL3 ChIPs in two 6×amiBPM lines (E, F), significant enrichment was detectable in α-WRI1 ChIP samples when compared to WT (E, F). ChIP-qPCR experiments were repeated at least three times independently. Error bar indicates the value of standard error. Asterisk indicates a statistical significant difference (One-Way ANOVA, p<0.05) compared to individual control.

Figure 12A:
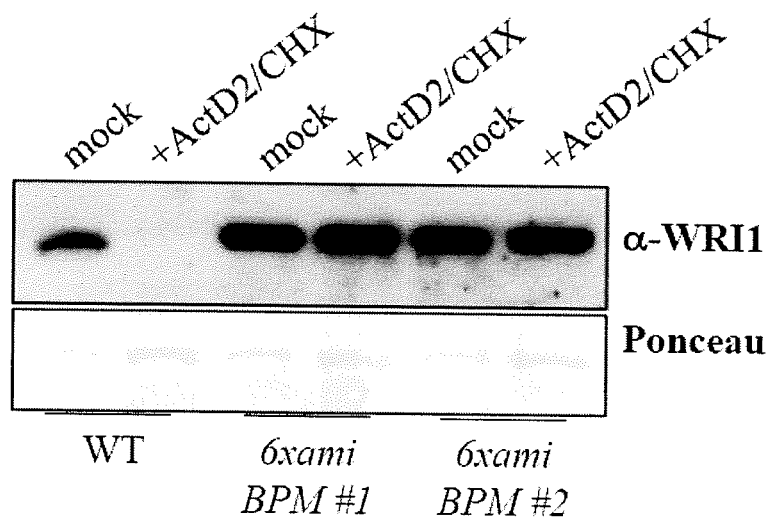
Figure 12B:
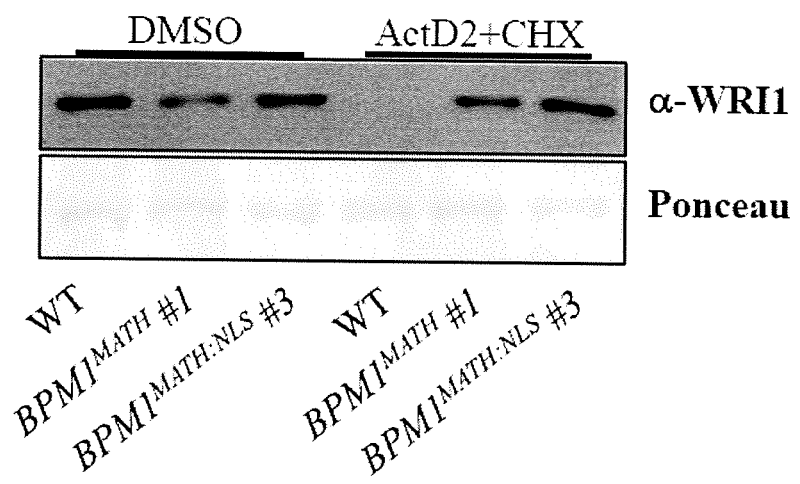

FIG. 12A-B: Stability assays of WRI1 in WT, 6×amiBPM, and MATH overexpressing lines. In comparison to WT, WRI1 protein is stabilized in both (A) 6×amiBPM and (B) MATH overexpressing plants.

FIG. 13A-D: Seed weight, size, and fatty acid content in WT, wri1-3, and 6×amiBPM plants. (A, B) In comparison to WT, seed weight and size is significantly reduced in wri1-3, while it is increased in both 6×amiBPM lines, and to a greater extend in 6×amiBPM#1 then it is in #2 (data in (A) represent average of n=5 measurements of 20 seeds. Scale bar in (B) represents 1 mm. (C) Seeds in 6×amiBPM lines contain higher WRI1 levels which correlate with expression of the WRI1 target genes BCCP1 and AtGLB1. (D) Differences in total fatty acid contents for WT, wri1-3, and the two 6×amiBPM lines correlated with seed weights and sizes. Data represent average of n=5 measurements on 30 seeds. The asterisk shows the statistical significant difference to WT (p<0.05, T-test).

Figure 14:
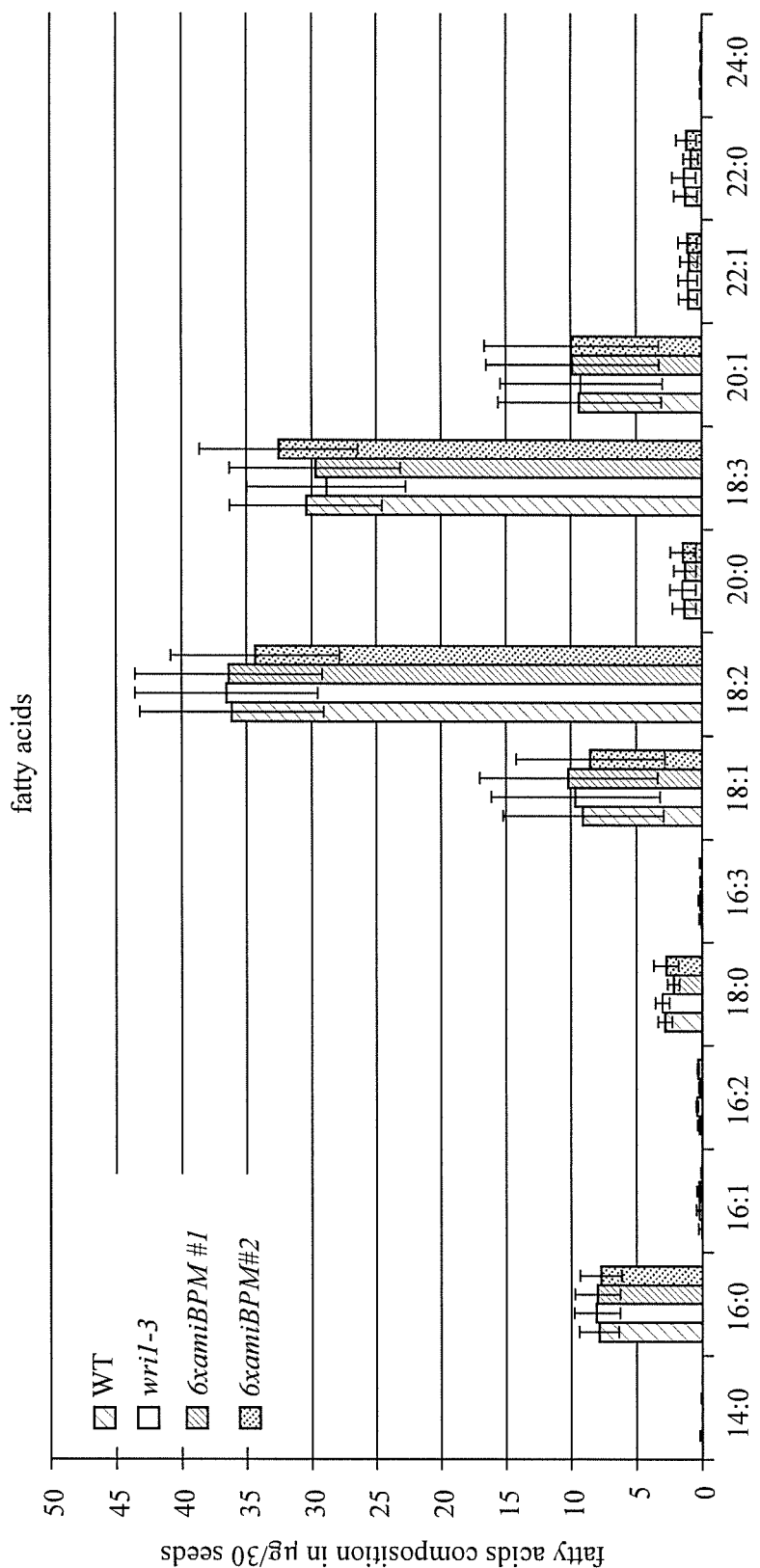
Figure 14:
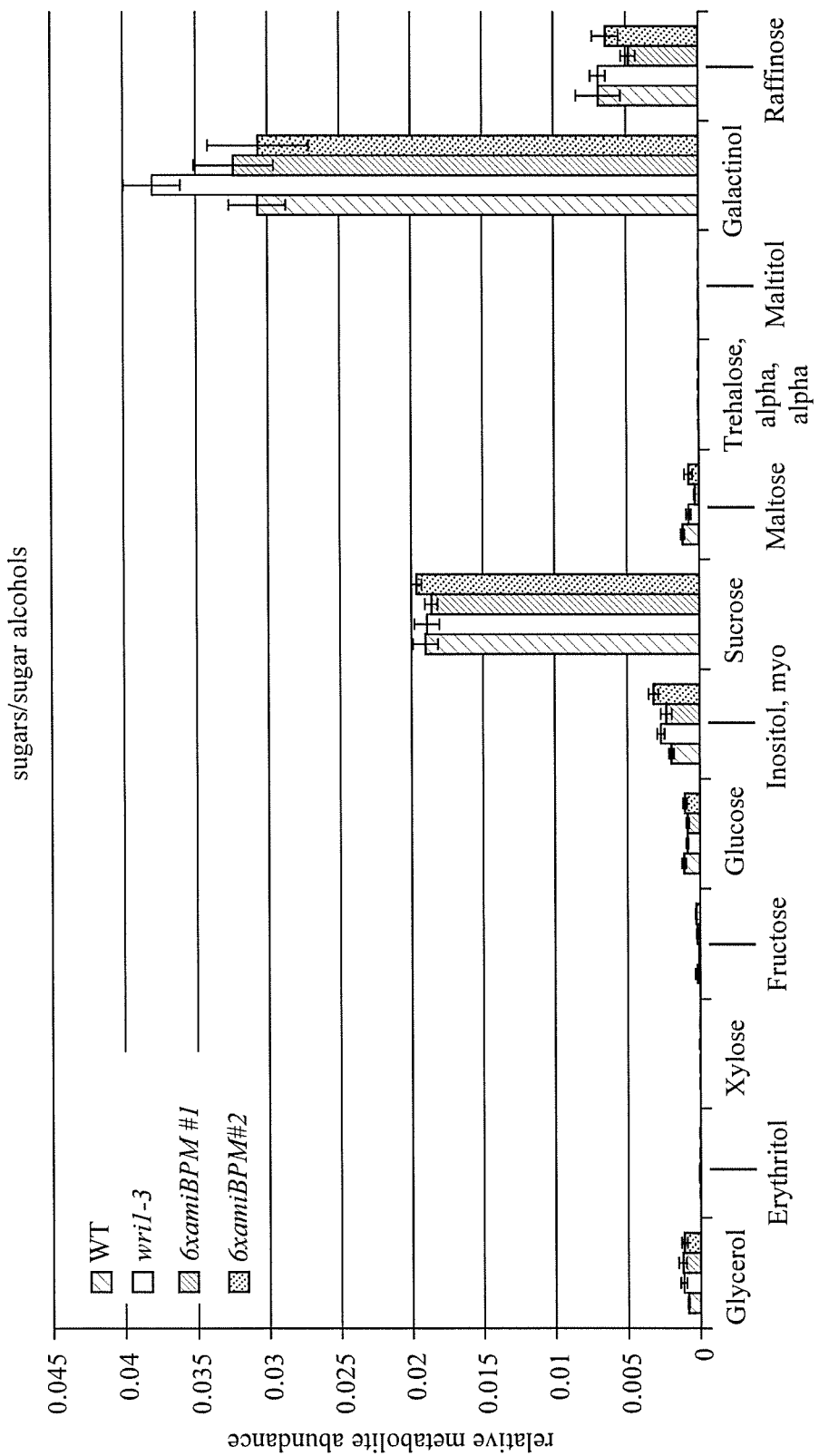
Figure 14:
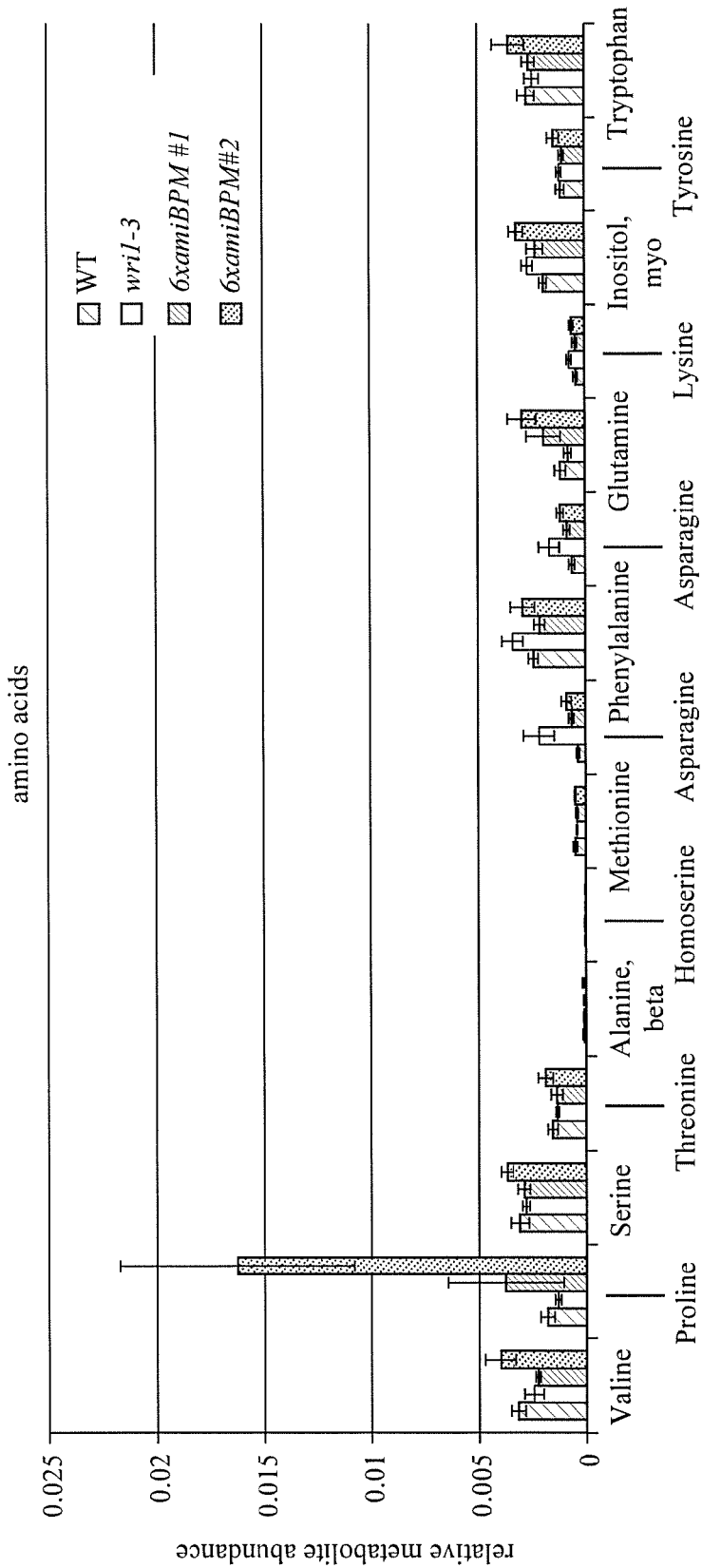
Figure 14:
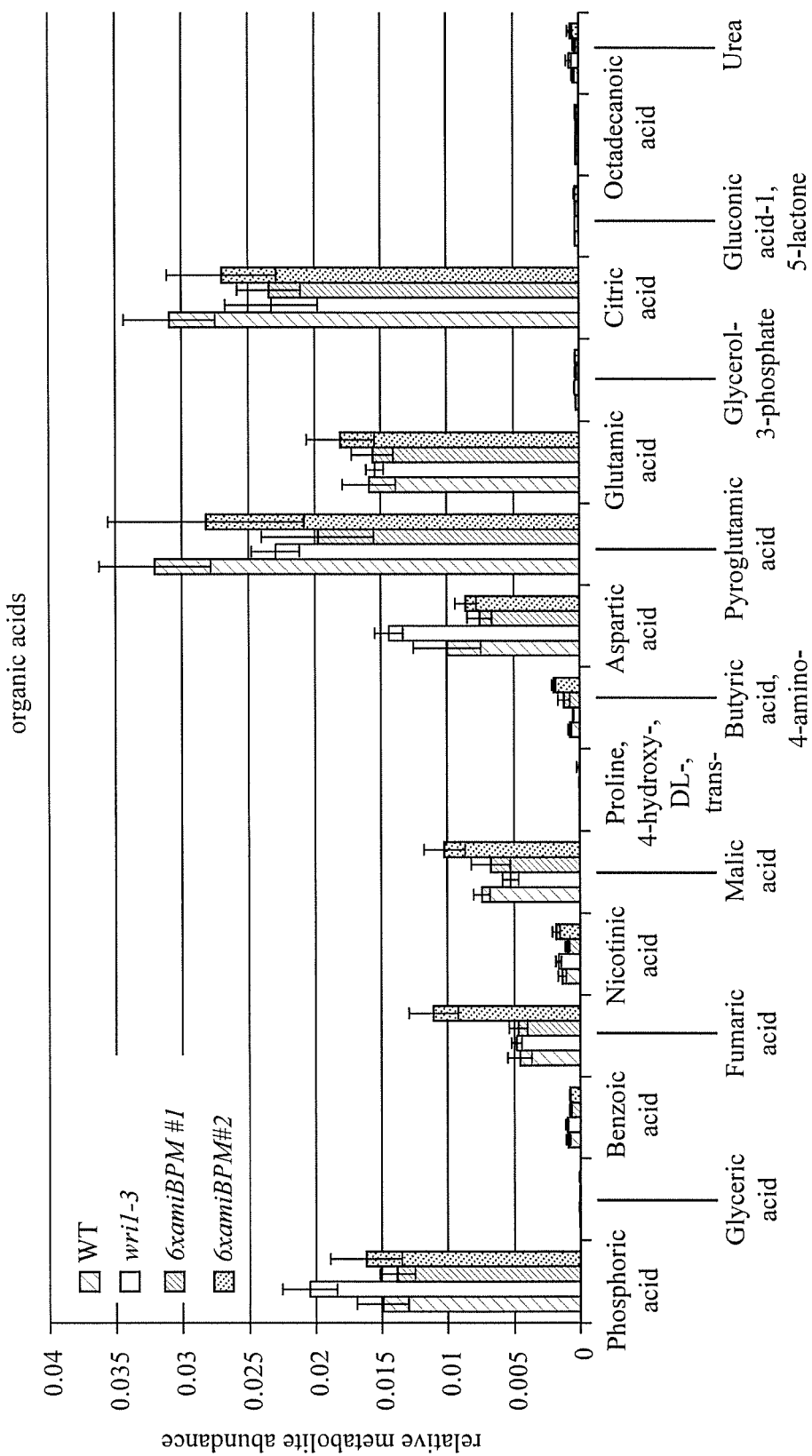

FIG. 14: Fatty acid profile and metabolic profile in seeds of WT, wri1-3, and two 6×amiBPM lines. All extractions and measurements were done from mature and desiccated seeds from WT, wri1-3, and 6×amiBPM lines. In the graph for fatty acids, numbers indicate the type of fatty acid (carbon chain length and number of double bonds). All values are based on five independent samples. Error bar indicates the value of standard deviation.

FIG. 15A-E: Seed phenotype analyzes for 6×amiBPM #3. (A) WRI1 protein is elevated in the mutant line in comparison to WT, which (B,C) correlates with seed size and weight, and (D) increased expression of BCCP1 and AtGLB1. (E) Fatty acid levels are significantly increased in 6×amiBPM #3 in comparison to WT (p<0.05, T-test).

Figure 16A:
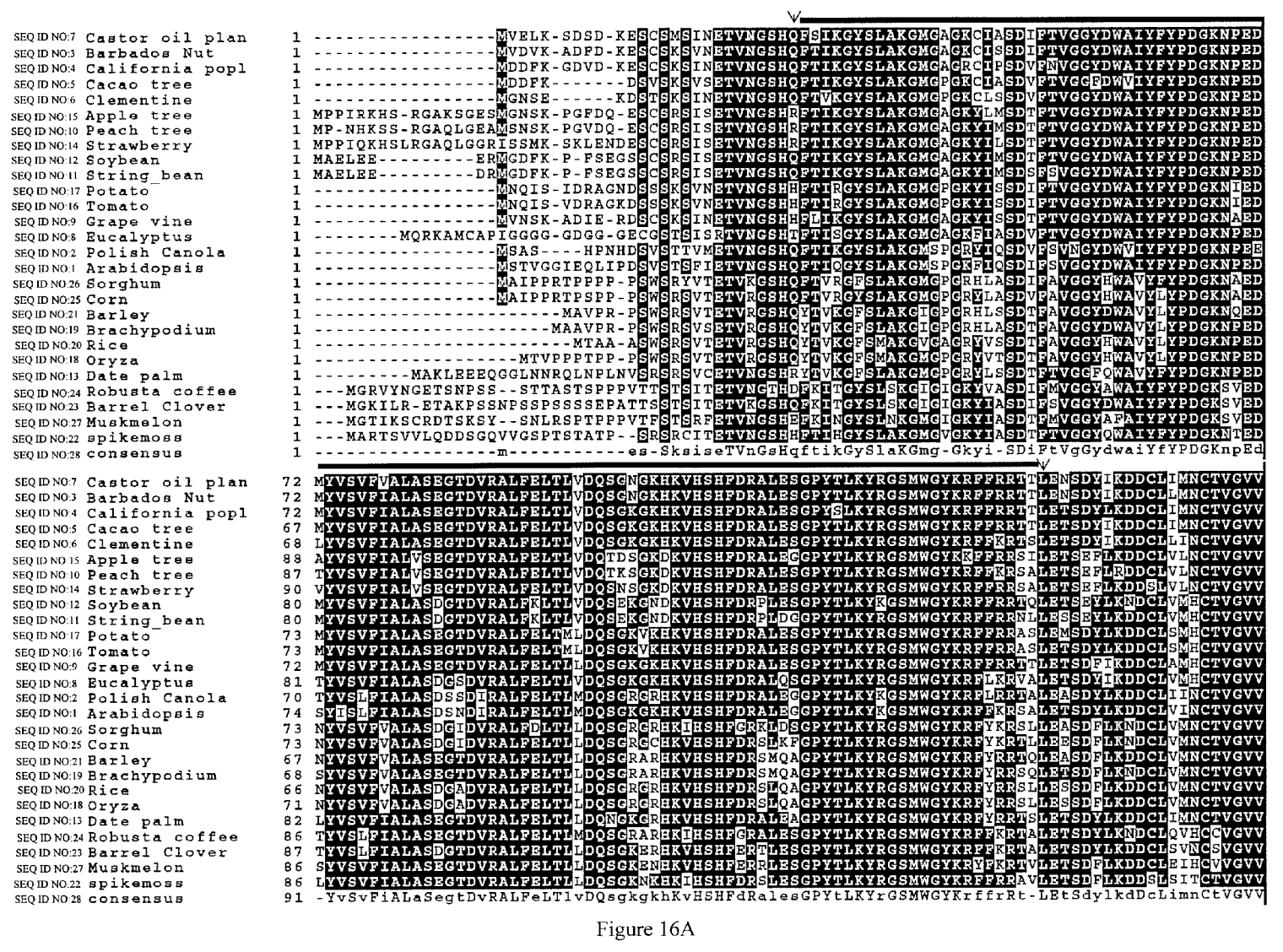
Figure 16B:
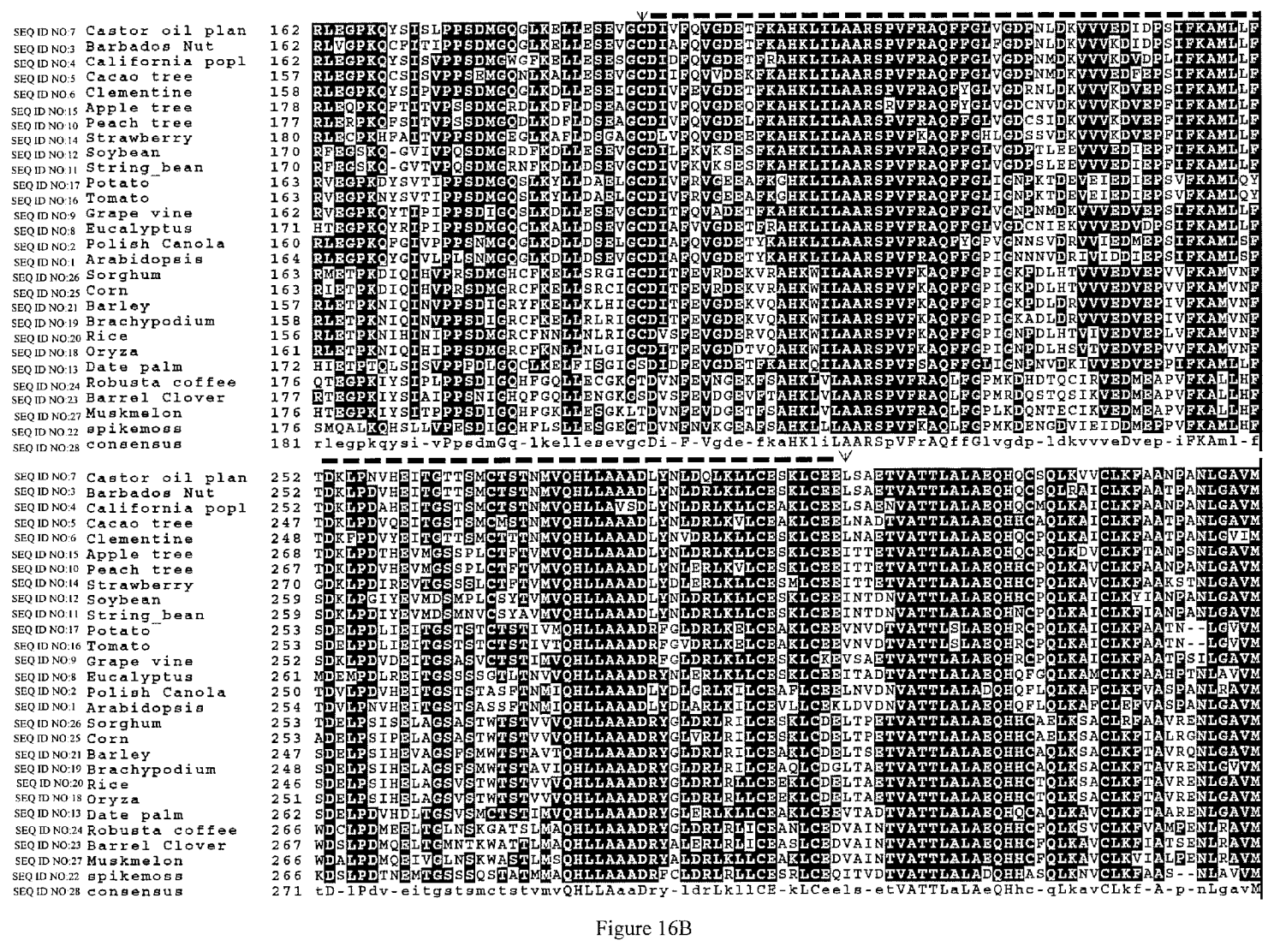
Figure 16C:
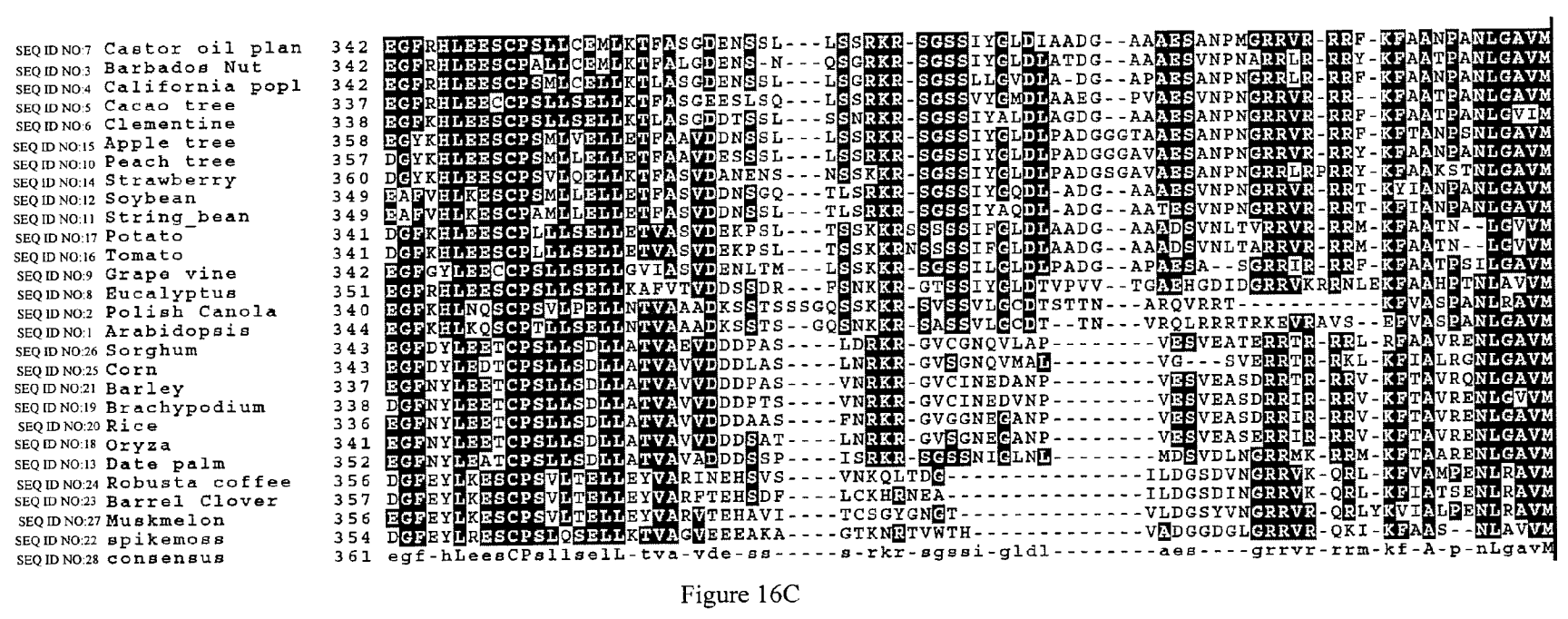

FIGS. 16A-C: Sequence alignment of full length BPM proteins from 27 different plant species (SEQ ID NOs. 1 to 27) and a consensus sequence (SEQ ID NO. 28). Amino acid residues with black background color are fully conserved, those with a dark gray background are highly conserved. Arrows at the top of the alignment indicate start and end of either the predicted MATH (black solid line) or BTB/POZ (black dotted line) domains in the *Arabidopsis thaliana* BPM3 protein. (A) shows the predicted MATH domain and surrounding sequence. (B) shows the predicted BTB/POZ domain and surrounding sequence. (C) shows the c-terminal sequence of the BPM proteins. For example, in *Arabidopsis* the predicted MATH domain comprises residues 29-141 and the BTB/POZ domain comprises residues 194-303. The following are the Latin names of the different species listed as well as the accession numbers (AccNo) of the corresponding BPM proteins: *Arabidopsis: Arabidopsis thaliana*; AccNo BAH19418 (SEQ ID NO:1); Polish Canola: *Brassica rapa*; AccNo XP_009141835 (SEQ ID NO:2). Barbados Nut: *Jatropha curcas*; AccNo KDP44889.1 (SEQ ID NO:3). California poplar: *Populus trichocarpa*; AccNo XP_002311186 (SEQ ID NO:4). Cacao tree: *Theobroma cacao* AccNo XP_007009287 (SEQ ID NO:5). Clementine: *Citrus clementina*; AccNo XP_006435614 (SEQ ID NO:6). Castor oil plant: *Ricinus communis*; AccNo XP_002524218 (SEQ ID NO:7). Eucalyptus: *Eucalyptus grandis*; AccNo KCW65573 (SEQ ID NO:8). Grape vine: *Vitis vinifera*; AccNo XP_002282536 (SEQ ID NO:9). Peach: *Prunus persica*; AccNo XP_007218050 (SEQ ID NO:10). String bean: *Phaseolus vulgaris*; AccNo XP_007163464 (SEQ ID NO:11). Soybean: *Glycine max* AccNo XP_003552772 (SEQ ID NO:12). Date palm: *Phoenix dactylifera*; AccNo XP_008785535 (SEQ ID NO:13). Strawberry: *Fragaria* vesca subsp. *Vesca*; AccNo XP_004307466 (SEQ ID NO:14). Apple: *Malus domestica*; AccNo XP_008372026 (SEQ ID NO:15). Tomato: *Solanum lycopersicum*; AccNo XP_004239913 (SEQ ID NO:16). Potato: *Solanum tuberosum*; AccNo XP_006355691 (SEQ ID NO:17). *Oryza: Oryza brachyantha*; AccNo XP_006657384 (SEQ ID NO:18). *Brachypodium: Brachypodium distachyon*; AccNo XP_003557713 (SEQ ID NO:19). Rice: *Oryza sativa* Japonica Group; AccNo NP 001058677 (SEQ ID NO:20). Barley: *Hordeum vulgare* subsp. *vulgare*; AccNo BAJ94248 (SEQ ID NO:21). Spikemoss: *Selaginella moellendorffii*; AccNo XP_002961582 (SEQ ID NO:22). Barrel Clover: *Medicago truncatula*; AccNo KEH23724 (SEQ ID NO:23). Robusta coffee: *Coffea canephora*; AccNo CDP03595 (SEQ ID NO:24). Corn: *Zea mays;* AccNo NP_001142069 (SEQ ID NO:25). *Sorghum: Sorghum bicolor*; AccNo XP_002461292 (SEQ ID NO:26). Muskmelon: *Cucumis melo*; AccNo XP_008458543 (SEQ ID NO:27). A consensus sequence is also shown (SEQ ID NO:28).

Figure 17:
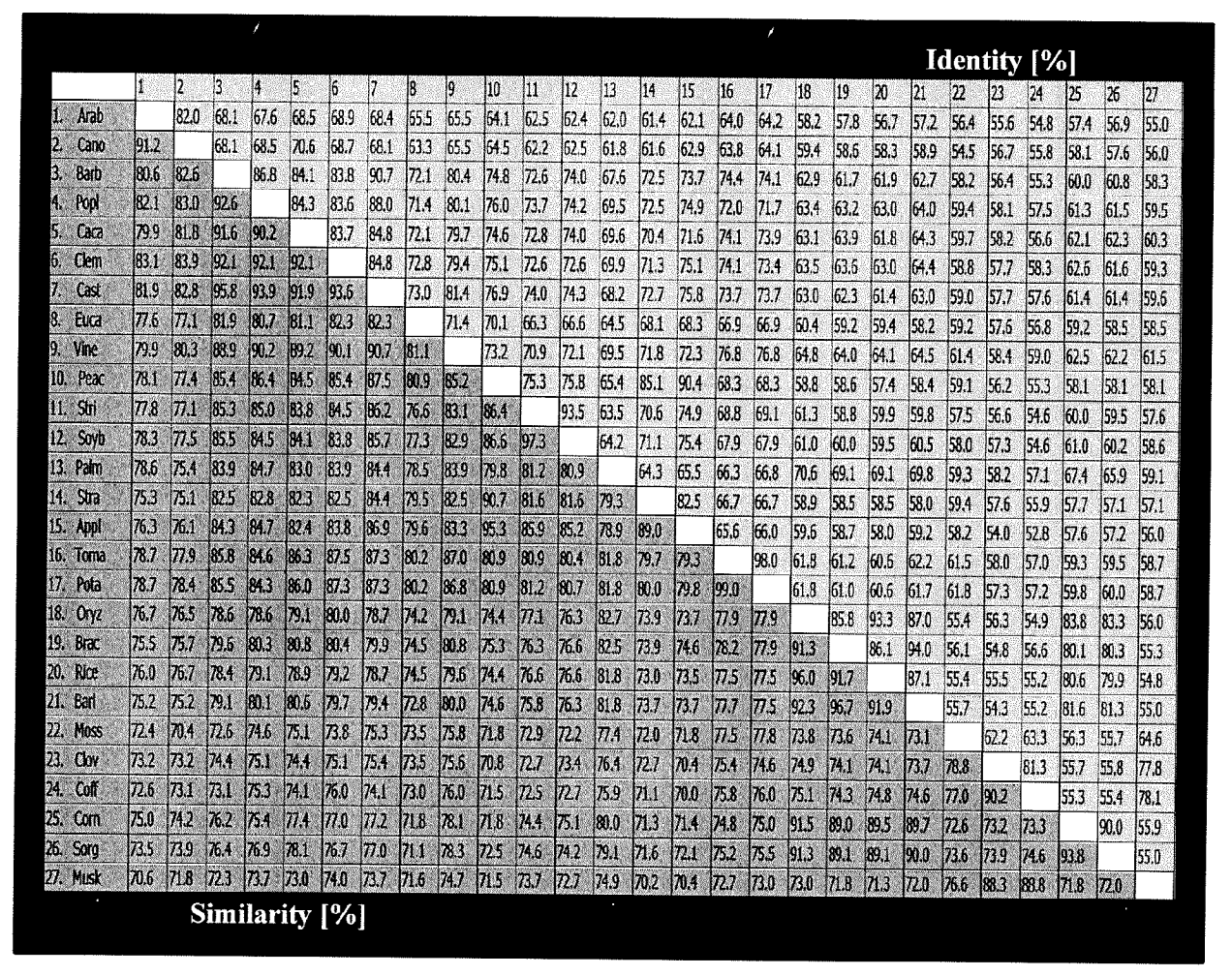

FIG. 17: Comparison of protein identities and similarities of BPM proteins from 27 different plant species. Arab: *Arabidopsis*. Cano: Polish Canola. Barb: Barbados Nut. Popl: California poplar. Caca: Cacao tree. Clem: Clementine. Cast: Castor oil plant. Euca: *Eucalyptus*. Vine: Grape vine. Peac: Peach. Stri: String bean. Soy: Soybean. Palm: Date palm. Stra: Strawberry. Appl: Apple. Toma: Tomato. Pota: Potato. Oryz: *Oryza*. Brac: *Brachypodium*. Rice: Rice. Barl: Barley. Moss: Spikemoss. Cloy: Barrel Clover. Coff: Robusta coffee. Corn: Corn. Sorg: *Sorghum*. Musk: Muskmelon. For specific latin names and accession numbers, see FIG. 16.

Figure 18B:
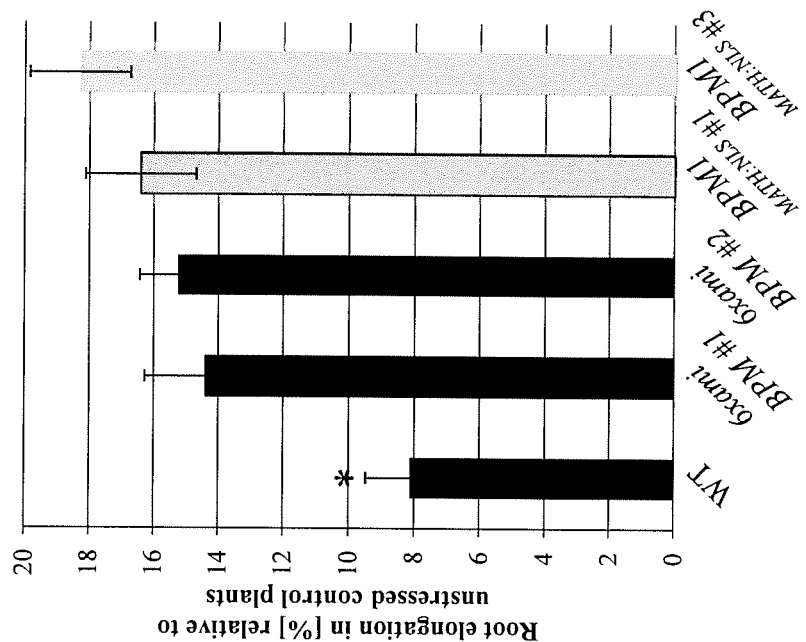
Figure 18A:
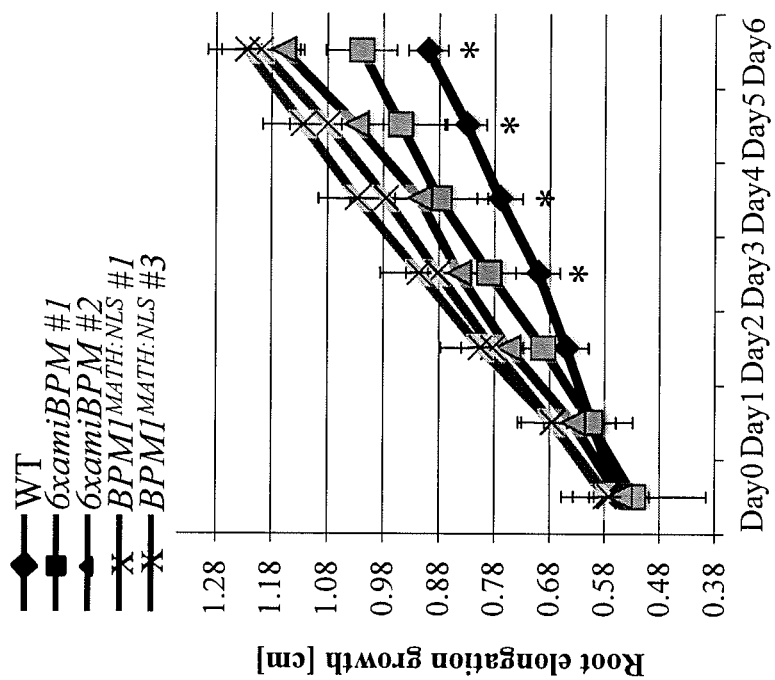

FIGS. 18A-B: Salt stress assay. (A) For salt stress tolerance assays, wild type (WT) and bpm mutants (6×amiBPM and BPM$^{MATH:NLS}$) were plated on solid minimal culture medium, and grown vertically for five days. Afterwards, they were carefully transferred to plates that were supplemented with 150 mM NaCl. The root length was measured for six days by tracking root tips. n=30 (B) Wild type root elongation growth at day six was significantly more inhibited under salt stress conditions than in bpm mutant plants. Asterisks indicate the statistical significant difference of at least P<0.05 (one-way analysis of variance) of WT plants in comparison to mutants.

Figure 19:
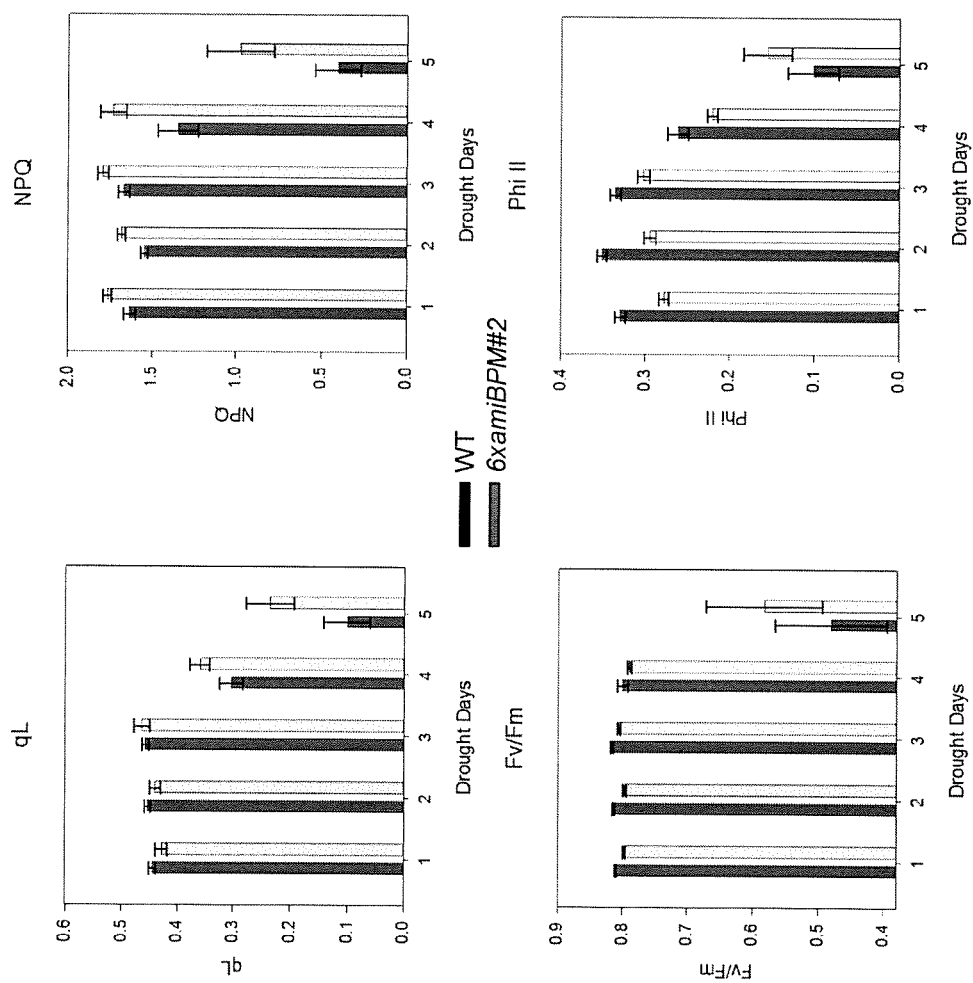

FIG. 19: Photosynthetic parameters of dark adapted plants exposed to drought stress. Plants were grown for three weeks in soil under standard growth conditions (long day (16 h light: 8 h dark)). Drought stress was applied by withholding water over a period of 5 days which is indicated on the X-axis. At day four significant changes were observed between wild type and 6×amiBPM plants (n=12). The changes indicate increased sensitivity of the mutant towards drought stress. qL; Estimates the fraction of open PSII centers on the basis of the lake model for PSII. NPQ; Non-photochemical quenching. Monitors the apparent rate constant for heat loss from PSII. Fv/Fm Maximum quantum efficiency of PSII photochemistry. Maximum efficiency at which light absorbed by PSII is used for reduction of Qa. Healthy plants are usually between 0.8 and 0.85. Phi II; PSII operating efficiency. Estimates the efficiency at which light absorbed by PSII is used for Qa reduction, and provides an estimate of linear electron flux through PSII.

Figure 20A:
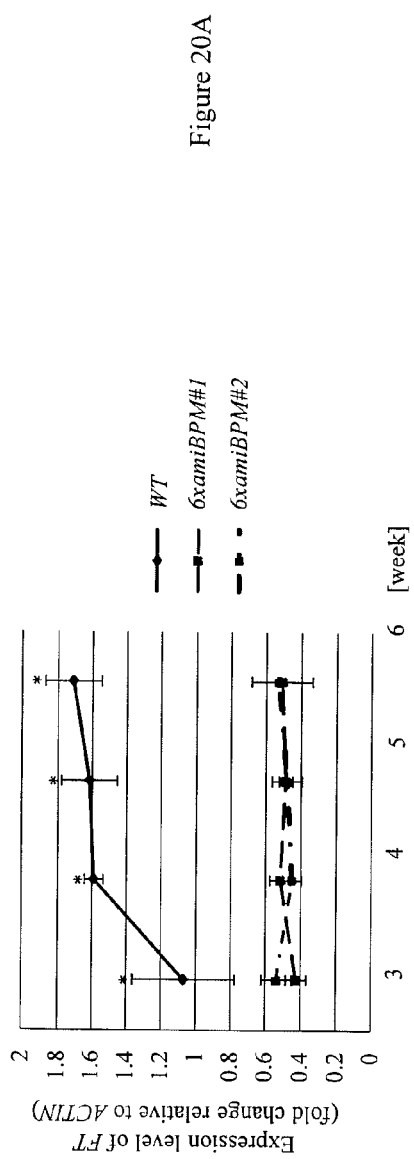
Figure 20B:
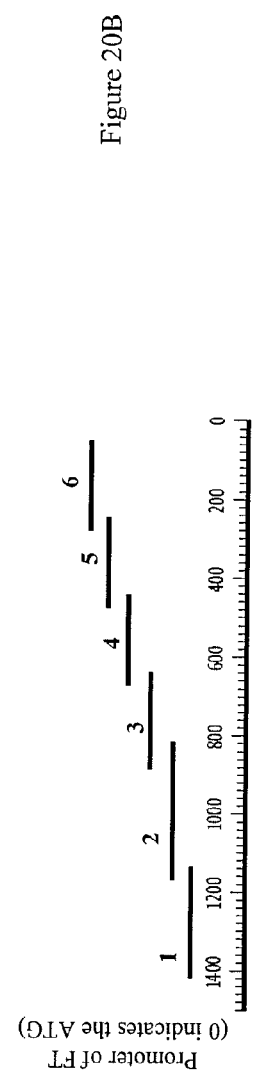

FIGS. 20A-B: Flowering phenotype analysis of WT, and 6×amiBPM mutants. (A) Expression level of Flowering Locus T (FT), a key regulator of the flowering time point, in rosette leaves at the end of the third, fourth, fifth, and sixth week after germination in wild type (WT) and 6×amiBPM plants. FT expression is significantly down regulated in 6×amiBPM plants when compared to WT which is in agreement with the late flowering phenotype of the mutants. (B) Schematic drawing of six different FT promoter regions analyzed via qPCR after α-CUL3 ChIP experiments. "0" indicates location of the start codon. (C) Significant enrichments were detectable in regions 1, 5 and 6 in WT, but not in a 6×amiBPM#1 control, indicating that CRL3$^{BPM}$ E3 ligases are directly involved in controlling FT expression. "NC" indicates negative control primer set afterwards of FT gene's ATG code. Asterisks indicate significant differences of mutant plants to WT (one-way ANOVA; P<0.05).

FIGS. 21A-E: Inducible 6×amiBPM constructs allow controlled increase in seed size. A, treatment of plants with estradiol over a time period of 24 hours leads to a significant down-regulation of all six BPM genes. B, pMDC7:6× amiBPM plants that carry an estradiol (E) inducible construct are indistinguishable from wild type (WT) when not treated with estradiol. Bar represents 5 cm. C-E, Plants carrying an estradiol (E) inducible 6×amiBPM construct were sprayed daily for around two weeks, starting at the onset of flowering with 10 mM estradiol (+E). The plants were indistinguishable in development from WT, except that seeds in E-treated 6×amiBPM plants were significantly larger then WT seeds (C, E), and heavier (D; data shown represent the average weight of 30 seeds). Bar represents 1 mm.

FIGS. 22A-J: Nucleotide sequence of full length BPM proteins from 27 different plant species (SEQ ID NOs. 68 to 94). Nucleotide sequences corresponding to the amino acid sequences listed in FIG. 16A-C.

DETAILED DESCRIPTION

Embodiments of the invention provide transgenic plants, wherein the expression of at least one BPM protein has been down-regulated or its activity reduced, resulting in enhanced yield-related traits, in particular but without limitation, increased seed oil production, as compared to a control plant. Control plants of the invention may be non-transgenic plants or plants wherein the expression or activity of a BPM protein has not been reduced or decreased by genetic engineering. Further embodiments of the invention provide methods for enhancing yield-related traits, in particular producing and recovering the seed oil from transgenic plants, wherein the expression of at least one BPM (BTB/POZ-MATH) protein is down-regulated or its activity reduced.

The following definitions are used throughout:

The terms "protein", "polypeptide" and "peptide" refer to contiguous chains of amino acids that are covalently bonded (linked) to each other by peptide (amide) bonds. In general, a peptide contains up to about 50 amino acids and a polypeptide contains about 50 or more amino acids. Proteins may contain one or more than one polypeptide. Those of skill in the art will recognize that these definitions are considered somewhat arbitrary, and these terms may be used interchangeably herein. The terms encompass amino acid polymers that are synthesized (transcribed and translated) in vivo and amino acid polymers that are chemically synthesized using procedures well known to those skilled in the art.

As used herein, the terms "nucleic acid" or "polynucleotide" or "nucleic acid molecule" refer to deoxyribonucleotides or ribonucleotides and polymers thereof in either single- or double-stranded form. Exemplary nucleic acids include DNA (including cDNA), RNA (e.g. mRNA, tRNA, rRNA, microRNA, amiRNA, antisense RNA, RNAi, etc.), and hybrids thereof.

The term "gene" means a segment of DNA that encodes a biologically active RNA, which may be further translated into a polypeptide chain. The term may or may not include regions preceding and following the coding region as well as intervening sequences (introns) between individual coding segments (exons). As used herein, a gene may be a recombinant or genetically engineered DNA sequence that encodes a polypeptide of interest from which introns have been eliminated.

The term "consensus sequence" or "motif" refers to a short conserved region in the sequence of evolutionary related proteins. Motifs are frequently highly conserved parts of domains, but may also include only part of the domain, or be located outside of a conserved domain.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell. The term "transformant" refers to a cell, tissue or organism that has undergone transformation.

As used herein, the term "transgenic" refers to cells, cell cultures, organisms (e.g., plants), and progeny which comprise a modified or foreign (heterologous) gene, wherein the modified or foreign gene is not originally present in the host organism. The term "transgenic" also refers to modification of an endogenous gene through the introduction of a transgene that modifies the endogenous gene in a plant. Transgenic organisms may receive the transgene by one of the various methods of transformation, but may also receive the transgene via conventional breeding techniques whereby at least one of the parent organisms comprises such a transgene.

"Recombinant" refers to a product of genetic engineering, e.g. a nucleic acid such as recombinant DNA, a protein that results from the expression of recombinant DNA, and recombinant cells or organisms that are transformed with recombinant DNA.

As used herein, the terms "plant" and "plant tissue" refer to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath. Plants also include vegetables and fruit plants. "Lower plants" is a collective term for three main groups of plants (mosses, liverworts and lichens) which do not have roots and produce spores to reproduce, rather than flowers. "Higher plants" refers to plants that have vascular tissue (as known as tracheophytes). "Seed producing plants" is a term referring to those plants that produce seed (Spermatophytes) and includes "Flowering plants", which refers to seed-producing plants, also known as Angiospermae or Magnoliophyta, as well as the Gymnospermae. Plants may be grown (e.g. in a field or a greenhouse) for production of food, fuel or fiber or other uses (e.g. wood, ornamentals). All such plants are encompassed by the present invention.

Exemplary plants or plant cells that may be utilized in the practice of the invention include but are not limited to: oil seed plants, canola, safflower, camelina, soybean, corn, sunflower, peanut, sesame, cotton rice, wheat, etc. Generally, oil seed plants (which may be trees) are cultivated so that oil, especially edible oil, can be produced from the seeds, nuts, tubers, etc. of the plants. Exemplary oil seed plants include but are not limited to: coconut, corn, cotton, olive, palm, peanut (ground nut), various rapeseed plants including canola, safflower, sesame, flax, soybean, sunflower, and the like. Various plant species that produce nuts from which oils are extracted may also be employed, including those that produce hazelnuts (e.g. from the common hazel), almond, beech (e.g. which produce *Fagus sylvatica* nuts), cashew macadamia, mongongo (or manketti, seeds of the *Schinziophyton rautanenii* tree), pecan, pine, pistachio, walnut, etc. Various citrus plants and trees produce seeds which are used to prepare edible oils, e.g. lemon, orange oil, grapefruit, sea-buckthorn, etc. Various melons and gourds may be utilized, e.g. watermelon (e.g. *Citrullus vulgaris*), members of the Cucurbitaceae family including gourds, melons, pumpkins, and squashes; the bitter gourd (*Momordica charantia*), bottle gourd (e.g. *Lagenaria siceraria*), buffalo gourd (*Cucurbita foetidissima*), butternut squash (e.g. *Cucurbita moschata*), egusi (*Cucumeropsis mannii naudin*, pumpkin, etc. Other plants and/or trees that may be utilized include borage (e.g. *Borago officinalis*), blackcurrant, evening primrose (e.g. *Oenothera biennis*), açai (e.g. any of several species of the Açai palm (Euterpe), black seed (e.g. from *Nigella sativa*), blackcurrant (e.g. *Ribes nigrum*), flax (linseed, e.g. *Linum usitatissimum*), carob, amaranth (e.g. from *Amaranthus cruentus* and *Amaranthus hypochondriacus*), apricot, apple, argan (e.g. from *Argania spinosa*), avocado, babassu r.g. *Attalea speciosa*), the seeds of *Moringa oleifera*, from which "ben" oil is extracted, species of genus *Shorea*, cape chestnut, the cacao plant, cocklebur (e.g. species of genus *Xanthium*), poppy, the *Attalea cohune* (cohune palm), coriander, date, *Irvingia gabonensis*, *Camelina sativa*, grape, hemp, *Ceiba pentandra*, *Hibiscus cannabinus*, *Lallemantia iberica*, *Trichilia emetica*, *Sclerocarya birrea*, meadowfoam, mustard, nutmeg (e.g. from cogeners of genus *Myristica*), okra (e.g. *Abelmoschus esculentus*), papaya, perilla, persimmon (e.g. *Diospyros virginiana*), *Caryocar brasiliense*, pili nut (e.g. *Canarium ovatum*), pomegranate (e.g. *Punica granatum*), prune quinoa, ramtil (e.g. several species of genus *Guizotia abyssinica* (*Niger* pea), rice, *Prinsepia utilis*, shea, *Sacha inchi*, sapote (e.g. *Jessenia bataua*), arugula (e.g. *Eruca sativa*), tea (Camellia), thistle (e.g. *Silybum marianum*), *Cyperus esculentus*, tobacco (e.g. *Nicotiana tabacum* and other *Nicotiana* species), tomato, and wheat, among others.

In some aspects, embodiments of the invention provide products produced by plants or from plants or parts of plants, for example, oils produced from the seeds or nuts of the transgenic plants. Exemplary oils of the invention include but are not limited to: Coconut oil, Corn oil, Cottonseed oil, Olive oil, Palm oil, Peanut oil (Ground nut oil), Rapeseed oil (including Canola oil) Safflower oil, Sesame oil, Soybean oil, and Sunflower oil. Various nut oils are also contemplated, including but not limited to: Almond oil, Beech nut oil, Cashew oil, Hazelnut oil, Macadamia oil, Mongongo nut oil (or manketti oil), Pecan oil, Pine nut oil, Pistachio oil, and Walnut oil. Various Citrus oils are also contemplated, including but not limited to: Grapefruit seed oil, Lemon oil, Orange oil, and sea-buckthorn oil. Oils from melon and gourd seeds are also contemplated, including but not limited to: Cucurbitaceae oils from e.g. gourds, melons, pumpkins, and squashes such as Watermelon seed oil, Bitter gourd oil, Bottle gourd oil, Buffalo gourd oil, Butternut squash seed oil, Egusi seed oil, and Pumpkin seed oil, Various other plant-derived oils are also encompassed by the invention, including but not limited to: Açai oil, *Arabidopsis* oil, Black seed oil, Blackcurrant seed oil, Borage seed oil, Evening primrose oil, Flaxseed oil (linseed oil), Carob seed pods, Apricot oil, Apple seed oil, Argan oil, Avocado oil, Babassu oil, Ben oil, Borneo tallow nut oil, Cape chestnut oil, Carob pod oil (Algaroba oil), Cocoa butter, Cocklebur oil, Cohune oil, Coriander seed oil Date seed oil, Dika oil, False flax oil Grape seed oil, Hemp oil, Kapok seed oil, Kenaf seed oil, Lallemantia oil, Mafura oil, Manila oil, Meadowfoam seed oil, Mustard oil (pressed), Poppyseed oil, Nutmeg butter, Okra seed oil, Papaya seed oil, Perilla seed oil, Persimmon seed oil, Pequi oil, Pili nut oil, Pomegranate seed oil, Prune kernel oil, Quinoa oil, Ramtil oil, Rice bran oil Royle oil, Sacha inchi oil, Sapote oil, Seje oil, Shea butter, Taramira oil, Tea seed oil (Camellia oil), Thistle oil, Tigernut oil (or nut-sedge oil) Tobacco seed oil, Tomato seed oil, and Wheat germ oil, etc.

It is an object of the invention to provide transgenic plants having enhanced yield-related traits as compared to a non-transgenic plant or other control plant which has not been similarly genetically engineered according to the teachings provided herein. Yield-related traits include, but are not limited to, seed oil production, flowering, stress-tolerance, and increased growth rate. In exemplary embodiments, the transgenic plants have increased seed oil production as compared to control plants (e.g., non-transgenic plants or plants not genetically engineered as described herein).

The plants of the present invention have been genetically engineered using molecular biology techniques to down-regulate the expression or reduce the activity of at least one BPM protein. Methods of producing transgenic plants are well known to those of ordinary skill in the art. Transgenic plants can be produced by a variety of different transformation methods including, but not limited to, electroporation; microinjection; microprojectile bombardment, also known as particle acceleration or biolistic bombardment, e.g. using needle-like crystals ("whiskers") of silicon carbide; viral-mediated transformation; Agrobacterium-, Rhizobium-, Mesorhizobium- and Sinorfizobium-mediated transformation. See, for example, U.S. Pat. Nos. 5,405,765; 5,472,869; 5,538,877; 5,538,880; 5,550,318; 5,641,664; 5,736,369; 5,736369; and US patent applications 2005/0289672 and 2005/0289667; each of which is expressly incorporated herein by reference in entirety. Progeny of the transgenic plants of the invention are also encompassed.

BPM proteins are found in almost all plants and the exemplary amino acid sequences of BPM proteins from 27 different species and a consensus sequence are shown in FIGS. 16A-C. The corresponding nucleotide sequences are shown in FIGS. 22A-J. The species listed in FIGS. 16A-C contain members of the Eudicots as well as monocot groups and one spikemoss. The spikemoss is an ancient plant with members of this family existing before Angio- and Gymnosperms were present. The alignment as shown in FIG. 16 indicates that BPMs are functionally conserved. FIG. 17 compares the full length BPM proteins shown in FIGS. 16A-C for identity and similarity.

Aspects of the invention related to the down-regulation of at least one BPM protein in a transgenic plant. The term "down-regulation" refers to a decrease in endogenous gene expression and/or polypeptide levels as compared to a control, wherein the expression levels in the control have not been modulated. The reduction may be at least about 10% or more reduced compared to that of a non-transgenic control plant, preferably at least 40% and more preferably at least 60%. Methods of decreasing expression of proteins in plants are well known in the art and include, but are not limited to artificial microRNA (amiRNA), antisense RNA, RNAi or co-suppression, and T-DNA insertion. In exemplary embodiments, amiRNA is introduced into the plant to down-regulate expression of at least one BPM protein. Other methods for down-regulating expression of proteins, for example the use of CRISPR-Cas9 nucleases, can be used in the practice of this invention and the invention encompasses each of these methods (Hsu et al., 2014). One of ordinary skill in the art would be able to adapt the various known biological methods for silencing so as to reduce the expression of a gene in a plant or in parts thereof.

Additional aspects of the invention relate to the reduced activity of at least one BPM protein. The term "reduced activity" refers to the functional aspects of the BPM protein. For example, "reduced activity" is construed to mean that the ability of the BPM protein to assemble with cullin, to interact with other BTB/POZ proteins, and/or to function as an adaptor to allow binding of a substrate and delivery to the CRL3 core for ubiquitylation is fully or partially inhibited. Methods of altering the activity of a protein are known in the art and include, but are not limited to reducing expression (for example, amiRNA), substrate competition (for example, MATH domain overexpression), targeted mutation of amino acid residues required for binding to substrates, and targeted mutation of amino acid residues in substrate proteins required for recognition (by the MATH domain for example). In exemplary embodiments, an exogenous BPM domain, preferably the MATH domain, is expressed in the plant to compete with at least one BPM protein for binding with a substrate.

Exemplary amino acid sequences are provided, but those of skill in the art will recognize that various other modified forms (variants or derivatives) of the amino acid sequences disclosed herein may be made, and the invention encompasses all such variants/derivatives, as long as the resulting molecule retains a desired level of activity as described herein. Exemplary encoding nucleotide sequences are also provided, but those of skill in the art will recognize that, due to the redundancy of the genetic code, other nucleotide sequences may also encode the same protein/polypeptide.

The nucleic acid molecules described herein may be modified, for example, by codon optimization to facilitate expression in heterologous cells. This type of modification changes or alters the nucleotide sequence that encodes a protein of interest to use, throughout the sequence, codons that are more-commonly used in the transgenic expression host cell. In addition, changes may be made to the nucleotide sequence that encodes the protein to adjust the relative concentration of A/T and G/C base pairs to ratios that are more similar to those of the expression host.

In addition, nucleotide sequences encoding MATH domains of the invention may be further modified to encode other sequences such as those described above as being beneficial or desirable for inclusion in the plants of the invention, e.g. sequences which target or direct the polypeptide to a particular location or locations within the expression host cell, etc.

The invention also encompasses vectors that comprise the nucleic acid sequences described herein. "Vector" refers broadly to any plasmid or virus encoding an exogenous nucleic acid. (However, the term may also be construed to include non-plasmid and non-viral compounds which facilitate transfer of nucleic acid into virions or cells, such as, for example, polylysine compounds and the like.) The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art. Examples of viral vectors include, but are not limited to recombinant vaccinia, adeno-, retro-, adeno-associated, avian pox and other viral vectors. Examples of non-viral vectors include, but are not limited to, liposomes, polyamine derivatives of DNA, and the like.

Embodiments of the invention provide transgenic plants with enhanced yield-related traits as compared to non-transgenic plants and methods for producing the same. In preferred embodiments, the transgenic plants have increased seed oil production. The amount of seed oil that can be recovered from plants of the present invention is more than about 1% in comparison to the oil recovered from non-transgenic plants, preferably more than about 25%, and more preferably more than about 50%. The more severe the down-regulation of BPMs or the reduction of the activity of BPMs, the higher the amount of seed oil that may be recovered from the plant. Methods of recovery of oil from a plant are known in the art and can be performed substantially as described in Focks and Benning, 1998. Methods of cultivating plants under conditions promoting plant growth and development are also known in the art.

Embodiments of the invention provide novel biotechnological approaches to improve yield-related traits in plants, in particular seed oil production, with beneficial impacts for biofuel or food-related products. Embodiments of the invention have many applications including, but not limited to, producing food, feed, or an industrial product comprising obtaining a plant or a part thereof, as herein described, including plants wherein the expression of at least one BPM protein is down-regulated or its activity reduced and preparing the food, feed or industrial product from the plant or part thereof. The food or feed may be oil, meal, grain, starch, flour or protein; or the industrial product may be biofuel, fiber, industrial chemicals, a pharmaceutical or a nutraceutical.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. *Arabidopsis* BPM Proteins Function as Substrate Adaptors to a CUL3-Based E3 Ligase Affecting Fatty Acid Metabolism in Plants Summary Regulation of transcriptional processes is a critical mechanism that enables efficient coordination of the synthesis of required proteins in response to environmental and cellular changes. Transcription factors require accurate activity control because they play a critical role as key mediators assuring specific expression of target genes. In this example, it is shown that Cul3-based E3 ligases can interact with a broad range of ERF/AP2 transcription factors, mediated by MATH-BTB/POZ proteins. The assembly with an E3 ligase causes degradation of their substrates via the 26S proteasome, as demonstrated for the WRINKLED1 ERF/AP2 protein. Furthermore, loss of MATH-BTB/POZ proteins widely affects plant development and causes changed fatty acid contents in mutant seeds. Overall the work provides a novel link between fatty acid metabolism and E3 ligase activities in plants, and establishes Cul3-based E3 ligases as key regulators in transcriptional processes that involve ERF/AP2 family members.

Materials and Methods

Plant Materials and Growth Conditions

*Arabidopsis thaliana* wild-type ecotype Columbia plants and plants of the different genetic backgrounds were grown either on *Arabidopsis thaliana* (AT) medium without supplement of Suc (Estelle and Somerville, 1987) in a growth chamber at 22° C. with 120 µmol/m²/s light intensity or in soil in a greenhouse at 20° C. under long-day conditions (16 hours light/8 hours dark).

Clone Constructions

The cDNAs of BPM1$^{MATH}$, BPM1$^{MTH:NLS}$, CUL3s, ERF/AP2s, and BPMs were cloned into pDONR221 (Invitrogen). For Y2H studies, the corresponding cDNAs were shuffled into destination vectors pACT2 (prey) and pBTM116-D9 (bait) by Gateway technology (Invitrogen) as described (Weber et al., 2005). pDEST15 (Invitrogen) and pET-58-DEST (Merck) were used to express and purify GST- and His-tagged proteins in *Escherichia coli*, respectively; where necessary, elution of GST proteins from glutathione-agarose beads was done following standard procedures. pMDC43 was used for expression in plants and for subcellular localization studies as described (Curtis and Grossniklaus, 2003). The NLS sequence was adopted from Howard et al. (1992), extended, and attached to the MATH domain in a four-step-based PCR process. To generate artificial microRNAs, a protocol from the WMD2 microRNA designer Web page; see FIG. 6) was followed using pRS300 as starting vector. For expression in plants, ami constructs were first cloned into pDONR221 before being shuffled into the binary vector pGBW14. For primers used see Table 1 below.

TABLE 1

Primers used for different PCR-based approaches.

| Name of Primer | Sequence of Primer (5'-3') |
|---|---|
| Cloning of constructs | |
| T7BPM1MATHFW (SEQ ID NO: 29) | TAATACGACTCACTATAGGGAGAATGTTCAAGATCTGTGGGTAC |
| BPM1MATHRW (SEQ ID NO: 30) | CTACATTTCTAGACTGGACCTCCTG |
| BPM1-MATH-RW-NLS (SEQ ID NO: 31) | TCGTCCTCAGTGGACGCTTAGAGAGCACTTCTAGACTGGACCTCCTG |
| NLS-1RW (SEQ ID NO: 32) | ACGCTTACGCTCAGATGGCTCACCGTCGTCGTCCTCACGTGGACGCTTAG |
| NLS-RW2 (SEQ ID NO: 33) | CACGACCGTCCTTAGAACGCTCGTCACGCTCACGCTTACGCTCAGATGGC |
| Attb2stop-NLS (SEQ ID NO: 34) | AGAAAGCTGGGTCACGACGGTTACCACCACGACCGTCC |
| WRI1-FW (SEQ ID NO: 35) | ATGAAGAAGCGCTTAACCAC |
| WRI-RW (SEQ ID NO: 36) | TCAGACCAAATAGTTACAAG |
| qRT-PCR | |
| ACTIN2-qRT FW (SEQ ID NO: 37) | CCTGCCATGTATGTTGCCATT |
| ACTIN2-qRT RW (SEQ ID NO: 38) | AATCGAGCACAATACCGGTTGT |
| BPM1-qRT-FW (SEQ ID NO: 39) | ATTGGCGTCTACTCTTGT |
| BPM1-qRT-RW (SEQ ID NO: 40) | AATGATGCTGCTCTGCTA |
| BPM2-qRT-FW (SEQ ID NO: 41) | TAATCGGCACAGACTTGA |
| BPM2-qRT-RW (SEQ ID NO: 42) | ACTCGCATATTGTTCTAAGC |
| BPM3-qRT-FW (SEQ ID NO: 43) | CACCAGTTCACGATTCAAG |
| BPM3-qRT-RW (SEQ ID NO: 44) | CCACCAACGGAGAAGATAT |
| BPM4-qRT-FW (SEQ ID NO: 45) | TCCTGATGGCAAGAATCC |
| BPM4-qRT-RW (SEQ ID NO: 46) | CGAAGTGGCTATGAACCT |
| BPM5-qRT-FW (SEQ ID NO: 47) | TTAGGCTCAGGTTGTTGT |
| BPM5-qRT-RW (SEQ ID NO: 48) | TCATCCTTCATCTGTTGGTA |
| BPM6-qRT-FW (SEQ ID NO: 49) | GCATAAGGTTCATAGCCATT |
| BPM6-qRT-RW (SEQ ID NO: 50) | AGATGTCTCAAGCAAGGA |
| WRI1-qRT-FW (SEQ ID NO: 51) | GAGCAACAAGAAGCAGAG |
| WRI1-qRT-RW (SEQ ID NO: 52) | CCACAACGATCCATTTCC |
| BCCP1-qRT-FW (SEQ ID NO: 53) | CAGCCAAATCGTCACT |
| BCCP1-qRT-RW (SEQ ID NO: 54) | GTTCCGGTATGGTCAG |
| AtGLB1-qRT-FW (SEQ ID NO: 55) | CTTTCACCGTCTTAGGAACAAACAG |
| AtGLB1-qRT-RW (SEQ ID NO: 56) | TAGGAACAGAGTTTCGATGTCTGAGAAC |
| BPM1-MATH-qRTFW (SEQ ID NO: 57) | CGGAGGATAACTCGTCTT |
| BPM1-MATH-qRTRW (SEQ ID NO: 58) | AATGGCTATGAACCTTATGC |
| ChIP-qPCR | |
| EF1-qRT-FW (SEQ ID NO: 59) | CTGGAGGTTTTGAGGCTGGTTA |
| EF1-qRT-RW (SEQ ID NO: 60) | CCAAGGGTGAAAGCAAGAAGA |
| ProBCCP1-qRT-FW (SEQ ID NO: 61) | AAGTGAACTGTTGTTGTT |
| ProBCCP1-qRT-RW (SEQ ID NO: 62) | CGTCTTCTTATTGTTATTGG |
| Pro-GLB1-qRT-FW (SEQ ID NO: 63) | TTCCAATAATTACCTCCTT |
| Pro-GLB1-qRT-RW (SEQ ID NO: 64) | TTTAACACAACTTTCAAAG |

Subcellular Localization Studies

The fluorescent fusion proteins GFP:WRI1, GFP:BPM1$^{MATH}$, and BPM1$^{MATH:NLS}$ were transiently expressed in Nicotiana benthamiana epidermal cells following the method described by Sparkes et al. (2006). GFP expression was detected and documented with a Zeiss LSM 510 Meta confocal microscope.

Interaction and Complex Assembly Studies

Y2H studies were followed as described by Weber et al. (2005). SDII selection medium supplemented with uracil and His was used as a transformation control, while for interaction studies, SDIV minimal medium was chosen without uracil and His supplements. Photos were taken from single spots 7 days after plating. FPLC was performed with 2 mg protein injections and a flow rate of 50 μL/min using an AKTA FPLC system (GE Healthcare Science) and as described by Leuendorf et al. (2010). Pull-down analysis and IP studies were followed as described before (Hellmann et al., 2003; Bernhardt et al., 2006). Extraction and washing buffers contained at all times 1 mM PMSF (Sigma-Aldrich) and 10 μM MG132 (Sigma-Aldrich) to prevent proteolytic and proteasomal activities, respectively. For pull-down analysis with GST- and His-tagged proteins, GST-containing proteins were first eluted from glutathione-agarose beads before incubated with His:WRI1 that remained attached to tetradentated-chelated nickel resin. In general, proteins were incubated at least 1.5 h at 4° C. under shaking conditions before being centrifuged. Precipitates were washed no less than three times to remove unspecific bindings, before they were taken up in Laemmli buffer (Laemmli, 1970) and boiled (10 min, 95° C.). IPs were followed as described by Bernhardt et al. (2006). In brief, 1 mg of fresh protein extracts from 2-week-old seedlings were precleaned with 30 μL protein-A-agarose beads (Santa Cruz Biotechnology; 1.5 h, 4° C.). The beads were centrifuged, and the supernatant was transferred into a fresh tube and incubated first with α-WRI1 (1.5 h, 4° C.) before 30 μL protein-A-agarose beads were added (1.5 h, 4° C.). After brief centrifugation, four washing steps followed, after which precipitates were taken up in Laemmli buffer and boiled as described above. For pull-down and IP studies, precipitates were further analyzed by SDS-PAGE and protein gel blotting using standard procedures. Where applicable, membranes were stained with Ponceau S to detect transferred proteins. For immunodetection, custom-made (α-CUL3 [rabbit] and α-WRI1 [rabbit]; GeneScript) or commercially available antibodies (GST, secondary α-rabbit IgG-horseradish peroxidase; Santa Cruz) in combination with an ECL Plus Western Blotting Detection Kit (GE Healthcare Life Science) were used.

Stability Assays

For stability assays, *Arabidopsis* seedlings were cultured on solid AT medium for 2 weeks before being transferred to 5 mL AT liquid medium. Plants were incubated for 3 h with the transcriptional inhibitor ActD2 (Sigma-Aldrich; final concentration 10 μg/mL) and/or the proteasomal inhibitor MG132 (Sigma-Aldrich; 20 μM/mL, 6 h) before CHX (Sigma-Aldrich; 100 μM/mL, 3 h) was added to inhibit translation. DMSO was used as mock control and as a dissolvent for all inhibitors. Protein gel blot analysis and protein detection were conducted using standard procedures. The antibodies against WRI1 and CUL3 were designed and produced by GeneScript and used in a 1:1000 dilution. Protein detection was followed as described in the ECL Plus Western Blotting Detection Kit manual (GE Healthcare Life Science).

RNA Isolation and Expression Analysis

Total *Arabidopsis* RNA was extracted following the protocol of the Isolate RNA kit from Bioline; reverse transcription was done according to the manual for the high-capacity cDNA reverse transcription kit (Applied Biosystems). qRT-PCR reactions (95° C., 7 min; 95° C., 15 s; 60° C., 1 min; 40 cycles) were performed using the SYBR green method on a 7500 Fast Real-Time PCR system (Applied Biosystems). Relative gene expression analyses were calculated by the full quantification method with ACTIN2 as the internal control gene. Fourteen 2-week-old seedlings were pooled for each replicate. At least three biological replicates were performed for each individual experiment. Primers used for qRT-PCR are shown in Table 1 above.

ChIP Assays

For ChIP assays, an established protocol was followed (Morohashi et al., 2009). In brief, 60 mg (fresh weight) of 15-day-old seedlings were harvested for each ChIP experiment and cross-linked for 10 min under vacuum in cross-link buffer containing 1% formaldehyde as described by Morohashi et al. (2009). Cross-linked samples were incubated in 100 mM Gly for 5 min under a vacuum, thoroughly washed in double-distilled water, and snap frozen in liquid nitrogen. Frozen tissues were ground into fine powder and dissolved in nuclear isolation buffer (Morohashi et al., 2009) supplemented with 1× protease inhibitor cocktail (Sigma-Aldrich). After filtering through single-layered Miracloth (Merck), the samples were centrifuged (10 min, 1200 g, 4° C.). Pellets were resuspended in nuclear isolation buffer supplemented with 0.3% Triton X-100 and centrifuged again (10 min, 10,000 g, 4° C.). After resuspension in lysis buffer, the purified nuclei were then sonicated (three times, 20 s, 9 W; Fisher Scientific Model 100 dismembrator) to yield chromatin fragments of 300 to 500 bps. Sonicated chromatin fragments (2 mg) were first precleared with protein-A-agarose beads (Sigma-Aldrich) (1.5 h, 4° C.) before being incubated with specific antibodies (1 mg/mL; 1.5 h, 4° C.), followed by a fresh batch of protein-A-agarose beads (30 μL; 1.5 h, 4° C.) to IP protein-DNA complexes. After IP, cross-linking was reversed by incubating samples overnight at 65° C. in elution buffer (1% SDS, 0.1 M NaHCO$_3$, and 0.25 mg/mL proteinase K; Morohashi et al., 2009), after which RNaseA (1 mg/mL) was added (30 min; room temperature). As input control for data normalization, a portion of sonicated, cross-linked, and precleared DNA was treated accordingly except for undergoing an IP. Samples were further cleaned up using a DNA purification kit (NuCleo-Spin Extraction II; Macherey-Nagel) and quantified to use equal amounts of template (50 ng/reaction) for qRT-PCR analysis. To amplify promoter sequences that contain an AW-box recognized by WRI1 (Maeo et al., 2009), specific primers were designed (Table 1). EF1 was selected as a reference gene for internal control. qRT-PCR reactions (95° C., 10 min; 95° C., 15 s; 60° C., 1 min; 50 cycles) were done as described above and repeated with at least three independent biological replicates.

Metabolic Analysis

Metabolic profiling of 2-week-old seedlings grown on ATS plate (100 mg fresh weight) and seed samples (50 mg dry weight) of all backgrounds used in this study were analyzed according to earlier described protocols (Roessner-Tunali et al., 2003). Seed fatty acids were extracted exactly as described before (Focks and Benning, 1998). For quantification with gas chromatography, pentadecanoic acid was used as an internal standard (Browse et al., 1985).

Accession Numbers

Sequence data from this Example can be found in the GenBank/EMBL data libraries under the following accession numbers: ACTIN2, At3g18780; IAA5, At1g15580; BPM1, At5g19000; BPM2, At3g06190; BPM3, At2g39760; BPM4, At3g03740; BPM5, At5g21010; BPM6, At3g43700; DREB1a, At4g25480; ERF1, At3g23240; ERF4, At3g15210; RAV1, At1g13260; WRI1, At3g54320; BCCP1, At5g16390; and GLB1, At2g16060.

Results

BPM Proteins Interact Broadly with ERF/AP2 Transcription Factors

We have earlier described that BPM proteins assemble with several, but not all members, of the A6 group of ERF/AP2 transcription factors (Weber and Hellmann, 2009). According to Sakuma and co-workers, the ERF/AP2 superfamily can be divided into five subgroups: AP-2, RAV, DREB, ERF, and others (Sakuma et al., 2002). The A6 group belongs to the ERF subfamily. To investigate how broadly BPM proteins assemble with ERF/AP2 transcription factors, we also tested in yeast-2-hybrid (Y2H) assays additional members outside the A6 group using BPM1 as prey (FIG.

2A). The ERF subfamily member ERF1 (At3g23240) showed weak interaction, while the ERF-subfamily members WRI1 (At3g54320) and ERF4 (At3g15210), showed a strong interaction with BPM1 in the Y2H assay. WRI1 also tested positively for self-assembly in the yeast assay (FIG. 2B). Finally, DREB1a (At4g25480), which belongs to the DREB subfamily, and also RAV1 (At1g13260), a member of the RAV-subfamily, strongly interacted with BPM1 (FIG. 2A). Since BPMs interact also with CUL3 proteins, we tested interaction of the different ERF/AP2 transcription factors with CUL3a, and did not observe any in the yeast system (data not shown). We therefore concluded that a large number of ERF/AP2 transcription factors is recognized by BPM proteins in Arabidopsis.

CUL3 and BPM Proteins Assemble in Planta with WRI1

To identify and demonstrate basic principles of CRL3$^{BPM}$ complex assembly with substrates, we focused on a single well-described protein, WRI1, which is a key player in fatty acid and carbohydrate metabolism (Cernac and Benning, 2004; Baud et al., 2009).

In agreement with findings from the Y2H assays, pull-down experiments using a GST:WRI1 fusion protein can co-precipitate in vitro translated BPM1 from rabbit reticulolysates (FIG. 2C). For further investigation of in planta complex assembly, specific peptide-based antibodies were raised against CUL3 and WRI1 (FIG. 1). The antibody against CUL3 does not distinguish between CUL3a and b (FIG. 1 A,C); however transient expression experiments in tobacco clearly demonstrated specificity of the α-CUL3 antibody. We only observed a single band of around 85 kDa appearing on Western blots with wild type (WT) or cul3 mutant plant extracts (FIG. 1B). Likewise, only a single band was detectable when the α-WRI1 antibody was used on total plant extracts from WT plants, and which was missing in a wri1-3 mutant when the α-WRI1 antibody was used on total plant extracts (FIG. 1E).

Figure 3A:
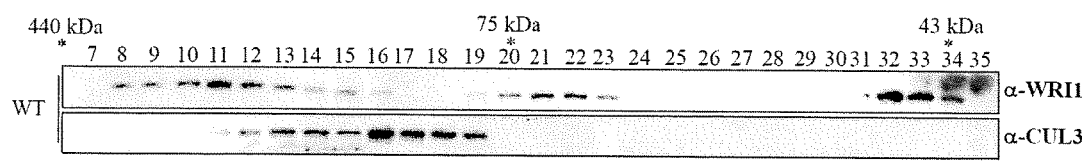
FIG. 3A-B: FPLC analysis and subcellular localization of WRI1. (A) Western blot analysis of FPLC fractions from two-week-old *Arabidopsis* WT plantlets tested with either α-WRI1 or α-CUL3, showed co-migration of the two proteins in fractions between 70 and 150 kDa. WRI1 is also present in fractions corresponding to proteins of around 40-50 kDa, and in fractions higher than 150 kDa indicating that the protein assembles also in complexes distinct from CUL3. (B) Transient expression analysis of GFP:WRI1 in tobacco shows that the fusion protein is located in the nucleus (green fluorescence derives from GFP; blue fluorescence from DAPI staining).
Figure 3B:
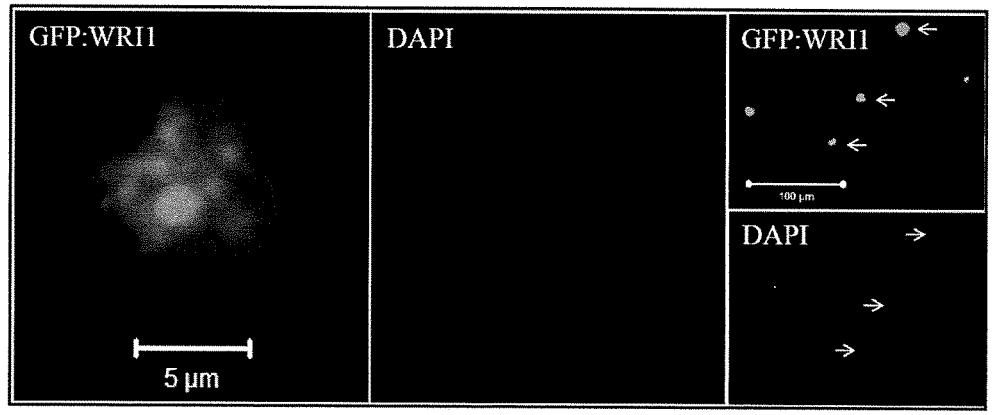

Pulldown experiments using GST:WRI1 against WT plant extract showed that the fusion protein precipitates both endogenous WRI1 and CUL3, however, this was not the case with GST alone (FIG. 2D). In addition, pulldown analysis with GST- and His-tag proteins expressed in and purified from E. coli demonstrated that BPM proteins are necessary to bridge assembly between WRI1 and CUL3 proteins. Here His:WRI1 is only capable of co-precipitating GST:CUL3a, if GST:BPM1 protein is present in the assay but not with GST alone (FIG. 2F). Also, immunoprecipitation (IP) studies using the α-WRI1 antibody successfully precipitated CUL3 from plant extracts in WT background (FIG. 2G). We also observed in FPLC studies co-migration of WRI1 with CUL3 (FIG. 3A), and detected GFP:WRI1 localized to the nucleus, as has been earlier shown for most BPM proteins and CUL3a (FIG. 3B; (Weber and Hellmann, 2009)). Overall these studies demonstrate that WRI1 assembles with CUL3 proteins in planta, and support the working hypothesis that the assembly is mediated by BPM proteins.

WRI1 is a CUL3-Dependent Target of the 26S Proteasome

Figure 4A:
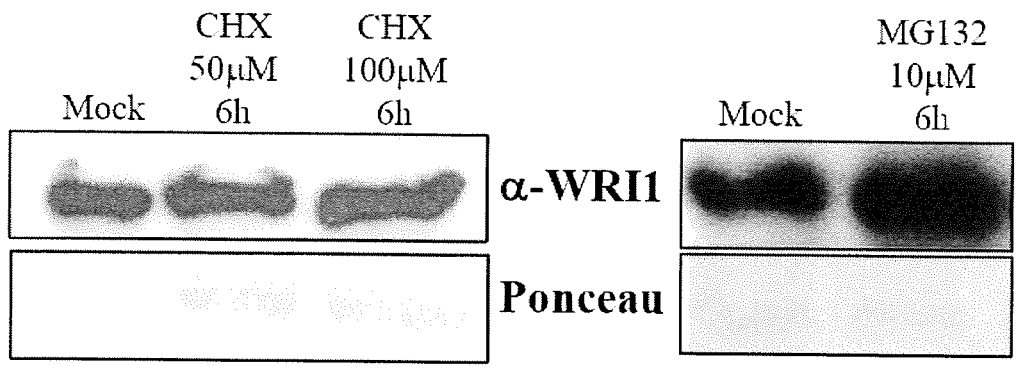
FIG. 4A-C: CHX treatment does not reduce the protein level of WRI1 but it induces its transcription level. (A) WRI1 protein levels do not decline 6 h after CHX treatment (both with 50 μM or 100 μM). (B) CHX but not MG132 treatment up-regulates WRI1 expression (p<0.01). (C) IAA5 (auxin-responsive protein IAA5) was used as positive control for CHX treatment. The expression of IAA5 was strongly induced by CHX treatment (p<0.01). In all cases two-week-old seedlings were used. Error bars illustrate standard error.

One outcome of BPM assembly with CUL3 proteins is the proteolytic degradation of their substrates. Consequently, stability assays were performed using the translational inhibitor cycloheximide (CHX) and the proteasomal inhibitor MG132. In initial experiments, CHX treatments did not point to instability of the WRI1 protein (FIG. 4A), although accumulation of WRI1 was observed when plants were treated with MG132 (FIG. 4A).

Figure 4B:
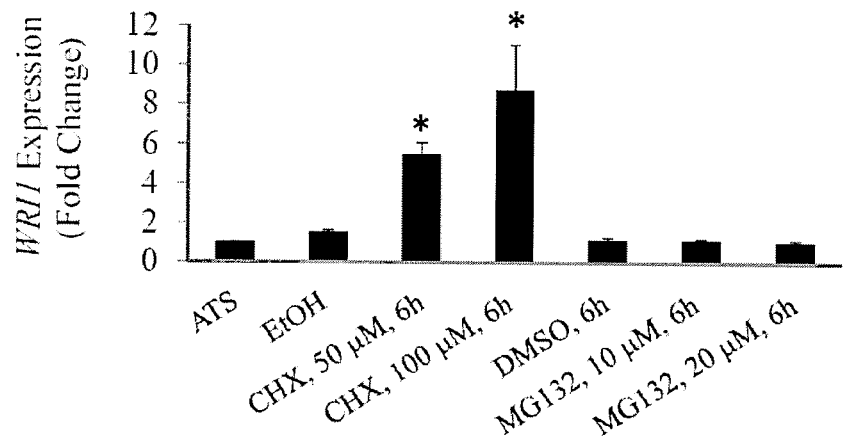
Figure 4C:
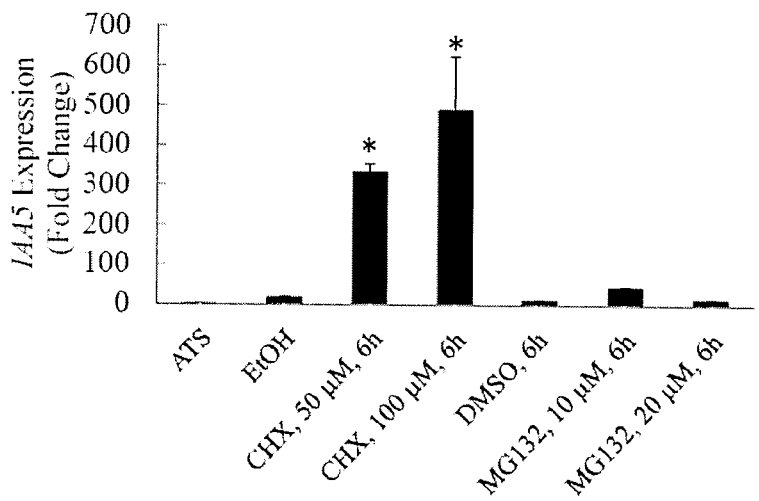

To further characterize this phenomenon, WRI1 expression was tested in plants treated with CHX or with the proteasomal inhibitor. While plants incubated with MG132 did not show any change in WRI1 expression, CHX caused a strong up-regulation of the WRI1 gene (FIG. 4B). It was therefore decided to pre-treat plants with the transcriptional inhibitor actinomycin D2 (ActD2) before CHX was given. Under these conditions WRI1 protein was completely gone after 6 h treatment, and its disappearance was blocked by co-incubation with MG132 (FIG. 5A), demonstrating that WRI1 is unstable in a 26S proteasome-dependent manner. Notably, the accumulation of WRI1 protein in samples treated with all three inhibitors is most likely due to pre-treatment of plants with ActD2 and MG132 for three hours before CHX was supplemented.

A cul3$^{hyp}$ double mutant was previously described that is knocked-out for CUL3b and partially functional for CUL3a (Thomann et al., 2009). We took advantage of this mutant to investigate whether WRI1 is stabilized in this genetic background and to prove that the instability is mediated by a CUL3-based complex. Western-blot analysis on WT and cul3$^{hyp}$ plant extracts showed that WRI1 was present in the mutant in higher amounts than in WT (FIG. 5B). This was not based on increased transcriptional activities in the mutant since no significant difference in WRI1 expression was detectable in either plant (FIG. 5C). Stability assays with ActD2 and CHX showed no considerable change in protein content over six hour treatments in the mutant, while WRI1 was not detectable in WT extracts (FIG. 5D), revealing that WRI1 is instable in a 26S proteasome- and CUL3-dependent manner.

BPM Proteins Bridge the Assembly Between WRI1 and CUL3 and are Broadly Important for Development.

The results show that BPM proteins assemble with a broad range of ERF/AP2 transcription factors and that, if ERF/AP2 proteins are in complex with CUL3s, the BPMs likely function as their bridging substrate receptors. Since WRI1 is unstable, and because complex formation requires presence of a functional CUL3 protein in the plant, it was necessary to investigate whether loss of BPM proteins is also stabilizing WRI1.

Two strategies were followed to support the hypothesis that BPM proteins function as substrate receptors and are required for mediating WRI1 instability. First, because of a lack of T-DNA insertion mutants for nearly all BPM genes, a 35S artificial microRNA (amiRNA) construct was designed to down-regulate expression of all six members, based on predictions from the WMD 2—Web MicroRNA Designer; FIG. 6) (the lines are further denoted as 6×amiBPM). Second, the MATH domain from BPM1 was cloned under the control of a 35S promoter and behind a GFP reporter, and with (further denoted as BPM1$^{MATH:NLS}$) or without (BPM1$^{MATH}$) a nuclear localization signal attached to the end of the domain to affect subcellular localization. The MATH construct was generated to impose a competition in the plant where endogenous BPM proteins have reduced access to WRI1 and thus, hypothetically cause its stabilization.

Figure 7A:
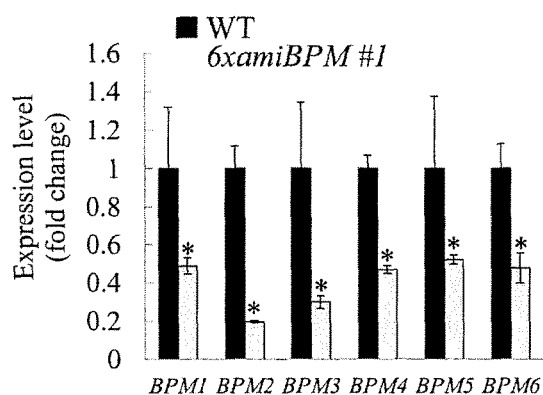
Figure 7B:
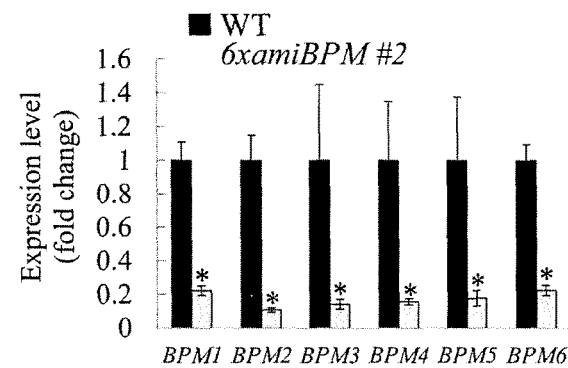
Figure 7C:
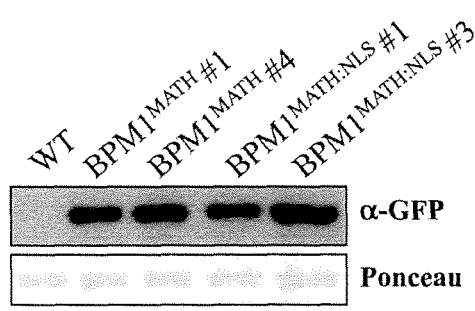
Figure 7D:
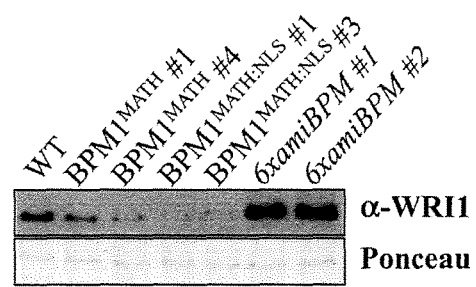

Several independent plant lines were successfully generated, and two independent lines of the T4 generation were chosen for each construct for further analysis. In both 6×amiBPM lines a significant down-regulation in gene expression of all BPMs was measurable (FIG. 7A,B), while the BPM1$^{MATH}$ and BPM1$^{MATH:NLS}$ lines showed strong expression of the transgene (FIG. 7C). In addition, based on the GFP reporter, BPM1$^{MATH}$ constructs were detectable throughout the cell, including the nucleus (FIG. 8A), while BPM1$^{MATH:NLS}$ was exclusively present in the nucleus (FIG. 8B). Analysis of T4-generation plants showed that the 6×amiBPM lines consistently had higher WRI1 protein levels comparable to cul3$^{hyp}$ mutants, while surprisingly all MATH-overexpression lines had significantly less WRI1 protein (FIG. 7D). Although the absolute degree of WRI1 reduction in MATH-overexpression lines varied among tested plants, we never observed any levels that equaled or exceeded those in WT. Also of note is that this is not based on reduced WRI1 expression, since the gene is actually up-regulated in BPM1$^{MATH}$ and BPM1$^{MATH:NLS}$ lines (FIG. 8C).

Figure 9A:
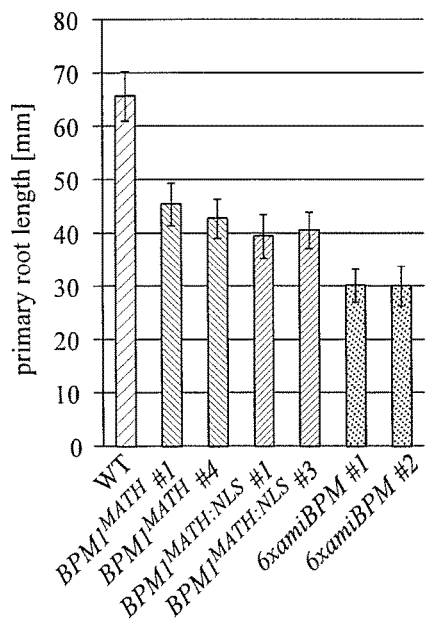
Figure 9B:
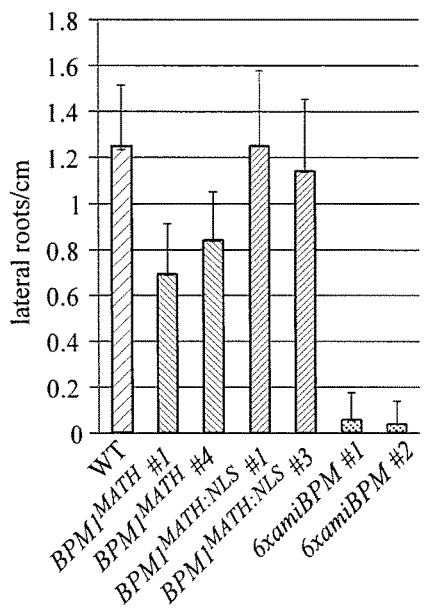
Figure 9C:
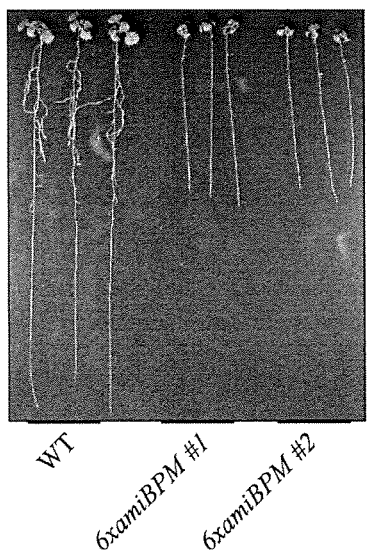
Figure 9D:
Figure 9E:
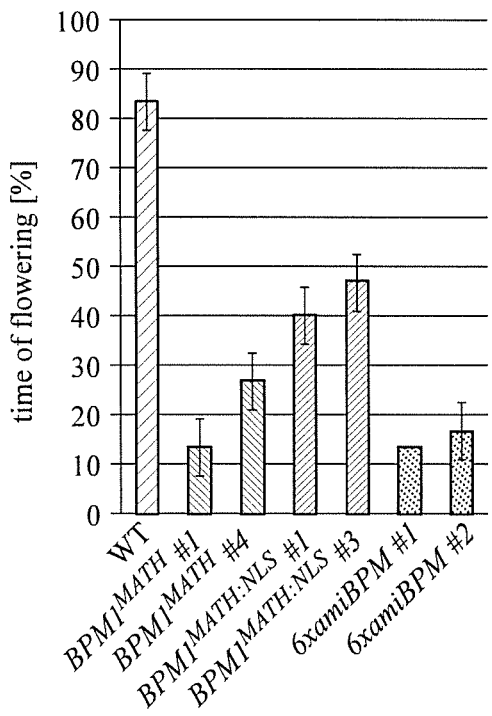
Figure 9F:
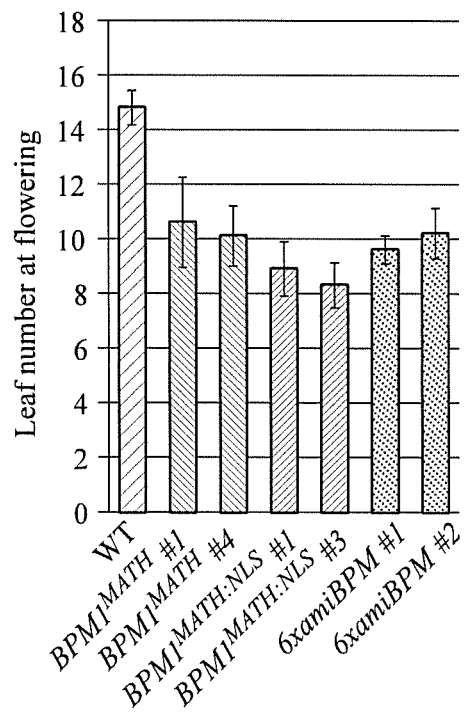
Figure 9G:
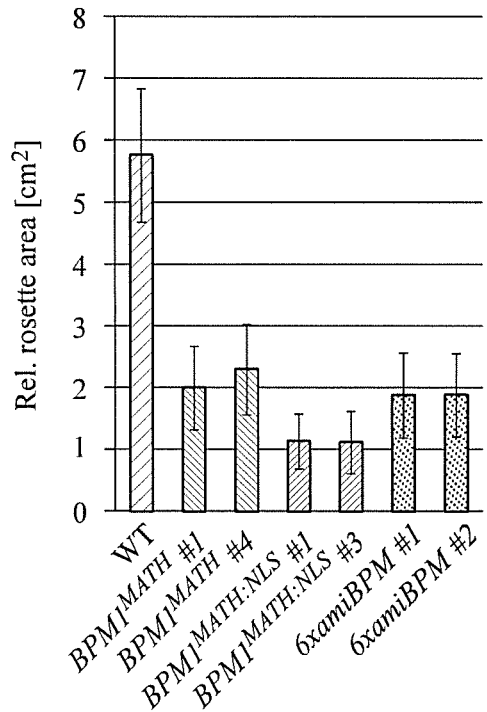

The different plant lines were broadly affected in development. Primary root growth was significantly delayed in all six lines, and most strongly in the two 6×amiBPM lines (FIG. 9A). While lateral roots emerged at a lower frequency in the BPM1$^{MATH}$ lines, no significant changes were detectable in plants expressing the BPM1$^{MATH:NLS}$ construct (FIG. 9B). The 6×amiBPM plants developed very low numbers of lateral roots (FIG. 9B,C), and all transgenic lines were affected in shoot development. In addition all were late flowering, most strongly pronounced in BPM1$^{MATH}$ and 6×amiBPM lines (FIG. 9D,E), with less leaves present at the beginning of flowering (FIG. 4F), and a reduced rosette size (FIG. 9D,G). Besides being smaller and present in fewer numbers, the leaves of transgenic plants also had a tendency to develop wider blades then WT (FIG. 10).

To characterize the extent WRI1 protein stability is affected in the different lines, stability assays were performed on selected plants (FIG. 11 and FIG. 12). The assays consistently showed that in either the 6×amiBPM or MATH-overexpressing backgrounds, WRI1 was highly stable in comparison to WT (FIG. 11A; FIG. 12A, B).

IP experiments were carried out on two MATH-overexpressing and two 6×amiBPM lines. As shown in FIG. 11B, CUL3 protein was precipitated from WT plant extracts, while no precipitated CUL3 was detectable in either the MATH-overexpressing or the 6×amiBPM lines. These findings together with stability assays demonstrate that the BPM proteins are required (i) for assembly of WRI1 into a complex with CUL3, and (ii) for mediation of the transcription factor's degradation.

WRI1 Activity is Affected by CRL3$^{BPM}$

We showed stabilization of WRI1 and an effect on its protein content in the plant in three different genetic backgrounds. In both cul3$^{hyp}$ double mutants and 6×amiBPM lines, WRI1 levels are increased, while in MATH-lines WRI1 amounts are decreased. In 6×amiBPM lines BPM expression is reduced, and in the cul3$^{hyp}$ and MATH-backgrounds BPM protein levels are likely unchanged. However, based on each genetic background, the assembly of WRI1 into a CUL3-based complex is differently affected by either reduced CUL3 availability and/or functionality (cul3$^{hyp}$), reduced BPM content (6×amiBPM), or reduced accessibility of BPMs to WRI1 (MATH-overexpressing lines). To show how these situations differently affect WRI1 transcriptional activities, expression of two confirmed WRI1 targets, BCCP1 and AtGLB1, were tested (Baud et al., 2009; Maeo et al., 2009). BCCP1 (At5 g16390), which encodes for a biotin carboxyl carrier protein, and AtGLB1 (At4g01900), which encodes for a PII protein, are both critical players in fatty acid biosynthesis, but also participate in carbon and nitrogen metabolism (Tissot et al., 1998; Chen et al., 2006).

qRT-PCR analysis showed loss of BCCP1 and AtGLB1 expression in the wri1-3 null mutant compared to WT (FIG. 11C). Expression of both genes in MATH-overexpressing lines was similarly reduced. In contrast, both genes were strongly up-regulated in 6×amiBPM lines correlating with changes in WRI1 protein content. Interestingly, no change in BCCP1 and AtGLB1 expression in comparison to WT was noticeable in the cul3$^{hyp}$ line, despite the fact that WRI1 protein levels were elevated comparable to 6×amiBPM lines. These findings indicate, based on the presumed presence (cul3$^{hyp}$) or absence (6×amiBPM), that BPM proteins also negatively affect transcriptional activity of their target proteins.

CUL3 Assembles with WRI1 at the DNA Level

Figure 11D:
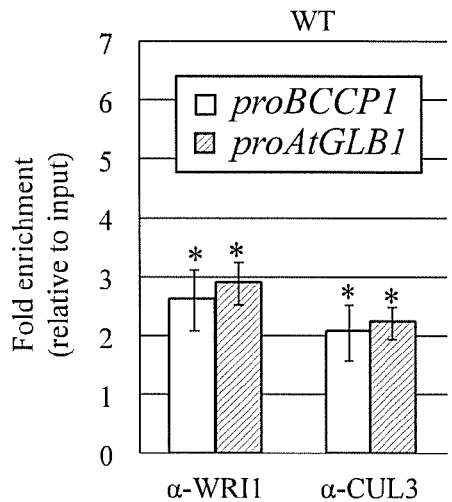
Figure 11E:
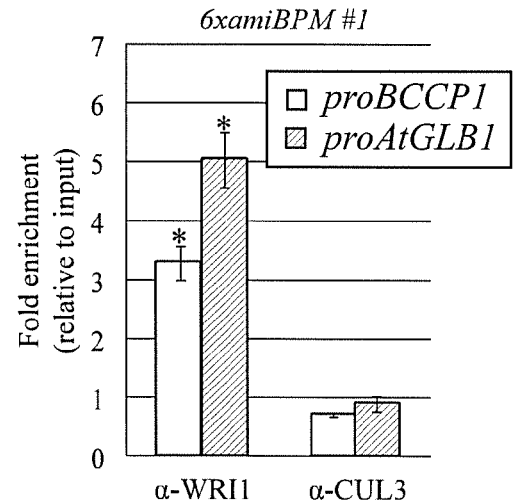
Figure 11F:
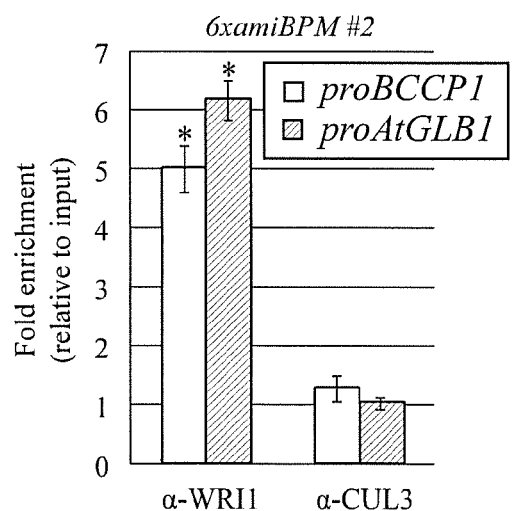
Figure 11G:
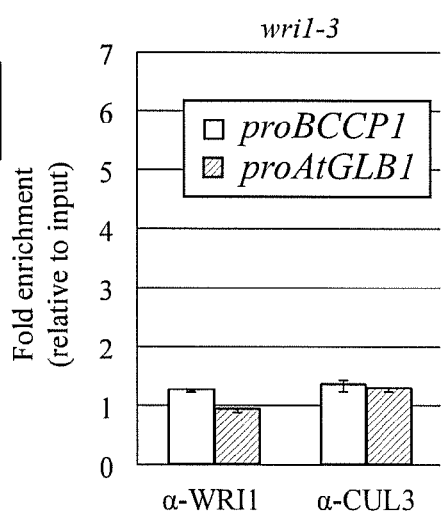

To show whether CUL3 forms a complex with WRI1 at the DNA level we performed chromosomal immunoprecipitation experiments (ChIP) (Morohashi et al. 2009). In WT plants, α-WRI1 and α-CUL3 based ChIP experiments resulted in a two to three-fold enrichment of WRI1 binding sites (proBCCP1 and proAtGLB1), respectively (FIG. 11D), while no enrichment was detectable in the wri1-3 null mutant, which served as a negative control (FIG. 11G). Interestingly, α-WRI1 ChIP in the two 6×amiBPM lines yielded higher levels of proAtGLB1 and proBCCP1 sites which was in agreement with higher WRI1 protein levels in these plants (FIG. 11E, F), as well as increased transcription of the corresponding genes (FIG. 11C). Finally, ChIP using the α-CUL3 antibody in 6×amiBPM lines did not lead to any enrichment of proAtGLB1 and proBCCP1 sites (FIG. 11E, F), which corroborates the finding that loss of BPMs disrupt the ability of CUL3 to assemble into a complex with WRI1 (FIG. 11B). Overall these results show that CUL3 proteins form a complex with WRI1 at the DNA level, and that this assembly requires BPM proteins.

Reduced BPM Content Affects Fatty Acid Metabolism in Seeds

Figure 13A:
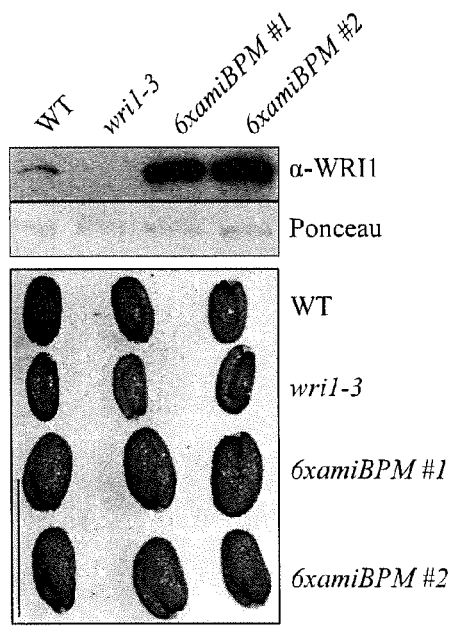
Figure 13B:
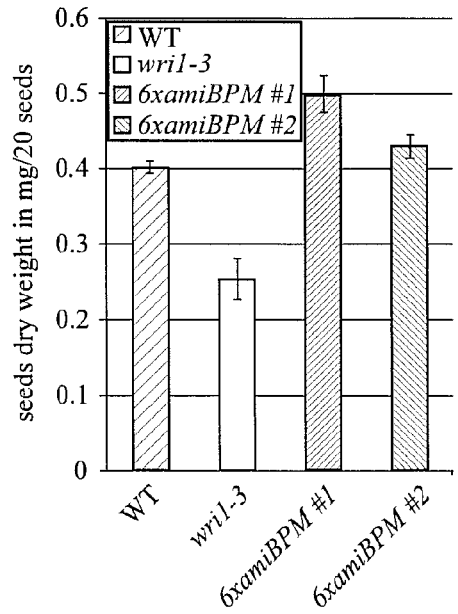
Figure 13C:
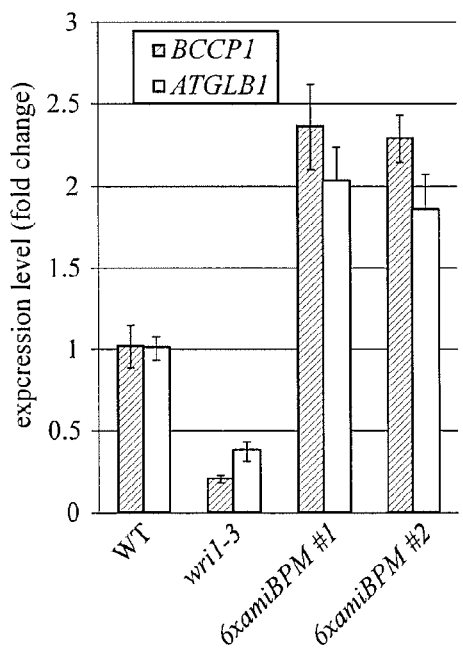
Figure 13D:
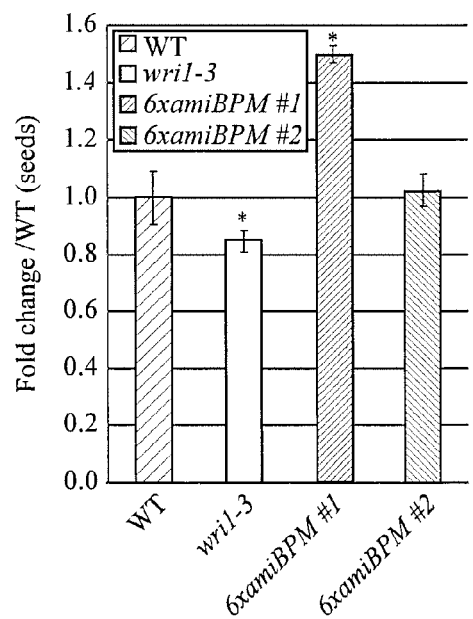

The finding that a reduced BPM expression in 6×amiBPM lines increases both WRI1 protein content and expression of WRI1 target genes was intriguing as it opened up the possibility that seeds of 6×amiBPM lines may also contain elevated levels of fatty acids due to augmented levels of active WRI1 (Baud et al., 2009). In agreement with this idea, both 6×amiBPM lines showed significant increases in seed weights and size when compared to WT seeds (FIG. 13A,B). However, changes were much more pronounced in 6×amiBPM #1 than in 6×amiBPM #2 plants, which may be due to different activities of the 35S promoter in seeds of the two lines. They also showed increased WRI1 content in seeds and elevated expression of the two target genes BCCP1 and AtGLB1 (FIG. 13C). Similar to increases in weight, both lines also showed altered total fatty acid contents (FIG. 13D); and while changes in 6×amiBPM #2 plants were only very mild and furthermore non-significant (~96 µg/30 seeds in average versus ~93 µg/30 seeds in WT), the total fatty acid content in 6×amiBPM #1 seeds was increased by around 50% (~140 µg/30 seeds) when compared to WT. The wri1-3 line was used in these experiments as a control, and showed a significant reduction in both seed weight and total fatty acid contents (~79 µg/30 seeds) when compared to WT and the two 6×amiBPM lines. While changes were observable for total fatty acid content measurements of individual fatty acids did not detect any significant changes (FIG. 14). In addition, no significant changes were observed in a general metabolic profile (amino and organic acids as well as soluble sugar) for wri1-3 or the two amiBPM lines when compared to WT (FIG. 14), indicating that the changes in seed size and weight for the mutants are primarily based on aberrant fatty acid contents. Overall these data further underscore that BPM proteins are critical regulators of WRI1 activity, and that their loss positively affects both WRI1 stability as well as its actions.

Figure 15A:
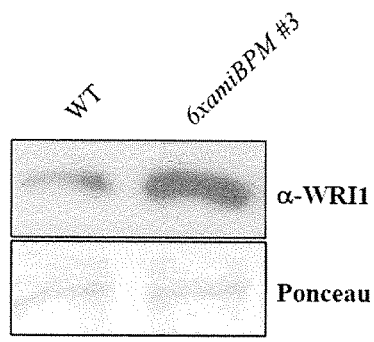
Figure 15B:
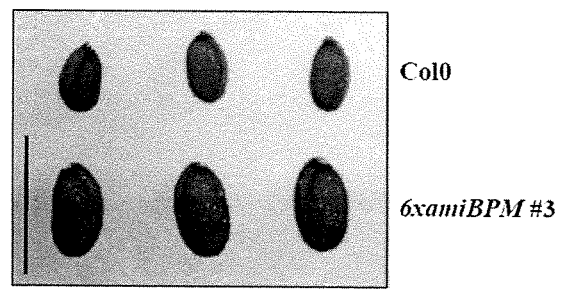
Figure 15C:
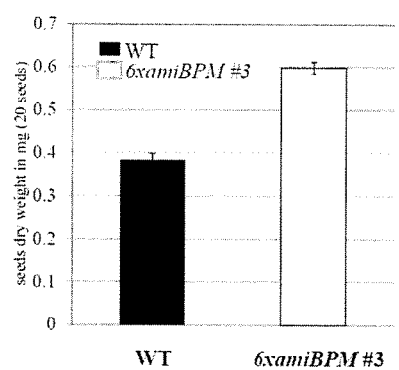
Figure 15D:
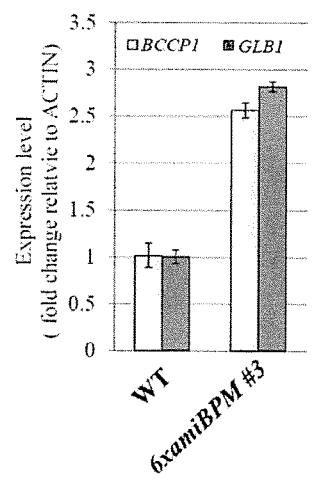
Figure 15E:
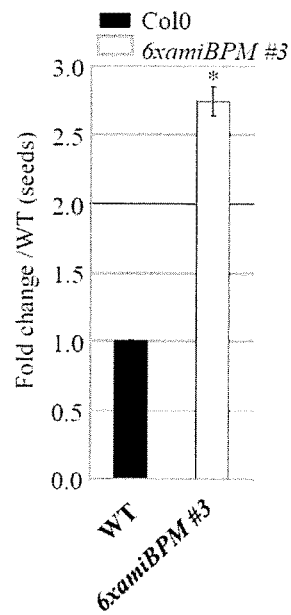

Because seeds of the two 6×amiBPM lines varied significantly in their weight and fatty acid content, we included a third 6×amiBPM line in our analysis to ensure that loss of BPMs is leading in a reproducible manner to increases in fatty acid content and seed size. As observed for the other two lines, 6×amiBPM #3 seeds are also increased in size (FIG. 15B) as well as in dry weight (FIG. 15C), and this correlated with elevated WRI1 content (FIG. 15A), as well as up-regulated expression of BCCP1 and AtGLB1 (FIG. 15D). Likewise, we also observed a significant increase in fatty acid content in these seeds in comparison to WT (FIG. 15E), substantiating findings for 6×amiBPM #1 plants that reduced BPM activity likely result in higher fatty acid levels in seeds.

Discussion

This example shows that BPM proteins have the ability to interact with a broad-range of ERF/AP2 proteins. Y2H studies indicate that many ERF/AP2 proteins are targeted in *Arabidopsis* by a CRL3$^{BPM}$ complex. IP and pull down studies in this work underscore that WRI1 assembles in vitro and in the plant into a complex with CUL3, and the missing CUL3-WRI1 assembly in 6×amiBPM and MATH-overexpressing backgrounds emphasizes that BPM proteins are required for this step. The studies further show that the interaction of BPMs with WRI1 results in the destabilization of their substrate. This is supported by the finding that WRI1 is stabilized in a cul3$^{hyp}$ background, as well as in MATH overexpression and 6×amiBPM plants. Moreover, the ChIP data strongly supports our conclusion that WRI1-CRL3$^{BPM}$ assembly occurs at the DNA level. Consequently, BPM proteins can be considered as negative regulators of WRI1 activities by mediating assembly with the CRL3 core, and ultimately causing its degradation via the 26S proteasome. This is also supported by the finding that fatty acid levels are significantly increased in seeds of 6×amiBPM #1 and #3 plants. These changes resemble earlier descriptions for plants overexpressing WRI1 (Cernac and Benning. 2004). However, it is significant to note that similar changes can be accomplished in *Arabidopsis* without ectopically expressing a transgenic WRI1 in seeds. The fact that overall metabolic changes were mostly restricted to total fatty acid contents also indicates that the function of BPM proteins in seeds is strongly connected with WRI1 activity. In this context, it is of note that WRI1 has very recently been described as part of a small gene family with a total of four members in *Arabidopsis* (To et al. 2012). Although WRI1 is the primary member that controls fatty acid biosynthesis in seeds, the other members also contribute to this pathway but in other tissues (To et al. 2012). The current findings also support the earlier suggestion that instability of RAP2.4, another BPM interacting protein, is mediated by a CRL3$^{BPM}$ ligase (Weber and Hellmann, 2009). Overall, it is likely that a general consequence of BPM interaction with ERF/AP2 transcription factors is degradation of the latter.

In this context, it is also important to note that the BPM family members have very recently been established as regulators of an ABA response by targeting the Homeodomain-Leucine Zipper transcription factor AtHB6 for degradation (Lechner et al., 2011). Consequently, plants with reduced levels of BPM1, 4, 5, and 6 (amiR-bpm) display aberrant responses in stomatal opening (Lechner et al., 2011); however, germinating amiR-bpm seedlings only display increased ABA resistance when combined with an AtHB6 overexpression background. The finding that a member of another transcription factor family is a substrate of BPM proteins, further increases the number of potential substrate proteins that are targeted by CRL3$^{BPM}$ for degradation. Furthermore, many members of the ERF/AP2 family have been described in context with stress tolerance including the ones tested in this study. For example DREB1a is a classical regulator of drought and cold tolerance responses in plants (Sakuma et al., 2002; Miura et al., 2007). ERF1 is known to play a role in biotic stress (Lorenzo et al., 2003; Zhang et al., 2011), and RAV1 has been described in context with senescence and different abiotic stress conditions (Sohn et al., 2006; Woo et al., 2010; Yun et al., 2010). It is therefore likely that both MATH overexpression and 6×amiBPM plants display different sensitivities towards stress such as cold or drought, and treatments with phytohormones such as ethylene or jasmonic acids, in addition to ABA.

It is also noteworthy that degradation of WRI1 appears to occur continuously rather than being stimulated by a specific signal, and this also holds true for RAP2.4 and AtHB6 (Weber and Hellmann, 2009; Lechner et al., 2011). It is unlikely that the cell is degrading these proteins always to the same amount since this seems to be a quite inefficient and unexceptional approach to control protein amounts. Rather one would expect that specific signals are in place that slow down turnover of CRL3$^{BPM}$ substrates similar to ethylene signal transduction, where ethylene disrupts proteasomal degradation of E1N3 mediated by the F-box proteins EBF1 and EBF2 (Guo and Ecker, 2003; Potuschak et al. 2003). In fact, ABA treatment has a stabilizing impact on AtHB6, but the kind of signal that may have a similar impact on WRI1 or RAP2.4 remains unclear.

The wide-ranging developmental changes in both 6×amiBPM, as well as MATH overexpression lines, emphasizes that the BPM family is widely required for plant development. amiR-BPM plants showed a reduced shoot growth (Lechner et al., 2011), which we also observed for 6×amiBPM lines. Interestingly, we could not detect any problems in fertility as observed by Lechner and co-workers for amiR-bpm plants. In addition, 6×amiBPM plants had a strongly reduced root development and fewer leaves, and it remains open whether these changes were also seen by Lechner et al (2011). Moreover, changes in root development were not apparent in MATH overexpression lines, indicating that reduced BPM expression and binding competition approaches differently affected the developmental program of the root in the corresponding plants.

The different approaches followed in this work to affect CRL3$^{BPM}$-WRI1 interplay revealed two additional interesting aspects about the function of BPM proteins besides being substrate receptors to a CRL3$^{BPM}$ ligase. First, comparing cul3$^{hyp}$ and 6×amiBPM plants clearly demonstrated that in both genetic backgrounds WRI1 protein content is increased due to greater stability of the transcription factor. However, the transcriptional activity of WRI1 was only elevated in 6×amiBPM plants but not in cul3$^{hyp}$, as indicated by the changed versus unchanged transcriptional levels of AtGLB1 and BCCP1. Given that in the cul3$^{hyp}$ mutant BPM protein levels are likely normal, these findings indicate that BPM proteins negatively interfere with WRI1 activity, most likely by binding to the transcription factor, while more active WRI1 is available in 6×amiBPM plants. Secondly, the reduced WRI1 amount was quite surprising and unexpected. Because WRI1 expression was up-regulated in MATH overexpressors, one may suggest that the reduced WRI1 content was sensed by the cell, and that changes on the transcriptional level represent a feedback-loop response. In addition, these data also clearly indicate that the MATH domain also interfered with post-transcriptional processes, and thus point out that BPM proteins may have even further diverse roles in addition to targeting ERF/AP2 or AtHB6 transcription factors for ubiquitylation and proteasomal degradation.

Finally, the ChIP data strongly indicate that CRL3$^{BPM}$ E3 ligase assembles with WRI1 at the DNA level while the transcription factor is bound to its target sites. In summary, the current work reveals a new link between fatty acid metabolism and CUL3-based E3 ligase activities. The work also confirms that BPM proteins function in planta as substrate receptor proteins to a CRL3$^{BPM}$ ligase with the purpose to destabilize bound substrates. These findings further indicate that a large number of ERF/AP2 proteins are targets of BPM proteins, and that this complex plays a major role in plant development and stress tolerance by broadly regulating transcriptional, and potentially post-transcriptional, processes in the plant.

Example 2. Modulation of BPM Expression or Activity Enhances Several Yield-Related Traits The transgenic plants (6xamiBPM and BPM$^{MATH:NLS}$) as described in Example 1 were tested under varying conditions to assess the effects on several yield-related traits. For salt stress tolerance assays, wild type (WT) and transgenic plants (6xamiBPM and BPM$^{MATH:NLS}$) were plated on solid minimal culture medium, and grown vertically for five days. Afterwards, they were carefully transferred to plates that were supplemented with 150 mM NaCl. The transgenic plants had significantly increased root growth from day 3 to 6 after the addition of salt as compared to the WT plants (FIG. 18A). Wild type root elongation growth at day six was significantly more inhibited under salt stress conditions than in transgenic plants (FIG. 18B).

The 6xamiBPM plants were then tested under drought conditions. After withholding water for four days, significant changes were observed between WT and 6xamiBPM plants which indicate increased sensitivity of the transgenic plant towards drought stress (FIG. 19).

Figure 20C:
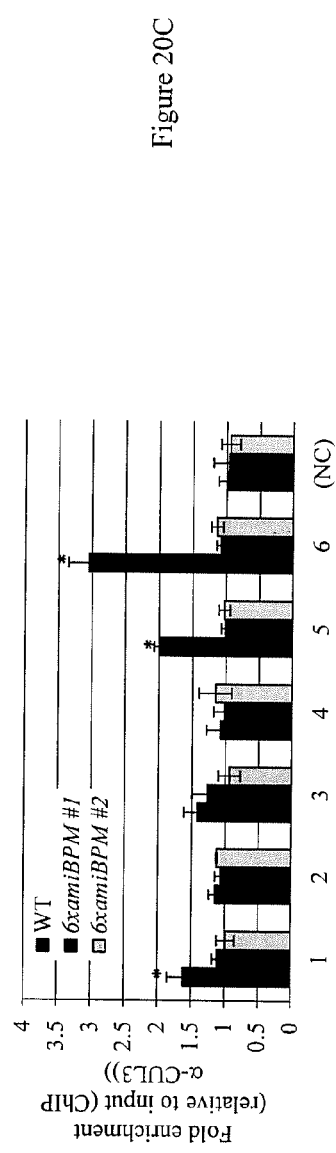
Figure 21A:
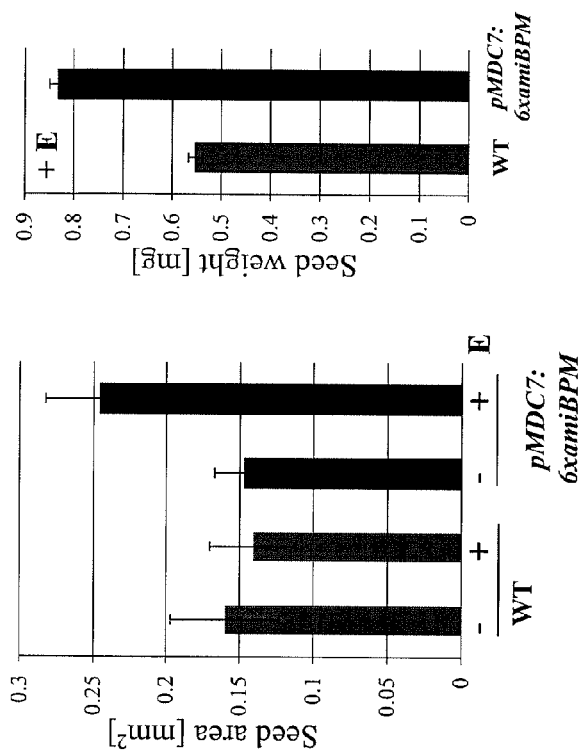
Figure 21B:
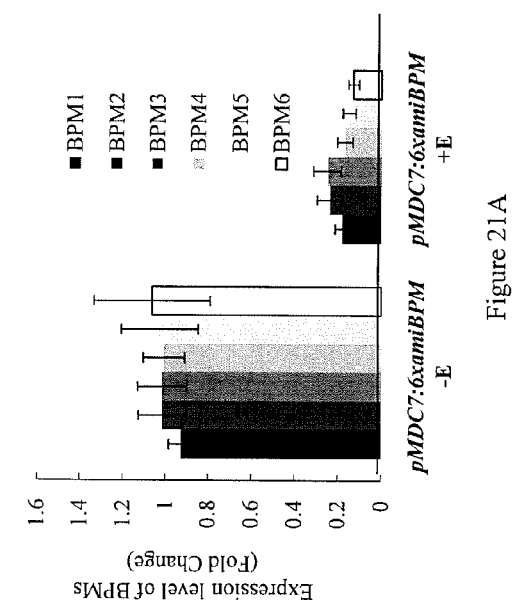
Figures 21C, 21D:
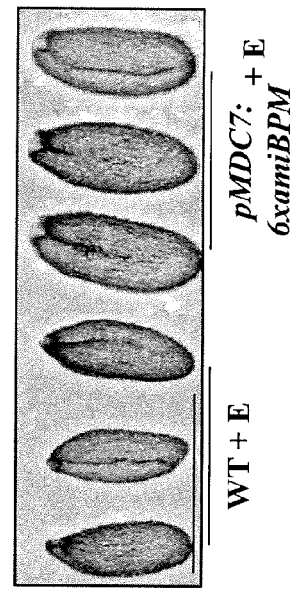
Figure 21E:
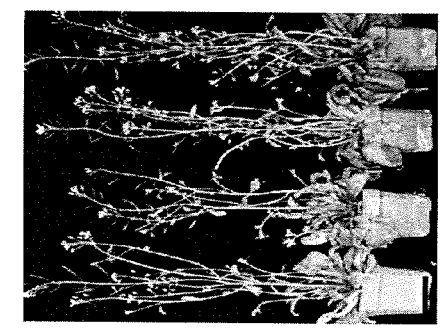

The 6xamiBPM plants were also found to affect the flowering phenotype as compared to WT plants. Expression of Flowering Locus T (FT), a key regulator of the flowering time point, is significantly down regulated in 6xamiBPM plants when compared to WT which is in agreement with the late flowering phenotype of the transgenic plants (FIG. 20A). FIG. 20B shows a schematic drawing of six different FT promoter regions analyzed via qPCR after α-CUL3 ChIP experiment. Significant enrichments were detectable in regions 1, 5 and 6 in WT, but not in a 6xamiBPM#1 control, indicating that CRL3$^{BPM}$ E3 ligases are directly involved in controlling FT expression (FIG. 20C).

Inducible 6xamiBPM constructs were generated and shown to allow for controlled increase in seed size (FIG. 21). Treatment of plants with estradiol over a time period of 24 hours leads to a significant down-regulation of all six BPM genes (FIG. 21A). pMDC7:6xamiBPM plants that carry an estradiol inducible construct are indistinguishable from wild type plants when not treated with estradiol (FIG. 21B). When the transgenic plants were sprayed with estradiol for about 2 weeks, the seeds in estradiol-treated 6xamiBPM plants were significantly larger (FIGS. 21C and E), and heavier (FIG. 21D) than WT seeds.

REFERENCES

Bates, P., Stymie, S., and Ohlrogge, J. (2013) Biochemical pathways in seed oil synthesis. *Current Opinion in Plant Biology*. 16: 358-364.

Baud, S., Wuilleme, S., To, A., Rochat, C., and Lepiniec, L. (2009) Role of WRINKLED1 in the transcriptional regulation of glycolytic and fatty acid biosynthetic genes in *Arabidopsis. Plant J.* 60: 933-947.

Bernhardt, A., et al. (2006) CUL4 associates with DDB1 and DET1 and its downregulation affects diverse aspects of development in *Arabidopsis thaliana. Plant J.* 47: 591-603.

Bohnert et al. (1995) Adaptations to Environmental Stresses, Plant Cell 7 (7), 1099-1111

Boyer, (1982) Plant Productivity and Environment, Science 218, 443-448

Browse, J., McCourt., P., J. and Somerville, C. R. (1985) A mutant of *arabidopsis* lacking a chloroplast-specific lipid. *Anal. Biochem.* 152: 141-145

Cernac, A., and Benning, C. (2004) WRINKLED1 encodes an AP2/EREB domain protein involved in the control of storage compound biosynthesis in *Arabidopsis. Plant J.* 40: 575-585.

Chen, Y. M., et al. (2006) The PII signal transduction protein of *Arabidopsis thaliana* forms an arginine-regulated complex with plastid N-acetyl glutamate kinase. *J Biol Chem.* 281: 5726-5733.

Curtis, M. D. and Grossniklaus, U. (2003) A Gateway cloning vector set for high-throughput functional analysis of genes in planta. *Plant Physiol.* 133: 462-469.

Dieterle, M., et al. (2005) Molecular and functional characterization of *Arabidopsis* Cullin 3A. *Plant J.* 41: 386-399.

Estelle, M. A. and Somerville, C. (1987) Auxin resistant mutants of *Arabidopsis thaliana* with altered morphology. *Mol Gen Genet.* 206: 200-206.

Figueroa, P., et al. (2005) *Arabidopsis* has two redundant Cullin3 proteins that are essential for embryo development and that interact with RBX1 and BTB proteins to form multisubunit E3 ubiquitin ligase complexes in vivo. *Plant Cell.* 17: 1180-1195.

Focks, C. and Benning, C. (1998) wrinkled1: A novel, low-seed-oil mutant of *arabidopsis* with a deficiency in the seed-specific regulation of carbohydrate metabolism. *Plant Phys.* 118: 91-101.

Gingerich, D. J., et al. (2005) Cullins 3a and 3b assemble with members of the broad complex/tramtrack/bric-a-brac (BTB) protein family to form essential ubiquitin-protein ligases (E3s) in *Arabidopsis. J Biol Chem.* 280: 18810-18821.

Gingerich, D. J., Hanada, K., Shiu, S. H., and Vierstra, R. D. (2007) Large-scale, lineage-specific expansion of a bric-a-brac/tramtrack/broad complex ubiquitin-ligase gene family in rice. *Plant Cell.* 19: 2329-2348.

Guo, H., and Ecker, J. R. (2003) Plant responses to ethylene gas are mediated by SCF(EBF1/EBF2)-dependent proteolysis of EIN3 transcription factor. *Cell.* 115: 667-677.

Howard, E. A., Zupan, J. R., Citovsky, V., and Zambryski, P. C. (1992) The VirD2 protein of *A. tumefaciens* contains a C-terminal bipartite nuclear localization signal: implications for nuclear uptake of DNA in plant cells. *Cell.* 68:109-118.

Hsu, P. D., Lander, E. S., and Zhang, F. (2014) Development and Applications of CRISPR-Cas9 for Genome Engineering. *Cell* 157, 1262.

Hua, Z., and Vierstra, R. D. (2011) The cullin-RING ubiquitin-protein ligases. *Annu Rev Plant Biol.* 62: 299-334.

Juranić, M., Srilunchang K O, Krohn N G, Leljak-Levanic D, Sprunck S, and Dresselhaus T. (2012) Germline-specific MATH-BTB substrate adaptor MAB1 regulates spindle length and nuclei identity in maize Plant Cell 24:4974-4991.

Laemmli, U. K. (1970) Cleavage of structural proteins during the assembly of the head of bacteriophage T4. Nature 227: 680-685.

Lechner, E., et al. (2011) MATH/BTB CRL3 receptors target the homeodomain-leucine zipper ATHB6 to modulate abscisic acid signaling. Dev Cell. 21: 1116-1128.

Liu, J., Hua, W., Zhan, G., Wei, F., Wang, X., Liu, G., and Wang, H. (2010) Increasing seed mass and oil content in transgenic Arabidopsis by the overexpression of wri1-like gene from Brassica napus. Plant physiology and biochemistry: PPB/Societe francaise de physiologie vegetale 48, 9-15.

Lorenzo, O., Piqueras, R., Sanchez-Serrano, J. J., and Solano, R. (2003) ETHYLENE RESPONSE FACTOR1 integrates signals from ethylene and jasmonate pathways in plant defense. Plant Cell. 15: 165-178.

Maeo, K., et al. (2009) An AP2-type transcription factor, WRINKLED1, of Arabidopsis thaliana binds to the AW-box sequence conserved among proximal upstream regions of genes involved in fatty acid synthesis. Plant J. 60: 476-487.

Miura, K., et al. (2007) SIZ1-mediated sumoylation of ICE1 controls CBF3/DREB1A expression and freezing tolerance in Arabidopsis. Plant Cell. 19: 1403-1414.

Morohashi, K., Xie, Z., Grotewold, E. (2009) Gene-specific and genome-wide ChIP approaches to study plant transcriptional networks. Methods Mol. Biol. 553: 3-12.

Potuschak T, Lechner E, Parmentier Y, Yanagisawa S, Grava S, Koncz C, Genschik P. (2003) EIN3-dependent regulation of plant ethylene hormone signaling by two arabidopsis F box proteins: EBF1 and EBF2. Cell 115: 679-689.

Pouvreau, B., Baud, S., Vernoud, V., Morin, V., Py, C., Gendrot, G., Pichon, J. P., Rouster, J., Paul, W., and Rogowsky, P. M. (2011) Duplicate maize Wrinkled1 transcription factors activate target genes involved in seed oil biosynthesis. Plant physiology 156, 674-686.

Roessner-Tunali, U., et al. (2003) De novo amino acid biosynthesis in potato tubers is regulated by sucrose levels. Plant Physiol. 133: 683-692.

Sakuma, Y., et al. (2002) DNA-binding specificity of the ERF/AP2 domain of Arabidopsis DREBs, transcription factors involved in dehydration- and cold-inducible gene expression. Biochem Biophys Res Commun. 290: 998-1009.

Shen, B., Allen, W. B., Zheng, P., Li, C., Glassman, K., Ranch, J., Nubel, D., and Tarczynski, M. C. (2010) Expression of ZmLEC1 and ZmWRI1 increases seed oil production in maize. Plant physiology 153, 980-987.

Sohn, K. H., Lee, S. C., Jung, H. W., Hong, J. K., and Hwang, B. K. (2006) Expression and functional roles of the pepper pathogen-induced transcription factor RAV1 in bacterial disease resistance, and drought and salt stress tolerance. Plant Mol Biol. 61: 897-915.

Sparkes, L A., Runions, J., Kearns, A., and Hawes, C. (2006) Rapid, transient expression of fluorescent fusion proteins in tobacco plants and generation of stably transformed plants. Nature Protocols. 1: 2019-2025.

Thomann, A., et al. (2009) Arabidopsis CULLIN3 genes regulate primary root growth and patterning by ethylene-dependent and -independent mechanisms. PLoS Genet. 5: e1000328.

Tissot, G., Pepin, R., Job, D., Douce, R., and Alban, C. (1998) Purification and properties of the chloroplastic form of biotin holocarboxylase synthetase from Arabidopsis thaliana overexpressed in Escherichia coli. Eur J Biochem. 258: 586-596.

To, A., Joubes, J., Barthole, G., Lecureuil, A., Scagnelli, A., Jasinski, S., Lepiniec, L., Bauda, S. (2012) WRINKLED Transcription Factors Orchestrate Tissue-Specific Regulation of Fatty Acid Biosynthesis in Arabidopsis. Plant Cell 24: 5007-5023.

Weber, H., et al. (2005) Arabidopsis AtCUL3a and AtCUL3b form complexes with members of the BTB/POZ-MATH protein family. Plant Physiol. 137: 83-93.

Weber, H., and Hellmann, H. (2009) Arabidopsis thaliana BTB/POZ-MATH proteins interact with members of the ERF/AP2 transcription factor family. FEBS J. 276: 6624-6635.

Woo, H. R., et al. (2010) The RAV1 transcription factor positively regulates leaf senescence in Arabidopsis. J Exp Bot. 61: 3947-3957.

Yun, K. Y., et al. (2010) Transcriptional regulatory network triggered by oxidative signals configures the early response mechanisms of japonica rice to chilling stress. BMC Plant Biol. 10: 16.

Zhang, W., et al. (2011) LeERF-1, a novel AP2/ERF family gene within the B3 subcluster, is down-regulated by light signals in Lithospermum erythrorhizon. Plant Biol (Stuttg). 13: 343-348.

Zhao, L., et al. (2013) Phylogenetic Analysis of Brassica rapa MATH-Domain Proteins Current Genomics 14, 214-223.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A transgenic plant, wherein said plant is genetically engineered to express a nucleic acid so as to down-regulate expression or reduce the activity of all of the members of the BPM (BTB/POZ-MATH) protein family as compared to a control plant, wherein said transgenic plant exhibits enhanced yield-related traits as compared to said control plant, and wherein said enhanced yield-related traits are selected from the group consisting of increased seed oil production, increased salt stress-tolerance, and increased drought stress-tolerance as compared to said control plant.

2. The transgenic plant of claim 1, wherein said plant is of the Brassicaceae family.

3. The transgenic plant of claim 2, wherein said plant is *Arabidopsis Thaliana*.

4. The transgenic plant of claim 1, wherein said transgenic plant exhibits increased seed oil production as compared to said control plant.

5. A method for increasing seed oil production in a transgenic plant as compared to a control plant and recovering said seed oil, said method comprising: cultivating a transgenic plant under conditions promoting plant growth and development, wherein said transgenic plant is genetically engineered to express a nucleic acid so as to exhibit increased seed oil production as compared to a control plant by down-regulating expression or reducing the activity of all of the members of the BPM protein family as compared to a control plant; and recovering said seed oil from said transgenic plant.

6. The method of claim 5, wherein said plant is of the Brassicaceae family.

7. The method of claim 6, wherein said plant is *Arabidopsis Thaliana*.

8. A method for enhancing yield-related traits in a plant as compared to a control plant, said method comprising: genetically engineering said plant to express a nucleic acid so as to down-regulate expression or reduce the activity of all of the members of the BPM protein family as compared to a control plant, wherein said yield-related traits are selected from the group consisting of increased seed oil production, increased salt stress-tolerance, and increased drought stress-tolerance as compared to said control plant, and testing the genetically engineered plant to assess a yield-related trait selected from the group consisting of seed oil production, salt stress-tolerance, and drought stress-tolerance.

9. The method of claim 8, wherein said plant exhibits increased seed oil production as compared to a control plant.

10. The method of claim 8, wherein said plant is of the Brassicaceae family.

11. The method of claim 10, wherein said plant is *Arabidopsis Thaliana*.

12. The method of claim 8, wherein said step of genetically engineering comprises introducing artificial microRNA (amiRNA) to down-regulate all of the members of the BPM protein family.

13. A method for enhancing yield-related traits in a plant as compared to a control plant, said method comprising: genetically engineering said plant to express a nucleic acid so as to reduce the activity of at least one BPM protein as compared to a control plant, wherein said yield-related traits are selected from the group consisting of increased seed oil production, increased salt stress-tolerance, and increased drought stress-tolerance as compared to said control plant, wherein said step of genetically engineering comprises the expression of at least one exogenous MATH domain to compete with said BPM protein, and testing the genetically engineered plant to assess a yield-related trait selected from the group consisting of seed oil production, salt stress-tolerance, and drought stress-tolerance.

14. A product produced by or from a transgenic plant which is genetically engineered to express a nucleic acid so as to enhance yield-related traits by down-regulating expression or reducing the activity of all of the members of the BPM protein family as compared to a control plant, wherein said enhanced yield-related traits are selected from the group consisting of increased seed oil production, increased salt stress-tolerance, and increased drought stress-tolerance as compared to said control plant, and wherein the product comprises the expressed nucleic acid.

* * * * *